United States Patent
Anderberg et al.

(10) Patent No.: US 9,229,010 B2
(45) Date of Patent: Jan. 5, 2016

(54) METHODS AND COMPOSITIONS FOR DIAGNOSIS AND PROGNOSIS OF RENAL INJURY AND RENAL FAILURE

(75) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US)

(73) Assignee: ASTUTE MEDICAL, INC., San Diego, CA (US)

( * ) Notice: Subject to any disclaimer, the term of this patent is extended or adjusted under 35 U.S.C. 154(b) by 699 days.

(21) Appl. No.: 13/148,029

(22) PCT Filed: Feb. 5, 2010

(86) PCT No.: PCT/US2010/023292
§ 371 (c)(1),
(2), (4) Date: Sep. 8, 2011

(87) PCT Pub. No.: WO2010/091231
PCT Pub. Date: Aug. 12, 2010

(65) Prior Publication Data
US 2012/0190051 A1 Jul. 26, 2012

Related U.S. Application Data

(60) Provisional application No. 61/150,372, filed on Feb. 6, 2009, provisional application No. 61/150,374, filed on Feb. 6, 2009, provisional application No. 61/150,393, filed on Feb. 6, 2009, provisional application No. 61/162,396, filed on Mar. 23, 2009, provisional application No. 61/162,402, filed on Mar. 23, 2009, provisional application No. 61/166,333, filed on Apr. 3, 2009.

(51) Int. Cl.
*G01N 31/00* (2006.01)
*G01N 33/53* (2006.01)
*G01N 33/68* (2006.01)

(52) U.S. Cl.
CPC ...... *G01N 33/6893* (2013.01); *G01N 2800/347* (2013.01); *G01N 2800/60* (2013.01)

(58) Field of Classification Search
CPC ..................... G01N 33/6893; G01N 2800/347
See application file for complete search history.

(56) References Cited

U.S. PATENT DOCUMENTS

| | | | |
|---|---|---|---|
| 5,804,392 A | 9/1998 | Esmon et al. | |
| 6,218,122 B1 | 4/2001 | Friend et al. | |
| 6,664,385 B1 | 12/2003 | Sanicola-Nadel et al. | |
| 6,784,154 B2 | 8/2004 | Westenfelder | |
| 6,861,404 B1 | 3/2005 | Cohen et al. | |
| 6,941,172 B2 | 9/2005 | Nachum | |
| 7,138,230 B2 | 11/2006 | Hu et al. | |
| 7,141,382 B1 | 11/2006 | Parikh et al. | |
| 7,235,358 B2 | 6/2007 | Wohlgemuth et al. | |
| 7,608,413 B1 | 10/2009 | Joseloff et al. | |
| 7,662,578 B2 | 2/2010 | Devarajan | |
| 7,981,684 B2 | 7/2011 | Levin et al. | |
| 7,998,744 B2 | 8/2011 | Stevenson et al. | |
| 8,008,008 B2 | 8/2011 | Parr et al. | |
| 8,071,293 B2 | 12/2011 | High et al. | |
| 8,072,669 B2 * | 12/2011 | Zhou | 359/238 |
| 8,080,394 B2 | 12/2011 | Levy et al. | |
| 8,241,861 B1 | 8/2012 | Heinecke et al. | |
| 8,871,459 B2 * | 10/2014 | Anderberg et al. | 435/23 |
| 2003/0003588 A1 | 1/2003 | Comper | |
| 2004/0053309 A1 | 3/2004 | Holt et al. | |
| 2004/0106155 A1 | 6/2004 | Comper | |
| 2005/0002934 A1 | 1/2005 | Reed | |
| 2005/0048033 A1 | 3/2005 | Fraser et al. | |
| 2005/0112688 A1 | 5/2005 | Hu et al. | |
| 2005/0137481 A1 | 6/2005 | Sheard et al. | |
| 2005/0148029 A1 | 7/2005 | Buechler et al. | |
| 2005/0158801 A1 | 7/2005 | Hu et al. | |
| 2005/0256075 A1 | 11/2005 | Alitalo et al. | |
| 2005/0272101 A1 | 12/2005 | Devarajan et al. | |
| 2006/0003327 A1 | 1/2006 | Achiron et al. | |
| 2006/0057066 A1 | 3/2006 | Natsoulis et al. | |
| 2006/0088823 A1 | 4/2006 | Haab et al. | |
| 2006/0204951 A1 | 9/2006 | Folkman et al. | |
| 2006/0223077 A1 | 10/2006 | Ni et al. | |
| 2006/0240437 A1 | 10/2006 | Krolewski et al. | |
| 2006/0246485 A1 | 11/2006 | Sarwal et al. | |
| 2007/0031905 A1 | 2/2007 | Shariat | |

(Continued)

FOREIGN PATENT DOCUMENTS

| | | |
|---|---|---|
| CN | 1311691 A | 9/2001 |
| CN | 1791797 A | 6/2006 |

(Continued)

OTHER PUBLICATIONS

Kawai et al. (Am. Journal of Pathology, 2004, 165(5), 1603-1612).*
Extended European Search Report and Written Opinion issued in PCT/US2010044772 dated Dec. 3, 2012.
Voshol et al., Evaluation of Biomarker Discovery Approaches to Detect Protein Biomarkers of Acute Renal Allograft Rejection. J Proteome Res. Jul.-Aug. 2005;4(4):1192-1199.
Extended European Search Report and Written Opinion issued in PCT/US2010044708 dated Dec. 3, 2012.
Neziri et al., Cloning and molecular characterization of Dashurin encoded by C20orf116, a PCI-domain containing protein. Biochim Biophys Acta. Apr. 2010;1800(4):430-438.
Non Final Office Action issued by the US Patent and Trademark Office in U.S. Appl. No. 13/164,768 on Dec. 18, 2012.

(Continued)

*Primary Examiner* — Lisa Cook
(74) *Attorney, Agent, or Firm* — Michael A. Whittaker

(57) ABSTRACT

Disclosed are methods and compositions for monitoring, diagnosis, prognosis, and determination of treatment regimens in subjects suffering from or suspected of having a renal injury. In particular, disclosed are assays that detect one or more markers selected from the group consisting of Prostatic acid phosphatase, Lactotransfenin, Soluble erythropoietin receptor, Von Willebrand factor, Soluble endothelial protein C receptor, and Beta-2-glycoprotein 1 as diagnostic and prognostic biomarkers in renal injuries.

7 Claims, 80 Drawing Sheets

(56) References Cited

U.S. PATENT DOCUMENTS

| | | |
|---|---|---|
| 2007/0087387 A1 | 4/2007 | Devarajan et al. |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0248989 A1 | 10/2007 | Devarajan |
| 2007/0249002 A1 | 10/2007 | Hu et al. |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0133141 A1 | 6/2008 | Frost |
| 2008/0153092 A1 | 6/2008 | Kienle et al. |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0148539 A1 | 6/2009 | Elias et al. |
| 2009/0176656 A1 | 7/2009 | Halloran |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0190044 A1 | 7/2012 | Anderberg et al. |
| 2012/0190051 A1 | 7/2012 | Anderberg et al. |
| 2013/0035290 A1 | 2/2013 | Elias et al. |

FOREIGN PATENT DOCUMENTS

| | | |
|---|---|---|
| EP | 0828159 A1 | 3/1998 |
| EP | 1905846 A2 | 4/2008 |
| EP | 2261660 A1 | 12/2010 |
| EP | 2480882 A1 | 8/2012 |
| EP | 2513649 A1 | 10/2012 |
| RU | 2180965 C1 | 3/2002 |
| SU | 1429031 A1 | 10/1988 |
| WO | 9855508 A2 | 12/1998 |
| WO | 0010601 A1 | 3/2000 |
| WO | 03054004 A2 | 7/2003 |
| WO | 03075016 A1 | 9/2003 |
| WO | 2004005934 A2 | 1/2004 |
| WO | 2005087264 A1 | 9/2005 |
| WO | 2006083986 A3 | 8/2006 |
| WO | 2006125301 A1 | 11/2006 |
| WO | 2007013919 A2 | 2/2007 |
| WO | 2007041623 A2 | 4/2007 |
| WO | 2008060607 A2 | 5/2008 |
| WO | 2008084331 A2 | 7/2008 |
| WO | 2008104804 A2 | 9/2008 |
| WO | 2008116867 A1 | 10/2008 |
| WO | 2008122670 A2 | 10/2008 |
| WO | 2008154238 A1 | 12/2008 |
| WO | 2009038742 A2 | 3/2009 |
| WO | 2010025424 A1 | 3/2010 |
| WO | 2010025434 A1 | 3/2010 |
| WO | 2010048346 A1 | 4/2010 |
| WO | 2010048347 A2 | 4/2010 |
| WO | 2010054389 A1 | 5/2010 |
| WO | 2010091236 A1 | 8/2010 |
| WO | 2010111746 A1 | 10/2010 |
| WO | 2010128158 A1 | 11/2010 |
| WO | 2011035323 A1 | 3/2011 |
| WO | 2011075744 A1 | 6/2011 |

OTHER PUBLICATIONS

Non Final Office Action issued by the US Patent and Trademark Office in U.S. Appl. No. 13/061,413 on Jan. 2, 2013.
Norman et al., Progressive Renal Disease: Fibroblasts, Extracellular Matrix, and Integrins. Exp Nephrol. Mar.-Apr. 1999;7(2):167-177.
International Search Report and Written Opinion issued in 200980154224.5 dated Nov. 23, 2012.
English Translation of International Search Report and Written Opinion issued in 200980154224.5 dated Nov. 23, 2012.
Zhu et al., Expression of Urinary Epidermal Growth Factor and Renal Function. J Clin Urol Dec. 31, 1998;13(8):374-379.
Zhu et al., Expression of Urinary Epidermal Growth Factor and Renal Function. J Clin Urol Dec. 31, 1998;13(8):374-379 (abstract English translation).
Sun et al., A Survey on the Relationship between the Epidermal Growth Factor and Renal Function. Int J Transpl Hemopurific Dec. 31, 2006;4(1):41-44.
Sun et al., A Survey on the Relationship between the Epidermal Growth Factor and Renal Function. Int J Transpl Hemopurific Dec. 31, 2006;4(1):41-44 (abstract English translation).
Non Final Office Action issued in 2009801542245 dated Dec. 17, 2012.
Non Final Office Action issued by the US Patent and Trademark Office in U.S. Appl. No. 13/125,360 on Jan. 24, 2013.
Caron et al. Ischemic injury alters endothelial cell properties of kidney cortex:stimulation of MMP-9. Exp Cell Res. Oct. 15, 2005;301(1):105-116.
Non Final Office Action issued by the US Patent and Trademark Office in U.S. Appl. No. 13/508,363 on Feb. 1, 2013.
Non Final Office Action issued by the US Patent and Trademark Office in U.S. Appl. No. 13/577,243 on Feb. 14, 2013.
Non Final Office Action issued in Japanese Patent Application No. 2011-525262 on Feb. 5, 2013.
Non Final Office Action issued in Japanese Patent Application No. 2011-525262 on Feb. 5, 2013 (English translation).
International Search Report and Written Opinion issued in PCT/US2010/023292 on Apr. 30, 2010.
Response dated May 16, 2012 to Extended European Search Report and Written Opinion in PCT/US2009/055449.
Extended European Search Report and Written Opinion issued on Feb. 23, 2012 in PCT/US2009/065419.
Extended European Search Report and Written Opinion issued on Jul. 27, 2012 in PCT/US2010/023294.
Extended European Search Report and Written Opinion issued on Oct. 24, 2011 in PCT/US2009/055449.
Extended European Search Report and Written Opinion issued on Feb. 22, 2012 in PCT/US2009/055460.
Extended European Search Report and Written Opinion issued on Jul. 9, 2012 in PCT/US2009/061561.
Extended European Search Report and Written Opinion issued on Aug. 23, 2012 in PCT/US2009/061562.
Extended European Search Report and Written Opinion issued on Jul. 9, 2012 in PCT/US2010/023292.
Extended European Search Report and Written Opinion issued on Aug. 23, 2012 in PCT/US2010/023297.
Extended European Search Report and Written Opinion issued on Jun. 8, 2012 in PCT/US2009/063906.
International Preliminary Report on Patentability issued on Oct. 21, 2011 in PCT/US2010/023297.
International Preliminary Report on Patentability issued on Mar. 29, 2011 in PCT/US2010/049234.
International Preliminary Report on Patentability issued on May 18, 2012 in PCT/US2010/055730.
International Preliminary Report on Patentability issued on Mar. 10, 2011 in PCT/US2009/055449.

(56) References Cited

OTHER PUBLICATIONS

International Preliminary Report on Patentability issued on Mar. 10, 2011 in PCT/US2009/055460.
International Preliminary Report on Patentability issued on Aug. 16, 2012 in PCT/US2011/023830.
International Preliminary Report on Patentability issued on Aug. 16, 2012 in PCT/US2011/023831.
International Preliminary Report on Patentability issued on Aug. 16, 2012 in PCT/US2011/023832.
International Preliminary Report on Patentability issued on Apr. 5, 2012 in PCT/US2010/049695.
International Preliminary Report on Patentability issued on May 5, 2011 in PCT/US2009/061561.
International Preliminary Report on Patentability issued on May 5, 2011 in PCT/US2009/061562.
International Preliminary Report on Patentability issued on Jun. 3, 2011 in PCT/US2009/065419.
International Preliminary Report on Patentability issued on Jul. 5, 2012 in PCT/US2010/061377.
International Preliminary Report on Patentability issued on Aug. 18, 2011 in PCT/US2010/023292.
International Preliminary Report on Patentability issued on Aug. 18, 2011 in PCT/US2010/023294.
International Preliminary Report on Patentability issued on May 10, 2011 in PCT/US2009/063906.
International Search Report and Written Opinion issued on Dec. 3, 2010 in PCT/US2010/049234.
International Search Report and Written Opinion issued on Feb. 8, 2011 in PCT/US2010/055730.
International Search Report and Written Opinion issued on Oct. 28, 2010 in PCT/US2010/044772.
International Search Report and Written Opinion issued on Oct. 8, 2010 in PCT/US2010/044708.
International Search Report and Written Opinion issued on Dec. 10, 2009 in PCT/US2009/055449.
International Search Report and Written Opinion issued on Dec. 31, 2009 in PCT/US2009/055460.
International Search Report and Written Opinion issued on Dec. 3, 2010 in PCT/US2010/049695.
International Search Report and Written Opinion issued on Jan. 20, 2010 in PCT/US2009/061561.
International Search Report and Written Opinion issued on Apr. 13, 2010 in PCT/US2009/061562.
International Search Report and Written Opinion issued on Mar. 30, 2010 in PCT/US2009/065419.
International Search Report and Written Opinion issued on Mar. 8, 2011 in PCT/US2010/061377.
International Search Report and Written Opinion issued on Apr. 30, 2010 in PCT/US2010/023292.
International Search Report and Written Opinion issued on Apr. 22, 2010 in PCT/US2010/023294.
International Search Report and Written Opinion issued on Jun. 3, 2010 in PCT/US2010/023297.
International Search Report and Written Opinion issued on Jan. 15, 2010 in PCT/US2009/063906.
International Search Report and Written Opinion issued on Nov. 18, 2010 in PCT/US2010/046910.
International Search Report and Written Opinion issued on Jan. 18, 2012 in PCT/US2011/053015.
International Search Report and Written Opinion issued on Feb. 24, 2012 in PCT/US2011/055055.
International Search Report and Written Opinion issued on Jan. 19, 2011 in PCT/US2010/055721.
International Search Report and Written Opinion issued on May 10, 2012 in PCT/US2012/020571.
International Search Report and Written Opinion issued on Apr. 27, 2011 in PCT/US2011/023830.
International Search Report and Written Opinion issued on Apr. 27, 2011 in PCT/US2011/023831.
International Search Report and Written Opinion issued on Apr. 29, 2011 in PCT/US2011/023832.
International Search Report and Written Opinion issued on May 17, 2011 in PCT/US2011/026384.
Yuen et al., Ischemic and Nephrotoxic Acute Renal Failure are Distinguished by their Broad Transcriptomic Responses. Physiol Genomics. May 16, 2006;25(3):375-386.
Zager et al. Proximal tubular cytochrome c efflux: Determinant, and potential marker, of mitochondrial injury. Kidney Int. Jun. 2004;65(6):2123-2134.
Herget-Rosenthal et al. Early detection of acute renal failure by serum cystatin C. Kidney International. 2004, vol. 66, pp. 1115-1122, especially pp. 1115, 1116, and 1117.
Grigoryev et al., The Local and Systemic Inflammatory Transcriptome after Acute Kidney Injury. J Am Soc Nephrol. Mar. 2008;19(3):547-558.
Gümüs et al., Serum Levels of Total Acid Phosphatase, Prostatic Acid Phosphatase, Total and Free Prostate-Specific Antigen in Patients Within Chronic Hemodialysis Program. Braz J Urol, Mar.-Apr. 2001;27(2):133-135.
Gupta et al., Role of Protein C in Renal Dysfunction after Polymicrobial Sepsis. J Am Soc Nephrol. Mar. 2007;18(3):860-867.
Han et al, Urinary biomarkers in the early diagnosis of acute kidney injury, Kidney Int. Apr. 2008;73(7):863-869.
Han et al., Upregulation of hyaluronan and its binding receptors in an experimental model of chronic cyclosporine nephropathy. Nephrology (Carlton). Mar. 2010;15(2):216-224.
Han, Biomarkers for Early Detection of Acute Kidney Injury. Nephrology Rounds Apr. 2008;6(4):6 pp.
Harris et al., Growth Factors and Cytokines in Acute Renal Failure. Adv Ren Replace Ther. Apr. 1997;4(2 Suppl):43-53.
He et al., Interleukin-18 binding protein transgenic mice are protected against ischemic acute kidney injury. Am J Physiol Renal Physiol. Nov. 2008;295(5):F1414-F1421.
Herget-Rosenthal et al., Early detection of acute renal failure by serum cystatin C. Kidney Int. Sep. 2004;66(3):1115-1122.
Hidaka et al., Urinary clusterin levels in the rat correlate with the severity of tubular damage and may help to differentiate between glomerular and tubular injuries. Cell Tissue Res. Dec. 2002;310(3):289-296.
Hirschberg et al. Factors Predicting Poor Outcome in Patients with Acute Renal Failure (ARF). J. Am. Soc. Nephrol. Sep. 1, 1996;7(9):1374.
Hoste et al., RIFLE criteria for acute kidney injury are associated with hospital mortality in critically ill patients: a cohort analysis. Crit Care, 2006;10(3):R73 (10 pages).
Hugo and Daniel, Thrombospondin in Renal Disease. Nephron Exp Nephrol. 2009;111(3):e61-e66.
Hugo et al. ,Thrombospondin 1 precedes and predicts the development of tubulointerstitial fibrosis in glomerular disease in the rat. Kidney Int. Feb. 1998;53(2):302-311.
Jang and Rabb, The innate immune response in ischemic acute kidney injury. Clin Immunol. Jan. 2009;130(1):41-50.
Jonsson, The role of fibroblast growth factor 23 in renal disease. Nephrol. Dial. Transplant Mar. 2005;20(3):479-482.
Julian et al., Sources of Urinary Proteins and their Analysis by Urinary Proteomics for the Detection of Biomarkers of Disease. Proteomics Clin Appl., 2009;3(9):1029-1043.
Kadiroglu et al., The Evaluation of Effects of Demographic Features, Biochemical Parameters, and Cytokines on Clinical Outcomes in Patients with Acute Renal Failure. Ren Fail. 2007;29(4):503-508.
Kalousova et al., Soluble Receptor for Advanced Glycation End Products in Patients With Decreased Renal Function. Am. J. Kidney Dis.Mar. 2006;47(3): 406-411.
Kamata et al., Up-regulation of glomerular extracellular matrix and transforming growth factor-beta expression in RF/J mice. Kidney Int. Mar. 1999;55(3):864-876.
Kehoe et al. Elevated Plasma Renin Activity Associated with Renal Dysfunction. Nephron 1986;44:51-57 (abstract only).
Kellum et al. Definition and Classification of Acute Kidney Injury. Nephron Clin Pract 2008;109(4):c182-c187.
Kellum., Acute kidney injury, Crit Care Med, 2008;36(4):S141-S145.

(56) References Cited

OTHER PUBLICATIONS

Keyes and Bagshaw, Early diagnosis of acute kidney injury in critically ill patients. Expert Rev Mol Diagn. Jul. 2008;8(4):455-464.
Khanna et al., Expression of TGF-beta and fibrogenic genes in transplant recipients with tacrolimus and cyclosporine nephrotoxicity. Kidney Int. Dec. 2002;62(6):2257-2263.
Kharasch et al., Gene Expression Profiling of Nephrotoxicity from the Sevoflurane Degradation Product Fluoromethyl-2,2-difluoro-1-(trifluoromethyl)vinyl Ether ("Compound A") in Rats. Toxicol Sci. Apr. 2006;90(2):419-431.
Kiley and Chevalier, Urinary biomarkers: The future looks promising. Kidney Int. Jul. 2009;76( 2): 133-134.
Kilis-Pstrusinska et al., [Levels of selected soluble adhesion molecules in blood serum of children with chronic glomerulonephritis]. Pol Merkur Lekarski. Apr. 2001;10(58):247-249.
Kilis-Pstrusinska et al., Serum levels of soluble adhesion molecules in children with glomerulonephritis (GN). Nephrol Dialysis Transplant. Jun. 2001;16(6):A62.
Kinsey et al., Inflammation in Acute Kidney Injury. Nephron Exp Nephrol. 2008; 109(4):e102-e107.
Koo et al., Cadaver versus living donor kidneys: Impact of donor factors on antigen induction before transplantation. Kidney Int. Oct. 1999;56(4):1551-1559.
Landray et al., Inflammation, Endothelial Dysfunction, and Platelet Activation in Patients With Chronic Kidney Disease: The Chronic Renal Impairment in Birmingham (CRIB) Study. Am J Kidney Dis. Feb. 2004;43(2):244-253.
Lang et al., Heat Shock Protein 60 Is Released in Immune-Mediated Glomerulonephritis and Aggravates Disease: In Vivo Evidence for an Immunologic Danger Signal. J Am Soc Nephrol. Feb. 2005;16(2):383-391.
Lapsley et al., Beta2-glycoprotein-1 (apolipoprotein H) excretion in chronic renal tubular disorders: Comparison with other protein markers of tubular malfunction. J Clin Pathol. Oct. 1991;44(10):812-816.
Larsson et al., Circulating concentration of FGF-23 increases as renal function declines in patients with chronic kidney disease, but does not change in response to variation in Phosphate intake in healthy volunteers. Kidney Int. Dec. 2003;64(6):2272-2279.
Liu et al., Predictive and pathogenetic value of plasma biomarkers for acute kidney injury in patients with acute lung injury. Crit Care Med Dec. 2007;35(12):2755-2761.
Liu et al., Serum Interleukin-6 and interleukin-8 are early biomarkers of acute kidney injury and predict prolonged mechanical ventilation in children undergoing cardiac surgery: a case-control study. Critical Care 2009;13(4):R104 (9 pp.).
Lopes-Virella et al., Urinary high density lipoprotein in minimal change glomerular disease and chronic glomerulopathies. Clin Chim Acta. May 16, 1979;94(1):73-81.
Lu et al., Increased Macrophage Infiltration and Fractalkine Expression in Cisplatin-Induced Acute Renal Failure in Mice. J Pharmacol Exp Ther. Jan. 2008;324(1):111-117.
Malyszko et al., Visfatin and apelin, new adipocytokines, and their relation to endothelial function in patients with chronic renal failure. Adv Med Sci. 2008;53(1):32-36.
Matousovic et al., IgA-containing immune complexes in the urine of IgA nephropathy patients. Nephrol Dial Transplant Sep. 2006;21(9):2478-2484.
Mattes, Experience With a Biomarker Consortium. CPath Predictive Safety Training Consortium, Critical Path Institute:48 pp.
Melnikov et al., Impaired IL-18 processing protects caspase-1-deficient mice from ischemic acute renal failure. J Clin Invest, May 2001;107(9):1145-1152.
Milford et al., Prognostic Markers in Diarrhoea-Associated Haemolytic-Uraemic Syndrome: Initial Neutrophil Count, Human Neutrophil Elastase and Von Willebrand Factor Antigen. Nephrol Dial Transplant 1991;6(4):232-237.
Montagna et al., Impairment of cellular redox status and membrane protein activities in kidneys from rats with ischemic acute renal failure. Biochim Biophys Acta Aug. 14, 1998;1407(2):99-108.
Musial et al., Soluble adhesion molecules in chronic renal failure (CRF) children treated conservatively. Nephrol Dialysis Transplant. 2002;17(Abstracts Suppl 1):232.
Nguyen et al., Heparin-Binding EGF-Like Growth Factor Is Up-Regulated in the Obstructed Kidney in a Cell- and Region-Specific Manner and Acts to Inhibit Apoptosis. Am J Pathol. Mar. 2000;156(3):889-898.
Nishiyama et al., Up-Regulation of Galectin-3 in Acute Renal Failure of the Rat. Am J Pathol. Sep. 2000;157 (3):815-823.
Ohno et al., Prognostic significance of tenascin-C expression in clear cell renal cell carcinoma. Oncol Rep. 2008;20(3):511-516.
Ozer et al., A panel of urinary biomarkers to monitor reversibility of renal injury and a serum marker with improved potential to assess renal function. Nat Biotechnol. May 2010;28(5):486-494.
FDA, European Medicines Agency to Consider Additional Test Results When Assessing New Drug Safety—Collaborative effort by FDA and EMEA expected to yield additional safety data. http://www.natap.org/2008/newsUpdates/071608_01.htm dated Jun. 12, 2008.
Harpur et al., Biological Qualification of Biomarkers of Chemical-Induced Renal Toxicity in Two Strains of Male Rat. Toxicol Sci. Aug. 2011;122(2):235-252.
Final Office Action issued by the United States Patent and Trademark Office in U.S. Appl. No. 13/061,446 dated Jun. 7, 2013.
Non Final Office Action issued by the United States Patent and Trademark Office in U.S. Appl. No. 13/125,454 dated Mar. 5, 2013.
Thaker et al., Identification of thrombospondin 1 (TSP-1) as a novel mediator of cell injury in kidney ischemia. J Clin Invest. Dec. 2005;115(12):3451-3458.
Restriction Requirement issued by the United States Patent and Trademark Office in U.S. Appl. No. 13/061,413 dated Sep. 5, 2012.
Response to Restriction Requirement in U.S. Appl. No. 13/061,413 dated Oct. 16, 2012.
Response to Non Final Office Action issued in U.S. Appl. No. 13/061,413 dated Jul. 2, 2013.
Final Office Action issued by the United States Patent and Trademark Office in U.S. Appl. No. 13/061,413 dated Aug. 23, 2013.
Restriction Requirement issued by the United States Patent and Trademark Office in U.S. Appl. No. 13/148,031 dated Mar. 20, 2013.
Mast et al., Clinical utility of the soluble transferrin receptor and comparison with serum ferritin in several populations. Clin Chem. Jan. 1998;44(1):45-51.
Non Final Office Action issued by the United States Patent and Trademark Office in U.S. Appl. No. 13/389,363 dated Apr. 18, 2013.
Iglesias et al., Thyroid Dysfunction and Kidney Disease (Revised version). Eur J Endocrinol. Dec. 18, 2008:32 pages retrieved from URL://www.eje.org/contentlearly/2008/12/18/EJE-08-0837.full.pdf.
Rajashekar et al., Systemic diseases with renal manifestations. Prim Care. Jun. 2008;35(2):297-328.abstract retrieved from URL:www.ncbi.nlm.nih.gov/pubmed/18486717.
Rini et al., Renal cell carcinoma. Lancet. Mar. 28, 2009;373(9669):1119-1132.
Non Final Office Action issued by the United States Patent and Trademark Office in U.S. Appl. No. 13/125,360 dated Aug. 27, 2013.
Sharma et al. Two-dimensional fluorescence difference gel electrophoresis analysis of the urine proteome in human diabetic nephropathy. Proteomics. Jul. 2005;5(10):2648-2655.
Non Final Office Action issued by the United States Patent and Trademark Office in U.S. Appl. No. 13/130,474 dated Nov. 27, 2012.
Non Final Office Action issued by the United States Patent and Trademark Office in U.S. Appl. No. 13/148,030 dated May 1, 2013.
Malm et al., Changes in the plasma levels of vitamin K-dependent proteins C and S and of C4b-binding protein during pregnancy and oral contraception. Br J Haematol. Apr. 1988;68(4):437-443.
Matsuzaka et al., Relationship between vitamin K dependent coagulation factors and anticoagulants (protein C and protein S) in neonatal vitamin K deficiency. Arch Dis Child. Mar. 1993;68(3 Spec No.):297-302.
International Search Report and Written Opinion issued in PCT/US2013/028005 dated Jun. 18, 2013.
Maddens et al., Chitinase-like Proteins are Candidate Biomarkers for Sepsis-induced Acute Kidney Injury. Mol Cell Proteomics. Jan. 10, 2012;11(6):1-13.

(56) References Cited

OTHER PUBLICATIONS

Restriction Requirement issued by the United States Patent and Trademark Office in U.S. Appl. No. 13/517,244 dated Jul. 1, 2013.
Extended European Search Report and Written Opinion issued in EP 11751238 dated Aug. 13, 2013.
Haase et al., A comparison of the RIFLE and Acute Kidney Injury Network classifications for cardiac surgery-associated acute kidney injury: A prospective cohort study. J Thorac Cardiovasc Surg. Dec. 2009;138(6):1370-1376.
Zaffanello M et al., Early diagnosis of acute kidney injury with urinary biomarkers in the newborn. J Matern Fetal Neonatal Med. 2009;22 Suppl 3:62-66.
Extended European Search Report and Written Opinion issued in EP 11748210 dated Aug. 16, 2013.
Calabrese et al., Oxidative stress and cellular stress response in diabetic nephropathy. Database Biosis [Online]. Biosciences Information Service Jan. 2007; XP002705326. Database accession No. PREV200800097004 (abstract):3 pages & Cell Stress Chaperones. 2007 Winter;12(4):299-306.
Musial et al., The Heat Shock Protein Profile in Children with Chronic Kidney Disease. Perit Dial Int. Mar.-Apr. 2010;30(2):227-232.
Tao et al., Expression of 60-kDa and Inducible 70-kDa Stress Proteins in Gentamicin-Induced Acute Renal Failure. Clin Exp Nephrol. Jul. 1997;1:254-260.
International Preliminary Report on Patentability issued on Sep. 7, 2012 in PCT/US2011/026384.
Non-Final Office Action issued by the US Patent and Trademark Office on Nov. 16, 2012 in U.S. Appl. No. 13/389,351.
Non-Final Office Action issued by the US Patent and Trademark Office on Nov. 27, 2012 in U.S. Appl. No. 13/130,474.
Flynn et al., Urinary excretion of beta2 -glycoprotein-1 (apolipoprotein H) and other markers of tubular malfunction in "non-tubular" renal disease J Clin Pathol. Jul. 1992;45(7):561-567.
Kasahara et al Clinical Significance of Serum Oxidized Low-Density Lipoprotein/beta2-Giycoprotein I Complexes in Patients with Chronic Renal Diseases. Nephron Clin Pract. 2004;98(1):15-24.
Lapsley et al., Beta 2-glycoprotein-1 (apolipoprotein H) excretion in chronic renal tubular disorders: Comparison with other protein markers of tubular malfunction. J Clin Pathol. Oct. 1991;44(10):812-816.
Matsuda et al., Beta 2-Glycoprotein I -Dependent and -Independent Anticardiolipin Antibody in Patients with End-Stage Renal Disease. Thromb Res. Oct. 15, 1993;72(2):109-117.
Ramirez et al., Prospective Study on Autoantibodies Against Apolipoprotein H (beta2GPI) in Several Clinical Parameters From Patients With Terminal Renal Failure and Functioning Renal Transplants. Transplant Proc. Jul.-Aug. 2009;41(6):2370-2.
Zheng et al., Antiphospholipid antibody profiles in lupus nephritis with glomerular microthrombosis: a prospective study of 124 cases. Arthritis Res Ther. 2009;11(3):1-9.
International Search Report and Written Opinion issued in PCT/US2012/066152 dated Mar. 15, 2013.
Extended European Search Report and Written Opinion issued in EP 10817878 dated Apr. 15, 2013.
Mezzano et al., Endothelial Cell Markers in Chronic Uremia: Relationship with Hemostatic Defects and Severity of Renal Failure. Thromb Res. Dec. 15, 1997;88(6):465-472.
Tan et al., The level of urinary secretory immunoglobulin A (sIgA) of patients with IgA nephropathy is elevated and associated with pathological phenotypes. Clin Exp Immunol. Apr. 2009;156(1):111-116.
Zhang et al., The level of serum secretory IgA of patients with IgA nephropathy is elevated and associated with pathological phenotypes. Nephrol Dial Transplant. Jan. 2008;23(1):207-212.
Search Report and Written Opinion issued by SIPO in 2009801406946 dated Apr. 15, 2013—includes English translation.
Office Action issued by SIPO in 2009801406946 dated May 29, 2013—includes English translation.
Search Report and Written Opinion issued in PCT/US2013/023479 dated May 15, 2013.
Choi et al., Expression of Vascular Endothelial Growth Factor-C and Its Receptor mRNA in the Rat Kidney With Ischemia-Reperfusion Injury. Clinical Kidney J. Jun. 2, 2011;4(Suppl 2):2 pages.
Cooper, Effect of Tobacco Smoking on Renal Function. Indian J Med Res Sep. 2006;124(3):261-268.
Extended European Search Report and Written Opinion issued in EP 10829198 dated May 21, 2013.
Senatorski et al., Urine activity of cathepsin B, collagenase and urine excretion of TGF-beta1 and fibronectin in membranous glomerulonephritis. Res Exp Med (Berl). Dec. 1998;198(4):199-206.
Schaefer et al., Urinary excretion of cathepsin B and cystatins as parameters of tubular damage. Kidney Int Suppl. Nov. 1994;47:S64-S67.
Kos et al., Cathepsins B,H and L and Their Inhibitors Stefin A and Cystatin C in Sera of Melanoma Patients. Clin Cancer Res. Oct. 1997;3(10):1815-1822.
Nambi et al., Down regulation of kidney neutral endopeptidase mRNA, protein and activity during acute renal failure: possible mechanism for ischemia-induced acute renal failure in rats? Mol Cell Biochem. Jul. 1999;197(1-2):53-59.
Li et al., Predictive value of RIFLE classification on prognosis of critically ill patients with acute kidney injury treated with continuous renal replacement therapy. Chin Med J (Engl). May 5, 2009;122(9):1020-1025.
Extended European Search Report and Written Opinion issued in EP 10829191 dated May 24, 2013.
Berahovich et al., Proteolytic activation of alternative CCR1 ligands in inflammation. J Immunol. Jun. 1, 2005;174(11):7341-7351.
Hatta et al., Cytokine Array Comparisons of Plasma from Cycling Fertile Women on Cycle Day 5 and Ovulation. Am J Reprod Immunol. Sep. 2009;62(3):158-164.
Office Action and Search Report issued by SIPO in Application No. 200980140805.3 dated Apr. 23, 2013—includes English Translation rec'd May 16, 2013.
Mishra et al., Neutrophil gelatinase-associated lipocalin (NGAL) as a biomarker for acute renal injury after cardiac surgery. Lancet. Apr. 2-8, 2005;365(9466):1231-1238.
International Preliminary Report on Patentability issued in PCT/US2011/055055 dated May 24, 2013.
Extended European Search Report and Written Opinion issued in EP 10838357 dated Jun. 3, 2013.
Stenvinkel et al., High Serum Hyaluronan Indicates Poor Survival in Renal Replacement Therapy. Am J Kidney Dis. Dec. 1999;34(6):1083-1088.
Non-Final Office Action issued by the United States Patent and Trade Office in U.S. Appl. No. 13/577,242 dated Jun. 20, 2013.
Extended European Search Report and Written Opinion issued in EP 10818036 dated Jun. 6, 2013.
Extended European Search Report and Written Opinion issued in EP 11740470 dated Jun. 18, 2013.
Tary-Lehmann et al., Enzyme-Linked Immunosorbent Assay Spot Detection of Interferon-Gamma and Interleukin 5-Producing Cells as a Predictive Marker for Renal Allograft Failure. Transplantation. Jul. 27, 1998;66(2):219-224.
Kimmel et al., Immunologic function and survival in hemodialysis patients. Kidney Int. Jul. 1998;54(1):236-244.
Simmons et al., Plasma cytokine levels predict mortality in patients with acute renal failure. Kidney Int. Apr. 2004;65(4):1357-1365.
Search Report issued by SIPO in Application No. 200980149555.X dated May 23, 2013—includes English translation.
Cai, Detection and Application for the biomarker of Rental Injury in Early Stage. Laboratory Med Clinic. Jun. 2005;2(3):124-127—incl Engl transl abstract only.
Office Action issued by SIPO in Application No. 200980149555.X dated Jul. 1, 2013—includes English translation.
Search Report issued by SIPO in Application No. 201080014932.1 dated Jun. 9, 2013—includes English translation.
Office Action issued by SIPO in Application No. 201080014932.1 dated Jun. 25, 2013—includes English translation.
Jung et al., Diagnostic significance of urinary enzymes in detecting acute rejection crises in renal transplant recipients depending on

(56) References Cited

OTHER PUBLICATIONS expression of results illustrated through the example of alanine aminopeptidase. Clin Biochem. Aug. 1985;18(4):257-260.
Search Report issued by SIPO in Application No. 200980149636.X dated Jun. 17, 2013—includes English translation.
Office Action issued by SIPO in Application No. 200980149636.X dated Jul. 1, 2013—includes English translation.
Extended European Search Report and Written Opinion issued in EP 11740468 dated Jun. 13, 2013.
Fried et al., Inflammatory and Prothrombotic Markers and the Progression of Renal Disease in Elderly Individuals. J Am Soc Nephrol. Dec. 2004;15(12):3184-3191.
Edelstein, Biomarkers of Acute Kidney Injury. Adv Chronic Kidney Dis. Jul. 2008;15(3)222-234.
Extended European Search Report and Written Opinion issued in EP 11740469 dated Jun. 13, 2013.
Fujisaki et al., Infusion of radiocontrast agents induces exaggerated release of urinary endothelin in patients with impaired renal function. Clin Exp Nephrol. Dec. 2003;7(4):279-283.
Hirai et al., Plasma endothelin-1(ET-1) is a useful marker for renal dysfunction. Atheroscler Suppl. Jun. 19, 2006;7(3):60[Mo-P1:65].
Cottone et al., Endothelin-1 and F2-isoprostane relate to and predict renal dysfunction in hypertensive patients. Nephrol Dial Transpl. Feb. 2009;24(2):497-503.
Schulz et al., Endothelin-1 as an early prognostic marker in acute renal failure (ARF) and sepsis. Kidney Blood Press Res. 2000;23(3-5):341-342.
Search Report issued by SIPO in Application No. 201080057014.7 dated Jul. 8, 2013—includes English translation.
Office Action issued by SIPO in Application No. 201080057014.7 dated Jul. 18, 2013—includes English translation.
Extended European Search Report and Written Opinion issued in EP 10812639 dated Jul. 16, 2013.
Song et al., Expression of TRAIL, DR4, and DR5 in kidney and serum from patients receiving renal transplantation. Transplant Proc. Jun. 2004;36(5):1340-1343.
Parikh and Devarajan, New biomarkers of acute kidney injury. Crit Care Med 2008;36(4 Suppl):S159-S165.
Parikh et al., Urinary IL-18 is an early predictive biomarker of acute kidney injury after cardiac surgery. Kidney Int, 2006;70(1):199-203.
Perco et al., Protein biomarkers associated with acute renal failure and chronic kidney disease. Eur J Clin Invest. Nov. 2006;36(11):753-763.
Picard et al., Origin of renal myofibroblasts in the model of unilateral ureter obstruction in the rat. Histochem Cell Biol. Jul. 2008;130(1):141-155.
Price, Abrupt Changes in Prostate-Specific Antigen Concentration in Acute Renal Failure. Clin Chem. Jan. 1993;39(1):161-162.
Prozialeck and Edwards, Cell Adhesion Molecules in Chemically-Induced Renal Injury. Pharmacol Ther. Apr. 2007;114(1):74-93.
Radford et al. Predicting renal outcome in IgA nephropathy. J Am Soc Nephrol Feb. 1997;8(2):199-207.
Ramesh and Reeves, TNF-α mediates chemokine and cytokine expression and renal injury in cisplatin nephrotoxicity. J. Clin. Invest. Sep. 2002;110(6):835-842.
Ramesh et al., Endotoxin and cisplatin synergistically induce renal dysfunction and cytokine production in mice. Am J Physiol Renal Physiol. Jul. 2007;293(1):F325-F332.
Ramirez et al., Prospective Study on Autoantibodies Against Apolipoprotein H ( B2GPI) in Several Clinical Parameters From Patients With Terminal Renal Failure and Functioning Renal Transplants. Transplantation Proceedings Jul. 2009;41(6):2370-2372.
Ricci et al., The RIFLE criteria and mortality in acute kidney injury: A systematic review. Kidney Int Mar. 2008;73(5):538-546.
Rosenkranz et al., P-selectin deficiency exacerbates experimental glomerulonephritis: a protective role for endothelial P-selectin in inflammation. J Clin Invest. Mar. 1999;103(5):649-659.
Rouschop et al., Pre-transplant plasma and cellular levels of CD44 correlate with acute renal allograft rejection. Nephrol Dial Transplant Oct. 2005;20(10):2248-2254.

Rouschop et al., Renal expression of CD44 correlates with acute renal allograft rejection. Kidney Int. Sep. 2006;70(6):1127-1134.
Schena et al., EGF and MCP-1 Urinary Excretion Is a Suitable Prognostic Marker in Iga Nephropathy. J Am Soc of Nephrology; Meeting of the American Society of Nephrology. Sep. 1, 2002;13(Program and Abstracts Issue): 458A.
Schiffer et al., Activated Renal Macrophages Are Markers of Disease Onset and Disease Remission in Lupus Nephritis, J Immunol Feb. 1, 2008;180(3):1938-1947.
Schmaldienst et al., Angiogenin: a novel inhibitor of neutrophil-lactoferrin release during extracorporeal circulation. Kidney Blood Press Res. 2003;26(2):107-112.
Schmidt et al., Sexual hormone abnormalities in male patients with renal failure. Nephrol Dial Transplant. Mar. 2002;17(3):368-371.
Segawa et al., In situ expression and soluble form of P-selectin in human glomerulonephritis. Kidney Int. Oct. 1997;52(4):1054-1063.
Segerer et al., Chemokines, Chemokine Receptors, and Renal Disease: From Basic Science to Pathophysiologic and Therapeutic Studies. J Am Soc Nephrol Jan. 2000;11(1):152-176.
Severini and Aliberti, Diagnostic significance of urinary enzymes: Development of a high performance liquid chromatographic method for the measurement of urinary lysozyme. Clin Chim Acta Feb. 27, 1987;163(1):97-103.
Shlipak et al., Elevations of Inflammatory and Procoagulant Biomarkers in Elderly Persons With Renal Insufficiency. Circulation Jan. 2003;107(1):87-92.
Shoji et al., Plasma angiopoietin-like protein 3 (ANGPTL3) concentration is associated with uremic dyslipidemia. Atherosclerosis. Dec. 2009;207(2):579-584.
Stafford-Smith et al., Acute Kidney Injury and Chronic Kidney Disease After Cardiac Surgery. Adv Chronic Kidney Dis. Jul. 2008;15(3):257-277.
Stasko et al., Soluble P-Selectin During a Single Hemodialysis Session in Patients With Chronic Renal Failure and Erythropoietin Treatment. Clin Appl Thromb Hemost. Oct. 2007;13(4):410-415.
Stuard et al., Soluble adhesion molecules in chronic renal failure patients. Nephrol Dialysis Transplant. 1997;12(9):A100.
Supavekin et al., Differential gene expression following early renal ischemia/reperfusion. Kidney Int. May 2003;63(5):1714-1724.
Sutton et al., Injury of the renal microvascular endothelium alters barrier function after ischemia. Am J Physiol Renal Physiol Aug. 2003;285(2):F191-F198.
Sutton et al., Microvascular endothelial injury and dysfunction during ischemic acute renal failure. Kidney Int. Nov. 2002;62(5):1539-1549.
Sutton, Alteration of microvascular permeability in acute kidney injury. Microvasc Res. Jan. 2009;77(1):4-7.
Symon et al., The endogenous insulin-like growth factor system in radiocontrast nephropathy. Am. J. Physiol. Renal Physiol. Mar. 1998;274(3 Pt 2):F490-497.
Takada et al., The Cytokine-adhesion Molecule Cascade in Ischemia/Reperfusion Injury of the Rat Kidney. Inhibition by a Soluble P-selectin Ligand. J. Clin. Invest. Jun. 1997; 99(11):2682-2690.
Taulan et al., Comprehensive analysis of the renal transcriptional response to acute uranyl nitrate exposure. BMC Genomics Jan. 11, 2006;7(2) 14 pages.
Teppo et al., Soluble Intercellular Adhesion Molecule-1 (Sicam-1) after Kidney Transplantation: The Origin and Role of Urinary Sicam-1? Transplantation Apr. 27, 2001;71(8):1113-1119.
Thorburn et al., CXC and CC chemokines induced in human renal epithelial cells by inflammatory cytokines. APMIS Jul. 2009;117(7):477-487.
Timoshanko et al., Interleukin-12 from Intrinsic Cells Is an Effector of Renal Injury in Crescentic Glomerulonephritis. J. Am. Soc. Nephrol. Mar. 2001;12(3):464-471.
Torres et al., The ratio of epidermal growth factor to monocyte chemotactic peptide-1 in the urine predicts renal prognosis in IgA nephropathy. Kidney Int. Feb. 2008;73(3):327-333.
Vaidya and Bonventre, Mechanistic biomarkers for cytotoxic acute kidney injury. Expert Opin Drug Metab Toxicol. Oct. 2006;2(5):697-713.
Vaidya et al., Biomarkers of Acute Kidney Injury. Annu Rev Pharmacol Toxicol. Feb. 2008;48:463-493.

(56) References Cited

OTHER PUBLICATIONS

Vanhoutte et al., Biomarker discovery with SELDI-TOF MS in human urine associated with early renal injury: evaluation with computational analytical tools. Nephrol Dial Transplant Oct. 2007;22(10):2932-2943.
Villanueva et al., Ischemic acute renal failure induces the expression of a wide range of nephrogenic proteins. Am J Physiol Regul Integr Comp Physiol Apr. 2006;290(4):R861-R870.
Vonderscher, Biomarker of Drug Induced Kidney Injury Qualification for Regulatory Decision Making (CRADA). IOM/FDA, Silver Spring, MD Apr. 23, 2007:31 pp.
Waikar et al., Diagnosis, Epidemiology and Outcomes of Acute Kidney Injury. Clin J Am Soc Nephrol. May 2008;3(3):844-861.
Wan et al., The pathogenesis of septic acute renal failure. Curr Opin Crit Care Dec. 2003;9(6):496-502.
Wang et al., Netrin-1 and kidney injury. I. Netrin-1 protects against ischemia-reperfusion injury of the kidney. Am J Physiol Renal Physiol. Apr. 2008;294(4):F739-F747.
Wang et al., Validation of putative genomic biomarkers of nephrotoxicity in rats. Toxicology Apr. 18, 2008;246(2-3):91-100.
Wilson and Hadley, Urinary lysozyme. J Pediatr. Feb. 1950;36(2):199-211.
Winchester et al., Sorbents in Acute Renal Failure and End-Stage Renal Disease: Middle Molecule and Cytokine Removal. Blood Purif. 2004;22(1):73-77.
Yang et al. Frequency of anti-bactericidal/permeability-increasing protein (BPI) and anti-azurocidin in patients with renal disease. Clin. Exp. Immunol. Jul. 1996;105(1):125-131.
Yu et al., Urinary biomarkers trefoil factor 3 and albumin enable early detection of kidney tubular injury. Nat Biotechnol May 2010;128(5):470-477.
International Search Report and Written Opinion issued on Jun. 3, 2011 in PCT/US2011/026759.
International Search Report and Written Opinion issued on Sep. 7, 2012 in PCT/US2012/043279.
International Search Report and Written Opinion issued on Dec. 15, 2011 in PCT/US2011/001126.
International Search Report and Written Opinion issued on Nov. 25, 2011 in PCT/US2011/001127.
International Search Report and Written Opinion issued on Nov. 25, 2011 in PCT/US2011/001128.
International Search Report and Written Opinion issued on Nov. 25, 2011 in PCT/US2011/001125.
International Search Report and Written Opinion issued on Jun. 20, 2012 in PCT/US2012/020572.
International Search Report and Written Opinion issued on May 2, 2012 in PCT/US2012/022926.
International Search Report and Written Opinion issued on Sep. 21, 2012 in PCT/US2012/045583.
Non Final Office Action issued by the USPTO in U.S. Appl. No. 13/061,446 on Oct. 12, 2012.
Abd El Latif et al., Urinary epidermal growth factor excretion: A useful prognostic marker for progression of renal damage in children. J Med Sci Oct. 2007; 7(7): 1171-1176.
Abou-Shousha and Youssef, Interleukin-2 Regulatory Effect on P-Selectin and Interleukin-8 Production in Patients with Chronic Renal Failure. Egypt J Immunol. 2006;13(1):11-18.
Akcay et al., Mediators of Inflammation in Acute Kidney Injury. Mediators Inflamm. 2009;2009:137072 (12 pp.).
Albright, Acute Renal Failure: A Practical Update. Mayo Clin. Proc. Jan. 2001;76(1):67-74.
Anders et al., Chemokines and chemokine receptors are involved in the resolution or progression of renal disease. Kidney Int. Feb. 2003;63(2):401-415.
Anilkumar et al., Trimeric assembly of the C-terminal region of Thrombospondin-1 or Thrombospondin-2 is necessary for cell spreading and fascin spike organisation. J Cell Sci. Jun. 1, 2002;115(Pt 11):2357-2366.
Arribas and Esselens, ADAM17 as a Therapeutic Target in Multiple Diseases. Curr Pharm Des. 2009;15(20):2319-2335.

Arrizabalaga et al., Tubular and Interstitial Expression of ICAM-1 as a Marker of Renal Injury in IgA Nephropathy. Am J Nephrol May-Jun. 2003;23(3):121-128.
Bagshaw et al., Urinary biomarkers in septic acute kidney injury. Intensive Care Med. Jul. 2007;33(7):1285-1296.
Bajwa et al., Immune Mechanisms and Novel Pharmacological Therapies of Acute Kidney Injury. Curr Drug Targets Dec. 2009;10(12):1196-1204.
Barrera-Chimal et al., Hsp72 is an early and sensitive biomarker to detect acute kidney injury. EMBO Mol Med. Jan. 2011;3(1):5-20.
Beushausen, NWG Biomarker Objectives. ILSI Health and Environmental Sciences Institute, ILSI-HESI Annual Meeting 2006:17 pp.
Bicik et al., Role of Transforming Growth Factor-.beta.2 in, and a Possible Transforming Growth Factor-beta2 Gene Polymorphism as a Marker of, Renal Dysfunction in Essential Hypertension: A Study in Turkish Patients, Current Therapeutic Research, 2005;44(4):266-278.
Biotrin International, Biotrin Biomarkers: How late do you want to detect preclinical kidney damage? Biotrin's acute kidney injury test (AKI Test). Biotrin's Preclinical Kidney Biomarkers: 8 pp.
Bonomini et al., Serum Levels of Soluble Adhesion Molecules in Chronic Renal Failure and Dialysis Patients. Nephron. Aug. 1998;79(4):399-407.
Bonventre and Zuk, Ischemic acute renal failure: An inflammatory disease? Kidney Int. Aug. 2004;66(2):480-485.
Bonventre, Dedifferentiation and Proliferation of Surviving Epithelial Cells in Acute Renal Failure. J Am Soc Nephrol Jun. 2003;14 Suppl 1:S55-S61.
Bonventre, Pathophysiology of Acute Kidney Injury: Roles of Potential Inhibitors of Inflammation. Contrib Nephrol. 2007; 156: 39-46.
Burne et al., IL-1 and TNF independent pathways mediate ICAM-1/VCAM-1 up-regulation in ischemia reperfusion injury. J Leukoc Biol. Aug. 2001;70(2):192-198.
Burne-Taney and Rabb, The role of adhesion molecules and T cells in ischemic renal injury. Curr Opin Nephrol Hypertens. Jan. 2003;12(1):85-90.
Canani et al., The Fatty Acid-Binding Protein-2 A54T Polymorphism Is Associated With Renal Disease in Patients With Type 2 Diabetes. Diabetes Nov. 2005;54(11):3326-3330.
Catania et al., Role of matrix metalloproteinases in renal pathophysiologies. Am J Physiol Renal Physiol Mar. 2007;292(3):F905-F911.
Coca et al., Biomarkers for the diagnosis and risk stratification of acute kidney injury: A systematic review. Kidney Int May 2008;73(9):1008-1016.
Cruz et al., North East Italian Prospective Hospital Renal Outcome Survey on Acute Kidney Injury (NEiPHROS-AKI):Targeting the Problem with the RIFLE Criteria. Clin J Amer. Soc. Nephrol. May 2007;2(3):418-425.
Daha and Van Kooten, Is the proximal tubular cell a proinflammatory cell? Nephrol Dial Transplant 2000;15 Suppl 6:41-43.
De Sa et al., Leukocyte, platelet and endothelial activation in patients with acute renal failure treated by intermittent hemodialysis. Am J Nephrol. Jul.-Aug. 2001;21(4):264-273.
Devarajan and Williams, Proteomics for Biomarker Discovery in Acute Kidney Injury. Semin Nephrol. Nov. 2007;27(6):637-651.
Devarajan, Cellular and molecular derangements in acute tubular necrosis. Curr Opin Pediatr. Apr. 2005;17(2):193-199.
Devarajan, Novel biomarkers for the early prediction of acute kidney injury. Cancer Therapy Sep. 2005;3:477-488.
Devarajan, Update on Mechanisms of Ischemic Acute Kidney Injury. J Am Soc Nephrol. Jun. 2006;17(6):1503-1520.
Domanski et al., Purine and Cytokine Concentrations in the Renal Vein of the Allograft During Reperfusion. Transplant Proc. Jun. 2007;39(5):1319-1322.
FDA, European Medicines Agency to Consider Additional Test Results When Assessing New Drug Safety—Collaborative effort by FDA and EMEA expected to yield additional safety data. http://www.natap.org/2008/newsUpdates/071608_01.htm.
Ferguson et al., Biomarkers of nephrotoxic acute kidney injury. Toxicology Mar. 20, 2008;245(3):182-193.
Frangogiannis, Chemokines in ischemia and reperfusion. Thromb Haemost May 2007;97(5):738-747.

(56) References Cited

OTHER PUBLICATIONS

Furuichi et al., Chemokine/chemokine receptor-mediated inflammation regulates pathologic changes from acute kidney injury to chronic kidney disease. Clin Exp Nephrol Feb. 2009;13(1):9-14.
Furuichi et al., Roles of chemokines in renal ischemia/reperfusion injury. Front Biosci. May 1, 2008;13:4021-4028.
Galkina and Ley, Leukocyte Recruitment and Vascular Injury in Diabetic Nephropathy. J Am Soc Nephrol. Feb. 2006;17(2):368-377.
Garcia et al., Adenosine A2A receptor activation and macrophagemediated experimental glomerulonephritis. FASEB J. Feb. 2008;22(2):445-454.
Gbadegesin et al., Plasma and urinary soluble adhesion molecule expression is increased during first documented acute pyelonephritis. Arch Dis Child. Mar. 2002;86(3):218-221.
Goes et al., Effect of Recombinant Human Insulin-Like Growth Factor-1 on the Inflammatory Response to Acute Renal Injury. J Am Soc Nephrol. May 1996;7(5):710-720.
Office Action and Search Report issued by SIPO in Chinese patent application No. 201080013522.5 dated Jun. 11, 2015—incl Engl lang transl (SR only).
Examination Report issued by the Australian Patent Office in patent application No. 2010210535 dated Apr. 22, 2015.
Pitashny et al., Urinary Lipocalin-2 Is Associated With Renal Disease Activity in Human Lupus Nephritis. Arthritis Rheum. Jun. 2007;56(6):1894-1903.
Sesin et al., Shedding of endothelial protein C receptor contributes to vasculopathy and renal injury in lupus: In vivo and in vitro evidence. Kidney Int. Jul. 2005;68(1):110-120.
Zhang et al., Examination of plasma von Willebrand factor level and its clinical significance in patients with chronic renal failure. Clinical Focus, Oct. 20, 2007:1465—incl Engl lang transl abstract only.

* cited by examiner

Endothelial protein C receptor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 43.929 | 60.385 | 43.929 | 61.154 | 43.929 | 0.962 |
| average | 68.904 | 77.746 | 68.904 | 82.203 | 68.904 | 80.385 |
| stdev | 83.580 | 71.173 | 83.580 | 54.662 | 83.580 | na |
| p (t-test) |  | 0.672 |  | 0.504 |  | na |
| min | 0.962 | 2.885 | 0.962 | 0.068 | 0.962 | 80.385 |
| max | 491.892 | 266.981 | 491.892 | 187.645 | 491.892 | 80.385 |
| n (Samp) | 51 | 21 | 51 | 21 | 51 | 1 |
| n (Pat) | 40 | 21 | 40 | 21 | 40 | 1 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 54.309 | 20.808 | 54.309 | 58.077 | 54.309 | 50.484 |
| average | 76.435 | 27.244 | 76.435 | 72.976 | 76.435 | 50.484 |
| stdev | 73.686 | 26.662 | 73.686 | 57.184 | 73.686 | 30.484 |
| p (t-test) |  | 0.108 |  | 0.904 |  | 0.622 |
| min | 0.962 | 2.885 | 0.962 | 0.068 | 0.962 | 28.929 |
| max | 491.892 | 79.276 | 491.892 | 153.737 | 491.892 | 72.039 |
| n (Samp) | 92 | 6 | 92 | 7 | 92 | 2 |
| n (Pat) | 73 | 6 | 73 | 7 | 73 | 2 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 43.522 | 76.974 | 43.522 | 63.158 | 43.522 | 58.031 |
| average | 69.978 | 93.411 | 69.978 | 95.567 | 69.978 | 49.833 |
| stdev | 88.824 | 73.608 | 88.824 | 64.336 | 88.824 | 37.304 |
| p (t-test) |  | 0.352 |  | 0.275 |  | 0.658 |
| min | 11.218 | 21.189 | 11.218 | 23.476 | 11.218 | 2.885 |
| max | 491.892 | 266.981 | 491.892 | 258.333 | 491.892 | 80.385 |
| n (Samp) | 42 | 16 | 42 | 18 | 42 | 4 |
| n (Pat) | 33 | 16 | 33 | 18 | 33 | 4 | sCr or UO

| Time prior AKI stage | AUC | SE | nCohort 1 | nCohort 2 | p |
|---|---|---|---|---|---|
| 0 hours | 0.56 | 0.076 | 51 | 21 | 0.431 |
| 24 hours | 0.63 | 0.075 | 51 | 21 | 0.077 |
| 48 hours | 0.80 | 0.268 | 51 | 1 | 0.257 | sCr only

| Time prior AKI stage | AUC | SE | nCohort 1 | nCohort 2 | p |
|---|---|---|---|---|---|
| 0 hours | 0.19 | 0.070 | 92 | 6 | 0.000 |
| 24 hours | 0.51 | 0.114 | 92 | 7 | 0.946 |
| 48 hours | 0.43 | 0.195 | 92 | 2 | 0.718 |

UO only

| Time prior AKI stage | AUC | SE | nCohort 1 | nCohort 2 | p |
|---|---|---|---|---|---|
| 0 hours | 0.67 | 0.084 | 42 | 16 | 0.048 |
| 24 hours | 0.70 | 0.078 | 42 | 18 | 0.009 |
| 48 hours | 0.51 | 0.153 | 42 | 4 | 0.969 | sCr or UO

| Time prior AKI stage | Cutoff value | sens | spec | Quartile | OR | 95% CI of OR | |
|---|---|---|---|---|---|---|---|
| 0 hours | 27.898551 | 71% | 29% | 1 |  |  |  |
|  | 20.833333 | 86% | 20% | 2 | 0.7 | 0.2 | 2.4 |
|  | 19.664634 | 90% | 18% | 3 | 0.7 | 0.2 | 2.4 |
|  | 62.828947 | 48% | 71% | 4 | 2.1 | 0.8 | 5.6 |
|  | 75 | 43% | 80% |  |  |  |  |
|  | 174.51737 | 10% | 90% |  |  |  |  |

FIG. 1 - 1 sCr only

| | Time prior AKI stage | Cutoff value | sens | spec | Quartile | OR | 95% CI of OR | |
|---|---|---|---|---|---|---|---|---|
| | 24 hours | 47.463768 | 71% | 53% | 1 | | | |
| | | 38.928571 | 81% | 45% | 2 | 0.7 | 0.2 | 2.9 |
| | | 22.115385 | 90% | 25% | 3 | 1.3 | 0.4 | 4.3 |
| | | 62.828947 | 43% | 71% | 4 | 3.5 | 1.2 | 10.2 |
| | | 75 | 43% | 80% | | | | |
| | | 174.51737 | 5% | 90% | | | | |
| | 48 hours | 75 | 100% | 80% | 1 | | | |
| | | 75 | 100% | 80% | 2 | na | na | na |
| | | 75 | 100% | 80% | 3 | na | na | na |
| | | 62.828947 | 100% | 71% | 4 | na | na | na |
| | | 75 | 100% | 80% | | | | |
| | | 174.51737 | 0% | 90% | | | | |

UO only

| Time prior AKI stage | Cutoff value | sens | spec | Quartile | OR | 95% CI of OR | |
|---|---|---|---|---|---|---|---|
| 0 hours | 13.782051 | 83% | 4% | 1 | | | |
| | 13.782051 | 83% | 4% | 2 | na | na | na |
| | 0.9615385 | 100% | 1% | 3 | na | na | na |
| | 81.923077 | 0% | 71% | 4 | na | na | na |
| | 111.74377 | 0% | 80% | | | | |
| | 161.38996 | 0% | 90% | | | | |
| 24 hours | 55 | 71% | 51% | 1 | | | |
| | 11.217949 | 86% | 3% | 2 | 0.0 | 0.0 | na |
| | 0 | 100% | 0% | 3 | 1.0 | 0.1 | 8.1 |
| | 81.923077 | 43% | 71% | 4 | 1.5 | 0.2 | 9.2 |
| | 111.74377 | 29% | 80% | | | | |
| | 161.38996 | 0% | 90% | | | | |
| 48 hours | 28.623188 | 100% | 23% | 1 | | | |
| | 28.623188 | 100% | 23% | 2 | na | na | na |
| | 28.623188 | 100% | 23% | 3 | na | na | na |
| | 81.923077 | 0% | 71% | 4 | na | na | na |
| | 111.74377 | 0% | 80% | | | | |
| | 161.38996 | 0% | 90% | | | | |

| Time prior AKI stage | Cutoff value | sens | spec | Quartile | OR | 95% CI of OR | |
|---|---|---|---|---|---|---|---|
| 0 hours | 32.246377 | 75% | 38% | 1 | | | |
| | 30.072464 | 81% | 36% | 2 | 6.5 | 0.4 | 96.6 |
| | 26.449275 | 94% | 33% | 3 | 3.5 | 0.2 | 67.2 |
| | 59.539474 | 63% | 71% | 4 | 11.4 | 0.8 | 158.7 |
| | 75 | 50% | 81% | | | | |
| | 153.73665 | 13% | 90% | | | | |
| 24 hours | 53.618421 | 72% | 62% | 1 | | | |
| | 43.928571 | 83% | 52% | 2 | 1.6 | 0.2 | 11.4 |
| | 24.038462 | 94% | 31% | 3 | 3.3 | 0.6 | 18.1 |
| | 59.539474 | 61% | 71% | 4 | 7.4 | 1.4 | 38.9 |
| | 75 | 44% | 81% | | | | |
| | 153.73665 | 22% | 90% | | | | |
| 48 hours | 35.869565 | 75% | 40% | 1 | | | |
| | 0 | 100% | 0% | 2 | 0.9 | 0.0 | 66.6 |
| | 0 | 100% | 0% | 3 | 0.0 | 0.0 | na |
| | 59.539474 | 50% | 71% | 4 | 2.0 | 0.1 | 56.0 |
| | 75 | 50% | 81% | | | | |
| | 153.73665 | 0% | 90% | | | | |

FIG. 1 - 2

Erythropoietin receptor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 28.716 | 15.032 | 28.716 | 30.854 | 28.716 | 0.517 |
| average | 178.249 | 40.826 | 178.249 | 51.347 | 178.249 | 0.517 |
| stdev | 1018.857 | 51.724 | 1018.857 | 55.625 | 1018.857 | na |
| p (t-test) |  | 0.540 |  | 0.554 |  | na |
| min | 0.517 | 0.517 | 0.517 | 0.517 | 0.517 | 0.517 |
| max | 7307.410 | 163.136 | 7307.410 | 190.476 | 7307.410 | 0.517 |
| n (Samp) | 51 | 21 | 51 | 23 | 51 | 1 |
| n (Pat) | 39 | 21 | 39 | 23 | 39 | 1 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 20.270 | 23.597 | 20.270 | 38.766 | 20.270 | 57.010 |
| average | 116.048 | 54.648 | 116.048 | 70.648 | 116.048 | 57.010 |
| stdev | 759.083 | 68.689 | 759.083 | 72.286 | 759.083 | 51.958 |
| p (t-test) |  | 0.844 |  | 0.875 |  | 0.913 |
| min | 0.517 | 0.517 | 0.517 | 0.517 | 0.517 | 20.270 |
| max | 7307.410 | 150.424 | 7307.410 | 190.476 | 7307.410 | 93.750 |
| n (Samp) | 92 | 6 | 92 | 7 | 92 | 2 |
| n (Pat) | 72 | 6 | 72 | 7 | 72 | 2 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 42.187 | 17.651 | 42.187 | 30.854 | 42.187 | 49.738 |
| average | 220.621 | 41.168 | 220.621 | 58.131 | 220.621 | 62.604 |
| stdev | 1120.988 | 49.387 | 1120.988 | 60.332 | 1120.988 | 74.707 |
| p (t-test) |  | 0.527 |  | 0.511 |  | 0.782 |
| min | 0.517 | 0.517 | 0.517 | 0.517 | 0.517 | 0.517 |
| max | 7307.410 | 163.136 | 7307.410 | 190.476 | 7307.410 | 150.424 |
| n (Samp) | 42 | 16 | 42 | 21 | 42 | 4 |
| n (Pat) | 32 | 16 | 32 | 21 | 32 | 4 | sCr or UO

| Time prior AKI stage | AUC | SE | nCohort 1 | nCohort 2 | p |
| --- | --- | --- | --- | --- | --- |
| 0 hours | 0.47 | 0.075 | 51 | 21 | 0.698 |
| 24 hours | 0.54 | 0.073 | 51 | 23 | 0.550 |
| 48 hours | 0.16 | 0.142 | 51 | 1 | 0.016 | sCr only

| Time prior AKI stage | AUC | SE | nCohort 1 | nCohort 2 | p |
| --- | --- | --- | --- | --- | --- |
| 0 hours | 0.51 | 0.123 | 92 | 6 | 0.906 |
| 24 hours | 0.63 | 0.117 | 92 | 7 | 0.276 |
| 48 hours | 0.69 | 0.211 | 92 | 2 | 0.360 |

UO only

| Time prior AKI stage | AUC | SE | nCohort 1 | nCohort 2 | p |
| --- | --- | --- | --- | --- | --- |
| 0 hours | 0.42 | 0.082 | 42 | 16 | 0.319 |
| 24 hours | 0.50 | 0.078 | 42 | 21 | 0.988 |
| 48 hours | 0.50 | 0.153 | 42 | 4 | 0.984 | sCr or UO

| Time prior AKI stage | Cutoff value | sens | spec | Quartile | OR | 95% CI of OR | |
| --- | --- | --- | --- | --- | --- | --- | --- |
| 0 hours | 0 | 100% | 0% | 1 |  |  |  |
|  | 0 | 100% | 0% | 2 | 0.2 | 0.0 | 0.9 |
|  | 0 | 100% | 0% | 3 | 0.3 | 0.1 | 1.1 |
|  | 54.588608 | 33% | 71% | 4 | 1.6 | 0.6 | 3.8 |
|  | 78.125 | 14% | 80% |  |  |  |  |
|  | 88.541667 | 14% | 90% |  |  |  |  |
| 24 hours | 0 | 100% | 0% | 1 |  |  |  |

FIG. 1 - 3

|  | | Cutoff value | sens | spec | Quartile | OR | 95% CI of OR | |
|---|---|---|---|---|---|---|---|---|
|  | | 0 | 100% | 0% | 2 | 0.4 | 0.1 | 1.2 |
|  | | 0 | 100% | 0% | 3 | 0.6 | 0.2 | 1.6 |
|  | | 54.588608 | 39% | 71% | 4 | 0.9 | 0.4 | 2.3 |
|  | | 78.125 | 26% | 80% | | | | |
|  | | 88.541667 | 22% | 90% | | | | |
|  | 48 hours | 0 | 100% | 0% | 1 | | | |
|  | | 0 | 100% | 0% | 2 | na | na | na |
|  | | 0 | 100% | 0% | 3 | na | na | na |
|  | | 54.588608 | 0% | 71% | 4 | na | na | na |
|  | | 78.125 | 0% | 80% | | | | |
|  | | 88.541667 | 0% | 90% | | | | | sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.5 | 0.0 | 10.3 |
| | 0 | 100% | 0% | 3 | 0.5 | 0.0 | 10.8 |
| | 62.5 | 33% | 72% | 4 | 1.0 | 0.1 | 8.1 |
| | 78.125 | 33% | 82% | | | | |
| | 94.758065 | 33% | 90% | | | | |
| 24 hours | 28.716216 | 71% | 55% | 1 | | | |
| | 0 | 100% | 0% | 2 | 0.0 | 0.0 | na |
| | 0 | 100% | 0% | 3 | 1.0 | 0.1 | 8.1 |
| | 62.5 | 43% | 72% | 4 | 1.5 | 0.2 | 9.2 |
| | 78.125 | 43% | 82% | | | | |
| | 94.758065 | 43% | 90% | | | | |
| 48 hours | 15.031646 | 100% | 48% | 1 | | | |
| | 15.031646 | 100% | 48% | 2 | na | na | na |
| | 15.031646 | 100% | 48% | 3 | na | na | na |
| | 62.5 | 50% | 72% | 4 | na | na | na |
| | 78.125 | 50% | 82% | | | | |
| | 94.758065 | 0% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.8 | 0.2 | 3.4 |
| | 0 | 100% | 0% | 3 | 0.7 | 0.2 | 3.0 |
| | 66.532258 | 38% | 71% | 4 | 2.1 | 0.6 | 7.1 |
| | 88.541667 | 13% | 86% | | | | |
| | 109.375 | 13% | 90% | | | | |
| 24 hours | 7.1202532 | 76% | 24% | 1 | | | |
| | 0 | 100% | 0% | 2 | 1.2 | 0.4 | 3.6 |
| | 0 | 100% | 0% | 3 | 0.7 | 0.2 | 2.3 |
| | 66.532258 | 38% | 71% | 4 | 1.2 | 0.4 | 3.6 |
| | 88.541667 | 24% | 86% | | | | |
| | 109.375 | 19% | 90% | | | | |
| 48 hours | 0 | 100% | 0% | 1 | | | |
| | 0 | 100% | 0% | 2 | 0.0 | 0.0 | na |
| | 0 | 100% | 0% | 3 | 0.0 | 0.0 | na |
| | 66.532258 | 50% | 71% | 4 | 0.9 | 0.1 | 9.7 |
| | 88.541667 | 50% | 86% | | | | |
| | 109.375 | 25% | 90% | | | | |

FIG. 1 - 4

Intercellular adhesion molecule 1 sCr or UO

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 4822.109 | 4749.879 | 4822.109 | 4967.611 | 4822.109 | 5732.760 |
| average  | 5958.736 | 6285.863 | 5958.736 | 7704.852 | 5958.736 | 7129.626 |
| stdev    | 4520.021 | 4663.788 | 4520.021 | 13491.187| 4520.021 | 5612.053 |
| p (t-test) |        | 0.669    |          | 0.207    |          | 0.255    |
| min      | 143.975  | 484.285  | 143.975  | 17.651   | 143.975  | 972.754  |
| max      | 20734.291| 19407.277| 20734.291| 101592.853| 20734.291| 19763.346|
| n (Samp) | 118      | 51       | 118      | 56       | 118      | 26       |
| n (Pat)  | 99       | 51       | 99       | 56       | 99       | 26       | sCr only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 4929.400 | 2340.611 | 4929.400 | 2958.798 | 4929.400 | 3794.253 |
| average  | 6580.251 | 3663.674 | 6580.251 | 4770.984 | 6580.251 | 6101.965 |
| stdev    | 7582.775 | 3829.021 | 7582.775 | 4498.755 | 7582.775 | 4881.287 |
| p (t-test) |        | 0.117    |          | 0.261    |          | 0.816    |
| min      | 49.188   | 319.458  | 49.188   | 17.651   | 49.188   | 1667.339 |
| max      | 101592.853| 13756.150| 101592.853| 14369.565| 101592.853| 16638.114|
| n (Samp) | 256      | 17       | 256      | 23       | 256      | 14       |
| n (Pat)  | 160      | 17       | 160      | 23       | 160      | 14       |

UO only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 4667.045 | 6019.775 | 4667.045 | 5663.788 | 4667.045 | 5345.772 |
| average  | 5915.725 | 6699.792 | 5915.725 | 8485.414 | 5915.725 | 6591.910 |
| stdev    | 4761.338 | 4578.388 | 4761.338 | 14515.055| 4761.338 | 5384.027 |
| p (t-test) |        | 0.351    |          | 0.103    |          | 0.548    |
| min      | 143.975  | 484.285  | 143.975  | 255.128  | 143.975  | 972.754  |
| max      | 20734.291| 19407.277| 20734.291| 101592.853| 20734.291| 19763.346|
| n (Samp) | 106      | 45       | 106      | 47       | 106      | 23       |
| n (Pat)  | 84       | 45       | 84       | 47       | 84       | 23       | sCr or UO

| Time prior AKI stage | AUC | SE | nCohort 1 | nCohort 2 | p |
|---|---|---|---|---|---|
| 0 hours | 0.51 | 0.049 | 118 | 51 | 0.759 |
| 24 hours | 0.52 | 0.047 | 118 | 56 | 0.722 |
| 48 hours | 0.55 | 0.064 | 118 | 26 | 0.467 | sCr only

| Time prior AKI stage | AUC | SE | nCohort 1 | nCohort 2 | p |
|---|---|---|---|---|---|
| 0 hours | 0.30 | 0.056 | 256 | 17 | 0.000 |
| 24 hours | 0.38 | 0.057 | 256 | 23 | 0.035 |
| 48 hours | 0.48 | 0.079 | 256 | 14 | 0.831 |

UO only

| Time prior AKI stage | AUC | SE | nCohort 1 | nCohort 2 | p |
|---|---|---|---|---|---|
| 0 hours | 0.56 | 0.052 | 106 | 45 | 0.216 |
| 24 hours | 0.57 | 0.051 | 106 | 47 | 0.170 |
| 48 hours | 0.54 | 0.067 | 106 | 23 | 0.593 | sCr or UO

| Time prior AKI stage | Cutoff value | sens | spec | Quartile | OR | 95% CI of OR | |
|---|---|---|---|---|---|---|---|
| 0 hours | 3117.4003 | 71% | 34% | 1 | | | |
|  | 2243.5899 | 80% | 19% | 2 | 1.3 | 0.8 | 1.9 |
|  | 1768.7072 | 90% | 13% | 3 | 0.8 | 0.5 | 1.3 |
|  | 6867.8374 | 35% | 70% | 4 | 1.3 | 0.9 | 2.1 |
|  | 9273.1411 | 27% | 81% | | | | |
|  | 12344.643 | 16% | 91% | | | | |

FIG. 1 - 5

|  | Time prior AKI stage | Cutoff value | sens | spec | Quartile | OR | 95% CI of OR | |
|---|---|---|---|---|---|---|---|---|
|  | 24 hours | 3006.2743 | 71% | 32% | 1 | | | |
|  |  | 2557.6547 | 80% | 25% | 2 | 1.1 | 0.7 | 1.6 |
|  |  | 878.55325 | 91% | 4% | 3 | 1.0 | 0.6 | 1.5 |
|  |  | 6867.8374 | 30% | 70% | 4 | 1.3 | 0.9 | 2.0 |
|  |  | 9273.1411 | 25% | 81% | | | | |
|  |  | 12344.643 | 18% | 91% | | | | |
|  | 48 hours | 2740.7946 | 73% | 30% | 1 | | | |
|  |  | 2003.1475 | 81% | 14% | 2 | 0.4 | 0.1 | 1.1 |
|  |  | 1210.828 | 92% | 9% | 3 | 1.4 | 0.7 | 2.6 |
|  |  | 6867.8374 | 35% | 70% | 4 | 1.0 | 0.5 | 2.0 |
|  |  | 9273.1411 | 27% | 81% | | | | |
|  |  | 12344.643 | 19% | 91% | | | | | sCr only

| Time prior AKI stage | Cutoff value | sens | spec | Quartile | OR | 95% CI of OR | |
|---|---|---|---|---|---|---|---|
| 0 hours | 1815.9215 | 71% | 15% | 1 | | | |
|  | 1747.3469 | 82% | 14% | 2 | 0.5 | 0.0 | 10.0 |
|  | 484.28516 | 94% | 1% | 3 | 2.7 | 0.6 | 11.1 |
|  | 7429.533 | 12% | 70% | 4 | 5.1 | 1.4 | 18.0 |
|  | 10048.887 | 12% | 80% | | | | |
|  | 13216.773 | 6% | 90% | | | | |
| 24 hours | 1644.3701 | 74% | 14% | 1 | | | |
|  | 1017.2784 | 83% | 6% | 2 | 0.6 | 0.2 | 1.8 |
|  | 795.00903 | 91% | 4% | 3 | 1.2 | 0.6 | 2.7 |
|  | 7429.533 | 22% | 70% | 4 | 2.0 | 1.0 | 3.8 |
|  | 10048.887 | 17% | 80% | | | | |
|  | 13216.773 | 13% | 90% | | | | |
| 48 hours | 3348.3318 | 71% | 33% | 1 | | | |
|  | 2133.882 | 86% | 20% | 2 | 1.0 | 0.3 | 4.0 |
|  | 1774.5861 | 93% | 14% | 3 | 1.7 | 0.6 | 5.2 |
|  | 7429.533 | 29% | 70% | 4 | 1.0 | 0.3 | 4.0 |
|  | 10048.887 | 21% | 80% | | | | |
|  | 13216.773 | 14% | 90% | | | | |

UO only

| Time prior AKI stage | Cutoff value | sens | spec | Quartile | OR | 95% CI of OR | |
|---|---|---|---|---|---|---|---|
| 0 hours | 3329.4421 | 71% | 39% | 1 | | | |
|  | 2722.1633 | 80% | 34% | 2 | 1.7 | 1.0 | 2.9 |
|  | 1296.436 | 91% | 12% | 3 | 1.3 | 0.7 | 2.3 |
|  | 6539.8171 | 44% | 71% | 4 | 2.4 | 1.4 | 4.0 |
|  | 8936.5808 | 33% | 80% | | | | |
|  | 13284.487 | 11% | 91% | | | | |
| 24 hours | 3702.7733 | 70% | 42% | 1 | | | |
|  | 2618.5406 | 81% | 31% | 2 | 1.7 | 1.0 | 3.0 |
|  | 878.55325 | 91% | 7% | 3 | 1.7 | 1.0 | 3.0 |
|  | 6539.8171 | 43% | 71% | 4 | 2.3 | 1.4 | 4.0 |
|  | 8936.5808 | 28% | 80% | | | | |
|  | 13284.487 | 11% | 91% | | | | |
| 48 hours | 3282.8748 | 74% | 39% | 1 | | | |
|  | 2003.1475 | 83% | 17% | 2 | 1.0 | 0.4 | 2.5 |
|  | 1210.828 | 91% | 10% | 3 | 1.8 | 0.8 | 4.0 |
|  | 6539.8171 | 30% | 71% | 4 | 1.0 | 0.4 | 2.4 |
|  | 8936.5808 | 22% | 80% | | | | |
|  | 13284.487 | 13% | 91% | | | | |

FIG. 1 - 6

Lactotransferrin sCr or UO

|             | 0 hr prior to AKI stage | | 24 hr prior to AKI stage | | 48 hr prior to AKI stage | |
|---|---|---|---|---|---|---|
|             | Cohort 1 | Cohort 2 | Cohort 1 | Cohort 2 | Cohort 1 | Cohort 2 |
| median      | 39.773   | 50.021   | 39.773   | 39.223   | 39.773   | 37.343   |
| average     | 120.491  | 83.370   | 120.491  | 156.989  | 120.491  | 162.414  |
| stdev       | 738.191  | 121.800  | 738.191  | 331.383  | 738.191  | 546.410  |
| p (t-test)  |          | 0.722    |          | 0.725    |          | 0.785    |
| min         | 0.034    | 0.264    | 0.034    | 0.596    | 0.034    | 3.410    |
| max         | 7981.395 | 752.000  | 7981.395 | 2143.046 | 7981.395 | 2826.490 |
| n (Samp)    | 116      | 51       | 116      | 56       | 116      | 26       |
| n (Pat)     | 98       | 51       | 98       | 56       | 98       | 26       | sCr only

|             | 0 hr prior to AKI stage | | 24 hr prior to AKI stage | | 48 hr prior to AKI stage | |
|---|---|---|---|---|---|---|
|             | Cohort 1 | Cohort 2 | Cohort 1 | Cohort 2 | Cohort 1 | Cohort 2 |
| median      | 39.773   | 50.517   | 39.773   | 39.968   | 39.773   | 77.168   |
| average     | 129.351  | 53.641   | 129.351  | 165.909  | 129.351  | 96.364   |
| stdev       | 561.449  | 35.895   | 561.449  | 439.777  | 561.449  | 80.849   |
| p (t-test)  |          | 0.579    |          | 0.761    |          | 0.827    |
| min         | 0.034    | 1.988    | 0.034    | 1.565    | 0.034    | 3.410    |
| max         | 7981.395 | 104.402  | 7981.395 | 2143.046 | 7981.395 | 266.230  |
| n (Samp)    | 256      | 17       | 256      | 23       | 256      | 14       |
| n (Pat)     | 158      | 17       | 158      | 23       | 158      | 14       |

UO only

|             | 0 hr prior to AKI stage | | 24 hr prior to AKI stage | | 48 hr prior to AKI stage | |
|---|---|---|---|---|---|---|
|             | Cohort 1 | Cohort 2 | Cohort 1 | Cohort 2 | Cohort 1 | Cohort 2 |
| median      | 40.304   | 53.534   | 40.304   | 53.363   | 40.304   | 34.168   |
| average     | 144.317  | 97.892   | 144.317  | 133.790  | 144.317  | 175.412  |
| stdev       | 800.158  | 136.062  | 800.158  | 206.064  | 800.158  | 580.450  |
| p (t-test)  |          | 0.700    |          | 0.931    |          | 0.860    |
| min         | 0.034    | 0.264    | 0.034    | 0.596    | 0.034    | 4.872    |
| max         | 7981.395 | 752.000  | 7981.395 | 1014.570 | 7981.395 | 2826.490 |
| n (Samp)    | 105      | 45       | 105      | 45       | 105      | 23       |
| n (Pat)     | 84       | 45       | 84       | 45       | 84       | 23       | sCr or UO

| Time prior AKI stage | AUC | SE | nCohort 1 | nCohort 2 | p |
|---|---|---|---|---|---|
| 0 hours  | 0.58 | 0.049 | 116 | 51 | 0.119 |
| 24 hours | 0.59 | 0.047 | 116 | 56 | 0.070 |
| 48 hours | 0.54 | 0.064 | 116 | 26 | 0.512 | sCr only

| Time prior AKI stage | AUC | SE | nCohort 1 | nCohort 2 | p |
|---|---|---|---|---|---|
| 0 hours  | 0.51 | 0.073 | 256 | 17 | 0.865 |
| 24 hours | 0.54 | 0.064 | 256 | 23 | 0.577 |
| 48 hours | 0.65 | 0.082 | 256 | 14 | 0.072 |

UO only

| Time prior AKI stage | AUC | SE | nCohort 1 | nCohort 2 | p |
|---|---|---|---|---|---|
| 0 hours  | 0.61 | 0.052 | 105 | 45 | 0.037 |
| 24 hours | 0.62 | 0.051 | 105 | 45 | 0.023 |
| 48 hours | 0.54 | 0.068 | 105 | 23 | 0.562 | sCr or UO

| Time prior AKI stage | Cutoff value | sens | spec | Quartile | OR | 95% CI of OR | |
|---|---|---|---|---|---|---|---|
| 0 hours | 17.851931 | 71% | 35% | 1 |     |     |     |
|         | 13.620825 | 80% | 32% | 2 | 2.3 | 1.4 | 3.8 |
|         | 9.6548571 | 90% | 24% | 3 | 1.5 | 0.8 | 2.5 |
|         | 67.675531 | 43% | 71% | 4 | 2.8 | 1.7 | 4.6 |
|         | 94.231339 | 25% | 80% |   |     |     |     |
|         | 112.67707 | 20% | 91% |   |     |     |     |

FIG. 1 - 7

|  | Time prior AKI stage | Cutoff value | sens | spec | Quartile | OR | 95% CI of OR | |
|---|---|---|---|---|---|---|---|---|
| | 24 hours | 20.639446 | 71% | 41% | 1 | | | |
| | | 11.81696 | 80% | 30% | 2 | 1.9 | 1.2 | 2.9 |
| | | 4.9357657 | 91% | 10% | 3 | 0.6 | 0.3 | 1.0 |
| | | 67.675531 | 41% | 71% | 4 | 2.8 | 1.8 | 4.2 |
| | | 94.231339 | 38% | 80% | | | | |
| | | 112.67707 | 30% | 91% | | | | |
| | 48 hours | 21.915017 | 73% | 42% | 1 | | | |
| | | 7.5921674 | 81% | 22% | 2 | 1.2 | 0.6 | 2.4 |
| | | 4.8724396 | 92% | 10% | 3 | 0.8 | 0.3 | 1.9 |
| | | 67.675531 | 38% | 71% | 4 | 1.4 | 0.7 | 2.8 |
| | | 94.231339 | 23% | 80% | | | | |
| | | 112.67707 | 15% | 91% | | | | |
| sCr only | Time prior AKI stage | Cutoff value | sens | spec | Quartile | OR | 95% CI of OR | |
| | 0 hours | 34.168163 | 71% | 46% | 1 | | | |
| | | 12.977528 | 82% | 27% | 2 | 1.0 | 0.3 | 3.9 |
| | | 2.7344176 | 94% | 6% | 3 | 3.3 | 1.3 | 8.4 |
| | | 82.278359 | 35% | 70% | 4 | 0.6 | 0.1 | 3.5 |
| | | 110.58056 | 0% | 80% | | | | |
| | | 177.32683 | 0% | 90% | | | | |
| | 24 hours | 20.639446 | 74% | 37% | 1 | | | |
| | | 8.0510017 | 83% | 18% | 2 | 1.2 | 0.6 | 2.6 |
| | | 5.178951 | 91% | 11% | 3 | 1.2 | 0.6 | 2.6 |
| | | 82.278359 | 35% | 70% | 4 | 1.2 | 0.6 | 2.6 |
| | | 110.58056 | 22% | 80% | | | | |
| | | 177.32683 | 22% | 90% | | | | |
| | 48 hours | 52.373934 | 71% | 58% | 1 | | | |
| | | 32.271515 | 86% | 46% | 2 | 3.0 | 0.2 | 44.1 |
| | | 21.915017 | 93% | 38% | 3 | 5.3 | 0.5 | 59.5 |
| | | 82.278359 | 50% | 70% | 4 | 5.2 | 0.5 | 58.5 |
| | | 110.58056 | 29% | 80% | | | | |
| | | 177.32683 | 14% | 90% | | | | |
| UO only | Time prior AKI stage | Cutoff value | sens | spec | Quartile | OR | 95% CI of OR | |
| | 0 hours | 19.034353 | 71% | 35% | 1 | | | |
| | | 16.4864 | 80% | 32% | 2 | 2.7 | 1.4 | 5.0 |
| | | 9.728 | 91% | 21% | 3 | 1.7 | 0.8 | 3.3 |
| | | 63.154087 | 47% | 70% | 4 | 4.2 | 2.3 | 7.6 |
| | | 84.873371 | 38% | 80% | | | | |
| | | 110.58056 | 24% | 90% | | | | |
| | 24 hours | 24.180364 | 71% | 43% | 1 | | | |
| | | 16.4864 | 80% | 32% | 2 | 1.7 | 1.0 | 2.9 |
| | | 7.2355165 | 91% | 17% | 3 | 0.8 | 0.4 | 1.6 |
| | | 63.154087 | 47% | 70% | 4 | 3.3 | 1.9 | 5.5 |
| | | 84.873371 | 40% | 80% | | | | |
| | | 110.58056 | 36% | 90% | | | | |
| | 48 hours | 11.81696 | 74% | 28% | 1 | | | |
| | | 8.37632 | 83% | 19% | 2 | 1.5 | 0.7 | 3.4 |
| | | 5.9977143 | 91% | 14% | 3 | 0.6 | 0.2 | 1.8 |
| | | 63.154087 | 39% | 70% | 4 | 1.8 | 0.8 | 4.0 |
| | | 84.873371 | 30% | 80% | | | | |
| | | 110.58056 | 22% | 90% | | | | |

FIG. 1 - 8

Prostatic Acid Phosphatase sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4.495 | 9.470 | 4.495 | 6.460 | 4.495 | 8.710 |
| average | 24.231 | 33.377 | 24.231 | 40.086 | 24.231 | 24.383 |
| stdev | 70.981 | 66.711 | 70.981 | 96.501 | 70.981 | 48.277 |
| p (t-test) |  | 0.390 |  | 0.147 |  | 0.991 |
| min | 0.006 | 0.026 | 0.006 | 0.024 | 0.006 | 0.293 |
| max | 530.000 | 310.000 | 530.000 | 521.000 | 530.000 | 235.000 |
| n (Samp) | 248 | 53 | 248 | 62 | 248 | 27 |
| n (Pat) | 103 | 53 | 103 | 62 | 103 | 27 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 5.850 | 3.525 | 5.850 | 2.440 | 5.850 | 7.380 |
| average | 27.843 | 19.082 | 27.843 | 34.058 | 27.843 | 10.736 |
| stdev | 69.781 | 52.720 | 69.781 | 94.152 | 69.781 | 9.926 |
| p (t-test) |  | 0.580 |  | 0.666 |  | 0.360 |
| min | 0.006 | 0.000 | 0.006 | 0.104 | 0.006 | 0.057 |
| max | 530.000 | 237.000 | 530.000 | 469.000 | 530.000 | 31.100 |
| n (Samp) | 440 | 20 | 440 | 26 | 440 | 14 |
| n (Pat) | 169 | 20 | 169 | 26 | 169 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 3.760 | 10.500 | 3.760 | 8.355 | 3.760 | 6.380 |
| average | 16.262 | 34.131 | 16.262 | 44.849 | 16.262 | 24.810 |
| stdev | 53.571 | 64.385 | 53.571 | 104.231 | 53.571 | 50.431 |
| p (t-test) |  | 0.048 |  | 0.006 |  | 0.449 |
| min | 0.006 | 0.026 | 0.006 | 0.024 | 0.006 | 0.293 |
| max | 530.000 | 310.000 | 530.000 | 521.000 | 530.000 | 235.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
| --- | --- | --- | --- | --- | --- |
| 0 hours | 0.58 | 0.045 | 248 | 53 | 0.081 |
| 24 hours | 0.53 | 0.041 | 248 | 62 | 0.454 |
| 48 hours | 0.59 | 0.060 | 248 | 27 | 0.140 | sCr only

| Time prior AKI stage | AUC | SE | nCohort 1 | nCohort 2 | p |
| --- | --- | --- | --- | --- | --- |
| 0 hours | 0.40 | 0.061 | 440 | 20 | 0.111 |
| 24 hours | 0.45 | 0.056 | 440 | 26 | 0.372 |
| 48 hours | 0.52 | 0.079 | 440 | 14 | 0.774 |

UO only

| Time prior AKI stage | AUC | SE | nCohort 1 | nCohort 2 | p |
| --- | --- | --- | --- | --- | --- |
| 0 hours | 0.62 | 0.047 | 212 | 47 | 0.011 |
| 24 hours | 0.56 | 0.045 | 212 | 52 | 0.208 |
| 48 hours | 0.58 | 0.063 | 212 | 25 | 0.196 | sCr or UO

| Time prior AKI stage | Cutoff value | sens | spec | Quartile | OR | 95% CI of OR | |
| --- | --- | --- | --- | --- | --- | --- | --- |
| 0 hours | 2.48 | 72% | 37% | 1 |  |  |  |
|  | 0.425 | 83% | 13% | 2 | 0.5 | 0.3 | 0.9 |
|  | 0.158 | 91% | 7% | 3 | 1.2 | 0.8 | 1.7 |
|  | 11.6 | 42% | 71% | 4 | 1.9 | 1.4 | 2.6 |
|  | 18.7 | 36% | 80% |  |  |  |  |
|  | 41.8 | 19% | 90% |  |  |  |  |

FIG. 1 - 9 sCr only

|  | Cutoff value | sens | spec | Quartile | OR | 95% CI of OR | |
|---|---|---|---|---|---|---|---|
| 24 hours | 1.38 | 71% | 25% | 1 | | | |
| | 0.843 | 81% | 20% | 2 | 0.5 | 0.4 | 0.8 |
| | 0.471 | 90% | 15% | 3 | 0.5 | 0.3 | 0.7 |
| | 11.6 | 40% | 71% | 4 | 1.4 | 1.1 | 1.8 |
| | 18.7 | 29% | 80% | | | | |
| | 41.8 | 19% | 90% | | | | |
| 48 hours | 3.72 | 70% | 47% | 1 | | | |
| | 1.2 | 81% | 23% | 2 | 0.5 | 0.2 | 1.3 |
| | 0.755 | 93% | 19% | 3 | 1.4 | 0.7 | 2.6 |
| | 11.6 | 41% | 71% | 4 | 1.8 | 1.0 | 3.2 |
| | 18.7 | 33% | 80% | | | | |
| | 41.8 | 11% | 90% | | | | |

| Time prior AKI stage | Cutoff value | sens | spec | Quartile | OR | 95% CI of OR | |
|---|---|---|---|---|---|---|---|
| 0 hours | 1.23 | 70% | 23% | 1 | | | |
| | 0.394 | 80% | 12% | 2 | 1.7 | 0.6 | 5.0 |
| | 0.307 | 90% | 11% | 3 | 1.3 | 0.4 | 4.4 |
| | 18.1 | 15% | 70% | 4 | 2.8 | 1.1 | 7.1 |
| | 29.8 | 15% | 80% | | | | |
| | 55.9 | 5% | 90% | | | | |
| 24 hours | 1.38 | 73% | 25% | 1 | | | |
| | 1.05 | 85% | 21% | 2 | 1.0 | 0.4 | 2.3 |
| | 0.311 | 92% | 11% | 3 | 1.6 | 0.8 | 3.2 |
| | 18.1 | 23% | 70% | 4 | 1.7 | 0.8 | 3.3 |
| | 29.8 | 15% | 80% | | | | |
| | 55.9 | 15% | 90% | | | | |
| 48 hours | 5.21 | 71% | 48% | 1 | | | |
| | 2.19 | 86% | 32% | 2 | 2.0 | 0.4 | 9.1 |
| | 1.38 | 93% | 25% | 3 | 3.1 | 0.8 | 11.9 |
| | 18.1 | 21% | 70% | 4 | 1.0 | 0.1 | 7.3 |
| | 29.8 | 7% | 80% | | | | |
| | 55.9 | 0% | 90% | | | | |

UO only

| Time prior AKI stage | Cutoff value | sens | spec | Quartile | OR | 95% CI of OR | |
|---|---|---|---|---|---|---|---|
| 0 hours | 2.74 | 70% | 43% | 1 | | | |
| | 0.471 | 81% | 16% | 2 | 0.5 | 0.3 | 0.9 |
| | 0.158 | 91% | 9% | 3 | 0.8 | 0.5 | 1.2 |
| | 9.25 | 55% | 71% | 4 | 2.3 | 1.6 | 3.3 |
| | 13.8 | 43% | 80% | | | | |
| | 25.3 | 34% | 90% | | | | |
| 24 hours | 0.986 | 71% | 22% | 1 | | | |
| | 0.639 | 81% | 17% | 2 | 0.2 | 0.1 | 0.4 |
| | 0.311 | 90% | 13% | 3 | 0.3 | 0.2 | 0.5 |
| | 9.25 | 42% | 71% | 4 | 1.3 | 1.0 | 1.8 |
| | 13.8 | 42% | 80% | | | | |
| | 25.3 | 25% | 90% | | | | |
| 48 hours | 1.74 | 72% | 31% | 1 | | | |
| | 1.2 | 80% | 24% | 2 | 0.8 | 0.4 | 1.8 |
| | 0.74 | 92% | 20% | 3 | 0.8 | 0.4 | 1.8 |
| | 9.25 | 44% | 71% | 4 | 1.6 | 0.8 | 2.9 |
| | 13.8 | 36% | 80% | | | | |
| | 25.3 | 20% | 90% | | | | |

FIG. 1 - 10 von Willebrand Factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.006 | 0.009 | 0.006 | 0.011 | 0.006 | 0.010 |
| average | 0.028 | 0.017 | 0.028 | 0.226 | 0.028 | 0.017 |
| stdev | 0.154 | 0.025 | 0.154 | 1.585 | 0.154 | 0.016 |
| p (t-test) |  | 0.599 |  | 0.054 |  | 0.700 |
| min | 0.000 | 0.000 | 0.000 | 0.000 | 0.000 | 0.001 |
| max | 2.330 | 0.123 | 2.330 | 12.500 | 2.330 | 0.058 |
| n (Samp) | 248 | 53 | 248 | 62 | 248 | 27 |
| n (Pat) | 103 | 53 | 103 | 62 | 103 | 27 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.007 | 0.009 | 0.007 | 0.013 | 0.007 | 0.013 |
| average | 0.053 | 0.021 | 0.053 | 0.028 | 0.053 | 0.017 |
| stdev | 0.606 | 0.032 | 0.606 | 0.034 | 0.606 | 0.014 |
| p (t-test) |  | 0.815 |  | 0.830 |  | 0.826 |
| min | 0.000 | 0.000 | 0.000 | 0.001 | 0.000 | 0.001 |
| max | 12.500 | 0.123 | 12.500 | 0.162 | 12.500 | 0.045 |
| n (Samp) | 440 | 20 | 440 | 26 | 440 | 14 |
| n (Pat) | 169 | 20 | 169 | 26 | 169 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.007 | 0.009 | 0.007 | 0.012 | 0.007 | 0.010 |
| average | 0.031 | 0.018 | 0.031 | 0.263 | 0.031 | 0.019 |
| stdev | 0.166 | 0.024 | 0.166 | 1.730 | 0.166 | 0.021 |
| p (t-test) |  | 0.597 |  | 0.055 |  | 0.712 |
| min | 0.000 | 0.001 | 0.000 | 0.000 | 0.000 | 0.002 |
| max | 2.330 | 0.123 | 2.330 | 12.500 | 2.330 | 0.089 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
| --- | --- | --- | --- | --- | --- |
| 0 hours | 0.55 | 0.044 | 248 | 53 | 0.247 |
| 24 hours | 0.61 | 0.042 | 248 | 62 | 0.009 |
| 48 hours | 0.59 | 0.060 | 248 | 27 | 0.152 | sCr only

| Time prior AKI stage | AUC | SE | nCohort 1 | nCohort 2 | p |
| --- | --- | --- | --- | --- | --- |
| 0 hours | 0.53 | 0.067 | 440 | 20 | 0.642 |
| 24 hours | 0.63 | 0.060 | 440 | 26 | 0.035 |
| 48 hours | 0.62 | 0.081 | 440 | 14 | 0.151 |

UO only

| Time prior AKI stage | AUC | SE | nCohort 1 | nCohort 2 | p |
| --- | --- | --- | --- | --- | --- |
| 0 hours | 0.58 | 0.047 | 212 | 47 | 0.087 |
| 24 hours | 0.62 | 0.045 | 212 | 52 | 0.006 |
| 48 hours | 0.59 | 0.063 | 212 | 25 | 0.153 | sCr or UO

| Time prior AKI stage | Cutoff value | sens | spec | Quartile | OR | 95% CI of OR | |
| --- | --- | --- | --- | --- | --- | --- | --- |
| 0 hours | 0.00501 | 72% | 41% | 1 |  |  |  |
|  | 0.00398 | 81% | 35% | 2 | 1.0 | 0.6 | 1.6 |
|  | 0.00127 | 91% | 11% | 3 | 2.1 | 1.4 | 3.0 |
|  | 0.0142 | 32% | 70% | 4 | 1.6 | 1.1 | 2.4 |
|  | 0.019 | 19% | 81% |  |  |  |  |
|  | 0.049 | 11% | 90% |  |  |  |  |

FIG. 1 - 11

|  | Time prior AKI stage | Cutoff value | sens | spec | Quartile | OR | 95% CI of OR | |
|---|---|---|---|---|---|---|---|---|
|  | 24 hours | 0.00598 | 71% | 48% | 1 | | | |
|  | | 0.00379 | 81% | 33% | 2 | 1.1 | 0.7 | 1.7 |
|  | | 0.00183 | 90% | 18% | 3 | 1.9 | 1.3 | 2.8 |
|  | | 0.0142 | 39% | 70% | 4 | 3.0 | 2.1 | 4.2 |
|  | | 0.019 | 37% | 81% | | | | |
|  | | 0.049 | 18% | 90% | | | | |
|  | 48 hours | 0.00598 | 70% | 48% | 1 | | | |
|  | | 0.00334 | 81% | 30% | 2 | 0.8 | 0.3 | 2.0 |
|  | | 0.0017 | 93% | 16% | 3 | 1.9 | 1.0 | 3.7 |
|  | | 0.0142 | 41% | 70% | 4 | 1.9 | 1.0 | 3.7 |
|  | | 0.019 | 33% | 81% | | | | |
|  | | 0.049 | 4% | 90% | | | | |
| sCr only | Time prior AKI stage | Cutoff value | sens | spec | Quartile | OR | 95% CI of OR | |
|  | 0 hours | 0.00517 | 70% | 37% | 1 | | | |
|  | | 0.00267 | 80% | 21% | 2 | 0.8 | 0.3 | 2.0 |
|  | | 0.00141 | 90% | 11% | 3 | 1.0 | 0.4 | 2.3 |
|  | | 0.0146 | 35% | 70% | 4 | 1.2 | 0.6 | 2.6 |
|  | | 0.0219 | 30% | 80% | | | | |
|  | | 0.0491 | 10% | 90% | | | | |
|  | 24 hours | 0.00675 | 73% | 46% | 1 | | | |
|  | | 0.00442 | 81% | 33% | 2 | 1.0 | 0.4 | 2.7 |
|  | | 0.00183 | 92% | 16% | 3 | 1.5 | 0.7 | 3.6 |
|  | | 0.0146 | 46% | 70% | 4 | 3.2 | 1.6 | 6.4 |
|  | | 0.0219 | 46% | 80% | | | | |
|  | | 0.0491 | 19% | 90% | | | | |
|  | 48 hours | 0.0104 | 71% | 60% | 1 | | | |
|  | | 0.00398 | 86% | 30% | 2 | 0.5 | 0.0 | 9.6 |
|  | | 0.0017 | 93% | 15% | 3 | 3.7 | 1.0 | 13.4 |
|  | | 0.0146 | 43% | 70% | 4 | 2.0 | 0.4 | 9.1 |
|  | | 0.0219 | 29% | 80% | | | | |
|  | | 0.0491 | 0% | 90% | | | | |
| UO only | Time prior AKI stage | Cutoff value | sens | spec | Quartile | OR | 95% CI of OR | |
|  | 0 hours | 0.00683 | 70% | 51% | 1 | | | |
|  | | 0.00485 | 81% | 39% | 2 | 1.8 | 1.0 | 3.2 |
|  | | 0.00127 | 91% | 10% | 3 | 3.4 | 2.0 | 5.7 |
|  | | 0.0144 | 36% | 70% | 4 | 2.7 | 1.5 | 4.5 |
|  | | 0.0227 | 19% | 81% | | | | |
|  | | 0.0457 | 11% | 90% | | | | |
|  | 24 hours | 0.0071 | 71% | 53% | 1 | | | |
|  | | 0.00485 | 81% | 39% | 2 | 1.3 | 0.8 | 2.3 |
|  | | 0.00226 | 90% | 22% | 3 | 2.7 | 1.7 | 4.3 |
|  | | 0.0144 | 44% | 70% | 4 | 3.7 | 2.3 | 5.8 |
|  | | 0.0227 | 29% | 81% | | | | |
|  | | 0.0457 | 15% | 90% | | | | |
|  | 48 hours | 0.00598 | 72% | 47% | 1 | | | |
|  | | 0.00403 | 80% | 33% | 2 | 1.7 | 0.6 | 5.3 |
|  | | 0.00208 | 92% | 17% | 3 | 3.4 | 1.3 | 8.6 |
|  | | 0.0144 | 40% | 70% | 4 | 2.9 | 1.1 | 7.6 |
|  | | 0.0227 | 28% | 81% | | | | |
|  | | 0.0457 | 12% | 90% | | | | |

FIG. 1 - 12

Endothelial protein C receptor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 50.329 | 0.068 | 50.329 | 60.949 | 50.329 | 0.068 |
| average | 72.893 | 8.232 | 72.893 | 83.497 | 72.893 | 36.786 |
| stdev | 73.245 | na | 73.245 | 62.004 | 73.245 | na |
| p (t-test) |  | na |  | 0.586 |  | na |
| min | 0.068 | 8.232 | 0.068 | 25.357 | 0.068 | 36.786 |
| max | 491.892 | 8.232 | 491.892 | 258.333 | 491.892 | 36.786 |
| n (Samp) | 95 | 1 | 95 | 16 | 95 | 1 |
| n (Pat) | 73 | 1 | 73 | 16 | 73 | 1 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 54.309 | na | 54.309 | 55.000 | 54.309 | na |
| average | 74.596 | na | 74.596 | 68.999 | 74.596 | na |
| stdev | 71.935 | na | 71.935 | 52.073 | 71.935 | na |
| p (t-test) |  | na |  | 0.894 |  | na |
| min | 0.068 | na | 0.068 | 25.357 | 0.068 | na |
| max | 491.892 | na | 491.892 | 126.641 | 491.892 | na |
| n (Samp) | 110 | 0 | 110 | 3 | 110 | 0 |
| n (Pat) | 86 | 0 | 86 | 3 | 86 | 0 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 52.771 | 0.068 | 52.771 | 64.803 | 52.771 | 45.893 |
| average | 74.160 | 8.232 | 74.160 | 151.262 | 74.160 | 45.893 |
| stdev | 77.373 | na | 77.373 | 246.285 | 77.373 | 12.879 |
| p (t-test) |  | na |  | 0.025 |  | 0.609 |
| min | 0.068 | 8.232 | 0.068 | 28.623 | 0.068 | 36.786 |
| max | 491.892 | 8.232 | 491.892 | 1013.333 | 491.892 | 55.000 |
| n (Samp) | 78 | 1 | 78 | 15 | 78 | 2 |
| n (Pat) | 60 | 1 | 60 | 15 | 60 | 2 | sCr or UO

| Time prior AKI stage | AUC | SE | nCohort 1 | nCohort 2 | p |
|---|---|---|---|---|---|
| 0 hours | 0.02 | 0.025 | 95 | 1 | 0.000 |
| 24 hours | 0.60 | 0.080 | 95 | 16 | 0.204 |
| 48 hours | 0.37 | 0.254 | 95 | 1 | 0.604 | sCr only

| Time prior AKI stage | AUC | SE | nCohort 1 | nCohort 2 | p |
|---|---|---|---|---|---|
| 0 hours | nd | nd | 110 | 0 | nd |
| 24 hours | 0.52 | 0.171 | 110 | 3 | 0.916 |
| 48 hours | nd | nd | 110 | 0 | nd |

UO only

| Time prior AKI stage | AUC | SE | nCohort 1 | nCohort 2 | p |
|---|---|---|---|---|---|
| 0 hours | 0.03 | 0.031 | 78 | 1 | 0.000 |
| 24 hours | 0.66 | 0.082 | 78 | 15 | 0.054 |
| 48 hours | 0.45 | 0.199 | 78 | 2 | 0.785 | sCr or UO

| Time prior AKI stage | Cutoff value | sens | spec | Quartile | OR | 95% CI of OR | | |
|---|---|---|---|---|---|---|---|---|
| 0 hours | 0.9615385 | 100% | 2% | 1 |  |  |  |  |
|  | 0.9615385 | 100% | 2% | 2 | na | na | na | na |
|  | 0.9615385 | 100% | 2% | 3 | na | na | na | na |
|  | 80.384615 | 0% | 71% | 4 | na | na | na | na |
|  | 105.01931 | 0% | 81% |  |  |  |  |  |
|  | 158.30116 | 0% | 91% |  |  |  |  |  |

FIG. 2 - 1

|  | Time prior AKI stage | Cutoff value | sens | spec | Quartile | OR | 95% CI of OR | |
|---|---|---|---|---|---|---|---|---|
|  | 24 hours | 47.463768 | 75% | 47% | 1 |  |  |  |
|  |  | 35.869565 | 81% | 37% | 2 | 1.5 | 0.3 | 9.0 |
|  |  | 28.214286 | 94% | 26% | 3 | 4.2 | 1.0 | 17.4 |
|  |  | 80.384615 | 38% | 71% | 4 | 2.1 | 0.4 | 10.6 |
|  |  | 105.01931 | 25% | 81% |  |  |  |  |
|  |  | 158.30116 | 13% | 91% |  |  |  |  |
|  | 48 hours | 35.869565 | 100% | 37% | 1 |  |  |  |
|  |  | 35.869565 | 100% | 37% | 2 | na | na | na |
|  |  | 35.869565 | 100% | 37% | 3 | na | na | na |
|  |  | 80.384615 | 0% | 71% | 4 | na | na | na |
|  |  | 105.01931 | 0% | 81% |  |  |  |  |
|  |  | 158.30116 | 0% | 91% |  |  |  |  | sCr only

| Time prior AKI stage | Cutoff value | sens | spec | Quartile | OR | 95% CI of OR | |
|---|---|---|---|---|---|---|---|
| 0 hours | na | na | na | 1 |  |  |  |
|  | na | na | na | 2 | na | na | na |
|  | na | na | na | 3 | na | na | na |
|  | na | na | na | 4 | na | na | na |
|  | na | na | na |  |  |  |  |
|  | na | na | na |  |  |  |  |
| 24 hours | 24.038462 | 100% | 20% | 1 |  |  |  |
|  | 24.038462 | 100% | 20% | 2 | 0.0 | 0.0 | 58.3 |
|  | 24.038462 | 100% | 20% | 3 | 1.0 | 0.0 | 58.3 |
|  | 81.153846 | 33% | 70% | 4 | 1.0 | 0.0 | 56.0 |
|  | 105.01931 | 33% | 80% |  |  |  |  |
|  | 158.30116 | 0% | 90% |  |  |  |  |
| 48 hours | na | na | na | 1 |  |  |  |
|  | na | na | na | 2 | na | na | na |
|  | na | na | na | 3 | na | na | na |
|  | na | na | na | 4 | na | na | na |
|  | na | na | na |  |  |  |  |
|  | na | na | na |  |  |  |  |

UO only

| Time prior AKI stage | Cutoff value | sens | spec | Quartile | OR | 95% CI of OR | |
|---|---|---|---|---|---|---|---|
| 0 hours | 2.8846154 | 100% | 3% | 1 |  |  |  |
|  | 2.8846154 | 100% | 3% | 2 | na | na | na |
|  | 2.8846154 | 100% | 3% | 3 | na | na | na |
|  | 80.384615 | 0% | 71% | 4 | na | na | na |
|  | 105.01931 | 0% | 81% |  |  |  |  |
|  | 158.30116 | 0% | 91% |  |  |  |  |
| 24 hours | 56.25 | 73% | 55% | 1 |  |  |  |
|  | 47.463768 | 80% | 46% | 2 | 3.3 | 0.2 | 54.3 |
|  | 28.623188 | 93% | 28% | 3 | 7.8 | 0.6 | 93.8 |
|  | 80.384615 | 47% | 71% | 4 | 5.8 | 0.5 | 73.7 |
|  | 105.01931 | 33% | 81% |  |  |  |  |
|  | 158.30116 | 20% | 91% |  |  |  |  |
| 48 hours | 35.869565 | 100% | 36% | 1 |  |  |  |
|  | 35.869565 | 100% | 36% | 2 | na | na | na |
|  | 35.869565 | 100% | 36% | 3 | na | na | na |
|  | 80.384615 | 0% | 71% | 4 | na | na | na |
|  | 105.01931 | 0% | 81% |  |  |  |  |
|  | 158.30116 | 0% | 91% |  |  |  |  |

FIG. 2 - 2

Erythropoietin receptor sCr or UO

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 20.270   | 0.517    | 20.270   | 91.146   | 20.270   | 0.517    |
| average  | 112.572  | 94.758   | 112.572  | 86.707   | 112.572  | 98.958   |
| stdev    | 739.437  | na       | 739.437  | 60.643   | 739.437  | na       |
| p (t-test) |        | na       |          | 0.889    |          | na       |
| min      | 0.517    | 94.758   | 0.517    | 0.517    | 0.517    | 98.958   |
| max      | 7307.410 | 94.758   | 7307.410 | 180.085  | 7307.410 | 98.958   |
| n (Samp) | 97       | 1        | 97       | 16       | 97       | 1        |
| n (Pat)  | 73       | 1        | 73       | 16       | 73       | 1        | sCr only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 28.716   | na       | 28.716   | 104.167  | 28.716   | na       |
| average  | 108.007  | na       | 108.007  | 88.086   | 108.007  | na       |
| stdev    | 688.107  | na       | 688.107  | 51.125   | 688.107  | na       |
| p (t-test) |        | na       |          | 0.960    |          | na       |
| min      | 0.517    | na       | 0.517    | 30.854   | 0.517    | na       |
| max      | 7307.410 | na       | 7307.410 | 129.237  | 7307.410 | na       |
| n (Samp) | 112      | 0        | 112      | 3        | 112      | 0        |
| n (Pat)  | 86       | 0        | 86       | 3        | 86       | 0        |

UO only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 28.716   | 0.517    | 28.716   | 88.542   | 28.716   | 64.906   |
| average  | 132.319  | 94.758   | 132.319  | 83.871   | 132.319  | 64.906   |
| stdev    | 813.620  | na       | 813.620  | 61.664   | 813.620  | 48.157   |
| p (t-test) |        | na       |          | 0.819    |          | 0.908    |
| min      | 0.517    | 94.758   | 0.517    | 0.517    | 0.517    | 30.854   |
| max      | 7307.410 | 94.758   | 7307.410 | 180.085  | 7307.410 | 98.958   |
| n (Samp) | 80       | 1        | 80       | 15       | 80       | 2        |
| n (Pat)  | 60       | 1        | 60       | 15       | 60       | 2        | sCr or UO

| Time prior AKI stage | AUC  | SE    | nCohort 1 | nCohort 2 | p     |
|----------------------|------|-------|-----------|-----------|-------|
| 0 hours              | 0.90 | 0.210 | 97        | 1         | 0.059 |
| 24 hours             | 0.74 | 0.075 | 97        | 16        | 0.002 |
| 48 hours             | 0.90 | 0.206 | 97        | 1         | 0.051 | sCr only

| Time prior AKI stage | AUC  | SE    | nCohort 1 | nCohort 2 | p     |
|----------------------|------|-------|-----------|-----------|-------|
| 0 hours              | nd   | nd    | 112       | 0         | nd    |
| 24 hours             | 0.78 | 0.160 | 112       | 3         | 0.080 |
| 48 hours             | nd   | nd    | 112       | 0         | nd    |

UO only

| Time prior AKI stage | AUC  | SE    | nCohort 1 | nCohort 2 | p     |
|----------------------|------|-------|-----------|-----------|-------|
| 0 hours              | 0.88 | 0.228 | 80        | 1         | 0.099 |
| 24 hours             | 0.70 | 0.080 | 80        | 15        | 0.013 |
| 48 hours             | 0.70 | 0.210 | 80        | 2         | 0.334 | sCr or UO

| Time prior AKI stage | Cutoff value | sens | spec | Quartile | OR | 95% CI of OR | |
|----------------------|--------------|------|------|----------|----|----|----|
| 0 hours  | 90.725806 | 100% | 90% | 1 |    |    |    |
|          | 90.725806 | 100% | 90% | 2 | na | na | na |
|          | 90.725806 | 100% | 90% | 3 | na | na | na |
|          | 54.054054 | 100% | 70% | 4 | na | na | na |
|          | 74.596774 | 100% | 80% |   |    |    |    |
|          | 98.958333 | 0%   | 91% |   |    |    |    |
| 24 hours | 28.716216 | 75%  | 56% | 1 |    |    |    |

FIG. 2 - 3

|  |  | 22.943038 | 81% | 53% | 2 | 1.0 | 0.1 | 8.3 |
|  |  | 0 | 100% | 0% | 3 | 1.6 | 0.3 | 9.3 |
|  |  | 54.054054 | 69% | 70% | 4 | 5.9 | 1.5 | 23.0 |
|  |  | 74.596774 | 56% | 80% |  |  |  |  |
|  |  | 98.958333 | 44% | 91% |  |  |  |  |
|  | 48 hours | 90.725806 | 100% | 90% | 1 |  |  |  |
|  |  | 90.725806 | 100% | 90% | 2 | na | na | na |
|  |  | 90.725806 | 100% | 90% | 3 | na | na | na |
|  |  | 54.054054 | 100% | 70% | 4 | na | na | na |
|  |  | 74.596774 | 100% | 80% |  |  |  |  |
|  |  | 98.958333 | 0% | 91% |  |  |  |  |

UO only

| Time prior AKI stage | Cutoff value | sens | spec | Quartile | OR | 95% CI of OR | |
|---|---|---|---|---|---|---|---|
| 0 hours | 88.541667 | 100% | 88% | 1 |  |  |  |
|  | 88.541667 | 100% | 88% | 2 | na | na | na |
|  | 88.541667 | 100% | 88% | 3 | na | na | na |
|  | 62.5 | 100% | 73% | 4 | na | na | na |
|  | 78.125 | 100% | 81% |  |  |  |  |
|  | 109.375 | 0% | 90% |  |  |  |  |
| 24 hours | 28.716216 | 73% | 51% | 1 |  |  |  |
|  | 22.943038 | 80% | 49% | 2 | 1.5 | 0.2 | 9.3 |
|  | 0 | 100% | 0% | 3 | 1.0 | 0.1 | 8.1 |
|  | 62.5 | 67% | 73% | 4 | 5.3 | 1.2 | 22.2 |
|  | 78.125 | 53% | 81% |  |  |  |  |
|  | 109.375 | 33% | 90% |  |  |  |  |
| 48 hours | 28.716216 | 100% | 51% | 1 |  |  |  |
|  | 28.716216 | 100% | 51% | 2 | na | na | na |
|  | 28.716216 | 100% | 51% | 3 | na | na | na |
|  | 62.5 | 50% | 73% | 4 | na | na | na |
|  | 78.125 | 50% | 81% |  |  |  |  |
|  | 109.375 | 0% | 90% |  |  |  |  |

FIG. 2 - 4

Intercellular adhesion molecule 1 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4749.879 | 5068.987 | 4749.879 | 3830.843 | 4749.879 | 4278.585 |
| average | 6133.036 | 5108.270 | 6133.036 | 7776.837 | 6133.036 | 4365.820 |
| stdev | 4859.623 | 2684.272 | 4859.623 | 16847.250 | 4859.623 | 3439.120 |
| p (t-test) |  | 0.320 |  | 0.222 |  | 0.154 |
| min | 143.975 | 49.188 | 143.975 | 17.651 | 143.975 | 884.006 |
| max | 23945.523 | 9162.750 | 23945.523 | 101592.853 | 23945.523 | 12963.420 |
| n (Samp) | 247 | 23 | 247 | 35 | 247 | 16 |
| n (Pat) | 161 | 23 | 161 | 35 | 161 | 16 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4756.924 | 3271.166 | 4756.924 | 6266.884 | 4756.924 | 1770.488 |
| average | 6280.964 | 3271.166 | 6280.964 | 7081.972 | 6280.964 | 2457.922 |
| stdev | 7095.695 | 2542.503 | 7095.695 | 5657.135 | 7095.695 | 1491.164 |
| p (t-test) |  | 0.550 |  | 0.752 |  | 0.156 |
| min | 49.188 | 1473.344 | 49.188 | 17.651 | 49.188 | 932.744 |
| max | 101592.853 | 5068.987 | 101592.853 | 14369.565 | 101592.853 | 4811.596 |
| n (Samp) | 316 | 2 | 316 | 8 | 316 | 7 |
| n (Pat) | 190 | 2 | 190 | 8 | 190 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4891.600 | 5046.487 | 4891.600 | 3741.190 | 4891.600 | 5207.380 |
| average | 6284.356 | 5134.771 | 6284.356 | 7825.788 | 6284.356 | 5386.829 |
| stdev | 4926.338 | 2639.694 | 4926.338 | 18122.796 | 4926.338 | 3921.802 |
| p (t-test) |  | 0.272 |  | 0.313 |  | 0.505 |
| min | 143.975 | 49.188 | 143.975 | 255.128 | 143.975 | 884.006 |
| max | 23945.523 | 9162.750 | 23945.523 | 101592.853 | 23945.523 | 12963.420 |
| n (Samp) | 212 | 23 | 212 | 30 | 212 | 14 |
| n (Pat) | 133 | 23 | 133 | 30 | 133 | 14 | sCr or UO

| Time prior AKI stage | AUC | SE | nCohort 1 | nCohort 2 | p |
| --- | --- | --- | --- | --- | --- |
| 0 hours | 0.49 | 0.063 | 247 | 23 | 0.885 |
| 24 hours | 0.45 | 0.051 | 247 | 35 | 0.300 |
| 48 hours | 0.40 | 0.068 | 247 | 16 | 0.136 | sCr only

| Time prior AKI stage | AUC | SE | nCohort 1 | nCohort 2 | p |
| --- | --- | --- | --- | --- | --- |
| 0 hours | 0.33 | 0.168 | 316 | 2 | 0.317 |
| 24 hours | 0.55 | 0.106 | 316 | 8 | 0.625 |
| 48 hours | 0.24 | 0.073 | 316 | 7 | 0.000 |

UO only

| Time prior AKI stage | AUC | SE | nCohort 1 | nCohort 2 | p |
| --- | --- | --- | --- | --- | --- |
| 0 hours | 0.48 | 0.063 | 212 | 23 | 0.802 |
| 24 hours | 0.41 | 0.053 | 212 | 30 | 0.106 |
| 48 hours | 0.46 | 0.078 | 212 | 14 | 0.640 | sCr or UO

| Time prior AKI stage | Cutoff value | sens | spec | Quartile | OR | 95% CI of OR | |
| --- | --- | --- | --- | --- | --- | --- | --- |
| 0 hours | 3708.0684 | 74% | 41% | 1 |  |  |  |
|  | 1837.2172 | 83% | 16% | 2 | 3.8 | 1.5 | 9.5 |
|  | 1404.7125 | 91% | 13% | 3 | 1.7 | 0.6 | 5.2 |
|  | 7384.4411 | 22% | 70% | 4 | 1.7 | 0.6 | 5.3 |
|  | 10095.697 | 0% | 80% |  |  |  |  |
|  | 13351.36 | 0% | 90% |  |  |  |  |

FIG. 2 - 5

| | Time prior AKI stage | Cutoff value | sens | spec | Quartile | OR | 95% CI of OR | |
|---|---|---|---|---|---|---|---|---|
| | 24 hours | 2425.248 | 71% | 23% | 1 | | | |
| | | 1193.0554 | 80% | 11% | 2 | 1.0 | 0.6 | 1.8 |
| | | 808.35928 | 91% | 6% | 3 | 1.0 | 0.6 | 1.7 |
| | | 7384.4411 | 26% | 70% | 4 | 1.5 | 0.9 | 2.4 |
| | | 10095.697 | 20% | 80% | | | | |
| | | 13351.36 | 9% | 90% | | | | |
| | 48 hours | 1648.5508 | 75% | 14% | 1 | | | |
| | | 1106.0835 | 81% | 10% | 2 | 3.2 | 0.8 | 12.6 |
| | | 884.00556 | 94% | 6% | 3 | 1.0 | 0.1 | 7.5 |
| | | 7384.4411 | 13% | 70% | 4 | 3.3 | 0.8 | 12.8 |
| | | 10095.697 | 13% | 80% | | | | |
| | | 13351.36 | 0% | 90% | | | | | sCr only

| Time prior AKI stage | Cutoff value | sens | spec | Quartile | OR | 95% CI of OR | |
|---|---|---|---|---|---|---|---|
| 0 hours | 1404.7125 | 100% | 13% | 1 | | | |
| | 1404.7125 | 100% | 13% | 2 | na | na | na |
| | 1404.7125 | 100% | 13% | 3 | na | na | na |
| | 7088.3129 | 0% | 70% | 4 | na | na | na |
| | 9642.0131 | 0% | 80% | | | | |
| | 13216.773 | 0% | 90% | | | | |
| 24 hours | 3348.3318 | 75% | 37% | 1 | | | |
| | 884.00556 | 88% | 6% | 2 | 0.5 | 0.0 | 9.8 |
| | 0 | 100% | 0% | 3 | 1.0 | 0.1 | 7.5 |
| | 7088.3129 | 50% | 70% | 4 | 1.5 | 0.3 | 8.2 |
| | 9642.0131 | 38% | 80% | | | | |
| | 13216.773 | 25% | 90% | | | | |
| 48 hours | 1648.5508 | 71% | 15% | 1 | | | |
| | 1017.2784 | 86% | 8% | 2 | na | na | na |
| | 884.00556 | 100% | 6% | 3 | na | na | na |
| | 7088.3129 | 0% | 70% | 4 | na | na | na |
| | 9642.0131 | 0% | 80% | | | | |
| | 13216.773 | 0% | 90% | | | | |

UO only

| Time prior AKI stage | Cutoff value | sens | spec | Quartile | OR | 95% CI of OR | |
|---|---|---|---|---|---|---|---|
| 0 hours | 3708.0684 | 74% | 39% | 1 | | | |
| | 2243.5899 | 83% | 21% | 2 | 3.4 | 1.3 | 8.6 |
| | 1747.3469 | 91% | 14% | 3 | 2.1 | 0.7 | 6.1 |
| | 7577.8005 | 22% | 70% | 4 | 1.8 | 0.6 | 5.4 |
| | 10218.757 | 0% | 80% | | | | |
| | 13463.237 | 0% | 90% | | | | |
| 24 hours | 2425.248 | 70% | 22% | 1 | | | |
| | 1404.7125 | 80% | 12% | 2 | 1.0 | 0.5 | 2.1 |
| | 878.55325 | 90% | 7% | 3 | 1.0 | 0.5 | 2.1 |
| | 7577.8005 | 20% | 70% | 4 | 2.3 | 1.3 | 4.0 |
| | 10218.757 | 10% | 80% | | | | |
| | 13463.237 | 7% | 90% | | | | |
| 48 hours | 2797.6993 | 71% | 29% | 1 | | | |
| | 1106.0835 | 86% | 9% | 2 | 1.8 | 0.6 | 5.4 |
| | 884.00556 | 93% | 7% | 3 | 0.7 | 0.1 | 3.6 |
| | 7577.8005 | 21% | 70% | 4 | 1.4 | 0.4 | 4.7 |
| | 10218.757 | 14% | 80% | | | | |
| | 13463.237 | 0% | 90% | | | | |

FIG. 2 - 6

Lactotransferrin sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 36.887 | 78.341 | 36.887 | 82.075 | 36.887 | 88.387 |
| average | 119.269 | 83.910 | 119.269 | 232.803 | 119.269 | 91.862 |
| stdev | 565.405 | 69.613 | 565.405 | 475.549 | 565.405 | 71.532 |
| p (t-test) |  | 0.765 |  | 0.259 |  | 0.838 |
| min | 0.034 | 0.264 | 0.034 | 0.596 | 0.034 | 1.598 |
| max | 7981.395 | 287.712 | 7981.395 | 2508.696 | 7981.395 | 252.566 |
| n (Samp) | 241 | 23 | 241 | 35 | 241 | 18 |
| n (Pat) | 158 | 23 | 158 | 35 | 158 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 43.590 | 88.709 | 43.590 | 45.749 | 43.590 | 88.688 |
| average | 126.727 | 88.709 | 126.727 | 40.853 | 126.727 | 120.099 |
| stdev | 522.076 | 0.654 | 522.076 | 29.906 | 522.076 | 90.032 |
| p (t-test) |  | 0.918 |  | 0.643 |  | 0.973 |
| min | 0.034 | 88.246 | 0.034 | 1.565 | 0.034 | 3.410 |
| max | 7981.395 | 89.171 | 7981.395 | 82.075 | 7981.395 | 252.566 |
| n (Samp) | 313 | 2 | 313 | 8 | 313 | 7 |
| n (Pat) | 187 | 2 | 187 | 8 | 187 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 38.710 | 74.540 | 38.710 | 97.471 | 38.710 | 88.629 |
| average | 128.634 | 81.854 | 128.634 | 266.228 | 128.634 | 87.749 |
| stdev | 608.641 | 69.977 | 608.641 | 506.904 | 608.641 | 59.278 |
| p (t-test) |  | 0.713 |  | 0.239 |  | 0.789 |
| min | 0.034 | 0.264 | 0.034 | 0.596 | 0.034 | 1.598 |
| max | 7981.395 | 287.712 | 7981.395 | 2508.696 | 7981.395 | 223.790 |
| n (Samp) | 207 | 23 | 207 | 30 | 207 | 16 |
| n (Pat) | 131 | 23 | 131 | 30 | 131 | 16 | sCr or UO

| Time prior AKI stage | AUC | SE | nCohort 1 | nCohort 2 | p |
| --- | --- | --- | --- | --- | --- |
| 0 hours | 0.63 | 0.065 | 241 | 23 | 0.047 |
| 24 hours | 0.66 | 0.053 | 241 | 35 | 0.002 |
| 48 hours | 0.66 | 0.072 | 241 | 18 | 0.027 | sCr only

| Time prior AKI stage | AUC | SE | nCohort 1 | nCohort 2 | p |
| --- | --- | --- | --- | --- | --- |
| 0 hours | 0.73 | 0.205 | 313 | 2 | 0.271 |
| 24 hours | 0.43 | 0.098 | 313 | 8 | 0.489 |
| 48 hours | 0.69 | 0.113 | 313 | 7 | 0.098 |

UO only

| Time prior AKI stage | AUC | SE | nCohort 1 | nCohort 2 | p |
| --- | --- | --- | --- | --- | --- |
| 0 hours | 0.61 | 0.065 | 207 | 23 | 0.079 |
| 24 hours | 0.70 | 0.056 | 207 | 30 | 0.000 |
| 48 hours | 0.68 | 0.076 | 207 | 16 | 0.021 | sCr or UO

| Time prior AKI stage | Cutoff value | sens | spec | Quartile | OR | 95% CI of OR | |
| --- | --- | --- | --- | --- | --- | --- | --- |
| 0 hours | 41.916484 | 74% | 54% | 1 |  |  |  |
|  | 15.01184 | 83% | 32% | 2 | 0.5 | 0.1 | 2.2 |
|  | 3.4238654 | 91% | 7% | 3 | 1.6 | 0.6 | 3.7 |
|  | 69.14188 | 65% | 70% | 4 | 3.1 | 1.5 | 6.5 |
|  | 94.924245 | 30% | 80% |  |  |  |  |
|  | 156.83453 | 13% | 90% |  |  |  |  |

FIG. 2 - 7

| | | | | | | | |
|---|---|---|---|---|---|---|---|
| 24 hours | 52.12679 | 71% | 62% | 1 | | | |
| | 24.630132 | 80% | 42% | 2 | 0.6 | 0.3 | 1.6 |
| | 7.4496546 | 91% | 17% | 3 | 1.8 | 1.0 | 3.2 |
| | 69.14188 | 51% | 70% | 4 | 2.9 | 1.7 | 4.9 |
| | 94.924245 | 43% | 80% | | | | |
| | 156.83453 | 34% | 90% | | | | |
| 48 hours | 33.016242 | 72% | 48% | 1 | | | |
| | 22.047347 | 83% | 40% | 2 | 2.0 | 0.4 | 9.4 |
| | 2.9045645 | 94% | 6% | 3 | 1.0 | 0.1 | 7.4 |
| | 69.14188 | 56% | 70% | 4 | 5.6 | 1.6 | 19.5 |
| | 94.924245 | 44% | 80% | | | | |
| | 156.83453 | 17% | 90% | | | | | sCr only

| Time prior AKI stage | Cutoff value | sens | spec | Quartile | OR | 95% CI of OR | |
|---|---|---|---|---|---|---|---|
| 0 hours | 88.086243 | 100% | 72% | 1 | | | |
| | 88.086243 | 100% | 72% | 2 | na | na | na |
| | 88.086243 | 100% | 72% | 3 | na | na | na |
| | 84.665922 | 100% | 70% | 4 | na | na | na |
| | 110.58056 | 0% | 80% | | | | |
| | 184.36697 | 0% | 90% | | | | |
| 24 hours | 17.59232 | 75% | 31% | 1 | | | |
| | 8.0084875 | 88% | 17% | 2 | na | na | na |
| | 1.4945818 | 100% | 3% | 3 | na | na | na |
| | 84.665922 | 0% | 70% | 4 | na | na | na |
| | 110.58056 | 0% | 80% | | | | |
| | 184.36697 | 0% | 90% | | | | |
| 48 hours | 83.266935 | 71% | 70% | 1 | | | |
| | 58.662081 | 86% | 60% | 2 | 0.0 | 0.0 | na |
| | 2.9045645 | 100% | 6% | 3 | 3.1 | 0.2 | 44.2 |
| | 84.665922 | 57% | 70% | 4 | 3.1 | 0.2 | 44.2 |
| | 110.58056 | 43% | 80% | | | | |
| | 184.36697 | 29% | 90% | | | | |

UO only

| Time prior AKI stage | Cutoff value | sens | spec | Quartile | OR | 95% CI of OR | |
|---|---|---|---|---|---|---|---|
| 0 hours | 41.916484 | 74% | 54% | 1 | | | |
| | 15.01184 | 83% | 30% | 2 | 0.5 | 0.1 | 2.2 |
| | 3.4238654 | 91% | 6% | 3 | 2.2 | 1.0 | 4.9 |
| | 69.14188 | 61% | 70% | 4 | 2.4 | 1.1 | 5.3 |
| | 95.209739 | 30% | 80% | | | | |
| | 156.83453 | 13% | 90% | | | | |
| 24 hours | 53.431061 | 70% | 62% | 1 | | | |
| | 28.599824 | 80% | 44% | 2 | 0.7 | 0.2 | 2.5 |
| | 10.71104 | 90% | 21% | 3 | 2.2 | 1.0 | 4.8 |
| | 69.14188 | 60% | 70% | 4 | 4.6 | 2.3 | 9.2 |
| | 95.209739 | 50% | 80% | | | | |
| | 156.83453 | 40% | 90% | | | | |
| 48 hours | 33.016242 | 75% | 47% | 1 | | | |
| | 31.526788 | 81% | 46% | 2 | 4.2 | 0.3 | 51.8 |
| | 18.226171 | 94% | 34% | 3 | 4.2 | 0.3 | 51.8 |
| | 69.14188 | 56% | 70% | 4 | 7.7 | 0.8 | 78.2 |
| | 95.209739 | 44% | 80% | | | | |
| | 156.83453 | 13% | 90% | | | | |

FIG. 2 - 8

Prostatic Acid Phosphatase sCr or UO

|          | 0 hr prior to AKI stage | | 24 hr prior to AKI stage | | 48 hr prior to AKI stage | |
|----------|--------|--------|--------|--------|--------|--------|
|          | Cohort 1 | Cohort 2 | Cohort 1 | Cohort 2 | Cohort 1 | Cohort 2 |
| median   | 4.770  | 9.470  | 4.770  | 7.160  | 4.770  | 8.725  |
| average  | 22.695 | 31.702 | 22.695 | 54.991 | 22.695 | 30.405 |
| stdev    | 60.788 | 88.857 | 60.788 | 126.579 | 60.788 | 49.347 |
| p (t-test) |      | 0.470  |        | 0.007  |        | 0.596  |
| min      | 0.000  | 0.018  | 0.000  | 0.000  | 0.000  | 0.024  |
| max      | 530.000 | 469.000 | 530.000 | 521.000 | 530.000 | 165.000 |
| n (Samp) | 419    | 27     | 419    | 36     | 419    | 18     |
| n (Pat)  | 164    | 27     | 164    | 36     | 164    | 18     | sCr only

|          | 0 hr prior to AKI stage | | 24 hr prior to AKI stage | | 48 hr prior to AKI stage | |
|----------|--------|--------|--------|--------|--------|--------|
|          | Cohort 1 | Cohort 2 | Cohort 1 | Cohort 2 | Cohort 1 | Cohort 2 |
| median   | 5.660  | 0.728  | 5.660  | 0.377  | 5.660  | 6.520  |
| average  | 26.063 | 2.601  | 26.063 | 15.381 | 26.063 | 71.118 |
| stdev    | 65.744 | 3.002  | 65.744 | 29.041 | 65.744 | 175.497 |
| p (t-test) |      | 0.426  |        | 0.627  |        | 0.082  |
| min      | 0.000  | 0.311  | 0.000  | 0.000  | 0.000  | 0.057  |
| max      | 530.000 | 6.970 | 530.000 | 89.100 | 530.000 | 469.000 |
| n (Samp) | 518    | 5      | 518    | 9      | 518    | 7      |
| n (Pat)  | 199    | 5      | 199    | 9      | 199    | 7      |

UO only

|          | 0 hr prior to AKI stage | | 24 hr prior to AKI stage | | 48 hr prior to AKI stage | |
|----------|--------|--------|--------|--------|--------|--------|
|          | Cohort 1 | Cohort 2 | Cohort 1 | Cohort 2 | Cohort 1 | Cohort 2 |
| median   | 4.345  | 12.150 | 4.345  | 6.375  | 4.345  | 8.725  |
| average  | 18.404 | 37.135 | 18.404 | 61.630 | 18.404 | 33.471 |
| stdev    | 49.284 | 91.191 | 49.284 | 137.322 | 49.284 | 51.687 |
| p (t-test) |      | 0.083  |        | 0.000  |        | 0.233  |
| min      | 0.000  | 0.018  | 0.000  | 0.051  | 0.000  | 0.024  |
| max      | 530.000 | 469.000 | 530.000 | 521.000 | 530.000 | 165.000 |
| n (Samp) | 352    | 26     | 352    | 30     | 352    | 16     |
| n (Pat)  | 133    | 26     | 133    | 30     | 133    | 16     | sCr or UO

| Time prior AKI stage | AUC | SE | nCohort 1 | nCohort 2 | p |
|---|---|---|---|---|---|
| 0 hours | 0.56 | 0.059 | 419 | 27 | 0.325 |
| 24 hours | 0.50 | 0.050 | 419 | 36 | 0.927 |
| 48 hours | 0.59 | 0.072 | 419 | 18 | 0.192 | sCr only

| Time prior AKI stage | AUC | SE | nCohort 1 | nCohort 2 | p |
|---|---|---|---|---|---|
| 0 hours | 0.28 | 0.095 | 518 | 5 | 0.021 |
| 24 hours | 0.37 | 0.085 | 518 | 9 | 0.122 |
| 48 hours | 0.47 | 0.107 | 518 | 7 | 0.755 |

UO only

| Time prior AKI stage | AUC | SE | nCohort 1 | nCohort 2 | p |
|---|---|---|---|---|---|
| 0 hours | 0.62 | 0.061 | 352 | 26 | 0.045 |
| 24 hours | 0.53 | 0.056 | 352 | 30 | 0.591 |
| 48 hours | 0.62 | 0.076 | 352 | 16 | 0.128 | sCr or UO

| Time prior AKI stage | Cutoff value | sens | spec | Quartile | OR | 95% CI of OR | |
|---|---|---|---|---|---|---|---|
| 0 hours | 2.29 | 70% | 35% | 1 | | | |
|  | 0.803 | 81% | 19% | 2 | 0.6 | 0.2 | 1.2 |
|  | 0.471 | 93% | 14% | 3 | 0.8 | 0.4 | 1.6 |
|  | 12.3 | 44% | 70% | 4 | 1.5 | 0.9 | 2.4 |
|  | 21.6 | 37% | 80% | | | | |
|  | 45.4 | 7% | 90% | | | | |

FIG. 2 - 9

|  | Time prior AKI stage | Cutoff value | sens | spec | Quartile | OR | 95% CI of OR | |
|---|---|---|---|---|---|---|---|---|
|  | 24 hours | 0.669 | 72% | 16% | 1 |  |  |  |
|  |  | 0.307 | 81% | 10% | 2 | 0.3 | 0.1 | 0.6 |
|  |  | 0.102 | 92% | 5% | 3 | 0.5 | 0.3 | 0.8 |
|  |  | 12.3 | 42% | 70% | 4 | 0.9 | 0.6 | 1.3 |
|  |  | 21.6 | 28% | 80% |  |  |  |  |
|  |  | 45.4 | 19% | 90% |  |  |  |  |
|  | 48 hours | 6.36 | 72% | 57% | 1 |  |  |  |
|  |  | 2.29 | 83% | 35% | 2 | 0.3 | 0.0 | 4.6 |
|  |  | 0.0539 | 94% | 4% | 3 | 3.2 | 1.3 | 7.9 |
|  |  | 12.3 | 33% | 70% | 4 | 1.7 | 0.6 | 5.0 |
|  |  | 21.6 | 28% | 80% |  |  |  |  |
|  |  | 45.4 | 17% | 90% |  |  |  |  |
| sCr only | Time prior AKI stage | Cutoff value | sens | spec | Quartile | OR | 95% CI of OR | |
|  | 0 hours | 0.471 | 80% | 14% | 1 |  |  |  |
|  |  | 0.471 | 80% | 14% | 2 | na | na | na |
|  |  | 0.307 | 100% | 10% | 3 | na | na | na |
|  |  | 15.7 | 0% | 70% | 4 | na | na | na |
|  |  | 27.9 | 0% | 80% |  |  |  |  |
|  |  | 55.9 | 0% | 90% |  |  |  |  |
|  | 24 hours | 0.158 | 78% | 7% | 1 |  |  |  |
|  |  | 0.102 | 89% | 5% | 2 | 1.0 | 0.1 | 7.3 |
|  |  | 0 | 100% | 0% | 3 | 0.0 | 0.0 | na |
|  |  | 15.7 | 22% | 70% | 4 | 2.6 | 0.6 | 10.5 |
|  |  | 27.9 | 11% | 80% |  |  |  |  |
|  |  | 55.9 | 11% | 90% |  |  |  |  |
|  | 48 hours | 1.4 | 71% | 25% | 1 |  |  |  |
|  |  | 1.23 | 86% | 23% | 2 | 3.1 | 0.2 | 43.2 |
|  |  | 0.0539 | 100% | 4% | 3 | 1.0 | 0.0 | 52.3 |
|  |  | 15.7 | 14% | 70% | 4 | 2.0 | 0.1 | 39.6 |
|  |  | 27.9 | 14% | 80% |  |  |  |  |
|  |  | 55.9 | 14% | 90% |  |  |  |  |
| UO only | Time prior AKI stage | Cutoff value | sens | spec | Quartile | OR | 95% CI of OR | |
|  | 0 hours | 2.32 | 73% | 37% | 1 |  |  |  |
|  |  | 1.81 | 81% | 32% | 2 | 0.8 | 0.3 | 2.0 |
|  |  | 0.795 | 92% | 20% | 3 | 1.2 | 0.6 | 2.6 |
|  |  | 11.7 | 54% | 70% | 4 | 2.3 | 1.3 | 4.3 |
|  |  | 20.3 | 42% | 80% |  |  |  |  |
|  |  | 40.9 | 15% | 90% |  |  |  |  |
|  | 24 hours | 0.843 | 70% | 20% | 1 |  |  |  |
|  |  | 0.322 | 80% | 11% | 2 | 0.4 | 0.2 | 0.8 |
|  |  | 0.186 | 90% | 9% | 3 | 0.5 | 0.3 | 0.9 |
|  |  | 11.7 | 40% | 70% | 4 | 1.1 | 0.7 | 1.7 |
|  |  | 20.3 | 33% | 80% |  |  |  |  |
|  |  | 40.9 | 20% | 90% |  |  |  |  |
|  | 48 hours | 5.07 | 75% | 54% | 1 |  |  |  |
|  |  | 2.29 | 81% | 37% | 2 | 0.3 | 0.0 | 4.6 |
|  |  | 0.471 | 94% | 15% | 3 | 2.4 | 0.9 | 6.5 |
|  |  | 11.7 | 44% | 70% | 4 | 1.7 | 0.6 | 5.1 |
|  |  | 20.3 | 31% | 80% |  |  |  |  |
|  |  | 40.9 | 25% | 90% |  |  |  |  |

FIG. 2 - 10 von Willebrand Factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.007 | 0.010 | 0.007 | 0.010 | 0.007 | 0.013 |
| average | 0.023 | 0.016 | 0.023 | 0.387 | 0.023 | 0.034 |
| stdev | 0.119 | 0.019 | 0.119 | 2.078 | 0.119 | 0.058 |
| p (t-test) |  | 0.765 |  | 0.000 |  | 0.697 |
| min | 0.000 | 0.000 | 0.000 | 0.000 | 0.000 | 0.001 |
| max | 2.330 | 0.090 | 2.330 | 12.500 | 2.330 | 0.253 |
| n (Samp) | 419 | 27 | 419 | 36 | 419 | 18 |
| n (Pat) | 164 | 27 | 164 | 36 | 164 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.008 | 0.013 | 0.008 | 0.009 | 0.008 | 0.043 |
| average | 0.048 | 0.015 | 0.048 | 0.032 | 0.048 | 0.062 |
| stdev | 0.559 | 0.011 | 0.559 | 0.051 | 0.559 | 0.088 |
| p (t-test) |  | 0.894 |  | 0.934 |  | 0.947 |
| min | 0.000 | 0.000 | 0.000 | 0.002 | 0.000 | 0.002 |
| max | 12.500 | 0.031 | 12.500 | 0.162 | 12.500 | 0.253 |
| n (Samp) | 518 | 5 | 518 | 9 | 518 | 7 |
| n (Pat) | 199 | 5 | 199 | 9 | 199 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.007 | 0.010 | 0.007 | 0.013 | 0.007 | 0.013 |
| average | 0.025 | 0.018 | 0.025 | 0.456 | 0.025 | 0.021 |
| stdev | 0.130 | 0.019 | 0.130 | 2.277 | 0.130 | 0.018 |
| p (t-test) |  | 0.760 |  | 0.000 |  | 0.888 |
| min | 0.000 | 0.000 | 0.000 | 0.000 | 0.000 | 0.001 |
| max | 2.330 | 0.090 | 2.330 | 12.500 | 2.330 | 0.058 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.59 | 0.059 | 419 | 27 | 0.139 |
| 24 hours | 0.63 | 0.052 | 419 | 36 | 0.013 |
| 48 hours | 0.66 | 0.071 | 419 | 18 | 0.027 | sCr only

| Time prior AKI stage | AUC | SE | nCohort 1 | nCohort 2 | p |
| --- | --- | --- | --- | --- | --- |
| 0 hours | 0.57 | 0.134 | 518 | 5 | 0.612 |
| 24 hours | 0.60 | 0.101 | 518 | 9 | 0.319 |
| 48 hours | 0.72 | 0.110 | 518 | 7 | 0.045 |

UO only

| Time prior AKI stage | AUC | SE | nCohort 1 | nCohort 2 | p |
| --- | --- | --- | --- | --- | --- |
| 0 hours | 0.61 | 0.061 | 352 | 26 | 0.079 |
| 24 hours | 0.63 | 0.056 | 352 | 30 | 0.022 |
| 48 hours | 0.65 | 0.076 | 352 | 16 | 0.050 | sCr or UO

| Time prior AKI stage | Cutoff value | sens | spec | Quartile | OR | 95% CI of OR | |
| --- | --- | --- | --- | --- | --- | --- | --- |
| 0 hours | 0.00675 | 70% | 49% | 1 |  |  |  |
|  | 0.00648 | 81% | 48% | 2 | 2.4 | 0.9 | 6.3 |
|  | 0.00117 | 93% | 10% | 3 | 3.2 | 1.3 | 7.9 |
|  | 0.014 | 33% | 70% | 4 | 2.8 | 1.1 | 7.1 |
|  | 0.0202 | 19% | 80% |  |  |  |  |
|  | 0.0436 | 7% | 90% |  |  |  |  |

FIG. 2 - 11

|  | Time | Cutoff value | sens | spec | Quartile | OR | 95% CI of OR | |
|---|---|---|---|---|---|---|---|---|
|  | 24 hours | 0.0068 | 72% | 49% | 1 | | | |
|  |  | 0.00513 | 81% | 39% | 2 | 1.0 | 0.5 | 2.0 |
|  |  | 0.00183 | 92% | 17% | 3 | 1.5 | 0.9 | 2.7 |
|  |  | 0.014 | 47% | 70% | 4 | 2.7 | 1.6 | 4.4 |
|  |  | 0.0202 | 42% | 80% | | | | |
|  |  | 0.0436 | 28% | 90% | | | | |
|  | 48 hours | 0.0072 | 72% | 51% | 1 | | | |
|  |  | 0.006 | 83% | 46% | 2 | 0.7 | 0.1 | 3.5 |
|  |  | 0.0017 | 94% | 16% | 3 | 1.7 | 0.6 | 5.0 |
|  |  | 0.014 | 44% | 70% | 4 | 2.8 | 1.1 | 7.1 |
|  |  | 0.0202 | 44% | 80% | | | | |
|  |  | 0.0436 | 22% | 90% | | | | | sCr only

| Time prior AKI stage | Cutoff value | sens | spec | Quartile | OR | 95% CI of OR | |
|---|---|---|---|---|---|---|---|
| 0 hours | 0.00945 | 80% | 56% | 1 | | | |
|  | 0.00945 | 80% | 56% | 2 | 0.0 | 0.0 | na |
|  | 0 | 100% | 0% | 3 | 2.0 | 0.1 | 39.0 |
|  | 0.0153 | 40% | 70% | 4 | 2.0 | 0.1 | 39.0 |
|  | 0.0232 | 20% | 80% | | | | |
|  | 0.049 | 0% | 90% | | | | |
| 24 hours | 0.00688 | 78% | 46% | 1 | | | |
|  | 0.00317 | 89% | 22% | 2 | 0.5 | 0.0 | 9.6 |
|  | 0.00183 | 100% | 15% | 3 | 1.0 | 0.1 | 7.3 |
|  | 0.0153 | 44% | 70% | 4 | 2.0 | 0.4 | 9.0 |
|  | 0.0232 | 33% | 80% | | | | |
|  | 0.049 | 22% | 90% | | | | |
| 48 hours | 0.0121 | 71% | 64% | 1 | | | |
|  | 0.00969 | 86% | 57% | 2 | 0.0 | 0.0 | na |
|  | 0.0017 | 100% | 14% | 3 | 2.0 | 0.1 | 39.3 |
|  | 0.0153 | 57% | 70% | 4 | 4.1 | 0.3 | 48.5 |
|  | 0.0232 | 57% | 80% | | | | |
|  | 0.049 | 29% | 90% | | | | |

UO only

| Time prior AKI stage | Cutoff value | sens | spec | Quartile | OR | 95% CI of OR | |
|---|---|---|---|---|---|---|---|
| 0 hours | 0.00675 | 73% | 47% | 1 | | | |
|  | 0.00665 | 81% | 47% | 2 | 3.7 | 1.0 | 13.5 |
|  | 0.0049 | 92% | 37% | 3 | 4.3 | 1.2 | 15.2 |
|  | 0.0143 | 35% | 70% | 4 | 4.8 | 1.4 | 16.7 |
|  | 0.0214 | 23% | 80% | | | | |
|  | 0.0436 | 8% | 90% | | | | |
| 24 hours | 0.00745 | 70% | 52% | 1 | | | |
|  | 0.00513 | 83% | 38% | 2 | 1.3 | 0.5 | 3.2 |
|  | 0.00269 | 90% | 22% | 3 | 2.1 | 1.0 | 4.6 |
|  | 0.0143 | 50% | 70% | 4 | 3.6 | 1.8 | 7.1 |
|  | 0.0214 | 40% | 80% | | | | |
|  | 0.0436 | 27% | 90% | | | | |
| 48 hours | 0.0072 | 75% | 50% | 1 | | | |
|  | 0.00695 | 81% | 49% | 2 | 1.5 | 0.3 | 8.1 |
|  | 0.0023 | 94% | 21% | 3 | 2.0 | 0.5 | 9.3 |
|  | 0.0143 | 44% | 70% | 4 | 3.7 | 1.0 | 13.7 |
|  | 0.0214 | 44% | 80% | | | | |
|  | 0.0436 | 19% | 90% | | | | |

FIG. 2 - 12

Endothelial protein C receptor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 65.789 | 55.769 | 65.789 | 55.769 | 65.789 | 55.769 |
| average | 79.393 | 74.076 | 79.393 | 74.076 | 79.393 | 74.076 |
| stdev | 66.381 | 74.076 | 66.381 | 74.076 | 66.381 | 74.076 |
| p (t-test) |  | 0.838 |  | 0.838 |  | 0.838 |
| min | 14.329 | 2.885 | 14.329 | 2.885 | 14.329 | 2.885 |
| max | 266.981 | 258.333 | 266.981 | 258.333 | 266.981 | 258.333 |
| n (Samp) | 24 | 10 | 24 | 10 | 24 | 10 |
| n (Pat) | 24 | 10 | 24 | 10 | 24 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 39.226 | 25.357 | 39.226 | 25.357 | 39.226 | 25.357 |
| average | 74.570 | 27.747 | 74.570 | 27.747 | 74.570 | 27.747 |
| stdev | 82.989 | 26.140 | 82.989 | 26.140 | 82.989 | 26.140 |
| p (t-test) |  | 0.376 |  | 0.376 |  | 0.376 |
| min | 14.329 | 2.885 | 14.329 | 2.885 | 14.329 | 2.885 |
| max | 258.333 | 55.000 | 258.333 | 55.000 | 258.333 | 55.000 |
| n (Samp) | 8 | 3 | 8 | 3 | 8 | 3 |
| n (Pat) | 8 | 3 | 8 | 3 | 8 | 3 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 76.597 | 58.462 | 76.597 | 58.462 | 76.597 | 58.462 |
| average | 89.110 | 64.626 | 89.110 | 64.626 | 89.110 | 64.626 |
| stdev | 70.747 | 40.191 | 70.747 | 40.191 | 70.747 | 40.191 |
| p (t-test) |  | 0.433 |  | 0.433 |  | 0.433 |
| min | 21.189 | 15.705 | 21.189 | 15.705 | 21.189 | 15.705 |
| max | 266.981 | 130.502 | 266.981 | 130.502 | 266.981 | 130.502 |
| n (Samp) | 18 | 6 | 18 | 6 | 18 | 6 |
| n (Pat) | 18 | 6 | 18 | 6 | 18 | 6 | sCr or UO

| Time prior AKI stage | AUC | SE | nCohort 1 | nCohort 2 | p |
|---|---|---|---|---|---|
| 0 hours | 0.48 | 0.109 | 24 | 10 | 0.819 |
| 24 hours | 0.48 | 0.109 | 24 | 10 | 0.819 |
| 48 hours | 0.48 | 0.109 | 24 | 10 | 0.819 | sCr only

| Time prior AKI stage | AUC | SE | nCohort 1 | nCohort 2 | p |
|---|---|---|---|---|---|
| 0 hours | 0.33 | 0.181 | 8 | 3 | 0.358 |
| 24 hours | 0.33 | 0.181 | 8 | 3 | 0.358 |
| 48 hours | 0.33 | 0.181 | 8 | 3 | 0.358 |

UO only

| Time prior AKI stage | AUC | SE | nCohort 1 | nCohort 2 | p |
|---|---|---|---|---|---|
| 0 hours | 0.44 | 0.135 | 18 | 6 | 0.682 |
| 24 hours | 0.44 | 0.135 | 18 | 6 | 0.682 |
| 48 hours | 0.44 | 0.135 | 18 | 6 | 0.682 | sCr or UO

| Time prior AKI stage | Cutoff value | sens | spec | Quartile | OR | 95% CI of OR | |
|---|---|---|---|---|---|---|---|
| 0 hours | 36.785714 | 70% | 38% | 1 |  |  |  |
|  | 33.695652 | 80% | 38% | 2 | 1.2 | 0.1 | 15.2 |
|  | 14.329268 | 90% | 4% | 3 | 2.8 | 0.3 | 23.8 |
|  | 81.923077 | 30% | 71% | 4 | 1.2 | 0.1 | 15.2 |
|  | 124.55516 | 20% | 83% |  |  |  |  |

FIG. 3 - 1

|  | | 148.26255 | 10% | 92% | | | | |
|---|---|---|---|---|---|---|---|---|
|  | 24 hours | 36.785714 | 70% | 38% | 1 | | | |
|  | | 33.695652 | 80% | 38% | 2 | 1.2 | 0.1 | 15.2 |
|  | | 14.329268 | 90% | 4% | 3 | 2.8 | 0.3 | 23.8 |
|  | | 81.923077 | 30% | 71% | 4 | 1.2 | 0.1 | 15.2 |
|  | | 124.55516 | 20% | 83% | | | | |
|  | | 148.26255 | 10% | 92% | | | | |
|  | 48 hours | 36.785714 | 70% | 38% | 1 | | | |
|  | | 33.695652 | 80% | 38% | 2 | 1.2 | 0.1 | 15.2 |
|  | | 14.329268 | 90% | 4% | 3 | 2.8 | 0.3 | 23.8 |
|  | | 81.923077 | 30% | 71% | 4 | 1.2 | 0.1 | 15.2 |
|  | | 124.55516 | 20% | 83% | | | | |
|  | | 148.26255 | 10% | 92% | | | | |

UO only

| Time prior AKI stage | Cutoff value | sens | spec | Quartile | OR | 95% CI of OR | |
|---|---|---|---|---|---|---|---|
| 0 hours | 33.695652 | 83% | 33% | 1 | | | |
|  | 33.695652 | 83% | 33% | 2 | 1.0 | 0.0 | 110.4 |
|  | 0 | 100% | 0% | 3 | 5.0 | 0.1 | 194.0 |
|  | 105.01931 | 17% | 72% | 4 | 1.0 | 0.0 | 110.4 |
|  | 129.53737 | 17% | 83% | | | | |
|  | 238.67925 | 0% | 94% | | | | |
| 24 hours | 33.695652 | 83% | 33% | 1 | | | |
|  | 33.695652 | 83% | 33% | 2 | 1.0 | 0.0 | 110.4 |
|  | 0 | 100% | 0% | 3 | 5.0 | 0.1 | 194.0 |
|  | 105.01931 | 17% | 72% | 4 | 1.0 | 0.0 | 110.4 |
|  | 129.53737 | 17% | 83% | | | | |
|  | 238.67925 | 0% | 94% | | | | |
| 48 hours | 33.695652 | 83% | 33% | 1 | | | |
|  | 33.695652 | 83% | 33% | 2 | 1.0 | 0.0 | 110.4 |
|  | 0 | 100% | 0% | 3 | 5.0 | 0.1 | 194.0 |
|  | 105.01931 | 17% | 72% | 4 | 1.0 | 0.0 | 110.4 |
|  | 129.53737 | 17% | 83% | | | | |
|  | 238.67925 | 0% | 94% | | | | |

FIG. 3 - 2

Erythropoietin receptor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 20.270 | 88.542 | 20.270 | 88.542 | 20.270 | 88.542 |
| average | 41.677 | 82.893 | 41.677 | 82.893 | 41.677 | 82.893 |
| stdev | 52.703 | 70.492 | 52.703 | 70.492 | 52.703 | 70.492 |
| p (t-test) |  | 0.067 |  | 0.067 |  | 0.067 |
| min | 0.517 | 0.517 | 0.517 | 0.517 | 0.517 | 0.517 |
| max | 190.476 | 180.085 | 190.476 | 180.085 | 190.476 | 180.085 |
| n (Samp) | 25 | 10 | 25 | 10 | 25 | 10 |
| n (Pat) | 25 | 10 | 25 | 10 | 25 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 98.958 | 30.854 | 98.958 | 30.854 | 98.958 | 30.854 |
| average | 96.567 | 53.536 | 96.567 | 53.536 | 96.567 | 53.536 |
| stdev | 72.469 | 67.291 | 72.469 | 67.291 | 72.469 | 67.291 |
| p (t-test) |  | 0.388 |  | 0.388 |  | 0.388 |
| min | 0.517 | 0.517 | 0.517 | 0.517 | 0.517 | 0.517 |
| max | 190.476 | 129.237 | 190.476 | 129.237 | 190.476 | 129.237 |
| n (Samp) | 9 | 3 | 9 | 3 | 9 | 3 |
| n (Pat) | 9 | 3 | 9 | 3 | 9 | 3 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 15.032 | 94.506 | 15.032 | 94.506 | 15.032 | 94.506 |
| average | 25.104 | 86.419 | 25.104 | 86.419 | 25.104 | 86.419 |
| stdev | 29.731 | 71.343 | 29.731 | 71.343 | 29.731 | 71.343 |
| p (t-test) |  | 0.006 |  | 0.006 |  | 0.006 |
| min | 0.517 | 0.517 | 0.517 | 0.517 | 0.517 | 0.517 |
| max | 78.125 | 163.136 | 78.125 | 163.136 | 78.125 | 163.136 |
| n (Samp) | 18 | 6 | 18 | 6 | 18 | 6 |
| n (Pat) | 18 | 6 | 18 | 6 | 18 | 6 | sCr or UO

| Time prior AKI stage | AUC | SE | nCohort 1 | nCohort 2 | p |
| --- | --- | --- | --- | --- | --- |
| 0 hours | 0.69 | 0.105 | 25 | 10 | 0.078 |
| 24 hours | 0.69 | 0.105 | 25 | 10 | 0.078 |
| 48 hours | 0.69 | 0.105 | 25 | 10 | 0.078 | sCr only

| Time prior AKI stage | AUC | SE | nCohort 1 | nCohort 2 | p |
| --- | --- | --- | --- | --- | --- |
| 0 hours | 0.30 | 0.168 | 9 | 3 | 0.225 |
| 24 hours | 0.30 | 0.168 | 9 | 3 | 0.225 |
| 48 hours | 0.30 | 0.168 | 9 | 3 | 0.225 |

UO only

| Time prior AKI stage | AUC | SE | nCohort 1 | nCohort 2 | p |
| --- | --- | --- | --- | --- | --- |
| 0 hours | 0.77 | 0.124 | 18 | 6 | 0.030 |
| 24 hours | 0.77 | 0.124 | 18 | 6 | 0.030 |
| 48 hours | 0.77 | 0.124 | 18 | 6 | 0.030 | sCr or UO

| Time prior AKI stage | Cutoff value | sens | spec | Quartile | OR | 95% CI of OR | |
| --- | --- | --- | --- | --- | --- | --- | --- |
| 0 hours | 28.716216 | 70% | 60% | 1 |  |  |  |
|  | 3.3783784 | 80% | 40% | 2 | 2.0 | 0.1 | 66.2 |
|  | 0 | 100% | 0% | 3 | 2.0 | 0.1 | 66.2 |
|  | 66.532258 | 60% | 72% | 4 | 8.8 | 0.4 | 198.6 |
|  | 72.916667 | 60% | 80% |  |  |  |  |
|  | 134.92063 | 30% | 92% |  |  |  |  |
| 24 hours | 28.716216 | 70% | 60% | 1 |  |  |  |

FIG. 3 - 3

|  | | Cutoff value | sens | spec | Quartile | OR | 95% CI of OR | |
|---|---|---|---|---|---|---|---|---|
|  |  | 3.3783784 | 80% | 40% | 2 | 2.0 | 0.1 | 66.2 |
|  |  | 0 | 100% | 0% | 3 | 2.0 | 0.1 | 66.2 |
|  |  | 66.532258 | 60% | 72% | 4 | 8.8 | 0.4 | 198.6 |
|  |  | 72.916667 | 60% | 80% |  |  |  |  |
|  |  | 134.92063 | 30% | 92% |  |  |  |  |
|  | 48 hours | 28.716216 | 70% | 60% | 1 |  |  |  |
|  |  | 3.3783784 | 80% | 40% | 2 | 2.0 | 0.1 | 66.2 |
|  |  | 0 | 100% | 0% | 3 | 2.0 | 0.1 | 66.2 |
|  |  | 66.532258 | 60% | 72% | 4 | 8.8 | 0.4 | 198.6 |
|  |  | 72.916667 | 60% | 80% |  |  |  |  |
|  |  | 134.92063 | 30% | 92% |  |  |  |  |

UO only

| Time prior AKI stage | Cutoff value | sens | spec | Quartile | OR | 95% CI of OR | |
|---|---|---|---|---|---|---|---|
| 0 hours | 3.3783784 | 83% | 44% | 1 |  |  |  |
|  | 3.3783784 | 83% | 44% | 2 | 1.0 | 0.0 | 110.4 |
|  | 0 | 100% | 0% | 3 | 0.0 | 0.0 | na |
|  | 28.716216 | 67% | 72% | 4 | 10.0 | 0.2 | 457.0 |
|  | 70.564516 | 67% | 83% |  |  |  |  |
|  | 74.596774 | 67% | 94% |  |  |  |  |
| 24 hours | 3.3783784 | 83% | 44% | 1 |  |  |  |
|  | 3.3783784 | 83% | 44% | 2 | 1.0 | 0.0 | 110.4 |
|  | 0 | 100% | 0% | 3 | 0.0 | 0.0 | na |
|  | 28.716216 | 67% | 72% | 4 | 10.0 | 0.2 | 457.0 |
|  | 70.564516 | 67% | 83% |  |  |  |  |
|  | 74.596774 | 67% | 94% |  |  |  |  |
| 48 hours | 3.3783784 | 83% | 44% | 1 |  |  |  |
|  | 3.3783784 | 83% | 44% | 2 | 1.0 | 0.0 | 110.4 |
|  | 0 | 100% | 0% | 3 | 0.0 | 0.0 | na |
|  | 28.716216 | 67% | 72% | 4 | 10.0 | 0.2 | 457.0 |
|  | 70.564516 | 67% | 83% |  |  |  |  |
|  | 74.596774 | 67% | 94% |  |  |  |  |

FIG. 3 - 4

Lactotransferrin sCr or UO

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 31.489   | 85.077   | 31.489   | 85.077   | 31.489   | 85.077   |
| average  | 71.516   | 351.569  | 71.516   | 351.569  | 71.516   | 351.569  |
| stdev    | 120.120  | 883.335  | 120.120  | 883.335  | 120.120  | 883.335  |
| p (t-test) |        | 0.027    |          | 0.027    |          | 0.027    |
| min      | 1.495    | 5.878    | 1.495    | 5.878    | 1.495    | 5.878    |
| max      | 752.000  | 3665.116 | 752.000  | 3665.116 | 752.000  | 3665.116 |
| n (Samp) | 52       | 23       | 52       | 23       | 52       | 23       |
| n (Pat)  | 52       | 23       | 52       | 23       | 52       | 23       | sCr only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 47.787   | 73.616   | 47.787   | 73.616   | 47.787   | 73.616   |
| average  | 59.591   | 60.577   | 59.591   | 60.577   | 59.591   | 60.577   |
| stdev    | 57.139   | 33.877   | 57.139   | 33.877   | 57.139   | 33.877   |
| p (t-test) |        | 0.974    |          | 0.974    |          | 0.974    |
| min      | 1.988    | 11.345   | 1.988    | 11.345   | 1.988    | 11.345   |
| max      | 223.790  | 83.729   | 223.790  | 83.729   | 223.790  | 83.729   |
| n (Samp) | 19       | 4        | 19       | 4        | 19       | 4        |
| n (Pat)  | 19       | 4        | 19       | 4        | 19       | 4        |

UO only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 31.527   | 86.581   | 31.527   | 86.581   | 31.527   | 86.581   |
| average  | 87.231   | 419.668  | 87.231   | 419.668  | 87.231   | 419.668  |
| stdev    | 140.053  | 992.504  | 140.053  | 992.504  | 140.053  | 992.504  |
| p (t-test) |        | 0.034    |          | 0.034    |          | 0.034    |
| min      | 1.495    | 5.878    | 1.495    | 5.878    | 1.495    | 5.878    |
| max      | 752.000  | 3665.116 | 752.000  | 3665.116 | 752.000  | 3665.116 |
| n (Samp) | 43       | 18       | 43       | 18       | 43       | 18       |
| n (Pat)  | 43       | 18       | 43       | 18       | 43       | 18       | sCr or UO

| Time prior AKI stage | AUC | SE | nCohort 1 | nCohort 2 | p |
|---|---|---|---|---|---|
| 0 hours  | 0.68 | 0.070 | 52 | 23 | 0.011 |
| 24 hours | 0.68 | 0.070 | 52 | 23 | 0.011 |
| 48 hours | 0.68 | 0.070 | 52 | 23 | 0.011 | sCr only

| Time prior AKI stage | AUC | SE | nCohort 1 | nCohort 2 | p |
|---|---|---|---|---|---|
| 0 hours  | 0.55 | 0.165 | 19 | 4 | 0.749 |
| 24 hours | 0.55 | 0.165 | 19 | 4 | 0.749 |
| 48 hours | 0.55 | 0.165 | 19 | 4 | 0.749 |

UO only

| Time prior AKI stage | AUC | SE | nCohort 1 | nCohort 2 | p |
|---|---|---|---|---|---|
| 0 hours  | 0.66 | 0.080 | 43 | 18 | 0.041 |
| 24 hours | 0.66 | 0.080 | 43 | 18 | 0.041 |
| 48 hours | 0.66 | 0.080 | 43 | 18 | 0.041 | sCr or UO

| Time prior AKI stage | Cutoff value | sens | spec | Quartile | OR | 95% CI of OR | |
|---|---|---|---|---|---|---|---|
| 0 hours | 28.599824  | 74% | 48% | 1 |     |     |      |
|         | 17.732181  | 83% | 37% | 2 | 1.3 | 0.3 | 5.4  |
|         | 10.77248   | 91% | 19% | 3 | 2.3 | 0.7 | 8.1  |
|         | 73.751891  | 57% | 71% | 4 | 5.6 | 1.7 | 18.4 |
|         | 87.329391  | 48% | 81% |   |     |     |      |
|         | 165.77561  | 22% | 90% |   |     |     |      |

FIG. 3 - 5

|  | Time prior AKI stage | Cutoff value | sens | spec | Quartile | OR | 95% CI of OR | |
|---|---|---|---|---|---|---|---|---|
|  | 24 hours | 28.599824 | 74% | 48% | 1 | | | |
|  | | 17.732181 | 83% | 37% | 2 | 1.3 | 0.3 | 5.4 |
|  | | 10.77248 | 91% | 19% | 3 | 2.3 | 0.7 | 8.1 |
|  | | 73.751891 | 57% | 71% | 4 | 5.6 | 1.7 | 18.4 |
|  | | 87.329391 | 48% | 81% | | | | |
|  | | 165.77561 | 22% | 90% | | | | |
|  | 48 hours | 28.599824 | 74% | 48% | 1 | | | |
|  | | 17.732181 | 83% | 37% | 2 | 1.3 | 0.3 | 5.4 |
|  | | 10.77248 | 91% | 19% | 3 | 2.3 | 0.7 | 8.1 |
|  | | 73.751891 | 57% | 71% | 4 | 5.6 | 1.7 | 18.4 |
|  | | 87.329391 | 48% | 81% | | | | |
| sCr only | | 165.77561 | 22% | 90% | | | | |
|  | Time prior AKI stage | Cutoff value | sens | spec | Quartile | OR | 95% CI of OR | |
|  | 0 hours | 63.548753 | 75% | 68% | 1 | | | |
|  | | 2.9045645 | 100% | 11% | 2 | 0.0 | 0.0 | na |
|  | | 2.9045645 | 100% | 11% | 3 | 2.0 | 0.0 | 100.8 |
|  | | 83.266935 | 25% | 74% | 4 | 0.8 | 0.0 | 97.4 |
|  | | 101.34903 | 0% | 84% | | | | |
|  | | 156.1488 | 0% | 95% | | | | |
|  | 24 hours | 63.548753 | 75% | 68% | 1 | | | |
|  | | 2.9045645 | 100% | 11% | 2 | 0.0 | 0.0 | na |
|  | | 2.9045645 | 100% | 11% | 3 | 2.0 | 0.0 | 100.8 |
|  | | 83.266935 | 25% | 74% | 4 | 0.8 | 0.0 | 97.4 |
|  | | 101.34903 | 0% | 84% | | | | |
|  | | 156.1488 | 0% | 95% | | | | |
|  | 48 hours | 63.548753 | 75% | 68% | 1 | | | |
|  | | 2.9045645 | 100% | 11% | 2 | 0.0 | 0.0 | na |
|  | | 2.9045645 | 100% | 11% | 3 | 2.0 | 0.0 | 100.8 |
|  | | 83.266935 | 25% | 74% | 4 | 0.8 | 0.0 | 97.4 |
|  | | 101.34903 | 0% | 84% | | | | |
| UO only | | 156.1488 | 0% | 95% | | | | |
|  | Time prior AKI stage | Cutoff value | sens | spec | Quartile | OR | 95% CI of OR | |
|  | 0 hours | 50.765576 | 72% | 63% | 1 | | | |
|  | | 19.556624 | 83% | 40% | 2 | 1.6 | 0.2 | 11.4 |
|  | | 10.28096 | 94% | 19% | 3 | 5.7 | 1.1 | 29.8 |
|  | | 76.363749 | 61% | 72% | 4 | 3.9 | 0.7 | 20.4 |
|  | | 114.28351 | 33% | 81% | | | | |
|  | | 190.67626 | 22% | 91% | | | | |
|  | 24 hours | 50.765576 | 72% | 63% | 1 | | | |
|  | | 19.556624 | 83% | 40% | 2 | 1.6 | 0.2 | 11.4 |
|  | | 10.28096 | 94% | 19% | 3 | 5.7 | 1.1 | 29.8 |
|  | | 76.363749 | 61% | 72% | 4 | 3.9 | 0.7 | 20.4 |
|  | | 114.28351 | 33% | 81% | | | | |
|  | | 190.67626 | 22% | 91% | | | | |
|  | 48 hours | 50.765576 | 72% | 63% | 1 | | | |
|  | | 19.556624 | 83% | 40% | 2 | 1.6 | 0.2 | 11.4 |
|  | | 10.28096 | 94% | 19% | 3 | 5.7 | 1.1 | 29.8 |
|  | | 76.363749 | 61% | 72% | 4 | 3.9 | 0.7 | 20.4 |
|  | | 114.28351 | 33% | 81% | | | | |
|  | | 190.67626 | 22% | 91% | | | | |

FIG. 3 - 6

Prostatic Acid Phosphatase sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 6.285 | 10.780 | 6.285 | 10.780 | 6.285 | 10.780 |
| average | 27.111 | 32.250 | 27.111 | 32.250 | 27.111 | 32.250 |
| stdev | 55.574 | 66.832 | 55.574 | 66.832 | 55.574 | 66.832 |
| p (t-test) |  | 0.731 |  | 0.731 |  | 0.731 |
| min | 0.026 | 0.051 | 0.026 | 0.051 | 0.026 | 0.051 |
| max | 310.000 | 285.000 | 310.000 | 285.000 | 310.000 | 285.000 |
| n (Samp) | 54 | 22 | 54 | 22 | 54 | 22 |
| n (Pat) | 54 | 22 | 54 | 22 | 54 | 22 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 5.155 | 2.100 | 5.155 | 2.100 | 5.155 | 2.100 |
| average | 18.794 | 11.651 | 18.794 | 11.651 | 18.794 | 11.651 |
| stdev | 52.433 | 17.095 | 52.433 | 17.095 | 52.433 | 17.095 |
| p (t-test) |  | 0.770 |  | 0.770 |  | 0.770 |
| min | 0.000 | 0.377 | 0.000 | 0.377 | 0.000 | 0.377 |
| max | 237.000 | 40.600 | 237.000 | 40.600 | 237.000 | 40.600 |
| n (Samp) | 20 | 5 | 20 | 5 | 20 | 5 |
| n (Pat) | 20 | 5 | 20 | 5 | 20 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8.005 | 9.360 | 8.005 | 9.360 | 8.005 | 9.360 |
| average | 27.036 | 38.518 | 27.036 | 38.518 | 27.036 | 38.518 |
| stdev | 51.712 | 75.147 | 51.712 | 75.147 | 51.712 | 75.147 |
| p (t-test) |  | 0.498 |  | 0.498 |  | 0.498 |
| min | 0.026 | 0.051 | 0.026 | 0.051 | 0.026 | 0.051 |
| max | 310.000 | 285.000 | 310.000 | 285.000 | 310.000 | 285.000 |
| n (Samp) | 44 | 17 | 44 | 17 | 44 | 17 |
| n (Pat) | 44 | 17 | 44 | 17 | 44 | 17 | sCr or UO

| Time prior AKI stage | AUC | SE | nCohort 1 | nCohort 2 | p |
|---|---|---|---|---|---|
| 0 hours | 0.52 | 0.074 | 54 | 22 | 0.815 |
| 24 hours | 0.52 | 0.074 | 54 | 22 | 0.815 |
| 48 hours | 0.52 | 0.074 | 54 | 22 | 0.815 | sCr only

| Time prior AKI stage | AUC | SE | nCohort 1 | nCohort 2 | p |
|---|---|---|---|---|---|
| 0 hours | 0.54 | 0.149 | 20 | 5 | 0.788 |
| 24 hours | 0.54 | 0.149 | 20 | 5 | 0.788 |
| 48 hours | 0.54 | 0.149 | 20 | 5 | 0.788 |

UO only

| Time prior AKI stage | AUC | SE | nCohort 1 | nCohort 2 | p |
|---|---|---|---|---|---|
| 0 hours | 0.51 | 0.083 | 44 | 17 | 0.942 |
| 24 hours | 0.51 | 0.083 | 44 | 17 | 0.942 |
| 48 hours | 0.51 | 0.083 | 44 | 17 | 0.942 | sCr or UO

| Time prior AKI stage | Cutoff value | sens | spec | Quartile | OR | 95% CI of OR | |
|---|---|---|---|---|---|---|---|
| 0 hours | 2.29 | 73% | 31% | 1 |  |  |  |
|  | 0.167 | 82% | 13% | 2 | 1.0 | 0.3 | 2.9 |
|  | 0.157 | 91% | 13% | 3 | 1.6 | 0.6 | 4.3 |
|  | 19.3 | 27% | 70% | 4 | 1.0 | 0.3 | 2.9 |
|  | 41.8 | 18% | 81% |  |  |  |  |
|  | 64.9 | 9% | 91% |  |  |  |  |

FIG. 3 - 7

|  | | Cutoff value | sens | spec | Quartile | OR | 95% CI of OR | |
|---|---|---|---|---|---|---|---|---|
| | 24 hours | 2.29 | 73% | 31% | 1 | | | |
| | | 0.167 | 82% | 13% | 2 | 1.0 | 0.3 | 2.9 |
| | | 0.157 | 91% | 13% | 3 | 1.6 | 0.6 | 4.3 |
| | | 19.3 | 27% | 70% | 4 | 1.0 | 0.3 | 2.9 |
| | | 41.8 | 18% | 81% | | | | |
| | | 64.9 | 9% | 91% | | | | |
| | 48 hours | 2.29 | 73% | 31% | 1 | | | |
| | | 0.167 | 82% | 13% | 2 | 1.0 | 0.3 | 2.9 |
| | | 0.157 | 91% | 13% | 3 | 1.6 | 0.6 | 4.3 |
| | | 19.3 | 27% | 70% | 4 | 1.0 | 0.3 | 2.9 |
| | | 41.8 | 18% | 81% | | | | |
| | | 64.9 | 9% | 91% | | | | | sCr only

| Time prior AKI stage | Cutoff value | sens | spec | Quartile | OR | 95% CI of OR | |
|---|---|---|---|---|---|---|---|
| 0 hours | 0.395 | 80% | 30% | 1 | | | |
| | 0.395 | 80% | 30% | 2 | 2.5 | 0.1 | 114.2 |
| | 0.333 | 100% | 25% | 3 | 0.0 | 0.0 | na |
| | 6.92 | 40% | 70% | 4 | 2.0 | 0.0 | 82.9 |
| | 11.2 | 40% | 80% | | | | |
| | 27.9 | 20% | 90% | | | | |
| 24 hours | 0.395 | 80% | 30% | 1 | | | |
| | 0.395 | 80% | 30% | 2 | 2.5 | 0.1 | 114.2 |
| | 0.333 | 100% | 25% | 3 | 0.0 | 0.0 | na |
| | 6.92 | 40% | 70% | 4 | 2.0 | 0.0 | 82.9 |
| | 11.2 | 40% | 80% | | | | |
| | 27.9 | 20% | 90% | | | | |
| 48 hours | 0.395 | 80% | 30% | 1 | | | |
| | 0.395 | 80% | 30% | 2 | 2.5 | 0.1 | 114.2 |
| | 0.333 | 100% | 25% | 3 | 0.0 | 0.0 | na |
| | 6.92 | 40% | 70% | 4 | 2.0 | 0.0 | 82.9 |
| | 11.2 | 40% | 80% | | | | |
| | 27.9 | 20% | 90% | | | | |

UO only

| Time prior AKI stage | Cutoff value | sens | spec | Quartile | OR | 95% CI of OR | |
|---|---|---|---|---|---|---|---|
| 0 hours | 2.69 | 71% | 34% | 1 | | | |
| | 0.159 | 82% | 9% | 2 | 1.0 | 0.3 | 3.8 |
| | 0.0506 | 94% | 7% | 3 | 1.4 | 0.4 | 4.8 |
| | 21.6 | 29% | 70% | 4 | 0.9 | 0.2 | 3.4 |
| | 45.4 | 24% | 84% | | | | |
| | 64.9 | 12% | 91% | | | | |
| 24 hours | 2.69 | 71% | 34% | 1 | | | |
| | 0.159 | 82% | 9% | 2 | 1.0 | 0.3 | 3.8 |
| | 0.0506 | 94% | 7% | 3 | 1.4 | 0.4 | 4.8 |
| | 21.6 | 29% | 70% | 4 | 0.9 | 0.2 | 3.4 |
| | 45.4 | 24% | 84% | | | | |
| | 64.9 | 12% | 91% | | | | |
| 48 hours | 2.69 | 71% | 34% | 1 | | | |
| | 0.159 | 82% | 9% | 2 | 1.0 | 0.3 | 3.8 |
| | 0.0506 | 94% | 7% | 3 | 1.4 | 0.4 | 4.8 |
| | 21.6 | 29% | 70% | 4 | 0.9 | 0.2 | 3.4 |
| | 45.4 | 24% | 84% | | | | |
| | 64.9 | 12% | 91% | | | | |

FIG. 3 - 8

Erythropoietin receptor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 37.162 | 98.958 | 37.162 | 98.958 | 37.162 | 93.750 |
| average | 227.865 | 94.153 | 227.865 | 94.153 | 227.865 | 103.961 |
| stdev | 1164.013 | 38.050 | 1164.013 | 38.050 | 1164.013 | 42.292 |
| p (t-test) |  | 0.749 |  | 0.749 |  | 0.856 |
| min | 0.517 | 30.854 | 0.517 | 30.854 | 0.517 | 67.708 |
| max | 7307.410 | 150.424 | 7307.410 | 150.424 | 7307.410 | 150.424 |
| n (Samp) | 39 | 8 | 39 | 8 | 39 | 3 |
| n (Pat) | 39 | 8 | 39 | 8 | 39 | 3 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 29.785 | 116.702 | 29.785 | 116.702 | 29.785 | 0.517 |
| average | 143.240 | 103.671 | 143.240 | 103.671 | 143.240 | 150.424 |
| stdev | 857.249 | 52.096 | 857.249 | 52.096 | 857.249 | na |
| p (t-test) |  | 0.927 |  | 0.927 |  | na |
| min | 0.517 | 30.854 | 0.517 | 30.854 | 0.517 | 150.424 |
| max | 7307.410 | 150.424 | 7307.410 | 150.424 | 7307.410 | 150.424 |
| n (Samp) | 72 | 4 | 72 | 4 | 72 | 1 |
| n (Pat) | 72 | 4 | 72 | 4 | 72 | 1 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 50.366 | 93.750 | 50.366 | 93.750 | 50.366 | 93.750 |
| average | 284.128 | 97.793 | 284.128 | 97.793 | 284.128 | 103.961 |
| stdev | 1282.305 | 34.390 | 1282.305 | 34.390 | 1282.305 | 42.292 |
| p (t-test) |  | 0.750 |  | 0.750 |  | 0.812 |
| min | 0.517 | 67.708 | 0.517 | 67.708 | 0.517 | 67.708 |
| max | 7307.410 | 150.424 | 7307.410 | 150.424 | 7307.410 | 150.424 |
| n (Samp) | 32 | 5 | 32 | 5 | 32 | 3 |
| n (Pat) | 32 | 5 | 32 | 5 | 32 | 3 | sCr or UO

| Time prior AKI stage | AUC | SE | nCohort 1 | nCohort 2 | p |
| --- | --- | --- | --- | --- | --- |
| 0 hours | 0.82 | 0.095 | 39 | 8 | 0.001 |
| 24 hours | 0.82 | 0.095 | 39 | 8 | 0.001 |
| 48 hours | 0.85 | 0.141 | 39 | 3 | 0.012 | sCr only

| Time prior AKI stage | AUC | SE | nCohort 1 | nCohort 2 | p |
| --- | --- | --- | --- | --- | --- |
| 0 hours | 0.83 | 0.128 | 72 | 4 | 0.010 |
| 24 hours | 0.83 | 0.128 | 72 | 4 | 0.010 |
| 48 hours | 0.96 | 0.141 | 72 | 1 | 0.001 |

UO only

| Time prior AKI stage | AUC | SE | nCohort 1 | nCohort 2 | p |
| --- | --- | --- | --- | --- | --- |
| 0 hours | 0.77 | 0.130 | 32 | 5 | 0.036 |
| 24 hours | 0.77 | 0.130 | 32 | 5 | 0.036 |
| 48 hours | 0.79 | 0.161 | 32 | 3 | 0.070 |

FIG. 4 - 1

Intercellular adhesion molecule 1 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4808.185 | 4261.862 | 4808.185 | 4261.862 | 4808.185 | 3661.124 |
| average | 6137.573 | 13917.934 | 6137.573 | 13875.327 | 6137.573 | 4723.937 |
| stdev | 4688.216 | 27995.338 | 4688.216 | 28016.430 | 4688.216 | 3737.560 |
| p (t-test) |  | 0.012 |  | 0.012 |  | 0.408 |
| min | 143.975 | 17.651 | 143.975 | 17.651 | 143.975 | 17.651 |
| max | 20734.291 | 101592.853 | 20734.291 | 101592.853 | 20734.291 | 12963.420 |
| n (Samp) | 99 | 12 | 99 | 12 | 99 | 8 |
| n (Pat) | 99 | 12 | 99 | 12 | 99 | 8 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 5461.036 | 3544.236 | 5461.036 | 3544.236 | 5461.036 | 2238.250 |
| average | 7366.343 | 5789.497 | 7366.343 | 5789.497 | 7366.343 | 2009.717 |
| stdev | 8951.544 | 5869.092 | 8951.544 | 5869.092 | 8951.544 | 1810.865 |
| p (t-test) |  | 0.670 |  | 0.670 |  | 0.235 |
| min | 143.975 | 17.651 | 143.975 | 17.651 | 143.975 | 17.651 |
| max | 101592.853 | 14369.565 | 101592.853 | 14369.565 | 101592.853 | 3544.718 |
| n (Samp) | 160 | 6 | 160 | 6 | 160 | 4 |
| n (Pat) | 160 | 6 | 160 | 6 | 160 | 4 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4546.670 | 4261.862 | 4546.670 | 4261.862 | 4546.670 | 4261.862 |
| average | 6015.287 | 17158.252 | 6015.287 | 17094.341 | 6015.287 | 5704.855 |
| stdev | 4908.163 | 34292.217 | 4908.163 | 34326.147 | 4908.163 | 3700.611 |
| p (t-test) |  | 0.006 |  | 0.006 |  | 0.880 |
| min | 143.975 | 1444.029 | 143.975 | 932.744 | 143.975 | 3178.457 |
| max | 20734.291 | 101592.853 | 20734.291 | 101592.853 | 20734.291 | 12963.420 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
| --- | --- | --- | --- | --- | --- |
| 0 hours | 0.53 | 0.090 | 99 | 12 | 0.722 |
| 24 hours | 0.53 | 0.090 | 99 | 12 | 0.778 |
| 48 hours | 0.43 | 0.101 | 99 | 8 | 0.492 | sCr only

| Time prior AKI stage | AUC | SE | nCohort 1 | nCohort 2 | p |
| --- | --- | --- | --- | --- | --- |
| 0 hours | 0.41 | 0.112 | 160 | 6 | 0.433 |
| 24 hours | 0.41 | 0.112 | 160 | 6 | 0.433 |
| 48 hours | 0.17 | 0.073 | 160 | 4 | 0.000 |

UO only

| Time prior AKI stage | AUC | SE | nCohort 1 | nCohort 2 | p |
| --- | --- | --- | --- | --- | --- |
| 0 hours | 0.54 | 0.109 | 84 | 8 | 0.683 |
| 24 hours | 0.54 | 0.109 | 84 | 8 | 0.743 |
| 48 hours | 0.54 | 0.125 | 84 | 6 | 0.775 | sCr or UO

| Time prior AKI stage | Cutoff value | sens | spec | Quartile | OR | 95% CI of OR | |
| --- | --- | --- | --- | --- | --- | --- | --- |
| 0 hours | 3521.3941 | 75% | 37% | 1 |  |  |  |
|  | 3079.2743 | 83% | 32% | 2 | 2.1 | 0.4 | 10.6 |
|  | 1296.436 | 92% | 12% | 3 | 1.0 | 0.1 | 8.0 |
|  | 7429.533 | 33% | 71% | 4 | 2.1 | 0.4 | 10.6 |
|  | 9387.4752 | 33% | 81% |  |  |  |  |
|  | 12985.454 | 17% | 91% |  |  |  |  |

FIG. 4 - 2

|  | | Cutoff value | sens | spec | Quartile | OR | 95% CI of OR | |
|---|---|---|---|---|---|---|---|---|
| 24 hours | | 3521.3941 | 75% | 37% | 1 | | | |
| | | 3079.2743 | 83% | 32% | 2 | 2.1 | 0.4 | 10.6 |
| | | 878.55325 | 92% | 4% | 3 | 1.0 | 0.1 | 8.0 |
| | | 7429.533 | 33% | 71% | 4 | 2.1 | 0.4 | 10.6 |
| | | 9387.4752 | 33% | 81% | | | | |
| | | 12985.454 | 17% | 91% | | | | |
| 48 hours | | 3521.3941 | 75% | 37% | 1 | | | |
| | | 3079.2743 | 88% | 32% | 2 | 2.1 | 0.1 | 45.9 |
| | | 0 | 100% | 0% | 3 | 4.5 | 0.3 | 61.5 |
| | | 7429.533 | 13% | 71% | 4 | 1.0 | 0.0 | 61.1 |
| | | 9387.4752 | 13% | 81% | | | | |
| | | 12985.454 | 0% | 91% | | | | | sCr only

| Time prior AKI stage | Cutoff value | sens | spec | Quartile | OR | 95% CI of OR | |
|---|---|---|---|---|---|---|---|
| 0 hours | 1404.7125 | 83% | 9% | 1 | | | |
| | 1404.7125 | 83% | 9% | 2 | 0.0 | 0.0 | na |
| | 0 | 100% | 0% | 3 | 1.0 | 0.1 | 7.8 |
| | 8244.2153 | 33% | 70% | 4 | 1.0 | 0.1 | 8.0 |
| | 10929.185 | 33% | 80% | | | | |
| | 13774.777 | 17% | 90% | | | | |
| 24 hours | 1404.7125 | 83% | 9% | 1 | | | |
| | 1404.7125 | 83% | 9% | 2 | 0.0 | 0.0 | na |
| | 0 | 100% | 0% | 3 | 1.0 | 0.1 | 7.8 |
| | 8244.2153 | 33% | 70% | 4 | 1.0 | 0.1 | 8.0 |
| | 10929.185 | 33% | 80% | | | | |
| | 13774.777 | 17% | 90% | | | | |
| 48 hours | 878.55325 | 75% | 3% | 1 | | | |
| | 0 | 100% | 0% | 2 | na | na | na |
| | 0 | 100% | 0% | 3 | na | na | na |
| | 8244.2153 | 0% | 70% | 4 | na | na | na |
| | 10929.185 | 0% | 80% | | | | |
| | 13774.777 | 0% | 90% | | | | |

UO only

| Time prior AKI stage | Cutoff value | sens | spec | Quartile | OR | 95% CI of OR | |
|---|---|---|---|---|---|---|---|
| 0 hours | 3521.3941 | 75% | 40% | 1 | | | |
| | 3079.2743 | 88% | 37% | 2 | 3.3 | 0.2 | 54.3 |
| | 1296.436 | 100% | 14% | 3 | 2.1 | 0.1 | 47.6 |
| | 6633.7291 | 25% | 70% | 4 | 2.1 | 0.1 | 47.6 |
| | 9553.5484 | 25% | 81% | | | | |
| | 12985.454 | 13% | 90% | | | | |
| 24 hours | 3521.3941 | 75% | 40% | 1 | | | |
| | 3079.2743 | 88% | 37% | 2 | 3.3 | 0.2 | 54.3 |
| | 878.55325 | 100% | 7% | 3 | 2.1 | 0.1 | 47.6 |
| | 6633.7291 | 25% | 70% | 4 | 2.1 | 0.1 | 47.6 |
| | 9553.5484 | 25% | 81% | | | | |
| | 12985.454 | 13% | 90% | | | | |
| 48 hours | 3521.3941 | 83% | 40% | 1 | | | |
| | 3521.3941 | 83% | 40% | 2 | na | na | na |
| | 3079.2743 | 100% | 37% | 3 | na | na | na |
| | 6633.7291 | 17% | 70% | 4 | na | na | na |
| | 9553.5484 | 17% | 81% | | | | |
| | 12985.454 | 0% | 90% | | | | |

FIG. 4 - 3

Lactotransferrin sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 44.384 | 159.930 | 44.384 | 159.930 | 44.384 | 116.033 |
| average | 134.659 | 499.716 | 134.659 | 490.326 | 134.659 | 582.143 |
| stdev | 802.709 | 1018.167 | 802.709 | 1020.964 | 802.709 | 1253.066 |
| p (t-test) |  | 0.152 |  | 0.163 |  | 0.151 |
| min | 0.034 | 1.565 | 0.034 | 1.565 | 0.034 | 1.565 |
| max | 7981.395 | 3665.116 | 7981.395 | 3665.116 | 7981.395 | 3665.116 |
| n (Samp) | 98 | 12 | 98 | 12 | 98 | 8 |
| n (Pat) | 98 | 12 | 98 | 12 | 98 | 8 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 51.326 | 92.341 | 51.326 | 76.923 | 51.326 | 98.231 |
| average | 168.485 | 110.358 | 168.485 | 105.219 | 168.485 | 106.241 |
| stdev | 705.659 | 104.394 | 705.659 | 105.989 | 705.659 | 92.798 |
| p (t-test) |  | 0.841 |  | 0.827 |  | 0.861 |
| min | 0.034 | 1.565 | 0.034 | 1.565 | 0.034 | 1.565 |
| max | 7981.395 | 308.777 | 7981.395 | 308.777 | 7981.395 | 226.935 |
| n (Samp) | 158 | 6 | 158 | 6 | 158 | 4 |
| n (Pat) | 158 | 6 | 158 | 6 | 158 | 4 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 43.062 | 289.569 | 43.062 | 248.648 | 43.062 | 168.190 |
| average | 168.384 | 718.875 | 168.384 | 708.644 | 168.384 | 761.148 |
| stdev | 893.760 | 1209.784 | 893.760 | 1214.085 | 893.760 | 1429.573 |
| p (t-test) |  | 0.110 |  | 0.117 |  | 0.136 |
| min | 0.034 | 23.092 | 0.034 | 23.092 | 0.034 | 23.092 |
| max | 7981.395 | 3665.116 | 7981.395 | 3665.116 | 7981.395 | 3665.116 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
| --- | --- | --- | --- | --- | --- |
| 0 hours | 0.79 | 0.081 | 98 | 12 | 0.000 |
| 24 hours | 0.77 | 0.082 | 98 | 12 | 0.001 |
| 48 hours | 0.74 | 0.103 | 98 | 8 | 0.019 | sCr only

| Time prior AKI stage | AUC | SE | nCohort 1 | nCohort 2 | p |
| --- | --- | --- | --- | --- | --- |
| 0 hours | 0.62 | 0.125 | 158 | 6 | 0.352 |
| 24 hours | 0.59 | 0.124 | 158 | 6 | 0.461 |
| 48 hours | 0.60 | 0.152 | 158 | 4 | 0.525 |

UO only

| Time prior AKI stage | AUC | SE | nCohort 1 | nCohort 2 | p |
| --- | --- | --- | --- | --- | --- |
| 0 hours | 0.89 | 0.077 | 84 | 8 | 0.000 |
| 24 hours | 0.89 | 0.077 | 84 | 8 | 0.000 |
| 48 hours | 0.85 | 0.100 | 84 | 6 | 0.000 | sCr or UO

| Time prior AKI stage | Cutoff value | sens | spec | Quartile | OR | 95% CI of OR | |
| --- | --- | --- | --- | --- | --- | --- | --- |
| 0 hours | 84.873371 | 75% | 77% | 1 |  |  |  |
|  | 58.064804 | 83% | 64% | 2 | 1.0 | 0.0 | 56.3 |
|  | 21.915017 | 92% | 43% | 3 | 2.1 | 0.1 | 45.9 |
|  | 69.14188 | 75% | 70% | 4 | 10.4 | 1.0 | 112.2 |
|  | 95.209739 | 67% | 81% |  |  |  |  |
|  | 118.88319 | 50% | 91% |  |  |  |  |

FIG. 4 - 4

| | | | | | | | |
|---|---|---|---|---|---|---|---|
| 24 hours | 63.154087 | 75% | 67% | 1 | | | |
| | 58.064804 | 83% | 64% | 2 | 1.0 | 0.0 | 56.3 |
| | 21.915017 | 92% | 43% | 3 | 3.3 | 0.2 | 51.9 |
| | 69.14188 | 67% | 70% | 4 | 8.7 | 0.8 | 96.4 |
| | 95.209739 | 58% | 81% | | | | |
| | 118.88319 | 50% | 91% | | | | |
| 48 hours | 84.873371 | 75% | 77% | 1 | | | |
| | 21.915017 | 88% | 43% | 2 | 1.0 | 0.0 | 56.5 |
| | 1.3535835 | 100% | 5% | 3 | 1.0 | 0.0 | 59.0 |
| | 69.14188 | 75% | 70% | 4 | 5.7 | 0.5 | 70.6 |
| | 95.209739 | 63% | 81% | | | | |
| | 118.88319 | 50% | 91% | | | | | sCr only

| Time prior AKI stage | Cutoff value | sens | spec | Quartile | OR | 95% CI of OR | |
|---|---|---|---|---|---|---|---|
| 0 hours | 58.662081 | 83% | 56% | 1 | | | |
| | 58.662081 | 83% | 56% | 2 | 0.0 | 0.0 | na |
| | 1.4945818 | 100% | 4% | 3 | 4.3 | 0.3 | 55.5 |
| | 94.635559 | 50% | 70% | 4 | 1.0 | 0.0 | 55.6 |
| | 112.67707 | 17% | 80% | | | | |
| | 184.36697 | 17% | 91% | | | | |
| 24 hours | 58.662081 | 83% | 56% | 1 | | | |
| | 58.662081 | 83% | 56% | 2 | 0.0 | 0.0 | na |
| | 1.4945818 | 100% | 4% | 3 | 4.3 | 0.3 | 55.5 |
| | 94.635559 | 33% | 70% | 4 | 1.0 | 0.0 | 55.6 |
| | 112.67707 | 17% | 80% | | | | |
| | 184.36697 | 17% | 91% | | | | |
| 48 hours | 88.510404 | 75% | 68% | 1 | | | |
| | 1.4945818 | 100% | 4% | 2 | 0.0 | 0.0 | na |
| | 1.4945818 | 100% | 4% | 3 | 2.1 | 0.1 | 43.0 |
| | 94.635559 | 50% | 70% | 4 | 1.0 | 0.0 | 54.3 |
| | 112.67707 | 25% | 80% | | | | |
| | 184.36697 | 25% | 91% | | | | |

FIG. 4 - 5

Prostatic Acid Phosphatase sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 9.250 | 18.700 | 9.250 | 14.450 | 9.250 | 17.150 |
| average | 41.398 | 111.095 | 41.398 | 106.876 | 41.398 | 52.031 |
| stdev | 97.909 | 164.515 | 97.909 | 172.062 | 97.909 | 69.731 |
| p (t-test) |  | 0.016 |  | 0.029 |  | 0.739 |
| min | 0.024 | 2.320 | 0.024 | 0.311 | 0.024 | 0.104 |
| max | 530.000 | 521.000 | 530.000 | 521.000 | 530.000 | 205.000 |
| n (Samp) | 103 | 17 | 103 | 16 | 103 | 10 |
| n (Pat) | 103 | 17 | 103 | 16 | 103 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 13.800 | 12.215 | 13.800 | 11.220 | 13.800 | 15.000 |
| average | 47.957 | 91.925 | 47.957 | 89.664 | 47.957 | 138.863 |
| stdev | 98.983 | 166.977 | 98.983 | 168.263 | 98.983 | 203.607 |
| p (t-test) |  | 0.238 |  | 0.263 |  | 0.053 |
| min | 0.024 | 4.520 | 0.024 | 0.311 | 0.024 | 0.104 |
| max | 530.000 | 469.000 | 530.000 | 469.000 | 530.000 | 469.000 |
| n (Samp) | 169 | 8 | 169 | 8 | 169 | 5 |
| n (Pat) | 169 | 8 | 169 | 8 | 169 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8.880 | 66.600 | 8.880 | 27.150 | 8.880 | 19.300 |
| average | 31.621 | 147.948 | 31.621 | 146.692 | 31.621 | 42.887 |
| stdev | 81.735 | 189.553 | 81.735 | 202.523 | 81.735 | 51.169 |
| p (t-test) |  | 0.000 |  | 0.001 |  | 0.721 |
| min | 0.024 | 2.320 | 0.024 | 2.320 | 0.024 | 2.320 |
| max | 530.000 | 521.000 | 530.000 | 521.000 | 530.000 | 117.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
|---|---|---|---|---|---|
| 0 hours | 0.69 | 0.075 | 103 | 17 | 0.011 |
| 24 hours | 0.61 | 0.080 | 103 | 16 | 0.160 |
| 48 hours | 0.59 | 0.099 | 103 | 10 | 0.350 | sCr only

| Time prior AKI stage | AUC | SE | nCohort 1 | nCohort 2 | p |
|---|---|---|---|---|---|
| 0 hours | 0.55 | 0.107 | 169 | 8 | 0.659 |
| 24 hours | 0.47 | 0.102 | 169 | 8 | 0.745 |
| 48 hours | 0.55 | 0.135 | 169 | 5 | 0.696 |

UO only

| Time prior AKI stage | AUC | SE | nCohort 1 | nCohort 2 | p |
|---|---|---|---|---|---|
| 0 hours | 0.77 | 0.087 | 85 | 11 | 0.002 |
| 24 hours | 0.72 | 0.095 | 85 | 10 | 0.018 |
| 48 hours | 0.65 | 0.117 | 85 | 7 | 0.208 | sCr or UO

| Time prior AKI stage | Cutoff value | sens | spec | Quartile | OR | 95% CI of OR | |
|---|---|---|---|---|---|---|---|
| 0 hours | 9.87 | 71% | 52% | 1 |  |  |  |
|  | 7.95 | 82% | 48% | 2 | 5.8 | 0.5 | 70.5 |
|  | 4.47 | 94% | 34% | 3 | 3.2 | 0.2 | 50.6 |
|  | 20.9 | 47% | 71% | 4 | 10.5 | 1.0 | 111.9 |
|  | 32.9 | 47% | 81% |  |  |  |  |
|  | 84.7 | 35% | 90% |  |  |  |  |

FIG. 4 - 6

| | Cutoff value | sens | spec | Quartile | OR | 95% CI of OR | |
|---|---|---|---|---|---|---|---|
| 24 hours | 7.95 | 75% | 48% | 1 | | | |
| | 5.07 | 81% | 38% | 2 | 1.0 | 0.2 | 4.1 |
| | 0.311 | 94% | 7% | 3 | 1.3 | 0.4 | 4.9 |
| | 20.9 | 38% | 71% | 4 | 2.2 | 0.7 | 6.8 |
| | 32.9 | 38% | 81% | | | | |
| | 84.7 | 31% | 90% | | | | |
| 48 hours | 6.27 | 70% | 41% | 1 | | | |
| | 5.07 | 80% | 38% | 2 | 1.0 | 0.1 | 8.3 |
| | 2.17 | 90% | 21% | 3 | 1.0 | 0.1 | 8.3 |
| | 20.9 | 40% | 71% | 4 | 2.1 | 0.4 | 10.6 |
| | 32.9 | 40% | 81% | | | | |
| | 84.7 | 30% | 90% | | | | | sCr only

| Time prior AKI stage | Cutoff value | sens | spec | Quartile | OR | 95% CI of OR | |
|---|---|---|---|---|---|---|---|
| 0 hours | 8.04 | 75% | 38% | 1 | | | |
| | 5.07 | 88% | 31% | 2 | na | na | na |
| | 4.47 | 100% | 28% | 3 | na | na | na |
| | 31.8 | 25% | 70% | 4 | na | na | na |
| | 47.5 | 25% | 80% | | | | |
| | 121 | 25% | 91% | | | | |
| 24 hours | 5.07 | 75% | 31% | 1 | | | |
| | 0.311 | 88% | 5% | 2 | 1.0 | 0.1 | 8.0 |
| | 0.269 | 100% | 5% | 3 | 1.0 | 0.1 | 8.0 |
| | 31.8 | 25% | 70% | 4 | 1.0 | 0.1 | 8.0 |
| | 47.5 | 25% | 80% | | | | |
| | 121 | 25% | 91% | | | | |
| 48 hours | 5.07 | 80% | 31% | 1 | | | |
| | 5.07 | 80% | 31% | 2 | 1.0 | 0.0 | 54.0 |
| | 0.0506 | 100% | 2% | 3 | 1.0 | 0.0 | 55.3 |
| | 31.8 | 40% | 70% | 4 | 2.0 | 0.1 | 41.5 |
| | 47.5 | 40% | 80% | | | | |
| | 121 | 40% | 91% | | | | |

UO only

| Time prior AKI stage | Cutoff value | sens | spec | Quartile | OR | 95% CI of OR | |
|---|---|---|---|---|---|---|---|
| 0 hours | 12.1 | 73% | 60% | 1 | | | |
| | 9.87 | 82% | 55% | 2 | 1.0 | 0.0 | 59.8 |
| | 4.96 | 91% | 39% | 3 | 2.1 | 0.1 | 47.1 |
| | 15.7 | 64% | 71% | 4 | 9.5 | 0.8 | 108.7 |
| | 22.4 | 64% | 80% | | | | |
| | 48.9 | 55% | 91% | | | | |
| 24 hours | 12.1 | 70% | 60% | 1 | | | |
| | 8.88 | 80% | 51% | 2 | 2.0 | 0.1 | 45.2 |
| | 4.96 | 90% | 39% | 3 | 2.0 | 0.1 | 45.2 |
| | 15.7 | 60% | 71% | 4 | 5.8 | 0.5 | 73.7 |
| | 22.4 | 50% | 80% | | | | |
| | 48.9 | 40% | 91% | | | | |
| 48 hours | 6.27 | 71% | 42% | 1 | | | |
| | 4.96 | 86% | 39% | 2 | 2.1 | 0.1 | 47.6 |
| | 2.17 | 100% | 26% | 3 | 1.0 | 0.0 | 60.2 |
| | 15.7 | 57% | 71% | 4 | 3.3 | 0.2 | 54.3 |
| | 22.4 | 43% | 80% | | | | |
| | 48.9 | 29% | 91% | | | | |

FIG. 4 - 7 von Willebrand Factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.013 | 0.048 | 0.013 | 0.045 | 0.013 | 0.043 |
| average | 0.055 | 0.880 | 0.055 | 0.924 | 0.055 | 0.193 |
| stdev | 0.236 | 3.017 | 0.236 | 3.111 | 0.236 | 0.488 |
| p (t-test) |  | 0.006 |  | 0.005 |  | 0.119 |
| min | 0.000 | 0.003 | 0.000 | 0.003 | 0.000 | 0.003 |
| max | 2.330 | 12.500 | 2.330 | 12.500 | 2.330 | 1.580 |
| n (Samp) | 103 | 17 | 103 | 16 | 103 | 10 |
| n (Pat) | 103 | 17 | 103 | 16 | 103 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.014 | 0.043 | 0.014 | 0.043 | 0.014 | 0.043 |
| average | 0.121 | 0.249 | 0.121 | 0.247 | 0.121 | 0.348 |
| stdev | 0.976 | 0.540 | 0.976 | 0.541 | 0.976 | 0.689 |
| p (t-test) |  | 0.715 |  | 0.718 |  | 0.607 |
| min | 0.000 | 0.003 | 0.000 | 0.003 | 0.000 | 0.003 |
| max | 12.500 | 1.580 | 12.500 | 1.580 | 12.500 | 1.580 |
| n (Samp) | 169 | 8 | 169 | 8 | 169 | 5 |
| n (Pat) | 169 | 8 | 169 | 8 | 169 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.013 | 0.058 | 0.013 | 0.053 | 0.013 | 0.043 |
| average | 0.061 | 1.193 | 0.061 | 1.295 | 0.061 | 0.043 |
| stdev | 0.259 | 3.750 | 0.259 | 3.937 | 0.259 | 0.031 |
| p (t-test) |  | 0.006 |  | 0.004 |  | 0.860 |
| min | 0.000 | 0.010 | 0.000 | 0.010 | 0.000 | 0.010 |
| max | 2.330 | 12.500 | 2.330 | 12.500 | 2.330 | 0.090 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
| --- | --- | --- | --- | --- | --- |
| 0 hours | 0.79 | 0.068 | 103 | 17 | 0.000 |
| 24 hours | 0.76 | 0.072 | 103 | 16 | 0.000 |
| 48 hours | 0.69 | 0.096 | 103 | 10 | 0.050 | sCr only

| Time prior AKI stage | AUC | SE | nCohort 1 | nCohort 2 | p |
| --- | --- | --- | --- | --- | --- |
| 0 hours | 0.74 | 0.102 | 169 | 8 | 0.016 |
| 24 hours | 0.73 | 0.103 | 169 | 8 | 0.024 |
| 48 hours | 0.70 | 0.133 | 169 | 5 | 0.127 |

UO only

| Time prior AKI stage | AUC | SE | nCohort 1 | nCohort 2 | p |
| --- | --- | --- | --- | --- | --- |
| 0 hours | 0.83 | 0.079 | 85 | 11 | 0.000 |
| 24 hours | 0.80 | 0.087 | 85 | 10 | 0.001 |
| 48 hours | 0.71 | 0.113 | 85 | 7 | 0.063 | sCr or UO

| Time prior AKI stage | Cutoff value | sens | spec | Quartile | OR | 95% CI of OR | |
| --- | --- | --- | --- | --- | --- | --- | --- |
| 0 hours | 0.0391 | 71% | 79% | 1 |  |  |  |
|  | 0.0277 | 82% | 77% | 2 | 1.0 | 0.0 | 57.7 |
|  | 0.00903 | 94% | 45% | 3 | 7.3 | 0.6 | 82.8 |
|  | 0.0227 | 88% | 71% | 4 | 12.4 | 1.2 | 128.9 |
|  | 0.049 | 47% | 81% |  |  |  |  |
|  | 0.0825 | 35% | 90% |  |  |  |  |

FIG. 4 - 8

| | Cutoff value | sens | spec | Quartile | OR | 95% CI of OR | |
|---|---|---|---|---|---|---|---|
| 24 hours | 0.0227 | 75% | 71% | 1 | | | |
| | 0.0196 | 81% | 68% | 2 | 1.0 | 0.0 | 55.8 |
| | 0.00903 | 94% | 45% | 3 | 7.0 | 0.6 | 80.2 |
| | 0.0227 | 75% | 71% | 4 | 10.2 | 1.0 | 108.3 |
| | 0.049 | 44% | 81% | | | | |
| | 0.0825 | 25% | 90% | | | | |
| 48 hours | 0.0177 | 70% | 64% | 1 | | | |
| | 0.0113 | 80% | 47% | 2 | 2.1 | 0.1 | 45.6 |
| | 0.00903 | 90% | 45% | 3 | 1.0 | 0.0 | 58.3 |
| | 0.0227 | 60% | 71% | 4 | 7.0 | 0.6 | 81.2 |
| | 0.049 | 40% | 81% | | | | |
| | 0.0825 | 20% | 90% | | | | | sCr only

| Time prior AKI stage | Cutoff value | sens | spec | Quartile | OR | 95% CI of OR | |
|---|---|---|---|---|---|---|---|
| 0 hours | 0.0283 | 75% | 73% | 1 | | | |
| | 0.025 | 88% | 67% | 2 | 0.0 | 0.0 | na |
| | 0.00226 | 100% | 9% | 3 | 2.0 | 0.1 | 42.5 |
| | 0.0268 | 75% | 70% | 4 | 5.4 | 0.5 | 62.1 |
| | 0.0491 | 38% | 80% | | | | |
| | 0.0882 | 38% | 91% | | | | |
| 24 hours | 0.0234 | 75% | 67% | 1 | | | |
| | 0.0207 | 88% | 64% | 2 | 0.0 | 0.0 | na |
| | 0.00226 | 100% | 9% | 3 | 2.0 | 0.1 | 42.5 |
| | 0.0268 | 63% | 70% | 4 | 5.4 | 0.5 | 62.1 |
| | 0.0491 | 38% | 80% | | | | |
| | 0.0882 | 38% | 91% | | | | |
| 48 hours | 0.0416 | 80% | 78% | 1 | | | |
| | 0.0416 | 80% | 78% | 2 | 0.0 | 0.0 | na |
| | 0.00226 | 100% | 9% | 3 | 0.0 | 0.0 | na |
| | 0.0268 | 80% | 70% | 4 | 4.2 | 0.3 | 53.6 |
| | 0.0491 | 40% | 80% | | | | |
| | 0.0882 | 20% | 91% | | | | |

FIG. 4 - 9

Endothelial protein C receptor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 300.134 | 322.838 | 300.134 | 259.130 | 300.134 | 295.533 |
| average | 376.663 | 370.055 | 376.663 | 368.623 | 376.663 | 308.887 |
| stdev | 255.432 | 229.567 | 255.432 | 342.732 | 255.432 | 127.865 |
| p (t-test) |  | 0.879 |  | 0.867 |  | 0.201 |
| min | 9.942 | 50.726 | 9.942 | 70.603 | 9.942 | 162.252 |
| max | 1411.055 | 1427.189 | 1411.055 | 2040.151 | 1411.055 | 714.156 |
| n (Samp) | 103 | 48 | 103 | 56 | 103 | 25 |
| n (Pat) | 98 | 48 | 98 | 56 | 98 | 25 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 301.489 | 318.500 | 301.489 | 249.530 | 301.489 | 290.661 |
| average | 375.358 | 431.240 | 375.358 | 352.808 | 375.358 | 316.791 |
| stdev | 285.968 | 346.574 | 285.968 | 210.811 | 285.968 | 144.078 |
| p (t-test) |  | 0.456 |  | 0.731 |  | 0.482 |
| min | 9.942 | 50.726 | 9.942 | 106.659 | 9.942 | 127.341 |
| max | 2040.151 | 1427.189 | 2040.151 | 731.464 | 2040.151 | 621.974 |
| n (Samp) | 239 | 16 | 239 | 20 | 239 | 12 |
| n (Pat) | 159 | 16 | 159 | 20 | 159 | 12 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 308.294 | 303.794 | 308.294 | 260.000 | 308.294 | 295.533 |
| average | 384.836 | 320.271 | 384.836 | 365.614 | 384.836 | 313.955 |
| stdev | 250.732 | 140.890 | 250.732 | 365.653 | 250.732 | 149.348 |
| p (t-test) |  | 0.129 |  | 0.716 |  | 0.216 |
| min | 45.313 | 50.726 | 45.313 | 70.603 | 45.313 | 134.432 |
| max | 1411.055 | 621.484 | 1411.055 | 2040.151 | 1411.055 | 714.156 |
| n (Samp) | 96 | 40 | 96 | 45 | 96 | 21 |
| n (Pat) | 84 | 40 | 84 | 45 | 84 | 21 | sCr or UO

| Time prior AKI stage | AUC | SE | nCohort 1 | nCohort 2 | p |
|---|---|---|---|---|---|
| 0 hours | 0.52 | 0.051 | 103 | 48 | 0.667 |
| 24 hours | 0.44 | 0.047 | 103 | 56 | 0.219 |
| 48 hours | 0.45 | 0.063 | 103 | 25 | 0.450 | sCr only

| Time prior AKI stage | AUC | SE | nCohort 1 | nCohort 2 | p |
|---|---|---|---|---|---|
| 0 hours | 0.54 | 0.076 | 239 | 16 | 0.561 |
| 24 hours | 0.48 | 0.066 | 239 | 20 | 0.725 |
| 48 hours | 0.48 | 0.084 | 239 | 12 | 0.782 |

UO only

| Time prior AKI stage | AUC | SE | nCohort 1 | nCohort 2 | p |
|---|---|---|---|---|---|
| 0 hours | 0.46 | 0.054 | 96 | 40 | 0.467 |
| 24 hours | 0.42 | 0.050 | 96 | 45 | 0.102 |
| 48 hours | 0.43 | 0.067 | 96 | 21 | 0.318 | sCr or UO

| Time prior AKI stage | Cutoff value | sens | spec | Quartile | OR | 95% CI of OR | |
|---|---|---|---|---|---|---|---|
| 0 hours | 258.26667 | 71% | 36% | 1 |  |  |  |
|  | 218.51064 | 81% | 24% | 2 | 1.1 | 0.7 | 1.8 |
|  | 127.34091 | 92% | 6% | 3 | 1.8 | 1.1 | 2.9 |
|  | 422.20645 | 29% | 71% | 4 | 1.2 | 0.8 | 2.1 |
|  | 543.48387 | 13% | 81% |  |  |  |  |
|  | 666.4878 | 4% | 90% |  |  |  |  |

FIG. 5 - 1 sCr only

|  | Time prior AKI stage | Cutoff value | sens | spec | Quartile | OR | 95% CI of OR | |
|---|---|---|---|---|---|---|---|---|
|  | 24 hours | 218.99329 | 71% | 24% | 1 |  |  |  |
|  |  | 195.43624 | 80% | 20% | 2 | 1.1 | 0.7 | 1.8 |
|  |  | 150.34351 | 91% | 11% | 3 | 1.6 | 1.0 | 2.4 |
|  |  | 422.20645 | 23% | 71% | 4 | 1.5 | 0.9 | 2.3 |
|  |  | 543.48387 | 14% | 81% |  |  |  |  |
|  |  | 666.4878 | 13% | 90% |  |  |  |  |
|  | 48 hours | 228.21643 | 72% | 29% | 1 |  |  |  |
|  |  | 213.67021 | 80% | 23% | 2 | 2.3 | 1.0 | 5.7 |
|  |  | 177.91971 | 92% | 15% | 3 | 2.0 | 0.8 | 4.9 |
|  |  | 422.20645 | 16% | 71% | 4 | 1.6 | 0.6 | 4.2 |
|  |  | 543.48387 | 4% | 81% |  |  |  |  |
|  |  | 666.4878 | 4% | 90% |  |  |  |  |

UO only

| Time prior AKI stage | Cutoff value | sens | spec | Quartile | OR | 95% CI of OR | |
|---|---|---|---|---|---|---|---|
| 0 hours | 225.09018 | 75% | 27% | 1 |  |  |  |
|  | 220.73826 | 81% | 26% | 2 | 1.3 | 0.4 | 4.5 |
|  | 155.70455 | 94% | 10% | 3 | 1.3 | 0.4 | 4.5 |
|  | 401.14286 | 38% | 71% | 4 | 1.7 | 0.6 | 5.1 |
|  | 485.6129 | 31% | 80% |  |  |  |  |
|  | 663.50649 | 13% | 90% |  |  |  |  |
| 24 hours | 228.8 | 70% | 30% | 1 |  |  |  |
|  | 195.43624 | 80% | 18% | 2 | 0.1 | 0.0 | 1.3 |
|  | 124.97727 | 90% | 6% | 3 | 1.0 | 0.5 | 1.9 |
|  | 401.14286 | 35% | 71% | 4 | 0.7 | 0.3 | 1.5 |
|  | 485.6129 | 30% | 80% |  |  |  |  |
|  | 663.50649 | 15% | 90% |  |  |  |  |
| 48 hours | 248.73333 | 75% | 37% | 1 |  |  |  |
|  | 188.20455 | 83% | 16% | 2 | 2.1 | 0.4 | 9.6 |
|  | 175.07299 | 92% | 14% | 3 | 1.5 | 0.3 | 8.3 |
|  | 401.14286 | 17% | 71% | 4 | 1.6 | 0.3 | 8.5 |
|  | 485.6129 | 17% | 80% |  |  |  |  |
|  | 663.50649 | 0% | 90% |  |  |  |  |

| Time prior AKI stage | Cutoff value | sens | spec | Quartile | OR | 95% CI of OR | |
|---|---|---|---|---|---|---|---|
| 0 hours | 238.33333 | 70% | 32% | 1 |  |  |  |
|  | 213.67021 | 80% | 22% | 2 | 1.6 | 0.9 | 2.8 |
|  | 127.34091 | 90% | 5% | 3 | 1.6 | 0.9 | 2.8 |
|  | 437.30323 | 20% | 71% | 4 | 1.4 | 0.7 | 2.5 |
|  | 543.48387 | 8% | 80% |  |  |  |  |
|  | 680.86452 | 0% | 91% |  |  |  |  |
| 24 hours | 219.86577 | 71% | 24% | 1 |  |  |  |
|  | 202.41611 | 80% | 21% | 2 | 1.4 | 0.8 | 2.5 |
|  | 147.43182 | 91% | 9% | 3 | 2.6 | 1.5 | 4.5 |
|  | 437.30323 | 18% | 71% | 4 | 1.8 | 1.0 | 3.2 |
|  | 543.48387 | 11% | 80% |  |  |  |  |
|  | 680.86452 | 9% | 91% |  |  |  |  |
| 48 hours | 227.43487 | 71% | 26% | 1 |  |  |  |
|  | 180.85878 | 81% | 13% | 2 | 2.9 | 1.0 | 8.6 |
|  | 172.84091 | 90% | 13% | 3 | 1.9 | 0.6 | 6.2 |
|  | 437.30323 | 19% | 71% | 4 | 2.3 | 0.8 | 7.3 |
|  | 543.48387 | 10% | 80% |  |  |  |  |
|  | 680.86452 | 5% | 91% |  |  |  |  |

FIG. 5 - 2

Erythropoietin receptor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 290.373 | 259.902 | 290.373 | 164.120 | 290.373 | 472.159 |
| average | 1032.036 | 599.806 | 1032.036 | 350.893 | 1032.036 | 560.586 |
| stdev | 1811.528 | 684.326 | 1811.528 | 477.002 | 1811.528 | 444.842 |
| p (t-test) |  | 0.328 |  | 0.064 |  | 0.469 |
| min | 12.346 | 9.259 | 12.346 | 0.517 | 12.346 | 77.083 |
| max | 8263.287 | 2660.287 | 8263.287 | 1969.419 | 8263.287 | 1094.801 |
| n (Samp) | 55 | 18 | 55 | 26 | 55 | 8 |
| n (Pat) | 55 | 18 | 55 | 26 | 55 | 8 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 236.328 | 273.481 | 236.328 | 197.266 | 236.328 | 590.995 |
| average | 736.698 | 776.018 | 736.698 | 669.826 | 736.698 | 590.995 |
| stdev | 1392.724 | 981.406 | 1392.724 | 845.584 | 1392.724 | 570.628 |
| p (t-test) |  | 0.942 |  | 0.908 |  | 0.883 |
| min | 0.517 | 27.778 | 0.517 | 58.642 | 0.517 | 187.500 |
| max | 8263.287 | 2660.287 | 8263.287 | 1969.419 | 8263.287 | 994.490 |
| n (Samp) | 107 | 7 | 107 | 6 | 107 | 2 |
| n (Pat) | 92 | 7 | 92 | 6 | 92 | 2 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 395.028 | 246.324 | 395.028 | 154.412 | 395.028 | 236.328 |
| average | 1116.957 | 837.516 | 1116.957 | 593.099 | 1116.957 | 504.815 |
| stdev | 1655.909 | 1458.477 | 1655.909 | 1434.945 | 1655.909 | 448.490 |
| p (t-test) |  | 0.582 |  | 0.197 |  | 0.278 |
| min | 12.346 | 9.259 | 12.346 | 0.517 | 12.346 | 58.642 |
| max | 6805.195 | 5495.557 | 6805.195 | 6961.570 | 6805.195 | 1094.801 |
| n (Samp) | 49 | 13 | 49 | 23 | 49 | 9 |
| n (Pat) | 47 | 13 | 47 | 23 | 47 | 9 | sCr or UO

| Time prior AKI stage | AUC | SE | nCohort 1 | nCohort 2 | p |
|---|---|---|---|---|---|
| 0 hours | 0.50 | 0.079 | 55 | 18 | 0.980 |
| 24 hours | 0.34 | 0.062 | 55 | 26 | 0.011 |
| 48 hours | 0.52 | 0.111 | 55 | 8 | 0.846 | sCr only

| Time prior AKI stage | AUC | SE | nCohort 1 | nCohort 2 | p |
|---|---|---|---|---|---|
| 0 hours | 0.53 | 0.115 | 107 | 7 | 0.776 |
| 24 hours | 0.47 | 0.120 | 107 | 6 | 0.830 |
| 48 hours | 0.62 | 0.215 | 107 | 2 | 0.571 |

UO only

| Time prior AKI stage | AUC | SE | nCohort 1 | nCohort 2 | p |
|---|---|---|---|---|---|
| 0 hours | 0.47 | 0.090 | 49 | 13 | 0.739 |
| 24 hours | 0.34 | 0.066 | 49 | 23 | 0.013 |
| 48 hours | 0.43 | 0.101 | 49 | 9 | 0.471 | sCr or UO

| Time prior AKI stage | Cutoff value | sens | spec | Quartile | OR | 95% CI of OR | |
|---|---|---|---|---|---|---|---|
| 0 hours | 162.10938 | 72% | 31% | 1 |  |  |  |
|  | 158.08824 | 83% | 31% | 2 | 3.2 | 0.9 | 11.0 |
|  | 41.666667 | 94% | 5% | 3 | 1.4 | 0.3 | 5.9 |
|  | 548.19277 | 39% | 71% | 4 | 1.3 | 0.3 | 5.4 |
|  | 1003.8462 | 22% | 80% |  |  |  |  |
|  | 4001.6353 | 0% | 91% |  |  |  |  |
| 24 hours | 89.583333 | 73% | 13% | 1 |  |  |  |

FIG. 5 - 3

|  |  | 77.083333 | 81% | 11% | 2 | 0.8 | 0.3 | 2.5 |
|  |  | 32.407407 | 92% | 4% | 3 | 1.4 | 0.5 | 3.7 |
|  |  | 548.19277 | 19% | 71% | 4 | 3.9 | 1.6 | 9.7 |
|  |  | 1003.8462 | 8% | 80% |  |  |  |  |
|  |  | 4001.6353 | 0% | 91% |  |  |  |  |
|  | 48 hours | 166.01563 | 75% | 33% | 1 |  |  |  |
|  |  | 139.70588 | 88% | 20% | 2 | 0.9 | 0.1 | 8.8 |
|  |  | 71.969697 | 100% | 9% | 3 | 0.4 | 0.0 | 10.9 |
|  |  | 548.19277 | 50% | 71% | 4 | 1.5 | 0.2 | 10.4 |
|  |  | 1003.8462 | 25% | 80% |  |  |  |  |
|  |  | 4001.6353 | 0% | 91% |  |  |  |  | sCr only

| Time prior AKI stage | Cutoff value | sens | spec | Quartile | OR | 95% CI of OR | |
|---|---|---|---|---|---|---|---|
| 0 hours | 236.32813 | 71% | 51% | 1 |  |  |  |
|  | 41.666667 | 86% | 7% | 2 | 0.0 | 0.0 | na |
|  | 12.345679 | 100% | 3% | 3 | 1.6 | 0.3 | 9.3 |
|  | 486.18785 | 43% | 70% | 4 | 1.0 | 0.1 | 7.9 |
|  | 740.96386 | 29% | 80% |  |  |  |  |
|  | 1714.1026 | 14% | 91% |  |  |  |  |
| 24 hours | 77.083333 | 83% | 11% | 1 |  |  |  |
|  | 77.083333 | 83% | 11% | 2 | 0.0 | 0.0 | na |
|  | 41.666667 | 100% | 7% | 3 | 1.0 | 0.1 | 8.5 |
|  | 486.18785 | 33% | 70% | 4 | 1.0 | 0.1 | 8.5 |
|  | 740.96386 | 33% | 80% |  |  |  |  |
|  | 1714.1026 | 17% | 91% |  |  |  |  |
| 48 hours | 185.54688 | 100% | 42% | 1 |  |  |  |
|  | 185.54688 | 100% | 42% | 2 | na | na | na |
|  | 185.54688 | 100% | 42% | 3 | na | na | na |
|  | 486.18785 | 50% | 70% | 4 | na | na | na |
|  | 740.96386 | 50% | 80% |  |  |  |  |
|  | 1714.1026 | 0% | 91% |  |  |  |  |

UO only

| Time prior AKI stage | Cutoff value | sens | spec | Quartile | OR | 95% CI of OR | |
|---|---|---|---|---|---|---|---|
| 0 hours | 161.76471 | 77% | 29% | 1 |  |  |  |
|  | 158.08824 | 85% | 29% | 2 | 1.1 | 0.2 | 5.5 |
|  | 132.35294 | 92% | 16% | 3 | 2.0 | 0.5 | 7.8 |
|  | 1001.2821 | 23% | 71% | 4 | 0.7 | 0.1 | 4.6 |
|  | 1969.419 | 8% | 82% |  |  |  |  |
|  | 4106.296 | 8% | 92% |  |  |  |  |
| 24 hours | 89.583333 | 74% | 14% | 1 |  |  |  |
|  | 41.666667 | 83% | 6% | 2 | 1.9 | 0.5 | 7.2 |
|  | 32.407407 | 91% | 4% | 3 | 1.9 | 0.5 | 7.2 |
|  | 1001.2821 | 9% | 71% | 4 | 6.3 | 1.8 | 21.3 |
|  | 1969.419 | 4% | 82% |  |  |  |  |
|  | 4106.296 | 4% | 92% |  |  |  |  |
| 48 hours | 139.70588 | 78% | 20% | 1 |  |  |  |
|  | 71.969697 | 89% | 8% | 2 | 1.1 | 0.1 | 10.5 |
|  | 41.666667 | 100% | 6% | 3 | 1.0 | 0.1 | 9.6 |
|  | 1001.2821 | 22% | 71% | 4 | 1.8 | 0.2 | 12.6 |
|  | 1969.419 | 0% | 82% |  |  |  |  |
|  | 4106.296 | 0% | 92% |  |  |  |  |

FIG. 5 - 4

Intercellular adhesion molecule 1 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 204482.739 | 241775.543 | 204482.739 | 236464.429 | 204482.739 | 199424.854 |
| average | 260087.506 | 251803.999 | 260087.506 | 263768.024 | 260087.506 | 273925.681 |
| stdev | 170577.847 | 118772.456 | 170577.847 | 127195.740 | 170577.847 | 183615.648 |
| p (t-test) |  | 0.787 |  | 0.899 |  | 0.724 |
| min | 51907.253 | 77026.129 | 51907.253 | 96080.376 | 51907.253 | 74243.651 |
| max | 1060572.701 | 515627.792 | 1060572.701 | 557525.433 | 1060572.701 | 799828.062 |
| n (Samp) | 82 | 38 | 82 | 46 | 82 | 26 |
| n (Pat) | 75 | 38 | 75 | 46 | 75 | 26 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 205751.313 | 259285.036 | 205751.313 | 274982.680 | 205751.313 | 200566.044 |
| average | 249019.358 | 251315.582 | 249019.358 | 320208.747 | 249019.358 | 293700.982 |
| stdev | 145779.206 | 111831.165 | 145779.206 | 148066.411 | 145779.206 | 233747.892 |
| p (t-test) |  | 0.954 |  | 0.049 |  | 0.385 |
| min | 51907.253 | 107017.742 | 51907.253 | 131091.944 | 51907.253 | 133433.302 |
| max | 1060572.701 | 445880.550 | 1060572.701 | 653217.049 | 1060572.701 | 799828.062 |
| n (Samp) | 189 | 14 | 189 | 18 | 189 | 9 |
| n (Pat) | 129 | 14 | 129 | 18 | 129 | 9 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 228898.829 | 234819.365 | 228898.829 | 240236.907 | 228898.829 | 205637.010 |
| average | 282141.495 | 252614.984 | 282141.495 | 256908.914 | 282141.495 | 256146.022 |
| stdev | 151730.865 | 117957.093 | 151730.865 | 115893.741 | 151730.865 | 144257.263 |
| p (t-test) |  | 0.349 |  | 0.353 |  | 0.486 |
| min | 51907.253 | 77026.129 | 51907.253 | 96080.376 | 51907.253 | 74243.651 |
| max | 766357.408 | 515627.792 | 766357.408 | 557525.433 | 766357.408 | 621286.258 |
| n (Samp) | 74 | 29 | 74 | 42 | 74 | 21 |
| n (Pat) | 61 | 29 | 61 | 42 | 61 | 21 | sCr or UO

| Time prior AKI stage | AUC | SE | nCohort 1 | nCohort 2 | p |
| --- | --- | --- | --- | --- | --- |
| 0 hours | 0.53 | 0.057 | 82 | 38 | 0.659 |
| 24 hours | 0.55 | 0.054 | 82 | 46 | 0.376 |
| 48 hours | 0.51 | 0.066 | 82 | 26 | 0.833 | sCr only

| Time prior AKI stage | AUC | SE | nCohort 1 | nCohort 2 | p |
| --- | --- | --- | --- | --- | --- |
| 0 hours | 0.54 | 0.082 | 189 | 14 | 0.646 |
| 24 hours | 0.67 | 0.073 | 189 | 18 | 0.023 |
| 48 hours | 0.52 | 0.100 | 189 | 9 | 0.869 |

UO only

| Time prior AKI stage | AUC | SE | nCohort 1 | nCohort 2 | p |
| --- | --- | --- | --- | --- | --- |
| 0 hours | 0.46 | 0.063 | 74 | 29 | 0.527 |
| 24 hours | 0.47 | 0.056 | 74 | 42 | 0.582 |
| 48 hours | 0.45 | 0.070 | 74 | 21 | 0.470 | sCr or UO

| Time prior AKI stage | Cutoff value | sens | spec | Quartile | OR | 95% CI of OR | |
| --- | --- | --- | --- | --- | --- | --- | --- |
| 0 hours | 165000.58 | 71% | 33% | 1 |  |  |  |
|  | 134797.92 | 82% | 20% | 2 | 0.7 | 0.4 | 1.4 |
|  | 114036.08 | 92% | 10% | 3 | 2.0 | 1.2 | 3.6 |
|  | 286718.4 | 34% | 71% | 4 | 0.8 | 0.4 | 1.6 |
|  | 384550.39 | 18% | 80% |  |  |  |  |
|  | 480616.58 | 3% | 90% |  |  |  |  |

FIG. 5 - 5

| Time prior AKI stage | Cutoff value | sens | spec | Quartile | OR | 95% CI of OR | |
|---|---|---|---|---|---|---|---|
| 24 hours | 165000.58 | 72% | 33% | 1 | | | |
| | 145855.13 | 80% | 24% | 2 | 0.7 | 0.4 | 1.4 |
| | 130812.39 | 91% | 17% | 3 | 2.2 | 1.3 | 3.7 |
| | 286718.4 | 33% | 71% | 4 | 1.3 | 0.8 | 2.3 |
| | 384550.39 | 17% | 80% | | | | |
| | 480616.58 | 9% | 90% | | | | |
| 48 hours | 147933.77 | 73% | 26% | 1 | | | |
| | 147365.22 | 81% | 24% | 2 | 1.5 | 0.7 | 3.2 |
| | 120774.31 | 92% | 12% | 3 | 1.0 | 0.4 | 2.3 |
| | 286718.4 | 31% | 71% | 4 | 1.0 | 0.4 | 2.3 |
| | 384550.39 | 19% | 80% | | | | |
| | 480616.58 | 19% | 90% | | | | | sCr only

| Time prior AKI stage | Cutoff value | sens | spec | Quartile | OR | 95% CI of OR | |
|---|---|---|---|---|---|---|---|
| 0 hours | 172340.2 | 71% | 37% | 1 | | | |
| | 142255.12 | 86% | 23% | 2 | 0.5 | 0.1 | 2.2 |
| | 120774.31 | 93% | 12% | 3 | 1.3 | 0.5 | 3.3 |
| | 274234.91 | 36% | 70% | 4 | 0.7 | 0.2 | 2.5 |
| | 356991.98 | 21% | 80% | | | | |
| | 461132.6 | 0% | 90% | | | | |
| 24 hours | 203344.41 | 72% | 48% | 1 | | | |
| | 190803.13 | 83% | 44% | 2 | 5.3 | 0.5 | 60.6 |
| | 150701.45 | 94% | 28% | 3 | 4.2 | 0.3 | 52.3 |
| | 274234.91 | 50% | 70% | 4 | 9.1 | 0.9 | 89.7 |
| | 356991.98 | 33% | 80% | | | | |
| | 461132.6 | 17% | 90% | | | | |
| 48 hours | 147735.92 | 78% | 26% | 1 | | | |
| | 133567.47 | 89% | 20% | 2 | 1.5 | 0.3 | 8.3 |
| | 133292.55 | 100% | 19% | 3 | 1.0 | 0.1 | 7.7 |
| | 274234.91 | 22% | 70% | 4 | 1.0 | 0.1 | 7.5 |
| | 356991.98 | 22% | 80% | | | | |
| | 461132.6 | 22% | 90% | | | | |

UO only

| Time prior AKI stage | Cutoff value | sens | spec | Quartile | OR | 95% CI of OR | |
|---|---|---|---|---|---|---|---|
| 0 hours | 165000.58 | 72% | 24% | 1 | | | |
| | 134797.92 | 83% | 14% | 2 | 2.6 | 1.2 | 5.9 |
| | 102736.37 | 93% | 5% | 3 | 1.3 | 0.5 | 3.1 |
| | 341114.14 | 21% | 70% | 4 | 2.0 | 0.8 | 4.6 |
| | 425739.15 | 10% | 81% | | | | |
| | 488775.86 | 3% | 91% | | | | |
| 24 hours | 165000.58 | 71% | 24% | 1 | | | |
| | 145855.13 | 81% | 18% | 2 | 2.5 | 1.3 | 4.5 |
| | 130812.39 | 90% | 12% | 3 | 1.0 | 0.5 | 2.0 |
| | 341114.14 | 21% | 70% | 4 | 1.9 | 1.0 | 3.4 |
| | 425739.15 | 10% | 81% | | | | |
| | 488775.86 | 5% | 91% | | | | |
| 48 hours | 176846.29 | 71% | 31% | 1 | | | |
| | 147365.22 | 81% | 18% | 2 | 1.7 | 0.6 | 4.6 |
| | 120851.22 | 90% | 9% | 3 | 1.3 | 0.4 | 3.9 |
| | 341114.14 | 19% | 70% | 4 | 1.8 | 0.6 | 4.9 |
| | 425739.15 | 14% | 81% | | | | |
| | 488775.86 | 14% | 91% | | | | |

FIG. 5 - 6

Lactotransferrin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 189.238 | 169.432 | 189.238 | 157.709 | 189.238 | na |
| average | 410.560 | 219.736 | 410.560 | 402.839 | 410.560 | na |
| stdev | 475.369 | 146.921 | 475.369 | 447.822 | 475.369 | na |
| p (t-test) |  | 0.276 |  | 0.958 |  | na |
| min | 26.292 | 68.170 | 26.292 | 38.746 | 26.292 | na |
| max | 1474.768 | 474.937 | 1474.768 | 1361.350 | 1474.768 | na |
| n (Samp) | 26 | 8 | 26 | 17 | 26 | 0 |
| n (Pat) | 25 | 8 | 25 | 17 | 25 | 0 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 151.646 | 249.465 | 151.646 | 364.219 | 151.646 | 26.292 |
| average | 381.454 | 249.465 | 381.454 | 581.143 | 381.454 | 102.980 |
| stdev | 445.562 | 88.604 | 445.562 | 503.829 | 445.562 | na |
| p (t-test) |  | 0.680 |  | 0.234 |  | na |
| min | 26.292 | 186.813 | 26.292 | 75.132 | 26.292 | 102.980 |
| max | 1474.768 | 312.118 | 1474.768 | 1324.895 | 1474.768 | 102.980 |
| n (Samp) | 46 | 2 | 46 | 9 | 46 | 1 |
| n (Pat) | 44 | 2 | 44 | 9 | 44 | 1 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 237.743 | 152.051 | 237.743 | 118.210 | 237.743 | 26.292 |
| average | 417.246 | 206.539 | 417.246 | 283.252 | 417.246 | 162.964 |
| stdev | 461.939 | 153.486 | 461.939 | 422.509 | 461.939 | na |
| p (t-test) |  | 0.247 |  | 0.412 |  | na |
| min | 26.292 | 68.170 | 26.292 | 38.746 | 26.292 | 162.964 |
| max | 1474.768 | 474.937 | 1474.768 | 1361.350 | 1474.768 | 162.964 |
| n (Samp) | 27 | 7 | 27 | 11 | 27 | 1 |
| n (Pat) | 25 | 7 | 25 | 11 | 25 | 1 | sCr or UO

| Time prior AKI stage | AUC | SE | nCohort 1 | nCohort 2 | p |
|---|---|---|---|---|---|
| 0 hours | 0.50 | 0.118 | 26 | 8 | 0.968 |
| 24 hours | 0.50 | 0.091 | 26 | 17 | 0.980 |
| 48 hours | nd | nd | 26 | 0 | nd | sCr only

| Time prior AKI stage | AUC | SE | nCohort 1 | nCohort 2 | p |
|---|---|---|---|---|---|
| 0 hours | 0.63 | 0.217 | 46 | 2 | 0.549 |
| 24 hours | 0.63 | 0.108 | 46 | 9 | 0.225 |
| 48 hours | 0.33 | 0.240 | 46 | 1 | 0.469 |

UO only

| Time prior AKI stage | AUC | SE | nCohort 1 | nCohort 2 | p |
|---|---|---|---|---|---|
| 0 hours | 0.44 | 0.120 | 27 | 7 | 0.613 |
| 24 hours | 0.37 | 0.097 | 27 | 11 | 0.193 |
| 48 hours | 0.41 | 0.276 | 27 | 1 | 0.737 | sCr or UO

| Time prior AKI stage | Cutoff value | sens | spec | Quartile | OR | 95% CI of OR | |
|---|---|---|---|---|---|---|---|
| 0 hours | 99.064023 | 75% | 38% | 1 |  |  |  |
|  | 89.926346 | 88% | 31% | 2 | 1.2 | 0.1 | 15.2 |
|  | 63.818697 | 100% | 15% | 3 | 1.8 | 0.2 | 16.4 |
|  | 360.84388 | 25% | 73% | 4 | 0.5 | 0.0 | 16.6 |
|  | 742.27848 | 0% | 81% |  |  |  |  |
|  | 1266.1603 | 0% | 92% |  |  |  |  |

FIG. 5 - 7

|  | | | | | | | | |
|---|---|---|---|---|---|---|---|---|
| | 24 hours | 112.11785 | 71% | 38% | 1 | | | |
| | | 71.650992 | 82% | 19% | 2 | 0.5 | 0.1 | 2.3 |
| | | 38.745946 | 94% | 4% | 3 | 1.0 | 0.2 | 4.2 |
| | | 360.84388 | 35% | 73% | 4 | 0.8 | 0.2 | 3.7 |
| | | 742.27848 | 29% | 81% | | | | |
| | | 1266.1603 | 6% | 92% | | | | |
| | 48 hours | na | na | na | 1 | | | |
| | | na | na | na | 2 | na | na | na |
| | | na | na | na | 3 | na | na | na |
| | | na | na | na | 4 | na | na | na |
| | | na | na | na | | | | |
| | | na | na | na | | | | | sCr only

| Time prior AKI stage | Cutoff value | sens | spec | Quartile | OR | 95% CI of OR | |
|---|---|---|---|---|---|---|---|
| 0 hours | 182.77053 | 100% | 57% | 1 | | | |
| | 182.77053 | 100% | 57% | 2 | na | na | na |
| | 182.77053 | 100% | 57% | 3 | na | na | na |
| | 360.84388 | 0% | 72% | 4 | na | na | na |
| | 742.27848 | 0% | 80% | | | | |
| | 1214.8523 | 0% | 91% | | | | |
| 24 hours | 152.05053 | 78% | 52% | 1 | | | |
| | 75.132011 | 89% | 17% | 2 | 0.4 | 0.0 | 11.1 |
| | 71.650992 | 100% | 17% | 3 | 0.9 | 0.1 | 9.2 |
| | 360.84388 | 56% | 72% | 4 | 2.2 | 0.3 | 13.9 |
| | 742.27848 | 44% | 80% | | | | |
| | 1214.8523 | 11% | 91% | | | | |
| 48 hours | 99.064023 | 100% | 33% | 1 | | | |
| | 99.064023 | 100% | 33% | 2 | na | na | na |
| | 99.064023 | 100% | 33% | 3 | na | na | na |
| | 360.84388 | 0% | 72% | 4 | na | na | na |
| | 742.27848 | 0% | 80% | | | | |
| | 1214.8523 | 0% | 91% | | | | |

UO only

| Time prior AKI stage | Cutoff value | sens | spec | Quartile | OR | 95% CI of OR | |
|---|---|---|---|---|---|---|---|
| 0 hours | 99.064023 | 71% | 33% | 1 | | | |
| | 89.926346 | 86% | 30% | 2 | 1.1 | 0.0 | 97.4 |
| | 63.818697 | 100% | 15% | 3 | 6.4 | 0.3 | 140.2 |
| | 360.84388 | 29% | 70% | 4 | 1.1 | 0.0 | 97.4 |
| | 742.27848 | 0% | 81% | | | | |
| | 1266.1603 | 0% | 93% | | | | |
| 24 hours | 89.926346 | 73% | 30% | 1 | | | |
| | 42.482162 | 82% | 11% | 2 | 0.5 | 0.0 | 15.4 |
| | 38.745946 | 91% | 4% | 3 | 4.0 | 0.5 | 29.8 |
| | 360.84388 | 18% | 70% | 4 | 2.0 | 0.2 | 18.1 |
| | 742.27848 | 18% | 81% | | | | |
| | 1266.1603 | 9% | 93% | | | | |
| 48 hours | 141.94526 | 100% | 41% | 1 | | | |
| | 141.94526 | 100% | 41% | 2 | na | na | na |
| | 141.94526 | 100% | 41% | 3 | na | na | na |
| | 360.84388 | 0% | 70% | 4 | na | na | na |
| | 742.27848 | 0% | 81% | | | | |
| | 1266.1603 | 0% | 93% | | | | |

FIG. 5 - 8

Prostatic Acid Phosphatase sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.161 | 0.173 | 0.161 | 0.216 | 0.161 | 0.160 |
| average | 0.445 | 0.241 | 0.445 | 0.489 | 0.445 | 0.215 |
| stdev | 2.973 | 0.298 | 2.973 | 1.226 | 2.973 | 0.217 |
| p (t-test) |  | 0.610 |  | 0.909 |  | 0.694 |
| min | 0.025 | 0.037 | 0.025 | 0.034 | 0.025 | 0.030 |
| max | 47.000 | 1.950 | 47.000 | 8.660 | 47.000 | 1.020 |
| n (Samp) | 255 | 56 | 255 | 61 | 255 | 26 |
| n (Pat) | 111 | 56 | 111 | 61 | 111 | 26 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.177 | 0.192 | 0.177 | 0.184 | 0.177 | 0.151 |
| average | 0.399 | 0.448 | 0.399 | 0.197 | 0.399 | 0.223 |
| stdev | 2.271 | 1.214 | 2.271 | 0.120 | 2.271 | 0.192 |
| p (t-test) |  | 0.919 |  | 0.650 |  | 0.772 |
| min | 0.025 | 0.041 | 0.025 | 0.034 | 0.025 | 0.088 |
| max | 47.000 | 5.990 | 47.000 | 0.494 | 47.000 | 0.748 |
| n (Samp) | 457 | 23 | 457 | 26 | 457 | 14 |
| n (Pat) | 179 | 23 | 179 | 26 | 179 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.165 | 0.182 | 0.165 | 0.223 | 0.165 | 0.180 |
| average | 0.495 | 0.273 | 0.495 | 0.595 | 0.495 | 0.617 |
| stdev | 3.251 | 0.309 | 3.251 | 1.336 | 3.251 | 1.988 |
| p (t-test) |  | 0.627 |  | 0.826 |  | 0.861 |
| min | 0.000 | 0.037 | 0.000 | 0.036 | 0.000 | 0.030 |
| max | 47.000 | 1.950 | 47.000 | 8.660 | 47.000 | 9.690 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
| --- | --- | --- | --- | --- | --- |
| 0 hours | 0.48 | 0.042 | 255 | 56 | 0.579 |
| 24 hours | 0.56 | 0.042 | 255 | 61 | 0.152 |
| 48 hours | 0.47 | 0.058 | 255 | 26 | 0.560 | sCr only

| Time prior AKI stage | AUC | SE | nCohort 1 | nCohort 2 | p |
| --- | --- | --- | --- | --- | --- |
| 0 hours | 0.50 | 0.062 | 457 | 23 | 0.985 |
| 24 hours | 0.47 | 0.057 | 457 | 26 | 0.582 |
| 48 hours | 0.46 | 0.076 | 457 | 14 | 0.608 |

UO only

| Time prior AKI stage | AUC | SE | nCohort 1 | nCohort 2 | p |
| --- | --- | --- | --- | --- | --- |
| 0 hours | 0.53 | 0.046 | 213 | 51 | 0.503 |
| 24 hours | 0.59 | 0.045 | 213 | 53 | 0.042 |
| 48 hours | 0.49 | 0.063 | 213 | 23 | 0.865 | sCr or UO

| Time prior AKI stage | Cutoff value | sens | spec | Quartile | OR | 95% CI of OR | |
| --- | --- | --- | --- | --- | --- | --- | --- |
| 0 hours | 0.0937 | 71% | 17% | 1 |  |  |  |
|  | 0.0702 | 80% | 8% | 2 | 0.8 | 0.6 | 1.1 |
|  | 0.0465 | 91% | 2% | 3 | 0.5 | 0.3 | 0.8 |
|  | 0.218 | 32% | 70% | 4 | 1.2 | 0.9 | 1.6 |
|  | 0.266 | 23% | 80% |  |  |  |  |
|  | 0.426 | 13% | 90% |  |  |  |  |

FIG. 5 - 9

| | | | | | | | |
|---|---|---|---|---|---|---|---|
| 24 hours | 0.118 | 70% | 29% | 1 | | | |
| | 0.0762 | 80% | 11% | 2 | 0.2 | 0.1 | 0.4 |
| | 0.0527 | 90% | 3% | 3 | 0.9 | 0.6 | 1.2 |
| | 0.218 | 48% | 70% | 4 | 1.6 | 1.2 | 2.1 |
| | 0.266 | 39% | 80% | | | | |
| | 0.426 | 13% | 90% | | | | |
| 48 hours | 0.103 | 73% | 25% | 1 | | | |
| | 0.0884 | 81% | 13% | 2 | 1.0 | 0.5 | 2.1 |
| | 0.0697 | 92% | 8% | 3 | 1.2 | 0.6 | 2.3 |
| | 0.218 | 27% | 70% | 4 | 1.2 | 0.6 | 2.3 |
| | 0.266 | 19% | 80% | | | | |
| | 0.426 | 8% | 90% | | | | | sCr only

| Time prior AKI stage | Cutoff value | sens | spec | Quartile | OR | 95% CI of OR | |
|---|---|---|---|---|---|---|---|
| 0 hours | 0.122 | 74% | 28% | 1 | | | |
| | 0.0795 | 83% | 13% | 2 | 0.8 | 0.4 | 1.8 |
| | 0.0527 | 91% | 4% | 3 | 1.2 | 0.6 | 2.2 |
| | 0.245 | 35% | 70% | 4 | 0.8 | 0.4 | 1.8 |
| | 0.313 | 13% | 80% | | | | |
| | 0.467 | 9% | 90% | | | | |
| 24 hours | 0.125 | 73% | 29% | 1 | | | |
| | 0.0829 | 81% | 13% | 2 | 1.0 | 0.6 | 1.8 |
| | 0.0742 | 92% | 11% | 3 | 0.7 | 0.3 | 1.4 |
| | 0.245 | 27% | 70% | 4 | 1.0 | 0.6 | 1.8 |
| | 0.313 | 19% | 80% | | | | |
| | 0.467 | 4% | 90% | | | | |
| 48 hours | 0.105 | 71% | 23% | 1 | | | |
| | 0.0907 | 86% | 17% | 2 | 0.5 | 0.1 | 2.2 |
| | 0.0884 | 93% | 15% | 3 | 0.7 | 0.2 | 2.4 |
| | 0.245 | 29% | 70% | 4 | 1.3 | 0.5 | 3.2 |
| | 0.313 | 14% | 80% | | | | |
| | 0.467 | 14% | 90% | | | | |

UO only

| Time prior AKI stage | Cutoff value | sens | spec | Quartile | OR | 95% CI of OR | |
|---|---|---|---|---|---|---|---|
| 0 hours | 0.131 | 71% | 34% | 1 | | | |
| | 0.0896 | 80% | 16% | 2 | 0.6 | 0.4 | 1.0 |
| | 0.0568 | 92% | 4% | 3 | 0.8 | 0.5 | 1.2 |
| | 0.225 | 41% | 70% | 4 | 1.5 | 1.1 | 2.1 |
| | 0.285 | 29% | 80% | | | | |
| | 0.467 | 14% | 90% | | | | |
| 24 hours | 0.141 | 72% | 38% | 1 | | | |
| | 0.0829 | 81% | 14% | 2 | 0.4 | 0.2 | 0.7 |
| | 0.0527 | 92% | 3% | 3 | 0.9 | 0.6 | 1.3 |
| | 0.225 | 47% | 70% | 4 | 2.0 | 1.4 | 2.7 |
| | 0.285 | 36% | 80% | | | | |
| | 0.467 | 17% | 90% | | | | |
| 48 hours | 0.103 | 78% | 26% | 1 | | | |
| | 0.075 | 83% | 11% | 2 | 1.0 | 0.5 | 2.1 |
| | 0.0697 | 91% | 7% | 3 | 1.0 | 0.5 | 2.1 |
| | 0.225 | 30% | 70% | 4 | 0.8 | 0.4 | 1.8 |
| | 0.285 | 17% | 80% | | | | |
| | 0.467 | 9% | 90% | | | | |

FIG. 5 - 10 von Willebrand Factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 89.500 | 99.100 | 89.500 | 109.000 | 89.500 | 115.000 |
| average | 97.420 | 107.670 | 97.420 | 121.097 | 97.420 | 114.312 |
| stdev | 36.520 | 39.395 | 36.520 | 50.265 | 36.520 | 43.801 |
| p (t-test) |  | 0.062 |  | 0.000 |  | 0.028 |
| min | 25.000 | 37.100 | 25.000 | 40.900 | 25.000 | 58.000 |
| max | 278.000 | 214.000 | 278.000 | 328.000 | 278.000 | 215.000 |
| n (Samp) | 255 | 56 | 255 | 61 | 255 | 26 |
| n (Pat) | 111 | 56 | 111 | 61 | 111 | 26 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 93.700 | 110.000 | 93.700 | 115.500 | 93.700 | 109.000 |
| average | 99.954 | 120.257 | 99.954 | 127.904 | 99.954 | 126.871 |
| stdev | 39.860 | 42.795 | 39.860 | 47.309 | 39.860 | 52.383 |
| p (t-test) |  | 0.018 |  | 0.001 |  | 0.014 |
| min | 15.600 | 67.200 | 15.600 | 46.500 | 15.600 | 58.000 |
| max | 328.000 | 217.000 | 328.000 | 239.000 | 328.000 | 224.000 |
| n (Samp) | 457 | 23 | 457 | 26 | 457 | 14 |
| n (Pat) | 179 | 23 | 179 | 26 | 179 | 14 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 90.000 | 99.900 | 90.000 | 106.000 | 90.000 | 115.000 |
| average | 97.479 | 104.239 | 97.479 | 115.174 | 97.479 | 108.109 |
| stdev | 34.231 | 37.463 | 34.231 | 48.825 | 34.231 | 36.605 |
| p (t-test) |  | 0.215 |  | 0.002 |  | 0.161 |
| min | 25.000 | 37.100 | 25.000 | 40.900 | 25.000 | 59.300 |
| max | 240.000 | 214.000 | 240.000 | 328.000 | 240.000 | 201.000 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.59 | 0.043 | 255 | 56 | 0.029 |
| 24 hours | 0.66 | 0.041 | 255 | 61 | 0.000 |
| 48 hours | 0.61 | 0.061 | 255 | 26 | 0.068 | sCr only

| Time prior AKI stage | AUC | SE | nCohort 1 | nCohort 2 | p |
|---|---|---|---|---|---|
| 0 hours | 0.65 | 0.064 | 457 | 23 | 0.019 |
| 24 hours | 0.68 | 0.059 | 457 | 26 | 0.002 |
| 48 hours | 0.65 | 0.081 | 457 | 14 | 0.057 |

UO only

| Time prior AKI stage | AUC | SE | nCohort 1 | nCohort 2 | p |
|---|---|---|---|---|---|
| 0 hours | 0.57 | 0.046 | 213 | 51 | 0.142 |
| 24 hours | 0.62 | 0.045 | 213 | 53 | 0.007 |
| 48 hours | 0.59 | 0.065 | 213 | 23 | 0.176 | sCr or UO

| Time prior AKI stage | Cutoff value | sens | spec | Quartile | OR | 95% CI of OR | |
|---|---|---|---|---|---|---|---|
| 0 hours | 88 | 71% | 49% | 1 |  |  |  |
|  | 83.8 | 80% | 43% | 2 | 1.4 | 0.9 | 2.1 |
|  | 66.8 | 91% | 16% | 3 | 2.6 | 1.8 | 3.8 |
|  | 106 | 45% | 70% | 4 | 1.8 | 1.2 | 2.7 |
|  | 122 | 23% | 80% |  |  |  |  |
|  | 143 | 20% | 90% |  |  |  |  |

FIG. 5 - 11 sCr only

|  | | | | | | | |
|---|---|---|---|---|---|---|---|
| 24 hours | 96.2 | 70% | 59% | 1 | | | |
| | 81.4 | 80% | 37% | 2 | 1.1 | 0.7 | 1.9 |
| | 69.9 | 90% | 21% | 3 | 3.4 | 2.3 | 5.1 |
| | 106 | 52% | 70% | 4 | 3.4 | 2.3 | 5.1 |
| | 122 | 31% | 80% | | | | |
| | 143 | 21% | 90% | | | | |
| 48 hours | 81.3 | 73% | 37% | 1 | | | |
| | 72.3 | 81% | 25% | 2 | 0.5 | 0.2 | 1.4 |
| | 62.3 | 92% | 11% | 3 | 1.0 | 0.5 | 2.0 |
| | 106 | 58% | 70% | 4 | 2.0 | 1.1 | 3.5 |
| | 122 | 35% | 80% | | | | |
| | 143 | 19% | 90% | | | | |

UO only

| Time prior AKI stage | Cutoff value | sens | spec | Quartile | OR | 95% CI of OR | |
|---|---|---|---|---|---|---|---|
| 0 hours | 91.8 | 74% | 48% | 1 | | | |
| | 90 | 83% | 46% | 2 | 3.7 | 1.0 | 13.3 |
| | 84.6 | 91% | 39% | 3 | 2.6 | 0.6 | 10.5 |
| | 112 | 48% | 72% | 4 | 4.8 | 1.4 | 16.4 |
| | 123 | 30% | 80% | | | | |
| | 149 | 26% | 90% | | | | |
| 24 hours | 100 | 73% | 59% | 1 | | | |
| | 76.8 | 85% | 30% | 2 | 1.3 | 0.4 | 4.3 |
| | 66.5 | 92% | 17% | 3 | 2.4 | 0.9 | 6.3 |
| | 112 | 62% | 72% | 4 | 4.3 | 1.8 | 10.1 |
| | 123 | 46% | 80% | | | | |
| | 149 | 35% | 90% | | | | |
| 48 hours | 96.3 | 71% | 54% | 1 | | | |
| | 86 | 86% | 41% | 2 | 1.0 | 0.1 | 7.3 |
| | 70.4 | 93% | 21% | 3 | 2.5 | 0.6 | 10.4 |
| | 112 | 50% | 72% | 4 | 2.5 | 0.6 | 10.4 |
| | 123 | 36% | 80% | | | | |
| | 149 | 36% | 90% | | | | |

| Time prior AKI stage | Cutoff value | sens | spec | Quartile | OR | 95% CI of OR | |
|---|---|---|---|---|---|---|---|
| 0 hours | 86.4 | 71% | 44% | 1 | | | |
| | 75.7 | 80% | 29% | 2 | 1.1 | 0.7 | 1.7 |
| | 64.5 | 90% | 13% | 3 | 1.8 | 1.2 | 2.7 |
| | 107 | 41% | 71% | 4 | 1.5 | 1.0 | 2.3 |
| | 122 | 22% | 80% | | | | |
| | 147 | 10% | 90% | | | | |
| 24 hours | 93.4 | 72% | 55% | 1 | | | |
| | 81.3 | 81% | 36% | 2 | 0.7 | 0.4 | 1.3 |
| | 68.8 | 91% | 19% | 3 | 2.8 | 1.9 | 4.1 |
| | 107 | 47% | 71% | 4 | 2.2 | 1.4 | 3.2 |
| | 122 | 25% | 80% | | | | |
| | 147 | 13% | 90% | | | | |
| 48 hours | 75.2 | 74% | 29% | 1 | | | |
| | 68.5 | 83% | 19% | 2 | 0.3 | 0.1 | 1.2 |
| | 63.6 | 91% | 12% | 3 | 0.8 | 0.4 | 1.8 |
| | 107 | 61% | 71% | 4 | 1.8 | 1.0 | 3.3 |
| | 122 | 26% | 80% | | | | |
| | 147 | 9% | 90% | | | | |

FIG. 5 - 12

Endothelial protein C receptor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 307.167 | 264.840 | 307.167 | 260.000 | 307.167 | 272.911 |
| average | 363.211 | 318.003 | 363.211 | 357.369 | 363.211 | 451.633 |
| stdev | 219.064 | 223.825 | 219.064 | 414.446 | 219.064 | 411.063 |
| p (t-test) |  | 0.389 |  | 0.905 |  | 0.148 |
| min | 9.942 | 160.019 | 9.942 | 18.516 | 9.942 | 134.432 |
| max | 1427.189 | 1169.184 | 1427.189 | 2040.151 | 1427.189 | 1647.301 |
| n (Samp) | 230 | 19 | 230 | 29 | 230 | 16 |
| n (Pat) | 158 | 19 | 158 | 29 | 158 | 16 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 301.977 | 231.676 | 301.977 | 261.383 | 301.977 | 222.660 |
| average | 377.797 | 231.676 | 377.797 | 363.566 | 377.797 | 302.452 |
| stdev | 276.515 | 101.338 | 276.515 | 272.984 | 276.515 | 221.117 |
| p (t-test) |  | 0.456 |  | 0.893 |  | 0.545 |
| min | 9.942 | 160.019 | 9.942 | 106.659 | 9.942 | 175.649 |
| max | 2040.151 | 303.333 | 2040.151 | 787.839 | 2040.151 | 695.922 |
| n (Samp) | 294 | 2 | 294 | 7 | 294 | 5 |
| n (Pat) | 186 | 2 | 186 | 7 | 186 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 309.594 | 264.840 | 309.594 | 239.670 | 309.594 | 272.911 |
| average | 360.149 | 330.437 | 360.149 | 326.661 | 360.149 | 451.866 |
| stdev | 207.033 | 227.949 | 207.033 | 415.884 | 207.033 | 430.967 |
| p (t-test) |  | 0.554 |  | 0.499 |  | 0.146 |
| min | 45.313 | 160.763 | 45.313 | 18.516 | 45.313 | 134.432 |
| max | 1411.055 | 1169.184 | 1411.055 | 2040.151 | 1411.055 | 1647.301 |
| n (Samp) | 198 | 19 | 198 | 27 | 198 | 14 |
| n (Pat) | 132 | 19 | 132 | 27 | 132 | 14 | sCr or UO

| Time prior AKI stage | AUC | SE | nCohort 1 | nCohort 2 | p |
| --- | --- | --- | --- | --- | --- |
| 0 hours | 0.40 | 0.064 | 230 | 19 | 0.128 |
| 24 hours | 0.38 | 0.051 | 230 | 29 | 0.019 |
| 48 hours | 0.48 | 0.074 | 230 | 16 | 0.781 | sCr only

| Time prior AKI stage | AUC | SE | nCohort 1 | nCohort 2 | p |
| --- | --- | --- | --- | --- | --- |
| 0 hours | 0.30 | 0.158 | 294 | 2 | 0.212 |
| 24 hours | 0.46 | 0.107 | 294 | 7 | 0.709 |
| 48 hours | 0.34 | 0.109 | 294 | 5 | 0.151 |

UO only

| Time prior AKI stage | AUC | SE | nCohort 1 | nCohort 2 | p |
| --- | --- | --- | --- | --- | --- |
| 0 hours | 0.42 | 0.065 | 198 | 19 | 0.235 |
| 24 hours | 0.34 | 0.050 | 198 | 27 | 0.001 |
| 48 hours | 0.47 | 0.079 | 198 | 14 | 0.725 | sCr or UO

| Time prior AKI stage | Cutoff value | sens | spec | Quartile | OR | 95% CI of OR | |
| --- | --- | --- | --- | --- | --- | --- | --- |
| 0 hours | 232.95302 | 74% | 27% | 1 |  |  |  |
|  | 184.65909 | 84% | 12% | 2 | 3.3 | 0.8 | 12.9 |
|  | 160.01908 | 95% | 8% | 3 | 3.3 | 0.8 | 12.9 |
|  | 409.24675 | 11% | 70% | 4 | 2.7 | 0.6 | 11.3 |
|  | 503.06003 | 11% | 80% |  |  |  |  |
|  | 607.39355 | 5% | 90% |  |  |  |  |

FIG. 6 - 1

| | Time prior AKI stage | Cutoff value | sens | spec | Quartile | OR | 95% CI of OR | |
|---|---|---|---|---|---|---|---|---|
| | 24 hours | 124.97727 | 76% | 4% | 1 | | | |
| | | 108.43182 | 83% | 3% | 2 | 0.6 | 0.3 | 1.6 |
| | | 71.368243 | 93% | 2% | 3 | 1.2 | 0.6 | 2.3 |
| | | 409.24675 | 21% | 70% | 4 | 2.3 | 1.3 | 4.0 |
| | | 503.06003 | 14% | 80% | | | | |
| | | 607.39355 | 14% | 90% | | | | |
| | 48 hours | 175.64885 | 75% | 10% | 1 | | | |
| | | 172.84091 | 81% | 10% | 2 | 0.3 | 0.1 | 1.3 |
| | | 151.56818 | 94% | 8% | 3 | 0.0 | 0.0 | na |
| | | 409.24675 | 44% | 70% | 4 | 1.4 | 0.7 | 2.7 |
| | | 503.06003 | 25% | 80% | | | | |
| | | 607.39355 | 25% | 90% | | | | | sCr only

| Time prior AKI stage | Cutoff value | sens | spec | Quartile | OR | 95% CI of OR | |
|---|---|---|---|---|---|---|---|
| 0 hours | 155.70455 | 100% | 10% | 1 | | | |
| | 155.70455 | 100% | 10% | 2 | na | na | na |
| | 155.70455 | 100% | 10% | 3 | na | na | na |
| | 409.24675 | 0% | 70% | 4 | na | na | na |
| | 514.5974 | 0% | 80% | | | | |
| | 638.59355 | 0% | 90% | | | | |
| 24 hours | 239.6696 | 71% | 31% | 1 | | | |
| | 124.97727 | 86% | 5% | 2 | 0.5 | 0.0 | 10.0 |
| | 101.34091 | 100% | 4% | 3 | 1.0 | 0.1 | 7.6 |
| | 409.24675 | 29% | 70% | 4 | 1.0 | 0.1 | 7.6 |
| | 514.5974 | 29% | 80% | | | | |
| | 638.59355 | 29% | 90% | | | | |
| 48 hours | 188.20455 | 80% | 15% | 1 | | | |
| | 188.20455 | 80% | 15% | 2 | 0.0 | 0.0 | na |
| | 175.07299 | 100% | 13% | 3 | 1.0 | 0.0 | 53.1 |
| | 409.24675 | 20% | 70% | 4 | 3.1 | 0.2 | 45.0 |
| | 514.5974 | 20% | 80% | | | | |
| | 638.59355 | 20% | 90% | | | | |

UO only

| Time prior AKI stage | Cutoff value | sens | spec | Quartile | OR | 95% CI of OR | |
|---|---|---|---|---|---|---|---|
| 0 hours | 231.20805 | 74% | 28% | 1 | | | |
| | 184.65909 | 84% | 12% | 2 | 1.4 | 0.4 | 4.7 |
| | 172.84091 | 95% | 11% | 3 | 2.6 | 0.9 | 7.1 |
| | 409.24675 | 16% | 70% | 4 | 1.8 | 0.6 | 5.4 |
| | 503.06003 | 16% | 80% | | | | |
| | 611.95122 | 5% | 90% | | | | |
| 24 hours | 124.97727 | 70% | 4% | 1 | | | |
| | 95.962838 | 81% | 3% | 2 | 1.0 | 0.4 | 2.9 |
| | 71.368243 | 93% | 2% | 3 | 1.9 | 0.8 | 4.4 |
| | 409.24675 | 15% | 70% | 4 | 3.6 | 1.7 | 7.5 |
| | 503.06003 | 7% | 80% | | | | |
| | 611.95122 | 7% | 90% | | | | |
| 48 hours | 172.84091 | 71% | 11% | 1 | | | |
| | 155.70455 | 86% | 8% | 2 | 0.4 | 0.1 | 1.6 |
| | 150.38636 | 93% | 8% | 3 | 0.0 | 0.0 | na |
| | 409.24675 | 43% | 70% | 4 | 1.5 | 0.7 | 3.1 |
| | 503.06003 | 21% | 80% | | | | |
| | 611.95122 | 21% | 90% | | | | |

FIG. 6 - 2

Erythropoietin receptor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 274.862 | na | 274.862 | 156.882 | 274.862 | 135.398 |
| average | 901.480 | na | 901.480 | 431.324 | 901.480 | 137.301 |
| stdev | 1563.579 | na | 1563.579 | 963.525 | 1563.579 | 39.498 |
| p (t-test) |  | na |  | 0.275 |  | 0.332 |
| min | 0.517 | na | 0.517 | 0.517 | 0.517 | 90.909 |
| max | 8263.287 | na | 8263.287 | 3753.930 | 8263.287 | 187.500 |
| n (Samp) | 112 | 0 | 112 | 14 | 112 | 4 |
| n (Pat) | 93 | 0 | 93 | 14 | 93 | 4 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 256.211 | na | 256.211 | 205.078 | 256.211 | 123.071 |
| average | 866.276 | na | 866.276 | 199.947 | 866.276 | 123.071 |
| stdev | 1522.392 | na | 1522.392 | 117.920 | 1522.392 | 91.116 |
| p (t-test) |  | na |  | 0.452 |  | 0.493 |
| min | 0.517 | na | 0.517 | 79.545 | 0.517 | 58.642 |
| max | 8263.287 | na | 8263.287 | 315.217 | 8263.287 | 187.500 |
| n (Samp) | 127 | 0 | 127 | 3 | 127 | 2 |
| n (Pat) | 106 | 0 | 106 | 3 | 106 | 2 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 290.373 | na | 290.373 | 136.029 | 290.373 | 134.766 |
| average | 908.788 | na | 908.788 | 494.427 | 908.788 | 120.568 |
| stdev | 1493.466 | na | 1493.466 | 1087.967 | 1493.466 | 25.693 |
| p (t-test) |  | na |  | 0.375 |  | 0.365 |
| min | 0.517 | na | 0.517 | 0.517 | 0.517 | 90.909 |
| max | 6961.570 | na | 6961.570 | 3753.930 | 6961.570 | 136.029 |
| n (Samp) | 95 | 0 | 95 | 11 | 95 | 3 |
| n (Pat) | 78 | 0 | 78 | 11 | 78 | 3 | sCr or UO

| Time prior AKI stage | AUC | SE | nCohort 1 | nCohort 2 | p |
|---|---|---|---|---|---|
| 0 hours | nd | nd | 112 | 0 | nd |
| 24 hours | 0.32 | 0.068 | 112 | 14 | 0.008 |
| 48 hours | 0.21 | 0.090 | 112 | 4 | 0.001 | sCr only

| Time prior AKI stage | AUC | SE | nCohort 1 | nCohort 2 | p |
|---|---|---|---|---|---|
| 0 hours | nd | nd | 127 | 0 | nd |
| 24 hours | 0.36 | 0.146 | 127 | 3 | 0.341 |
| 48 hours | 0.23 | 0.132 | 127 | 2 | 0.041 |

UO only

| Time prior AKI stage | AUC | SE | nCohort 1 | nCohort 2 | p |
|---|---|---|---|---|---|
| 0 hours | nd | nd | 95 | 0 | nd |
| 24 hours | 0.32 | 0.076 | 95 | 11 | 0.017 |
| 48 hours | 0.18 | 0.092 | 95 | 3 | 0.001 | sCr or UO

| Time prior AKI stage | Cutoff value | sens | spec | Quartile | OR | 95% CI of OR | |
|---|---|---|---|---|---|---|---|
| 0 hours |  | na | na | na | 1 |  |  |  |
|  |  | na | na | na | 2 | na | na | na |
|  |  | na | na | na | 3 | na | na | na |
|  |  | na | na | na | 4 | na | na | na |
|  |  | na | na | na |  |  |  |  |
|  |  | na | na | na |  |  |  |  |
| 24 hours | 114.58333 | 71% | 15% | 1 |  |  |  |

FIG. 6 - 3

|  | | Cutoff value | sens | spec | Quartile | OR | 95% CI of OR | |
|---|---|---|---|---|---|---|---|---|
| | | 77.083333 | 86% | 13% | 2 | 3.3 | 0.2 | 51.8 |
| | | 41.666667 | 93% | 7% | 3 | 3.2 | 0.2 | 49.9 |
| | | 663.91185 | 7% | 71% | 4 | 9.0 | 0.8 | 98.2 |
| | | 1006.1162 | 7% | 80% | | | | |
| | | 2121.6678 | 7% | 90% | | | | |
| | 48 hours | 132.35294 | 75% | 18% | 1 | | | |
| | | 83.333333 | 100% | 14% | 2 | na | na | na |
| | | 83.333333 | 100% | 14% | 3 | na | na | na |
| | | 663.91185 | 0% | 71% | 4 | na | na | na |
| | | 1006.1162 | 0% | 80% | | | | |
| | | 2121.6678 | 0% | 90% | | | | |

UO only

| Time prior AKI stage | Cutoff value | sens | spec | Quartile | OR | 95% CI of OR | |
|---|---|---|---|---|---|---|---|
| 0 hours | na | na | na | 1 | | | |
| | na | na | na | 2 | na | na | na |
| | na | na | na | 3 | na | na | na |
| | na | na | na | 4 | na | na | na |
| | na | na | na | | | | |
| | na | na | na | | | | |
| 24 hours | 114.58333 | 73% | 17% | 1 | | | |
| | 97.916667 | 82% | 17% | 2 | 2.2 | 0.1 | 48.0 |
| | 41.666667 | 91% | 8% | 3 | 2.1 | 0.1 | 45.9 |
| | 707.98898 | 9% | 71% | 4 | 7.8 | 0.7 | 91.3 |
| | 1045.8716 | 9% | 80% | | | | |
| | 2611.6108 | 9% | 91% | | | | |
| 48 hours | 83.333333 | 100% | 16% | 1 | | | |
| | 83.333333 | 100% | 16% | 2 | na | na | na |
| | 83.333333 | 100% | 16% | 3 | na | na | na |
| | 707.98898 | 0% | 71% | 4 | na | na | na |
| | 1045.8716 | 0% | 80% | | | | |
| | 2611.6108 | 0% | 91% | | | | |

FIG. 6 - 4

Intercellular adhesion molecule 1 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 212720.282 | 195987.185 | 212720.282 | 204249.960 | 212720.282 | 196393.305 |
| average | 258888.313 | 270628.556 | 258888.313 | 243905.418 | 258888.313 | 261418.055 |
| stdev | 149719.996 | 161880.148 | 149719.996 | 111904.661 | 149719.996 | 176673.663 |
| p (t-test) |  | 0.839 |  | 0.643 |  | 0.948 |
| min | 51907.253 | 121487.749 | 51907.253 | 98212.086 | 51907.253 | 122320.133 |
| max | 1060572.701 | 482503.909 | 1060572.701 | 515627.792 | 1060572.701 | 807280.039 |
| n (Samp) | 192 | 7 | 192 | 23 | 192 | 17 |
| n (Pat) | 129 | 7 | 129 | 23 | 129 | 17 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 210350.573 | 143846.960 | 210350.573 | 245214.865 | 210350.573 | 221188.854 |
| average | 255004.781 | 204460.199 | 255004.781 | 322814.481 | 255004.781 | 313388.160 |
| stdev | 143929.862 | 124850.396 | 143929.862 | 183649.684 | 143929.862 | 251599.617 |
| p (t-test) |  | 0.546 |  | 0.224 |  | 0.338 |
| min | 51907.253 | 121487.749 | 51907.253 | 152881.538 | 51907.253 | 147933.768 |
| max | 1060572.701 | 348045.889 | 1060572.701 | 653217.049 | 1060572.701 | 807280.039 |
| n (Samp) | 235 | 3 | 235 | 7 | 235 | 6 |
| n (Pat) | 154 | 3 | 154 | 7 | 154 | 6 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 223529.275 | 335646.849 | 223529.275 | 209260.645 | 223529.275 | 252584.630 |
| average | 266850.987 | 320254.823 | 266850.987 | 243022.810 | 266850.987 | 253861.700 |
| stdev | 146387.464 | 185355.542 | 146387.464 | 107601.465 | 146387.464 | 126267.316 |
| p (t-test) |  | 0.474 |  | 0.493 |  | 0.756 |
| min | 51907.253 | 127221.684 | 51907.253 | 98212.086 | 51907.253 | 122320.133 |
| max | 799828.062 | 482503.909 | 799828.062 | 515627.792 | 799828.062 | 557525.433 |
| n (Samp) | 165 | 4 | 165 | 19 | 165 | 13 |
| n (Pat) | 106 | 4 | 106 | 19 | 106 | 13 | sCr or UO

| Time prior AKI stage | AUC | SE | nCohort 1 | nCohort 2 | p |
|---|---|---|---|---|---|
| 0 hours | 0.50 | 0.111 | 192 | 7 | 0.989 |
| 24 hours | 0.50 | 0.064 | 192 | 23 | 0.997 |
| 48 hours | 0.49 | 0.073 | 192 | 17 | 0.891 | sCr only

| Time prior AKI stage | AUC | SE | nCohort 1 | nCohort 2 | p |
|---|---|---|---|---|---|
| 0 hours | 0.37 | 0.147 | 235 | 3 | 0.389 |
| 24 hours | 0.62 | 0.115 | 235 | 7 | 0.309 |
| 48 hours | 0.55 | 0.123 | 235 | 6 | 0.679 |

UO only

| Time prior AKI stage | AUC | SE | nCohort 1 | nCohort 2 | p |
|---|---|---|---|---|---|
| 0 hours | 0.58 | 0.151 | 165 | 4 | 0.610 |
| 24 hours | 0.48 | 0.069 | 165 | 19 | 0.752 |
| 48 hours | 0.48 | 0.083 | 165 | 13 | 0.841 | sCr or UO

| Time prior AKI stage | Cutoff value | sens | spec | Quartile | OR | 95% CI of OR | |
|---|---|---|---|---|---|---|---|
| 0 hours | 142881.92 | 71% | 22% | 1 |  |  |  |
|  | 126735.51 | 86% | 14% | 2 | 0.0 | 0.0 | na |
|  | 120851.22 | 100% | 11% | 3 | 0.3 | 0.0 | 4.7 |
|  | 301522.93 | 43% | 70% | 4 | 1.0 | 0.3 | 4.1 |
|  | 377720.11 | 29% | 80% |  |  |  |  |
|  | 461132.6 | 29% | 90% |  |  |  |  |

FIG. 6 - 5

| Time prior AKI stage | Cutoff value | sens | spec | Quartile | OR | 95% CI of OR | |
|---|---|---|---|---|---|---|---|
| 24 hours | 171458.56 | 74% | 35% | 1 | | | |
| | 150701.45 | 83% | 28% | 2 | 1.2 | 0.6 | 2.7 |
| | 133433.3 | 91% | 18% | 3 | 1.7 | 0.8 | 3.5 |
| | 301522.93 | 26% | 70% | 4 | 0.8 | 0.3 | 2.1 |
| | 377720.11 | 17% | 80% | | | | |
| | 461132.6 | 4% | 90% | | | | |
| 48 hours | 150701.45 | 71% | 28% | 1 | | | |
| | 147735.92 | 82% | 27% | 2 | 1.8 | 0.6 | 5.5 |
| | 126735.51 | 94% | 14% | 3 | 2.2 | 0.8 | 6.3 |
| | 301522.93 | 24% | 70% | 4 | 1.0 | 0.3 | 4.1 |
| | 377720.11 | 12% | 80% | | | | |
| | 461132.6 | 12% | 90% | | | | | sCr only

| Time prior AKI stage | Cutoff value | sens | spec | Quartile | OR | 95% CI of OR | |
|---|---|---|---|---|---|---|---|
| 0 hours | 120851.22 | 100% | 11% | 1 | | | |
| | 120851.22 | 100% | 11% | 2 | 0.0 | 0.0 | na |
| | 120851.22 | 100% | 11% | 3 | 0.0 | 0.0 | na |
| | 288238.02 | 33% | 70% | 4 | 2.1 | 0.1 | 41.9 |
| | 363338.73 | 0% | 80% | | | | |
| | 461132.6 | 0% | 90% | | | | |
| 24 hours | 190803.13 | 71% | 42% | 1 | | | |
| | 172617.78 | 86% | 35% | 2 | na | na | na |
| | 150701.45 | 100% | 28% | 3 | na | na | na |
| | 288238.02 | 43% | 70% | 4 | na | na | na |
| | 363338.73 | 43% | 80% | | | | |
| | 461132.6 | 14% | 90% | | | | |
| 48 hours | 147933.77 | 83% | 27% | 1 | | | |
| | 147933.77 | 83% | 27% | 2 | na | na | na |
| | 147735.92 | 100% | 26% | 3 | na | na | na |
| | 288238.02 | 33% | 70% | 4 | na | na | na |
| | 363338.73 | 17% | 80% | | | | |
| | 461132.6 | 17% | 90% | | | | |

UO only

| Time prior AKI stage | Cutoff value | sens | spec | Quartile | OR | 95% CI of OR | |
|---|---|---|---|---|---|---|---|
| 0 hours | 195907.81 | 75% | 37% | 1 | | | |
| | 126735.51 | 100% | 12% | 2 | 1.0 | 0.0 | 55.5 |
| | 126735.51 | 100% | 12% | 3 | 0.0 | 0.0 | na |
| | 308717.07 | 50% | 70% | 4 | 2.0 | 0.1 | 41.6 |
| | 377720.11 | 50% | 80% | | | | |
| | 474692.34 | 50% | 90% | | | | |
| 24 hours | 171458.56 | 74% | 30% | 1 | | | |
| | 146350.44 | 84% | 19% | 2 | 2.2 | 0.7 | 6.3 |
| | 132077.56 | 95% | 14% | 3 | 1.7 | 0.6 | 5.5 |
| | 308717.07 | 26% | 70% | 4 | 1.7 | 0.6 | 5.5 |
| | 377720.11 | 11% | 80% | | | | |
| | 474692.34 | 5% | 90% | | | | |
| 48 hours | 150554.2 | 77% | 23% | 1 | | | |
| | 132077.56 | 85% | 14% | 2 | 1.4 | 0.4 | 4.8 |
| | 126735.51 | 92% | 12% | 3 | 0.7 | 0.1 | 3.7 |
| | 308717.07 | 23% | 70% | 4 | 1.4 | 0.4 | 4.8 |
| | 377720.11 | 15% | 80% | | | | |
| | 474692.34 | 8% | 90% | | | | |

FIG. 6 - 6

Lactotransferrin sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 198.131 | na | 198.131 | 111.248 | 198.131 | 26.292 |
| average | 404.005 | na | 404.005 | 342.527 | 404.005 | 162.964 |
| stdev | 442.278 | na | 442.278 | 407.022 | 442.278 | na |
| p (t-test) |  | na |  | 0.655 |  | na |
| min | 26.292 | na | 26.292 | 61.643 | 26.292 | 162.964 |
| max | 1474.768 | na | 1474.768 | 1168.270 | 1474.768 | 162.964 |
| n (Samp) | 46 | 0 | 46 | 13 | 46 | 1 |
| n (Pat) | 43 | 0 | 43 | 13 | 43 | 1 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 175.697 | na | 175.697 | 76.002 | 175.697 | na |
| average | 385.110 | na | 385.110 | 492.010 | 385.110 | na |
| stdev | 430.316 | na | 430.316 | 721.300 | 430.316 | na |
| p (t-test) |  | na |  | 0.685 |  | na |
| min | 26.292 | na | 26.292 | 75.132 | 26.292 | na |
| max | 1474.768 | na | 1474.768 | 1324.895 | 1474.768 | na |
| n (Samp) | 58 | 0 | 58 | 3 | 58 | 0 |
| n (Pat) | 54 | 0 | 54 | 3 | 54 | 0 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 191.259 | na | 191.259 | 111.248 | 191.259 | 26.292 |
| average | 377.491 | na | 377.491 | 344.903 | 377.491 | 162.964 |
| stdev | 436.242 | na | 436.242 | 405.417 | 436.242 | na |
| p (t-test) |  | na |  | 0.813 |  | na |
| min | 26.292 | na | 26.292 | 61.643 | 26.292 | 162.964 |
| max | 1474.768 | na | 1474.768 | 1168.270 | 1474.768 | 162.964 |
| n (Samp) | 40 | 0 | 40 | 13 | 40 | 1 |
| n (Pat) | 37 | 0 | 37 | 13 | 37 | 1 | sCr or UO

| Time prior AKI stage | AUC | SE | nCohort 1 | nCohort 2 | p |
| --- | --- | --- | --- | --- | --- |
| 0 hours | nd | nd | 46 | 0 | nd |
| 24 hours | 0.43 | 0.088 | 46 | 13 | 0.430 |
| 48 hours | 0.43 | 0.280 | 46 | 1 | 0.816 | sCr only

| Time prior AKI stage | AUC | SE | nCohort 1 | nCohort 2 | p |
| --- | --- | --- | --- | --- | --- |
| 0 hours | nd | nd | 58 | 0 | nd |
| 24 hours | 0.42 | 0.161 | 58 | 3 | 0.618 |
| 48 hours | nd | nd | 58 | 0 | nd |

UO only

| Time prior AKI stage | AUC | SE | nCohort 1 | nCohort 2 | p |
| --- | --- | --- | --- | --- | --- |
| 0 hours | nd | nd | 40 | 0 | nd |
| 24 hours | 0.46 | 0.091 | 40 | 13 | 0.643 |
| 48 hours | 0.45 | 0.285 | 40 | 1 | 0.861 | sCr or UO

| Time prior AKI stage | Cutoff value | sens | spec | Quartile | OR | 95% CI of OR |
| --- | --- | --- | --- | --- | --- | --- |
| 0 hours | na | na | na | 1 |  |  |
|  | na | na | na | 2 | na | na na |
|  | na | na | na | 3 | na | na na |
|  | na | na | na | 4 | na | na na |
|  | na | na | na |  |  |  |
|  | na | na | na |  |  |  |

FIG. 6 - 7 sCr only

|  | | | | | | | |
|---|---|---|---|---|---|---|---|
| 24 hours | 90.361473 | 77% | 24% | 1 | | | |
| | 89.926346 | 85% | 24% | 2 | 0.3 | 0.0 | 5.3 |
| | 71.650992 | 92% | 17% | 3 | 2.7 | 0.7 | 10.4 |
| | 362.19409 | 31% | 72% | 4 | 1.1 | 0.2 | 5.7 |
| | 763.88186 | 23% | 80% | | | | |
| | 1214.8523 | 0% | 91% | | | | |
| 48 hours | 157.70947 | 100% | 43% | 1 | | | |
| | 157.70947 | 100% | 43% | 2 | na | na | na |
| | 157.70947 | 100% | 43% | 3 | na | na | na |
| | 362.19409 | 0% | 72% | 4 | na | na | na |
| | 763.88186 | 0% | 80% | | | | |
| | 1214.8523 | 0% | 91% | | | | |

UO only

| Time prior AKI stage | Cutoff value | sens | spec | Quartile | OR | 95% CI of OR | |
|---|---|---|---|---|---|---|---|
| 0 hours | na | na | na | 1 | | | |
| | na | na | na | 2 | na | na | na |
| | na | na | na | 3 | na | na | na |
| | na | na | na | 4 | na | na | na |
| | na | na | na | | | | |
| | na | na | na | | | | |
| 24 hours | 71.650992 | 100% | 16% | 1 | | | |
| | 71.650992 | 100% | 16% | 2 | 0.0 | 0.0 | na |
| | 71.650992 | 100% | 16% | 3 | 0.0 | 0.0 | na |
| | 360.84388 | 33% | 71% | 4 | 2.3 | 0.1 | 57.8 |
| | 763.88186 | 33% | 81% | | | | |
| | 1168.27 | 33% | 91% | | | | |
| 48 hours | na | na | na | 1 | | | |
| | na | na | na | 2 | na | na | na |
| | na | na | na | 3 | na | na | na |
| | na | na | na | 4 | na | na | na |
| | na | na | na | | | | |
| | na | na | na | | | | |

| Time prior AKI stage | Cutoff value | sens | spec | Quartile | OR | 95% CI of OR | |
|---|---|---|---|---|---|---|---|
| 0 hours | na | na | na | 1 | | | |
| | na | na | na | 2 | na | na | na |
| | na | na | na | 3 | na | na | na |
| | na | na | na | 4 | na | na | na |
| | na | na | na | | | | |
| | na | na | na | | | | |
| 24 hours | 94.27762 | 77% | 28% | 1 | | | |
| | 90.361473 | 85% | 28% | 2 | 0.2 | 0.0 | 3.5 |
| | 89.926346 | 92% | 28% | 3 | 2.1 | 0.6 | 7.8 |
| | 312.11789 | 31% | 70% | 4 | 0.5 | 0.1 | 2.9 |
| | 666.66667 | 23% | 80% | | | | |
| | 1214.8523 | 0% | 90% | | | | |
| 48 hours | 152.05053 | 100% | 45% | 1 | | | |
| | 152.05053 | 100% | 45% | 2 | na | na | na |
| | 152.05053 | 100% | 45% | 3 | na | na | na |
| | 312.11789 | 0% | 70% | 4 | na | na | na |
| | 666.66667 | 0% | 80% | | | | |
| | 1214.8523 | 0% | 90% | | | | |

FIG. 6 - 8

Prostatic Acid Phosphatase sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.167 | 0.184 | 0.167 | 0.247 | 0.167 | 0.252 |
| average | 0.383 | 0.460 | 0.383 | 0.404 | 0.383 | 0.950 |
| stdev | 2.325 | 1.108 | 2.325 | 0.456 | 2.325 | 2.303 |
| p (t-test) |  | 0.861 |  | 0.955 |  | 0.310 |
| min | 0.000 | 0.047 | 0.000 | 0.036 | 0.000 | 0.030 |
| max | 47.000 | 5.990 | 47.000 | 2.510 | 47.000 | 9.690 |
| n (Samp) | 434 | 28 | 434 | 36 | 434 | 18 |
| n (Pat) | 173 | 28 | 173 | 36 | 173 | 18 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.174 | 0.412 | 0.174 | 0.210 | 0.174 | 0.192 |
| average | 0.388 | 1.269 | 0.388 | 0.453 | 0.388 | 0.198 |
| stdev | 2.126 | 2.317 | 2.126 | 0.733 | 2.126 | 0.116 |
| p (t-test) |  | 0.313 |  | 0.923 |  | 0.814 |
| min | 0.000 | 0.080 | 0.000 | 0.084 | 0.000 | 0.076 |
| max | 47.000 | 5.990 | 47.000 | 2.510 | 47.000 | 0.384 |
| n (Samp) | 542 | 6 | 542 | 10 | 542 | 7 |
| n (Pat) | 208 | 6 | 208 | 10 | 208 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.167 | 0.173 | 0.167 | 0.278 | 0.167 | 0.280 |
| average | 0.420 | 0.264 | 0.420 | 0.487 | 0.420 | 1.542 |
| stdev | 2.565 | 0.252 | 2.565 | 0.737 | 2.565 | 2.711 |
| p (t-test) |  | 0.753 |  | 0.882 |  | 0.089 |
| min | 0.000 | 0.047 | 0.000 | 0.036 | 0.000 | 0.030 |
| max | 47.000 | 1.180 | 47.000 | 4.210 | 47.000 | 9.690 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.56 | 0.058 | 434 | 28 | 0.315 |
| 24 hours | 0.65 | 0.051 | 434 | 36 | 0.003 |
| 48 hours | 0.63 | 0.072 | 434 | 18 | 0.067 | sCr only

| Time prior AKI stage | AUC | SE | nCohort 1 | nCohort 2 | p |
|---|---|---|---|---|---|
| 0 hours | 0.75 | 0.116 | 542 | 6 | 0.029 |
| 24 hours | 0.59 | 0.095 | 542 | 10 | 0.364 |
| 48 hours | 0.49 | 0.109 | 542 | 7 | 0.951 |

UO only

| Time prior AKI stage | AUC | SE | nCohort 1 | nCohort 2 | p |
|---|---|---|---|---|---|
| 0 hours | 0.54 | 0.059 | 356 | 27 | 0.535 |
| 24 hours | 0.68 | 0.054 | 356 | 32 | 0.001 |
| 48 hours | 0.68 | 0.075 | 356 | 16 | 0.017 | sCr or UO

| Time prior AKI stage | Cutoff value | sens | spec | Quartile | OR | 95% CI of OR | |
|---|---|---|---|---|---|---|---|
| 0 hours | 0.14 | 71% | 36% | 1 |  |  |  |
|  | 0.0896 | 82% | 18% | 2 | 1.0 | 0.5 | 2.0 |
|  | 0.0568 | 93% | 6% | 3 | 0.8 | 0.4 | 1.8 |
|  | 0.224 | 43% | 70% | 4 | 1.9 | 1.1 | 3.3 |
|  | 0.283 | 36% | 80% |  |  |  |  |
|  | 0.409 | 18% | 90% |  |  |  |  |

FIG. 6 - 9

| | Time prior AKI stage | Cutoff value | sens | spec | Quartile | OR | 95% CI of OR | |
|---|---|---|---|---|---|---|---|---|
| | 24 hours | 0.16 | 72% | 48% | 1 | | | |
| | | 0.141 | 81% | 38% | 2 | 0.8 | 0.4 | 1.7 |
| | | 0.0751 | 92% | 13% | 3 | 1.4 | 0.7 | 2.5 |
| | | 0.224 | 61% | 70% | 4 | 3.1 | 1.9 | 5.0 |
| | | 0.283 | 42% | 80% | | | | |
| | | 0.409 | 28% | 90% | | | | |
| | 48 hours | 0.191 | 72% | 58% | 1 | | | |
| | | 0.118 | 83% | 29% | 2 | 0.7 | 0.1 | 3.5 |
| | | 0.041 | 94% | 2% | 3 | 1.3 | 0.4 | 4.4 |
| | | 0.224 | 56% | 70% | 4 | 3.2 | 1.3 | 7.9 |
| | | 0.283 | 39% | 80% | | | | |
| | | 0.409 | 17% | 90% | | | | | sCr only

| Time prior AKI stage | Cutoff value | sens | spec | Quartile | OR | 95% CI of OR | |
|---|---|---|---|---|---|---|---|
| 0 hours | 0.262 | 83% | 74% | 1 | | | |
| | 0.262 | 83% | 74% | 2 | 0.0 | 0.0 | na |
| | 0.0795 | 100% | 14% | 3 | 1.0 | 0.0 | 51.9 |
| | 0.243 | 83% | 70% | 4 | 4.1 | 0.3 | 48.8 |
| | 0.313 | 67% | 80% | | | | |
| | 0.465 | 17% | 90% | | | | |
| 24 hours | 0.181 | 70% | 51% | 1 | | | |
| | 0.126 | 80% | 29% | 2 | 0.5 | 0.0 | 9.7 |
| | 0.0964 | 90% | 20% | 3 | 2.0 | 0.5 | 9.1 |
| | 0.243 | 40% | 70% | 4 | 1.5 | 0.3 | 8.0 |
| | 0.313 | 30% | 80% | | | | |
| | 0.465 | 20% | 90% | | | | |
| 48 hours | 0.105 | 71% | 24% | 1 | | | |
| | 0.0884 | 86% | 16% | 2 | 1.0 | 0.1 | 7.4 |
| | 0.0751 | 100% | 13% | 3 | 0.0 | 0.0 | na |
| | 0.243 | 43% | 70% | 4 | 1.5 | 0.3 | 8.0 |
| | 0.313 | 14% | 80% | | | | |
| | 0.465 | 0% | 90% | | | | |

UO only

| Time prior AKI stage | Cutoff value | sens | spec | Quartile | OR | 95% CI of OR | |
|---|---|---|---|---|---|---|---|
| 0 hours | 0.14 | 70% | 37% | 1 | | | |
| | 0.0896 | 81% | 18% | 2 | 1.0 | 0.5 | 2.0 |
| | 0.0568 | 93% | 6% | 3 | 1.0 | 0.5 | 2.0 |
| | 0.225 | 41% | 70% | 4 | 1.5 | 0.9 | 2.8 |
| | 0.283 | 30% | 80% | | | | |
| | 0.409 | 15% | 90% | | | | |
| 24 hours | 0.204 | 72% | 63% | 1 | | | |
| | 0.149 | 81% | 42% | 2 | 0.8 | 0.3 | 2.0 |
| | 0.0751 | 91% | 13% | 3 | 1.2 | 0.6 | 2.6 |
| | 0.225 | 63% | 70% | 4 | 3.9 | 2.2 | 6.8 |
| | 0.283 | 47% | 80% | | | | |
| | 0.409 | 31% | 90% | | | | |
| 48 hours | 0.196 | 75% | 61% | 1 | | | |
| | 0.131 | 81% | 34% | 2 | 1.0 | 0.1 | 7.4 |
| | 0.041 | 94% | 2% | 3 | 1.5 | 0.3 | 8.1 |
| | 0.225 | 63% | 70% | 4 | 4.9 | 1.4 | 16.9 |
| | 0.283 | 50% | 80% | | | | |
| | 0.409 | 31% | 90% | | | | |

FIG. 6 - 10 von Willebrand Factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 93.350 | 98.950 | 93.350 | 106.000 | 93.350 | 114.000 |
| average | 99.462 | 107.729 | 99.462 | 124.542 | 99.462 | 113.367 |
| stdev | 36.124 | 40.861 | 36.124 | 63.075 | 36.124 | 48.944 |
| p (t-test) |  | 0.245 |  | 0.000 |  | 0.116 |
| min | 25.000 | 36.800 | 25.000 | 34.300 | 25.000 | 15.600 |
| max | 278.000 | 195.000 | 278.000 | 328.000 | 278.000 | 201.000 |
| n (Samp) | 434 | 28 | 434 | 36 | 434 | 18 |
| n (Pat) | 173 | 28 | 173 | 36 | 173 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 93.350 | 117.500 | 93.350 | 161.000 | 93.350 | 143.000 |
| average | 100.001 | 121.850 | 100.001 | 145.500 | 100.001 | 136.257 |
| stdev | 39.553 | 26.303 | 39.553 | 41.513 | 39.553 | 43.024 |
| p (t-test) |  | 0.178 |  | 0.000 |  | 0.016 |
| min | 15.600 | 94.100 | 15.600 | 59.600 | 15.600 | 83.800 |
| max | 328.000 | 166.000 | 328.000 | 195.000 | 328.000 | 194.000 |
| n (Samp) | 542 | 6 | 542 | 10 | 542 | 7 |
| n (Pat) | 208 | 6 | 208 | 10 | 208 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 93.900 | 97.900 | 93.900 | 98.650 | 93.900 | 105.500 |
| average | 98.210 | 107.078 | 98.210 | 121.256 | 98.210 | 109.269 |
| stdev | 33.015 | 41.446 | 33.015 | 64.423 | 33.015 | 49.003 |
| p (t-test) |  | 0.188 |  | 0.001 |  | 0.201 |
| min | 25.000 | 36.800 | 25.000 | 34.300 | 25.000 | 15.600 |
| max | 240.000 | 195.000 | 240.000 | 328.000 | 240.000 | 201.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
| --- | --- | --- | --- | --- | --- |
| 0 hours | 0.57 | 0.058 | 434 | 28 | 0.235 |
| 24 hours | 0.60 | 0.052 | 434 | 36 | 0.045 |
| 48 hours | 0.60 | 0.072 | 434 | 18 | 0.149 | sCr only

| Time prior AKI stage | AUC | SE | nCohort 1 | nCohort 2 | p |
| --- | --- | --- | --- | --- | --- |
| 0 hours | 0.73 | 0.118 | 542 | 6 | 0.051 |
| 24 hours | 0.80 | 0.085 | 542 | 10 | 0.001 |
| 48 hours | 0.74 | 0.108 | 542 | 7 | 0.023 |

UO only

| Time prior AKI stage | AUC | SE | nCohort 1 | nCohort 2 | p |
| --- | --- | --- | --- | --- | --- |
| 0 hours | 0.56 | 0.059 | 356 | 27 | 0.287 |
| 24 hours | 0.58 | 0.055 | 356 | 32 | 0.136 |
| 48 hours | 0.58 | 0.076 | 356 | 16 | 0.277 | sCr or UO

| Time prior AKI stage | Cutoff value | sens | spec | Quartile | OR | 95% CI of OR | |
| --- | --- | --- | --- | --- | --- | --- | --- |
| 0 hours | 90.5 | 71% | 47% | 1 |  |  |  |
|  | 76.3 | 82% | 29% | 2 | 1.8 | 0.8 | 4.0 |
|  | 58.5 | 93% | 8% | 3 | 2.1 | 1.0 | 4.5 |
|  | 112 | 32% | 71% | 4 | 2.3 | 1.1 | 4.9 |
|  | 123 | 25% | 80% |  |  |  |  |
|  | 148 | 18% | 90% |  |  |  |  |

FIG. 6 - 11

| | Time prior AKI stage | Cutoff value | sens | spec | Quartile | OR | 95% CI of OR | |
|---|---|---|---|---|---|---|---|---|
| | 24 hours | 85.4 | 72% | 40% | 1 | | | |
| | | 71.7 | 81% | 22% | 2 | 0.7 | 0.4 | 1.3 |
| | | 60.9 | 92% | 9% | 3 | 0.9 | 0.5 | 1.5 |
| | | 112 | 47% | 71% | 4 | 2.0 | 1.3 | 3.0 |
| | | 123 | 39% | 80% | | | | |
| | | 148 | 28% | 90% | | | | |
| | 48 hours | 86.9 | 72% | 41% | 1 | | | |
| | | 73 | 83% | 24% | 2 | 0.7 | 0.2 | 2.4 |
| | | 47 | 94% | 3% | 3 | 0.5 | 0.1 | 2.2 |
| | | 112 | 50% | 71% | 4 | 2.4 | 1.1 | 5.0 |
| | | 123 | 39% | 80% | | | | |
| | | 148 | 22% | 90% | | | | | sCr only

| Time prior AKI stage | Cutoff value | sens | spec | Quartile | OR | 95% CI of OR | |
|---|---|---|---|---|---|---|---|
| 0 hours | 99.9 | 83% | 58% | 1 | | | |
| | 99.9 | 83% | 58% | 2 | na | na | na |
| | 93.7 | 100% | 51% | 3 | na | na | na |
| | 112 | 67% | 71% | 4 | na | na | na |
| | 123 | 33% | 80% | | | | |
| | 149 | 17% | 90% | | | | |
| 24 hours | 142 | 70% | 88% | 1 | | | |
| | 124 | 80% | 81% | 2 | 0.0 | 0.0 | na |
| | 94.3 | 90% | 51% | 3 | 1.0 | 0.0 | 51.9 |
| | 112 | 80% | 71% | 4 | 8.4 | 0.9 | 78.7 |
| | 123 | 80% | 80% | | | | |
| | 149 | 60% | 90% | | | | |
| 48 hours | 109 | 71% | 68% | 1 | | | |
| | 87.9 | 86% | 43% | 2 | na | na | na |
| | 83.5 | 100% | 37% | 3 | na | na | na |
| | 112 | 57% | 71% | 4 | na | na | na |
| | 123 | 57% | 80% | | | | |
| | 149 | 43% | 90% | | | | |

UO only

| Time prior AKI stage | Cutoff value | sens | spec | Quartile | OR | 95% CI of OR | |
|---|---|---|---|---|---|---|---|
| 0 hours | 87.7 | 70% | 42% | 1 | | | |
| | 75.8 | 81% | 28% | 2 | 1.4 | 0.7 | 2.9 |
| | 58.5 | 93% | 8% | 3 | 1.4 | 0.7 | 2.9 |
| | 111 | 33% | 71% | 4 | 1.6 | 0.8 | 3.2 |
| | 121 | 26% | 81% | | | | |
| | 145 | 19% | 90% | | | | |
| 24 hours | 85.4 | 72% | 40% | 1 | | | |
| | 71.6 | 81% | 21% | 2 | 1.0 | 0.5 | 1.8 |
| | 63.6 | 91% | 12% | 3 | 0.7 | 0.3 | 1.4 |
| | 111 | 41% | 71% | 4 | 2.0 | 1.2 | 3.2 |
| | 121 | 31% | 81% | | | | |
| | 145 | 22% | 90% | | | | |
| 48 hours | 86.9 | 75% | 40% | 1 | | | |
| | 73 | 81% | 22% | 2 | 0.5 | 0.1 | 2.2 |
| | 47 | 94% | 3% | 3 | 0.7 | 0.2 | 2.4 |
| | 111 | 44% | 71% | 4 | 1.8 | 0.8 | 4.1 |
| | 121 | 38% | 81% | | | | |
| | 145 | 19% | 90% | | | | |

FIG. 6 - 12

Endothelial protein C receptor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 348.048 | 246.289 | 348.048 | 246.289 | 348.048 | 246.289 |
| average | 388.855 | 259.168 | 388.855 | 259.168 | 388.855 | 259.168 |
| stdev | 224.593 | 172.646 | 224.593 | 172.646 | 224.593 | 172.646 |
| p (t-test) |  | 0.038 |  | 0.038 |  | 0.038 |
| min | 50.726 | 18.516 | 50.726 | 18.516 | 50.726 | 18.516 |
| max | 1427.189 | 575.377 | 1427.189 | 575.377 | 1427.189 | 575.377 |
| n (Samp) | 52 | 16 | 52 | 16 | 52 | 16 |
| n (Pat) | 52 | 16 | 52 | 16 | 52 | 16 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 324.133 | 242.021 | 324.133 | 242.021 | 324.133 | 242.021 |
| average | 431.867 | 242.021 | 431.867 | 242.021 | 431.867 | 242.021 |
| stdev | 320.686 | 27.382 | 320.686 | 27.382 | 320.686 | 27.382 |
| p (t-test) |  | 0.423 |  | 0.423 |  | 0.423 |
| min | 50.726 | 222.660 | 50.726 | 222.660 | 50.726 | 222.660 |
| max | 1427.189 | 261.383 | 1427.189 | 261.383 | 1427.189 | 261.383 |
| n (Samp) | 19 | 2 | 19 | 2 | 19 | 2 |
| n (Pat) | 19 | 2 | 19 | 2 | 19 | 2 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 343.612 | 218.056 | 343.612 | 218.056 | 343.612 | 218.056 |
| average | 350.231 | 238.936 | 350.231 | 238.936 | 350.231 | 238.936 |
| stdev | 152.796 | 162.756 | 152.796 | 162.756 | 152.796 | 162.756 |
| p (t-test) |  | 0.028 |  | 0.028 |  | 0.028 |
| min | 50.726 | 18.516 | 50.726 | 18.516 | 50.726 | 18.516 |
| max | 754.335 | 492.312 | 754.335 | 492.312 | 754.335 | 492.312 |
| n (Samp) | 41 | 13 | 41 | 13 | 41 | 13 |
| n (Pat) | 41 | 13 | 41 | 13 | 41 | 13 | sCr or UO

| Time prior AKI stage | AUC | SE | nCohort 1 | nCohort 2 | p |
| --- | --- | --- | --- | --- | --- |
| 0 hours | 0.31 | 0.071 | 52 | 16 | 0.009 |
| 24 hours | 0.31 | 0.071 | 52 | 16 | 0.009 |
| 48 hours | 0.31 | 0.071 | 52 | 16 | 0.009 | sCr only

| Time prior AKI stage | AUC | SE | nCohort 1 | nCohort 2 | p |
| --- | --- | --- | --- | --- | --- |
| 0 hours | 0.21 | 0.141 | 19 | 2 | 0.041 |
| 24 hours | 0.21 | 0.141 | 19 | 2 | 0.041 |
| 48 hours | 0.21 | 0.141 | 19 | 2 | 0.041 |

UO only

| Time prior AKI stage | AUC | SE | nCohort 1 | nCohort 2 | p |
| --- | --- | --- | --- | --- | --- |
| 0 hours | 0.30 | 0.078 | 41 | 13 | 0.012 |
| 24 hours | 0.30 | 0.078 | 41 | 13 | 0.012 |
| 48 hours | 0.30 | 0.078 | 41 | 13 | 0.012 | sCr or UO

| Time prior AKI stage | Cutoff value | sens | spec | Quartile | OR | 95% CI of OR | |
| --- | --- | --- | --- | --- | --- | --- | --- |
| 0 hours | 109.61364 | 75% | 4% | 1 |  |  |  |
|  | 101.34091 | 81% | 4% | 2 | 0.6 | 0.1 | 4.2 |
|  | 71.368243 | 94% | 4% | 3 | 1.0 | 0.2 | 4.9 |
|  | 426.46753 | 25% | 71% | 4 | 4.1 | 1.2 | 14.6 |

FIG. 7 - 1

|  | | Cutoff value | sens | spec | Quartile | OR | 95% CI of OR | |
|---|---|---|---|---|---|---|---|---|
| | | 514.5974 | 6% | 81% | | | | |
| | | 607.39355 | 0% | 90% | | | | |
| | 24 hours | 109.61364 | 75% | 4% | 1 | | | |
| | | 101.34091 | 81% | 4% | 2 | 0.6 | 0.1 | 4.2 |
| | | 71.368243 | 94% | 4% | 3 | 1.0 | 0.2 | 4.9 |
| | | 426.46753 | 25% | 71% | 4 | 4.1 | 1.2 | 14.6 |
| | | 514.5974 | 6% | 81% | | | | |
| | | 607.39355 | 0% | 90% | | | | |
| | 48 hours | 109.61364 | 75% | 4% | 1 | | | |
| | | 101.34091 | 81% | 4% | 2 | 0.6 | 0.1 | 4.2 |
| | | 71.368243 | 94% | 4% | 3 | 1.0 | 0.2 | 4.9 |
| | | 426.46753 | 25% | 71% | 4 | 4.1 | 1.2 | 14.6 |
| | | 514.5974 | 6% | 81% | | | | |
| | | 607.39355 | 0% | 90% | | | | |

UO only

| Time prior AKI stage | Cutoff value | sens | spec | Quartile | OR | 95% CI of OR | |
|---|---|---|---|---|---|---|---|
| 0 hours | 101.34091 | 77% | 5% | 1 | | | |
| | 77.077703 | 85% | 5% | 2 | 0.3 | 0.0 | 5.9 |
| | 71.368243 | 92% | 5% | 3 | 1.0 | 0.2 | 5.3 |
| | 417.35065 | 23% | 71% | 4 | 3.1 | 0.7 | 13.2 |
| | 482.58537 | 8% | 80% | | | | |
| | 544.98701 | 0% | 93% | | | | |
| 24 hours | 101.34091 | 77% | 5% | 1 | | | |
| | 77.077703 | 85% | 5% | 2 | 0.3 | 0.0 | 5.9 |
| | 71.368243 | 92% | 5% | 3 | 1.0 | 0.2 | 5.3 |
| | 417.35065 | 23% | 71% | 4 | 3.1 | 0.7 | 13.2 |
| | 482.58537 | 8% | 80% | | | | |
| | 544.98701 | 0% | 93% | | | | |
| 48 hours | 101.34091 | 77% | 5% | 1 | | | |
| | 77.077703 | 85% | 5% | 2 | 0.3 | 0.0 | 5.9 |
| | 71.368243 | 92% | 5% | 3 | 1.0 | 0.2 | 5.3 |
| | 417.35065 | 23% | 71% | 4 | 3.1 | 0.7 | 13.2 |
| | 482.58537 | 8% | 80% | | | | |
| | 544.98701 | 0% | 93% | | | | |

FIG. 7 - 2

Erythropoietin receptor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 242.647 | 254.240 | 242.647 | 254.240 | 242.647 | 254.240 |
| average | 838.906 | 1290.891 | 838.906 | 1290.891 | 838.906 | 1290.891 |
| stdev | 1460.675 | 1710.982 | 1460.675 | 1710.982 | 1460.675 | 1710.982 |
| p (t-test) |  | 0.517 |  | 0.517 |  | 0.517 |
| min | 9.259 | 126.953 | 9.259 | 126.953 | 9.259 | 126.953 |
| max | 6961.570 | 3753.930 | 6961.570 | 3753.930 | 6961.570 | 3753.930 |
| n (Samp) | 24 | 6 | 24 | 6 | 24 | 6 |
| n (Pat) | 24 | 6 | 24 | 6 | 24 | 6 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 450.790 | na | 450.790 | na | 450.790 | na |
| average | 1569.698 | na | 1569.698 | na | 1569.698 | na |
| stdev | 2215.935 | na | 2215.935 | na | 2215.935 | na |
| p (t-test) |  | na |  | na |  | na |
| min | 27.778 | na | 27.778 | na | 27.778 | na |
| max | 6961.570 | na | 6961.570 | na | 6961.570 | na |
| n (Samp) | 10 | 0 | 10 | 0 | 10 | 0 |
| n (Pat) | 10 | 0 | 10 | 0 | 10 | 0 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 236.328 | 177.734 | 236.328 | 177.734 | 236.328 | 177.734 |
| average | 775.297 | 905.079 | 775.297 | 905.079 | 775.297 | 905.079 |
| stdev | 1310.562 | 1594.660 | 1310.562 | 1594.660 | 1310.562 | 1594.660 |
| p (t-test) |  | 0.854 |  | 0.854 |  | 0.854 |
| min | 9.259 | 126.953 | 9.259 | 126.953 | 9.259 | 126.953 |
| max | 5495.557 | 3753.930 | 5495.557 | 3753.930 | 5495.557 | 3753.930 |
| n (Samp) | 17 | 5 | 17 | 5 | 17 | 5 |
| n (Pat) | 17 | 5 | 17 | 5 | 17 | 5 | sCr or UO

| Time prior AKI stage | AUC | SE | nCohort 1 | nCohort 2 | p |
| --- | --- | --- | --- | --- | --- |
| 0 hours | 0.53 | 0.135 | 24 | 6 | 0.837 |
| 24 hours | 0.53 | 0.135 | 24 | 6 | 0.837 |
| 48 hours | 0.53 | 0.135 | 24 | 6 | 0.837 | sCr only

| Time prior AKI stage | AUC | SE | nCohort 1 | nCohort 2 | p |
| --- | --- | --- | --- | --- | --- |
| 0 hours | nd | nd | 10 | 0 | nd |
| 24 hours | nd | nd | 10 | 0 | nd |
| 48 hours | nd | nd | 10 | 0 | nd |

UO only

| Time prior AKI stage | AUC | SE | nCohort 1 | nCohort 2 | p |
| --- | --- | --- | --- | --- | --- |
| 0 hours | 0.42 | 0.144 | 17 | 5 | 0.595 |
| 24 hours | 0.42 | 0.144 | 17 | 5 | 0.595 |
| 48 hours | 0.42 | 0.144 | 17 | 5 | 0.595 | sCr or UO

| Time prior AKI stage | Cutoff value | sens | spec | Quartile | OR | 95% CI of OR | |
| --- | --- | --- | --- | --- | --- | --- | --- |
| 0 hours | 126.95313 | 83% | 17% | 1 |  |  |  |
|  | 126.95313 | 83% | 17% | 2 | 0.4 | 0.0 | 13.2 |
|  | 125 | 100% | 17% | 3 | 0.4 | 0.0 | 16.2 |
|  | 634.93976 | 33% | 71% | 4 | 0.8 | 0.1 | 12.1 |
|  | 1406.7278 | 33% | 83% |  |  |  |  |
|  | 1714.1026 | 33% | 92% |  |  |  |  |
| 24 hours | 126.95313 | 83% | 17% | 1 |  |  |  |

FIG. 7 - 3

|  |  | Cutoff value | sens | spec | Quartile | OR | 95% CI of OR | |
|---|---|---|---|---|---|---|---|---|
|  |  | 126.95313 | 83% | 17% | 2 | 0.4 | 0.0 | 13.2 |
|  |  | 125 | 100% | 17% | 3 | 0.4 | 0.0 | 16.2 |
|  |  | 634.93976 | 33% | 71% | 4 | 0.8 | 0.1 | 12.1 |
|  |  | 1406.7278 | 33% | 83% |  |  |  |  |
|  |  | 1714.1026 | 33% | 92% |  |  |  |  |
|  | 48 hours | 126.95313 | 83% | 17% | 1 |  |  |  |
|  |  | 126.95313 | 83% | 17% | 2 | 0.4 | 0.0 | 13.2 |
|  |  | 125 | 100% | 17% | 3 | 0.4 | 0.0 | 16.2 |
|  |  | 634.93976 | 33% | 71% | 4 | 0.8 | 0.1 | 12.1 |
|  |  | 1406.7278 | 33% | 83% |  |  |  |  |
|  |  | 1714.1026 | 33% | 92% |  |  |  |  |

UO only

| Time prior AKI stage | Cutoff value | sens | spec | Quartile | OR | 95% CI of OR | |
|---|---|---|---|---|---|---|---|
| 0 hours | 126.95313 | 80% | 12% | 1 |  |  |  |
|  | 126.95313 | 80% | 12% | 2 | 1.3 | 0.0 | 152.2 |
|  | 125 | 100% | 12% | 3 | 1.0 | 0.0 | 110.4 |
|  | 634.93976 | 20% | 71% | 4 | 3.3 | 0.1 | 179.3 |
|  | 1065.3846 | 20% | 82% |  |  |  |  |
|  | 1714.1026 | 20% | 94% |  |  |  |  |
| 24 hours | 126.95313 | 80% | 12% | 1 |  |  |  |
|  | 126.95313 | 80% | 12% | 2 | 1.3 | 0.0 | 152.2 |
|  | 125 | 100% | 12% | 3 | 1.0 | 0.0 | 110.4 |
|  | 634.93976 | 20% | 71% | 4 | 3.3 | 0.1 | 179.3 |
|  | 1065.3846 | 20% | 82% |  |  |  |  |
|  | 1714.1026 | 20% | 94% |  |  |  |  |
| 48 hours | 126.95313 | 80% | 12% | 1 |  |  |  |
|  | 126.95313 | 80% | 12% | 2 | 1.3 | 0.0 | 152.2 |
|  | 125 | 100% | 12% | 3 | 1.0 | 0.0 | 110.4 |
|  | 634.93976 | 20% | 71% | 4 | 3.3 | 0.1 | 179.3 |
|  | 1065.3846 | 20% | 82% |  |  |  |  |
|  | 1714.1026 | 20% | 94% |  |  |  |  |

FIG. 7 - 4

Lactotransferrin sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 237.743 | 111.248 | 237.743 | 111.248 | 237.743 | 111.248 |
| average | 306.729 | 310.281 | 306.729 | 310.281 | 306.729 | 310.281 |
| stdev | 249.940 | 403.603 | 249.940 | 403.603 | 249.940 | 403.603 |
| p (t-test) |  | 0.985 |  | 0.985 |  | 0.985 |
| min | 68.170 | 69.910 | 68.170 | 69.910 | 68.170 | 69.910 |
| max | 828.017 | 1168.270 | 828.017 | 1168.270 | 828.017 | 1168.270 |
| n (Samp) | 7 | 7 | 7 | 7 | 7 | 7 |
| n (Pat) | 7 | 7 | 7 | 7 | 7 | 7 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 212.278 | na | 212.278 | na | 212.278 | na |
| average | 224.909 | na | 224.909 | na | 224.909 | na |
| stdev | 65.976 | na | 65.976 | na | 65.976 | na |
| p (t-test) |  | na |  | na |  | na |
| min | 162.964 | na | 162.964 | na | 162.964 | na |
| max | 312.118 | na | 312.118 | na | 312.118 | na |
| n (Samp) | 4 | 0 | 4 | 0 | 4 | 0 |
| n (Pat) | 4 | 0 | 4 | 0 | 4 | 0 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 186.813 | 102.763 | 186.813 | 102.763 | 186.813 | 102.763 |
| average | 319.449 | 334.834 | 319.449 | 334.834 | 319.449 | 334.834 |
| stdev | 303.819 | 436.361 | 303.819 | 436.361 | 303.819 | 436.361 |
| p (t-test) |  | 0.949 |  | 0.949 |  | 0.949 |
| min | 68.170 | 69.910 | 68.170 | 69.910 | 68.170 | 69.910 |
| max | 828.017 | 1168.270 | 828.017 | 1168.270 | 828.017 | 1168.270 |
| n (Samp) | 5 | 6 | 5 | 6 | 5 | 6 |
| n (Pat) | 5 | 6 | 5 | 6 | 5 | 6 | sCr or UO

| Time prior AKI stage | AUC | SE | nCohort 1 | nCohort 2 | p |
| --- | --- | --- | --- | --- | --- |
| 0 hours | 0.39 | 0.155 | 7 | 7 | 0.469 |
| 24 hours | 0.39 | 0.155 | 7 | 7 | 0.469 |
| 48 hours | 0.39 | 0.155 | 7 | 7 | 0.469 | sCr only

| Time prior AKI stage | AUC | SE | nCohort 1 | nCohort 2 | p |
| --- | --- | --- | --- | --- | --- |
| 0 hours | nd | nd | 4 | 0 | nd |
| 24 hours | nd | nd | 4 | 0 | nd |
| 48 hours | nd | nd | 4 | 0 | nd |

UO only

| Time prior AKI stage | AUC | SE | nCohort 1 | nCohort 2 | p |
| --- | --- | --- | --- | --- | --- |
| 0 hours | 0.43 | 0.181 | 5 | 6 | 0.713 |
| 24 hours | 0.43 | 0.181 | 5 | 6 | 0.713 |
| 48 hours | 0.43 | 0.181 | 5 | 6 | 0.713 | sCr or UO

| Time prior AKI stage | Cutoff value | sens | spec | Quartile | OR | 95% CI of OR | |
| --- | --- | --- | --- | --- | --- | --- | --- |
| 0 hours | 90.361473 | 71% | 14% | 1 |  |  |  |
|  | 69.910482 | 86% | 14% | 2 | 0.0 | 0.0 | na |
|  | 68.169972 | 100% | 14% | 3 | 3.0 | 0.0 | 290.6 |
|  | 312.11789 | 29% | 71% | 4 | 2.0 | 0.0 | 268.6 |
|  | 362.19409 | 29% | 86% |  |  |  |  |
|  | 828.01688 | 14% | 100% |  |  |  |  |

FIG. 7 - 5

|  | | Cutoff value | sens | spec | Quartile | OR | 95% CI of OR | |
|---|---|---|---|---|---|---|---|---|
|  | 24 hours | 90.361473 | 71% | 14% | 1 | | | |
|  | | 69.910482 | 86% | 14% | 2 | 0.0 | 0.0 | na |
|  | | 68.169972 | 100% | 14% | 3 | 3.0 | 0.0 | 290.6 |
|  | | 312.11789 | 29% | 71% | 4 | 2.0 | 0.0 | 268.6 |
|  | | 362.19409 | 29% | 86% | | | | |
|  | | 828.01688 | 14% | 100% | | | | |
|  | 48 hours | 90.361473 | 71% | 14% | 1 | | | |
|  | | 69.910482 | 86% | 14% | 2 | 0.0 | 0.0 | na |
|  | | 68.169972 | 100% | 14% | 3 | 3.0 | 0.0 | 290.6 |
|  | | 312.11789 | 29% | 71% | 4 | 2.0 | 0.0 | 268.6 |
|  | | 362.19409 | 29% | 86% | | | | |
|  | | 828.01688 | 14% | 100% | | | | |

UO only

| Time prior AKI stage | Cutoff value | sens | spec | Quartile | OR | 95% CI of OR | |
|---|---|---|---|---|---|---|---|
| 0 hours | 69.910482 | 83% | 20% | 1 | | | |
| | 69.910482 | 83% | 20% | 2 | 0.0 | 0.0 | na |
| | 68.169972 | 100% | 20% | 3 | na | na | na |
| | 362.19409 | 33% | 80% | 4 | 0.5 | 0.0 | 476.7 |
| | 362.19409 | 33% | 80% | | | | |
| | 828.01688 | 17% | 100% | | | | |
| 24 hours | 69.910482 | 83% | 20% | 1 | | | |
| | 69.910482 | 83% | 20% | 2 | 0.0 | 0.0 | na |
| | 68.169972 | 100% | 20% | 3 | na | na | na |
| | 362.19409 | 33% | 80% | 4 | 0.5 | 0.0 | 476.7 |
| | 362.19409 | 33% | 80% | | | | |
| | 828.01688 | 17% | 100% | | | | |
| 48 hours | 69.910482 | 83% | 20% | 1 | | | |
| | 69.910482 | 83% | 20% | 2 | 0.0 | 0.0 | na |
| | 68.169972 | 100% | 20% | 3 | na | na | na |
| | 362.19409 | 33% | 80% | 4 | 0.5 | 0.0 | 476.7 |
| | 362.19409 | 33% | 80% | | | | |
| | 828.01688 | 17% | 100% | | | | |

FIG. 7 - 6

Prostatic Acid Phosphatase sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.173 | 0.250 | 0.173 | 0.250 | 0.173 | 0.250 |
| average | 0.268 | 0.895 | 0.268 | 0.895 | 0.268 | 0.895 |
| stdev | 0.421 | 2.083 | 0.421 | 2.083 | 0.421 | 2.083 |
| p (t-test) |  | 0.034 |  | 0.034 |  | 0.034 |
| min | 0.037 | 0.041 | 0.037 | 0.041 | 0.037 | 0.041 |
| max | 2.470 | 9.690 | 2.470 | 9.690 | 2.470 | 9.690 |
| n (Samp) | 56 | 21 | 56 | 21 | 56 | 21 |
| n (Pat) | 56 | 21 | 56 | 21 | 56 | 21 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.173 | 0.265 | 0.173 | 0.265 | 0.173 | 0.265 |
| average | 0.664 | 0.714 | 0.664 | 0.714 | 0.664 | 0.714 |
| stdev | 2.082 | 1.004 | 2.082 | 1.004 | 2.082 | 1.004 |
| p (t-test) |  | 0.959 |  | 0.959 |  | 0.959 |
| min | 0.041 | 0.234 | 0.041 | 0.234 | 0.041 | 0.234 |
| max | 9.690 | 2.510 | 9.690 | 2.510 | 9.690 | 2.510 |
| n (Samp) | 21 | 5 | 21 | 5 | 21 | 5 |
| n (Pat) | 21 | 5 | 21 | 5 | 21 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.177 | 0.319 | 0.177 | 0.319 | 0.177 | 0.319 |
| average | 0.276 | 0.387 | 0.276 | 0.387 | 0.276 | 0.387 |
| stdev | 0.438 | 0.246 | 0.438 | 0.246 | 0.438 | 0.246 |
| p (t-test) |  | 0.328 |  | 0.328 |  | 0.328 |
| min | 0.037 | 0.041 | 0.037 | 0.041 | 0.037 | 0.041 |
| max | 2.470 | 0.885 | 2.470 | 0.885 | 2.470 | 0.885 |
| n (Samp) | 46 | 17 | 46 | 17 | 46 | 17 |
| n (Pat) | 46 | 17 | 46 | 17 | 46 | 17 | sCr or UO

| Time prior AKI stage | AUC | SE | nCohort 1 | nCohort 2 | p |
|---|---|---|---|---|---|
| 0 hours | 0.72 | 0.070 | 56 | 21 | 0.002 |
| 24 hours | 0.72 | 0.070 | 56 | 21 | 0.002 |
| 48 hours | 0.72 | 0.070 | 56 | 21 | 0.002 | sCr only

| Time prior AKI stage | AUC | SE | nCohort 1 | nCohort 2 | p |
|---|---|---|---|---|---|
| 0 hours | 0.85 | 0.115 | 21 | 5 | 0.002 |
| 24 hours | 0.85 | 0.115 | 21 | 5 | 0.002 |
| 48 hours | 0.85 | 0.115 | 21 | 5 | 0.002 |

UO only

| Time prior AKI stage | AUC | SE | nCohort 1 | nCohort 2 | p |
|---|---|---|---|---|---|
| 0 hours | 0.75 | 0.075 | 46 | 17 | 0.001 |
| 24 hours | 0.75 | 0.075 | 46 | 17 | 0.001 |
| 48 hours | 0.75 | 0.075 | 46 | 17 | 0.001 | sCr or UO

| Time prior AKI stage | Cutoff value | sens | spec | Quartile | OR | 95% CI of OR | |
|---|---|---|---|---|---|---|---|
| 0 hours | 0.215 | 71% | 71% | 1 |  |  |  |
|  | 0.151 | 81% | 46% | 2 | 2.3 | 0.4 | 12.6 |
|  | 0.141 | 90% | 41% | 3 | 3.0 | 0.6 | 15.5 |
|  | 0.215 | 71% | 71% | 4 | 8.5 | 1.9 | 37.6 |
|  | 0.269 | 48% | 80% |  |  |  |  |
|  | 0.439 | 33% | 91% |  |  |  |  |

FIG. 7 - 7

|  | | 24 hours | 0.215 | 71% | 71% | 1 | | | |
|---|---|---|---|---|---|---|---|---|---|
|  | | | 0.151 | 81% | 46% | 2 | 2.3 | 0.4 | 12.6 |
|  | | | 0.141 | 90% | 41% | 3 | 3.0 | 0.6 | 15.5 |
|  | | | 0.215 | 71% | 71% | 4 | 8.5 | 1.9 | 37.6 |
|  | | | 0.269 | 48% | 80% | | | | |
|  | | | 0.439 | 33% | 91% | | | | |
|  | | 48 hours | 0.215 | 71% | 71% | 1 | | | |
|  | | | 0.151 | 81% | 46% | 2 | 2.3 | 0.4 | 12.6 |
|  | | | 0.141 | 90% | 41% | 3 | 3.0 | 0.6 | 15.5 |
|  | | | 0.215 | 71% | 71% | 4 | 8.5 | 1.9 | 37.6 |
|  | | | 0.269 | 48% | 80% | | | | |
|  | | | 0.439 | 33% | 91% | | | | |

UO only

| Time prior AKI stage | Cutoff value | sens | spec | Quartile | OR | 95% CI of OR | |
|---|---|---|---|---|---|---|---|
| 0 hours | 0.226 | 71% | 72% | 1 | | | |
| | 0.215 | 82% | 67% | 2 | 2.0 | 0.1 | 50.1 |
| | 0.148 | 94% | 41% | 3 | 8.4 | 0.6 | 115.7 |
| | 0.226 | 71% | 72% | 4 | 14.0 | 1.1 | 186.6 |
| | 0.283 | 53% | 80% | | | | |
| | 0.39 | 29% | 91% | | | | |
| 24 hours | 0.226 | 71% | 72% | 1 | | | |
| | 0.215 | 82% | 67% | 2 | 2.0 | 0.1 | 50.1 |
| | 0.148 | 94% | 41% | 3 | 8.4 | 0.6 | 115.7 |
| | 0.226 | 71% | 72% | 4 | 14.0 | 1.1 | 186.6 |
| | 0.283 | 53% | 80% | | | | |
| | 0.39 | 29% | 91% | | | | |
| 48 hours | 0.226 | 71% | 72% | 1 | | | |
| | 0.215 | 82% | 67% | 2 | 2.0 | 0.1 | 50.1 |
| | 0.148 | 94% | 41% | 3 | 8.4 | 0.6 | 115.7 |
| | 0.226 | 71% | 72% | 4 | 14.0 | 1.1 | 186.6 |
| | 0.283 | 53% | 80% | | | | |
| | 0.39 | 29% | 91% | | | | |

FIG. 7 - 8

Erythropoietin receptor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 290.373 | 117.424 | 290.373 | 117.424 | 290.373 | na |
| average | 1032.036 | 206.018 | 1032.036 | 206.018 | 1032.036 | na |
| stdev | 1811.528 | 206.459 | 1811.528 | 206.459 | 1811.528 | na |
| p (t-test) |  | 0.437 |  | 0.437 |  | na |
| min | 12.346 | 58.642 | 12.346 | 58.642 | 12.346 | na |
| max | 8263.287 | 441.989 | 8263.287 | 441.989 | 8263.287 | na |
| n (Samp) | 55 | 3 | 55 | 3 | 55 | 0 |
| n (Pat) | 55 | 3 | 55 | 3 | 55 | 0 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 236.328 | 9.259 | 236.328 | 9.259 | 236.328 | 9.259 |
| average | 792.420 | 58.642 | 792.420 | 58.642 | 792.420 | 58.642 |
| stdev | 1489.255 | na | 1489.255 | na | 1489.255 | na |
| p (t-test) |  | na |  | na |  | na |
| min | 9.259 | 58.642 | 9.259 | 58.642 | 9.259 | 58.642 |
| max | 8263.287 | 58.642 | 8263.287 | 58.642 | 8263.287 | 58.642 |
| n (Samp) | 92 | 1 | 92 | 1 | 92 | 1 |
| n (Pat) | 92 | 1 | 92 | 1 | 92 | 1 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 352.484 | 117.424 | 352.484 | 117.424 | 352.484 | na |
| average | 1075.016 | 206.018 | 1075.016 | 206.018 | 1075.016 | na |
| stdev | 1674.425 | 206.459 | 1674.425 | 206.459 | 1674.425 | na |
| p (t-test) |  | 0.378 |  | 0.378 |  | na |
| min | 12.346 | 58.642 | 12.346 | 58.642 | 12.346 | na |
| max | 6805.195 | 441.989 | 6805.195 | 441.989 | 6805.195 | na |
| n (Samp) | 47 | 3 | 47 | 3 | 47 | 0 |
| n (Pat) | 47 | 3 | 47 | 3 | 47 | 0 | sCr or UO

| Time prior AKI stage | AUC | SE | nCohort 1 | nCohort 2 | p |
| --- | --- | --- | --- | --- | --- |
| 0 hours | 0.27 | 0.127 | 55 | 3 | 0.073 |
| 24 hours | 0.27 | 0.127 | 55 | 3 | 0.073 |
| 48 hours | nd | nd | 55 | 0 | nd | sCr only

| Time prior AKI stage | AUC | SE | nCohort 1 | nCohort 2 | p |
| --- | --- | --- | --- | --- | --- |
| 0 hours | 0.05 | 0.056 | 92 | 1 | 0.000 |
| 24 hours | 0.05 | 0.056 | 92 | 1 | 0.000 |
| 48 hours | 0.05 | 0.056 | 92 | 1 | 0.000 |

UO only

| Time prior AKI stage | AUC | SE | nCohort 1 | nCohort 2 | p |
| --- | --- | --- | --- | --- | --- |
| 0 hours | 0.27 | 0.127 | 47 | 3 | 0.070 |
| 24 hours | 0.27 | 0.127 | 47 | 3 | 0.070 |
| 48 hours | nd | nd | 47 | 0 | nd |

FIG. 8 - 1

Intercellular adhesion molecule 1 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 205637.010 | 319174.717 | 205637.010 | 319174.717 | 205637.010 | 319174.717 |
| average | 262966.542 | 382655.529 | 262966.542 | 382655.529 | 262966.542 | 436571.985 |
| stdev | 175123.670 | 210891.799 | 175123.670 | 210891.799 | 175123.670 | 328156.163 |
| p (t-test) |  | 0.061 |  | 0.061 |  | 0.107 |
| min | 51907.253 | 193433.392 | 51907.253 | 193433.392 | 51907.253 | 183261.199 |
| max | 1060572.701 | 807280.039 | 1060572.701 | 807280.039 | 1060572.701 | 807280.039 |
| n (Samp) | 75 | 9 | 75 | 9 | 75 | 3 |
| n (Pat) | 75 | 9 | 75 | 9 | 75 | 3 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 206039.902 | 403943.289 | 206039.902 | 403943.289 | 206039.902 | 569880.435 |
| average | 257720.863 | 478070.920 | 257720.863 | 478070.920 | 257720.863 | 569880.435 |
| stdev | 156303.703 | 248377.088 | 156303.703 | 248377.088 | 156303.703 | 335733.739 |
| p (t-test) |  | 0.003 |  | 0.003 |  | 0.007 |
| min | 51907.253 | 193433.392 | 51907.253 | 193433.392 | 51907.253 | 332480.831 |
| max | 1060572.701 | 807280.039 | 1060572.701 | 807280.039 | 1060572.701 | 807280.039 |
| n (Samp) | 129 | 5 | 129 | 5 | 129 | 2 |
| n (Pat) | 129 | 5 | 129 | 5 | 129 | 2 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 216297.678 | 292610.964 | 216297.678 | 292610.964 | 216297.678 | 319174.717 |
| average | 281083.446 | 365551.005 | 281083.446 | 365551.005 | 281083.446 | 436571.985 |
| stdev | 159164.302 | 221172.194 | 159164.302 | 221172.194 | 159164.302 | 328156.163 |
| p (t-test) |  | 0.235 |  | 0.235 |  | 0.121 |
| min | 51907.253 | 204249.960 | 51907.253 | 204249.960 | 51907.253 | 183261.199 |
| max | 766357.408 | 807280.039 | 766357.408 | 807280.039 | 766357.408 | 807280.039 |
| n (Samp) | 61 | 6 | 61 | 6 | 61 | 3 |
| n (Pat) | 61 | 6 | 61 | 6 | 61 | 3 | sCr or UO

| Time prior AKI stage | AUC | SE | nCohort 1 | nCohort 2 | p |
| --- | --- | --- | --- | --- | --- |
| 0 hours | 0.73 | 0.100 | 75 | 9 | 0.024 |
| 24 hours | 0.73 | 0.100 | 75 | 9 | 0.024 |
| 48 hours | 0.71 | 0.172 | 75 | 3 | 0.229 | sCr only

| Time prior AKI stage | AUC | SE | nCohort 1 | nCohort 2 | p |
| --- | --- | --- | --- | --- | --- |
| 0 hours | 0.80 | 0.121 | 129 | 5 | 0.014 |
| 24 hours | 0.80 | 0.121 | 129 | 5 | 0.014 |
| 48 hours | 0.88 | 0.158 | 129 | 2 | 0.016 |

UO only

| Time prior AKI stage | AUC | SE | nCohort 1 | nCohort 2 | p |
| --- | --- | --- | --- | --- | --- |
| 0 hours | 0.66 | 0.127 | 61 | 6 | 0.211 |
| 24 hours | 0.66 | 0.127 | 61 | 6 | 0.211 |
| 48 hours | 0.67 | 0.176 | 61 | 3 | 0.327 |

FIG. 8 - 2

Lactotransferrin sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 195.705 | 89.491 | 195.705 | 89.491 | 195.705 | 102.980 |
| average | 422.167 | 412.908 | 422.167 | 412.908 | 422.167 | 338.302 |
| stdev | 481.397 | 540.081 | 481.397 | 540.081 | 481.397 | 431.931 |
| p (t-test) |  | 0.967 |  | 0.967 |  | 0.776 |
| min | 26.292 | 61.643 | 26.292 | 61.643 | 26.292 | 75.132 |
| max | 1474.768 | 1324.895 | 1474.768 | 1324.895 | 1474.768 | 836.793 |
| n (Samp) | 25 | 6 | 25 | 6 | 25 | 3 |
| n (Pat) | 25 | 6 | 25 | 6 | 25 | 3 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 160.337 | 836.793 | 160.337 | 836.793 | 160.337 | 455.963 |
| average | 393.162 | 745.607 | 393.162 | 745.607 | 393.162 | 455.963 |
| stdev | 452.252 | 629.851 | 452.252 | 629.851 | 452.252 | 538.576 |
| p (t-test) |  | 0.207 |  | 0.207 |  | 0.849 |
| min | 26.292 | 75.132 | 26.292 | 75.132 | 26.292 | 75.132 |
| max | 1474.768 | 1324.895 | 1474.768 | 1324.895 | 1474.768 | 836.793 |
| n (Samp) | 44 | 3 | 44 | 3 | 44 | 2 |
| n (Pat) | 44 | 3 | 44 | 3 | 44 | 2 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 237.743 | 89.491 | 237.743 | 89.491 | 237.743 | 469.887 |
| average | 433.325 | 269.355 | 433.325 | 269.355 | 433.325 | 469.887 |
| stdev | 476.202 | 378.680 | 476.202 | 378.680 | 476.202 | 518.884 |
| p (t-test) |  | 0.519 |  | 0.519 |  | 0.918 |
| min | 26.292 | 61.643 | 26.292 | 61.643 | 26.292 | 102.980 |
| max | 1474.768 | 836.793 | 1474.768 | 836.793 | 1474.768 | 836.793 |
| n (Samp) | 25 | 4 | 25 | 4 | 25 | 2 |
| n (Pat) | 25 | 4 | 25 | 4 | 25 | 2 | sCr or UO

| Time prior AKI stage | AUC | SE | nCohort 1 | nCohort 2 | p |
| --- | --- | --- | --- | --- | --- |
| 0 hours | 0.44 | 0.129 | 25 | 6 | 0.642 |
| 24 hours | 0.44 | 0.129 | 25 | 6 | 0.642 |
| 48 hours | 0.47 | 0.176 | 25 | 3 | 0.850 | sCr only

| Time prior AKI stage | AUC | SE | nCohort 1 | nCohort 2 | p |
| --- | --- | --- | --- | --- | --- |
| 0 hours | 0.64 | 0.179 | 44 | 3 | 0.420 |
| 24 hours | 0.64 | 0.179 | 44 | 3 | 0.420 |
| 48 hours | 0.50 | 0.211 | 44 | 2 | 1.000 |

UO only

| Time prior AKI stage | AUC | SE | nCohort 1 | nCohort 2 | p |
| --- | --- | --- | --- | --- | --- |
| 0 hours | 0.37 | 0.142 | 25 | 4 | 0.360 |
| 24 hours | 0.37 | 0.142 | 25 | 4 | 0.360 |
| 48 hours | 0.58 | 0.222 | 25 | 2 | 0.718 | sCr or UO

| Time prior AKI stage | Cutoff value | sens | spec | Quartile | OR | 95% CI of OR | |
| --- | --- | --- | --- | --- | --- | --- | --- |
| 0 hours | 71.650992 | 83% | 20% | 1 |  |  |  |
|  | 71.650992 | 83% | 20% | 2 | 0.0 | 0.0 | na |
|  | 42.482162 | 100% | 12% | 3 | 1.0 | 0.1 | 13.6 |
|  | 360.84388 | 33% | 72% | 4 | 1.2 | 0.1 | 17.5 |
|  | 742.27848 | 33% | 80% |  |  |  |  |
|  | 1266.1603 | 17% | 92% |  |  |  |  |

FIG. 8 - 3

| | | | | | | | |
|---|---|---|---|---|---|---|---|
| 24 hours | 71.650992 | 83% | 20% | 1 | | | |
| | 71.650992 | 83% | 20% | 2 | 0.0 | 0.0 | na |
| | 42.482162 | 100% | 12% | 3 | 1.0 | 0.1 | 13.6 |
| | 360.84388 | 33% | 72% | 4 | 1.2 | 0.1 | 17.5 |
| | 742.27848 | 33% | 80% | | | | |
| | 1266.1603 | 17% | 92% | | | | |
| 48 hours | 71.650992 | 100% | 20% | 1 | | | |
| | 71.650992 | 100% | 20% | 2 | 0.0 | 0.0 | na |
| | 71.650992 | 100% | 20% | 3 | 1.0 | 0.0 | 96.9 |
| | 360.84388 | 33% | 72% | 4 | 1.0 | 0.0 | 96.9 |
| | 742.27848 | 33% | 80% | | | | |
| | 1266.1603 | 0% | 92% | | | | | sCr only

| Time prior AKI stage | Cutoff value | sens | spec | Quartile | OR | 95% CI of OR | |
|---|---|---|---|---|---|---|---|
| 0 hours | 71.650992 | 100% | 18% | 1 | | | |
| | 71.650992 | 100% | 18% | 2 | 0.0 | 0.0 | na |
| | 71.650992 | 100% | 18% | 3 | 0.0 | 0.0 | na |
| | 360.84388 | 67% | 70% | 4 | 2.0 | 0.1 | 56.0 |
| | 828.01688 | 67% | 82% | | | | |
| | 1214.8523 | 33% | 91% | | | | |
| 24 hours | 71.650992 | 100% | 18% | 1 | | | |
| | 71.650992 | 100% | 18% | 2 | 0.0 | 0.0 | na |
| | 71.650992 | 100% | 18% | 3 | 0.0 | 0.0 | na |
| | 360.84388 | 67% | 70% | 4 | 2.0 | 0.1 | 56.0 |
| | 828.01688 | 67% | 82% | | | | |
| | 1214.8523 | 33% | 91% | | | | |
| 48 hours | 71.650992 | 100% | 18% | 1 | | | |
| | 71.650992 | 100% | 18% | 2 | 0.0 | 0.0 | na |
| | 71.650992 | 100% | 18% | 3 | 0.0 | 0.0 | na |
| | 360.84388 | 50% | 70% | 4 | 1.1 | 0.0 | 80.6 |
| | 828.01688 | 50% | 82% | | | | |
| | 1214.8523 | 0% | 91% | | | | |

UO only

| Time prior AKI stage | Cutoff value | sens | spec | Quartile | OR | 95% CI of OR | |
|---|---|---|---|---|---|---|---|
| 0 hours | 71.650992 | 75% | 20% | 1 | | | |
| | 42.482162 | 100% | 12% | 2 | 0.0 | 0.0 | na |
| | 42.482162 | 100% | 12% | 3 | 1.2 | 0.0 | 107.9 |
| | 364.21941 | 25% | 72% | 4 | 2.8 | 0.1 | 103.7 |
| | 742.27848 | 25% | 80% | | | | |
| | 1266.1603 | 0% | 92% | | | | |
| 24 hours | 71.650992 | 75% | 20% | 1 | | | |
| | 42.482162 | 100% | 12% | 2 | 0.0 | 0.0 | na |
| | 42.482162 | 100% | 12% | 3 | 1.2 | 0.0 | 107.9 |
| | 364.21941 | 25% | 72% | 4 | 2.8 | 0.1 | 103.7 |
| | 742.27848 | 25% | 80% | | | | |
| | 1266.1603 | 0% | 92% | | | | |
| 48 hours | 99.064023 | 100% | 36% | 1 | | | |
| | 99.064023 | 100% | 36% | 2 | na | na | na |
| | 99.064023 | 100% | 36% | 3 | na | na | na |
| | 364.21941 | 50% | 72% | 4 | na | na | na |
| | 742.27848 | 50% | 80% | | | | |
| | 1266.1603 | 0% | 92% | | | | |

FIG. 8 - 4

Prostatic Acid Phosphatase sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.181 | 0.458 | 0.181 | 0.347 | 0.181 | 0.321 |
| average | 0.728 | 0.552 | 0.728 | 0.507 | 0.728 | 0.375 |
| stdev | 4.459 | 0.563 | 4.459 | 0.582 | 4.459 | 0.268 |
| p (t-test) |  | 0.872 |  | 0.839 |  | 0.803 |
| min | 0.025 | 0.084 | 0.025 | 0.076 | 0.025 | 0.030 |
| max | 47.000 | 2.510 | 47.000 | 2.510 | 47.000 | 1.020 |
| n (Samp) | 111 | 17 | 111 | 17 | 111 | 10 |
| n (Pat) | 111 | 17 | 111 | 17 | 111 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.215 | 0.471 | 0.215 | 0.471 | 0.215 | 0.351 |
| average | 0.665 | 0.661 | 0.665 | 0.661 | 0.665 | 0.347 |
| stdev | 3.580 | 0.760 | 3.580 | 0.760 | 3.580 | 0.179 |
| p (t-test) |  | 0.997 |  | 0.997 |  | 0.843 |
| min | 0.025 | 0.097 | 0.025 | 0.097 | 0.025 | 0.076 |
| max | 47.000 | 2.510 | 47.000 | 2.510 | 47.000 | 0.531 |
| n (Samp) | 179 | 8 | 179 | 8 | 179 | 5 |
| n (Pat) | 179 | 8 | 179 | 8 | 179 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.181 | 0.347 | 0.181 | 0.278 | 0.181 | 0.278 |
| average | 0.847 | 0.438 | 0.847 | 0.368 | 0.847 | 0.340 |
| stdev | 4.977 | 0.295 | 4.977 | 0.319 | 4.977 | 0.316 |
| p (t-test) |  | 0.787 |  | 0.752 |  | 0.789 |
| min | 0.000 | 0.084 | 0.000 | 0.076 | 0.000 | 0.030 |
| max | 47.000 | 1.020 | 47.000 | 1.020 | 47.000 | 1.020 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
| --- | --- | --- | --- | --- | --- |
| 0 hours | 0.75 | 0.072 | 111 | 17 | 0.001 |
| 24 hours | 0.68 | 0.076 | 111 | 17 | 0.020 |
| 48 hours | 0.70 | 0.096 | 111 | 10 | 0.042 | sCr only

| Time prior AKI stage | AUC | SE | nCohort 1 | nCohort 2 | p |
| --- | --- | --- | --- | --- | --- |
| 0 hours | 0.75 | 0.101 | 179 | 8 | 0.012 |
| 24 hours | 0.75 | 0.101 | 179 | 8 | 0.012 |
| 48 hours | 0.65 | 0.135 | 179 | 5 | 0.273 |

UO only

| Time prior AKI stage | AUC | SE | nCohort 1 | nCohort 2 | p |
| --- | --- | --- | --- | --- | --- |
| 0 hours | 0.73 | 0.090 | 89 | 11 | 0.010 |
| 24 hours | 0.62 | 0.095 | 89 | 11 | 0.196 |
| 48 hours | 0.63 | 0.117 | 89 | 7 | 0.285 | sCr or UO

| Time prior AKI stage | Cutoff value | sens | spec | Quartile | OR | 95% CI of OR | |
| --- | --- | --- | --- | --- | --- | --- | --- |
| 0 hours | 0.294 | 71% | 75% | 1 |  |  |  |
|  | 0.205 | 82% | 57% | 2 | 0.0 | 0.0 | na |
|  | 0.0964 | 94% | 17% | 3 | 2.8 | 0.6 | 12.6 |
|  | 0.266 | 76% | 70% | 4 | 6.8 | 1.8 | 25.8 |
|  | 0.344 | 65% | 80% |  |  |  |  |
|  | 0.584 | 18% | 90% |  |  |  |  |

FIG. 8 - 5

| | | Cutoff value | sens | spec | Quartile | OR | 95% CI of OR | |
|---|---|---|---|---|---|---|---|---|
| | 24 hours | 0.205 | 71% | 57% | 1 | | | |
| | | 0.163 | 82% | 45% | 2 | 0.3 | 0.0 | 4.8 |
| | | 0.0784 | 94% | 12% | 3 | 1.4 | 0.4 | 5.0 |
| | | 0.266 | 65% | 70% | 4 | 3.8 | 1.4 | 10.5 |
| | | 0.344 | 53% | 80% | | | | |
| | | 0.584 | 18% | 90% | | | | |
| | 48 hours | 0.272 | 70% | 73% | 1 | | | |
| | | 0.205 | 80% | 57% | 2 | 0.0 | 0.0 | na |
| | | 0.204 | 90% | 57% | 3 | 4.5 | 0.3 | 59.6 |
| | | 0.266 | 70% | 70% | 4 | 5.6 | 0.5 | 67.6 |
| | | 0.344 | 50% | 80% | | | | |
| | | 0.584 | 10% | 90% | | | | | sCr only

| Time prior AKI stage | Cutoff value | sens | spec | Quartile | OR | 95% CI of OR | |
|---|---|---|---|---|---|---|---|
| 0 hours | 0.422 | 75% | 82% | 1 | | | |
| | 0.293 | 88% | 68% | 2 | 0.0 | 0.0 | na |
| | 0.0964 | 100% | 16% | 3 | 1.0 | 0.0 | 53.7 |
| | 0.314 | 75% | 70% | 4 | 6.6 | 0.6 | 71.0 |
| | 0.4 | 75% | 80% | | | | |
| | 0.758 | 13% | 91% | | | | |
| 24 hours | 0.422 | 75% | 82% | 1 | | | |
| | 0.293 | 88% | 68% | 2 | 0.0 | 0.0 | na |
| | 0.0964 | 100% | 16% | 3 | 1.0 | 0.0 | 53.7 |
| | 0.314 | 75% | 70% | 4 | 6.6 | 0.6 | 71.0 |
| | 0.4 | 75% | 80% | | | | |
| | 0.758 | 13% | 91% | | | | |
| 48 hours | 0.293 | 80% | 68% | 1 | | | |
| | 0.293 | 80% | 68% | 2 | 0.0 | 0.0 | na |
| | 0.075 | 100% | 9% | 3 | 2.0 | 0.1 | 42.3 |
| | 0.314 | 60% | 70% | 4 | 2.0 | 0.1 | 42.3 |
| | 0.4 | 40% | 80% | | | | |
| | 0.758 | 0% | 91% | | | | |

UO only

| Time prior AKI stage | Cutoff value | sens | spec | Quartile | OR | 95% CI of OR | |
|---|---|---|---|---|---|---|---|
| 0 hours | 0.293 | 73% | 74% | 1 | | | |
| | 0.205 | 82% | 56% | 2 | 0.0 | 0.0 | na |
| | 0.199 | 91% | 56% | 3 | 4.6 | 0.3 | 63.1 |
| | 0.268 | 73% | 71% | 4 | 7.6 | 0.6 | 89.7 |
| | 0.344 | 55% | 81% | | | | |
| | 0.672 | 18% | 91% | | | | |
| 24 hours | 0.199 | 73% | 56% | 1 | | | |
| | 0.163 | 82% | 44% | 2 | 0.5 | 0.0 | 10.7 |
| | 0.0784 | 91% | 15% | 3 | 2.2 | 0.4 | 11.4 |
| | 0.268 | 55% | 71% | 4 | 2.2 | 0.4 | 11.4 |
| | 0.344 | 36% | 81% | | | | |
| | 0.672 | 18% | 91% | | | | |
| 48 hours | 0.205 | 71% | 56% | 1 | | | |
| | 0.199 | 86% | 56% | 2 | 0.0 | 0.0 | na |
| | 0.000342 | 100% | 1% | 3 | 4.6 | 0.3 | 64.0 |
| | 0.268 | 57% | 71% | 4 | 2.1 | 0.1 | 47.1 |
| | 0.344 | 29% | 81% | | | | |
| | 0.672 | 14% | 91% | | | | |

FIG. 8 - 6 von Willebrand Factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 104.000 | 143.000 | 104.000 | 143.000 | 104.000 | 136.000 |
| average | 111.046 | 163.035 | 111.046 | 161.765 | 111.046 | 150.470 |
| stdev | 39.391 | 60.467 | 39.391 | 60.189 | 39.391 | 48.453 |
| p (t-test) |  | 0.000 |  | 0.000 |  | 0.004 |
| min | 32.000 | 94.600 | 32.000 | 94.400 | 32.000 | 92.700 |
| max | 278.000 | 328.000 | 278.000 | 328.000 | 278.000 | 224.000 |
| n (Samp) | 111 | 17 | 111 | 17 | 111 | 10 |
| n (Pat) | 111 | 17 | 111 | 17 | 111 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 107.000 | 143.000 | 107.000 | 143.000 | 107.000 | 143.000 |
| average | 113.492 | 145.750 | 113.492 | 145.050 | 113.492 | 145.000 |
| stdev | 42.272 | 33.763 | 42.272 | 34.886 | 42.272 | 29.504 |
| p (t-test) |  | 0.035 |  | 0.039 |  | 0.100 |
| min | 32.000 | 100.000 | 32.000 | 94.400 | 32.000 | 117.000 |
| max | 328.000 | 210.000 | 328.000 | 210.000 | 328.000 | 194.000 |
| n (Samp) | 179 | 8 | 179 | 8 | 179 | 5 |
| n (Pat) | 179 | 8 | 179 | 8 | 179 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 104.000 | 143.000 | 104.000 | 143.000 | 104.000 | 129.000 |
| average | 109.143 | 175.691 | 109.143 | 174.236 | 109.143 | 155.814 |
| stdev | 36.579 | 71.199 | 36.579 | 70.589 | 36.579 | 58.185 |
| p (t-test) |  | 0.000 |  | 0.000 |  | 0.003 |
| min | 32.000 | 94.600 | 32.000 | 94.600 | 32.000 | 92.700 |
| max | 240.000 | 328.000 | 240.000 | 328.000 | 240.000 | 224.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
| --- | --- | --- | --- | --- | --- |
| 0 hours | 0.79 | 0.068 | 111 | 17 | 0.000 |
| 24 hours | 0.79 | 0.068 | 111 | 17 | 0.000 |
| 48 hours | 0.75 | 0.092 | 111 | 10 | 0.006 | sCr only

| Time prior AKI stage | AUC | SE | nCohort 1 | nCohort 2 | p |
| --- | --- | --- | --- | --- | --- |
| 0 hours | 0.76 | 0.100 | 179 | 8 | 0.008 |
| 24 hours | 0.75 | 0.101 | 179 | 8 | 0.012 |
| 48 hours | 0.78 | 0.123 | 179 | 5 | 0.022 |

UO only

| Time prior AKI stage | AUC | SE | nCohort 1 | nCohort 2 | p |
| --- | --- | --- | --- | --- | --- |
| 0 hours | 0.81 | 0.081 | 89 | 11 | 0.000 |
| 24 hours | 0.81 | 0.081 | 89 | 11 | 0.000 |
| 48 hours | 0.74 | 0.111 | 89 | 7 | 0.029 |

FIG. 8 - 7

SEQUENCE LISTING

<160> NUMBER OF SEQ ID NOS: 8

<210> SEQ ID NO 1
<211> LENGTH: 386
<212> TYPE: PRT
<213> ORGANISM: Homo sapiens

<400> SEQUENCE: 1

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser

```
                     85                   90                  95
Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
            115                 120                 125

Val Ser Ile Trp Asn Pro Ile Leu Leu Trp Gln Pro Ile Pro Val His
            130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
                180                 185                 190

Lys Leu Ser Gly Leu His Gly Gln Asp Leu Phe Gly Ile Trp Ser Lys
                195                 200                 205

Val Tyr Asp Pro Leu Tyr Cys Glu Ser Val His Asn Phe Thr Leu Pro
            210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
                260                 265                 270

Arg Ala Thr Gln Ile Pro Ser Tyr Lys Lys Leu Ile Met Tyr Ser Ala
                275                 280                 285

His Asp Thr Thr Val Ser Gly Leu Gln Met Ala Leu Asp Val Tyr Asn
            290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
                340                 345                 350

Leu Glu Arg Phe Ala Glu Leu Val Gly Pro Val Ile Pro Gln Asp Trp
                355                 360                 365

Ser Thr Glu Cys Met Thr Thr Asn Ser His Gln Gly Thr Glu Asp Ser
            370                 375                 380

Thr Asp
385

<210> SEQ ID NO 2
<211> LENGTH: 710
<212> TYPE: PRT
<213> ORGANISM: Homo sapiens

<400> SEQUENCE: 2

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser Gln
            20                  25                  30

Pro Glu Ala Thr Lys Cys Phe Gln Trp Gln Arg Asn Met Arg Lys Val
            35                  40                  45

Arg Gly Pro Pro Val Ser Cys Ile Lys Arg Asp Ser Pro Ile Gln Cys
        50                  55                  60
```

-continued

```
Ile Gln Ala Ile Ala Glu Asn Arg Ala Asp Ala Val Thr Leu Asp Gly
 65                  70                  75                  80

Gly Phe Ile Tyr Glu Ala Gly Leu Ala Pro Tyr Lys Leu Arg Pro Val
                 85                  90                  95

Ala Ala Glu Val Tyr Gly Thr Glu Arg Gln Pro Arg Thr His Tyr Tyr
            100                 105                 110

Ala Val Ala Val Val Lys Lys Gly Gly Ser Phe Gln Leu Asn Glu Leu
        115                 120                 125

Gln Gly Leu Lys Ser Cys His Thr Gly Leu Arg Arg Thr Ala Gly Trp
130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
        195                 200                 205

Phe Ser Tyr Ser Gly Ala Phe Lys Cys Leu Arg Asp Gly Ala Gly Asp
210                 215                 220

Val Ala Phe Ile Arg Glu Ser Thr Val Phe Glu Asp Leu Ser Asp Glu
225                 230                 235                 240

Ala Glu Arg Asp Glu Tyr Glu Leu Leu Cys Pro Asp Asn Thr Arg Lys
                245                 250                 255

Pro Val Asp Lys Phe Lys Asp Cys His Leu Ala Arg Val Pro Ser His
            260                 265                 270

Ala Val Val Ala Arg Ser Val Asn Gly Lys Glu Asp Ala Ile Trp Asn
        275                 280                 285

Leu Leu Arg Gln Ala Gln Glu Lys Phe Gly Lys Asp Lys Ser Pro Lys
290                 295                 300

Phe Gln Leu Phe Gly Ser Pro Ser Gly Gln Lys Asp Leu Leu Phe Lys
305                 310                 315                 320

Asp Ser Ala Ile Gly Phe Ser Arg Val Pro Pro Arg Ile Asp Ser Gly
                325                 330                 335

Leu Tyr Leu Gly Ser Gly Tyr Phe Thr Ala Ile Gln Asn Leu Arg Lys
            340                 345                 350

Ser Glu Glu Glu Val Ala Ala Arg Arg Ala Arg Val Val Trp Cys Ala
        355                 360                 365

Val Gly Glu Gln Glu Leu Arg Lys Cys Asn Gln Trp Ser Gly Leu Ser
370                 375                 380

Glu Gly Ser Val Thr Cys Ser Ser Ala Ser Thr Thr Glu Asp Cys Ile
385                 390                 395                 400

Ala Leu Val Leu Lys Gly Glu Ala Asp Ala Met Ser Leu Asp Gly Gly
                405                 410                 415

Tyr Val Tyr Thr Ala Gly Lys Cys Gly Leu Val Pro Val Leu Ala Glu
            420                 425                 430

Asn Tyr Lys Ser Gln Gln Ser Ser Asp Pro Asp Pro Asn Cys Val Asp
        435                 440                 445

Arg Pro Val Glu Gly Tyr Leu Ala Val Ala Val Val Arg Arg Ser Asp
450                 455                 460

Thr Ser Leu Thr Trp Asn Ser Val Lys Gly Lys Lys Ser Cys His Thr
465                 470                 475                 480

Ala Val Asp Arg Thr Ala Gly Trp Asn Ile Pro Met Gly Leu Leu Phe
```

```
                    485                 490                 495
Asn Gln Thr Gly Ser Cys Lys Phe Asp Glu Tyr Phe Ser Gln Ser Cys
                500                 505                 510

Ala Pro Gly Ser Asp Pro Arg Ser Asn Leu Cys Ala Leu Cys Ile Gly
            515                 520                 525

Asp Glu Gln Gly Glu Asn Lys Cys Val Pro Asn Ser Asn Glu Arg Tyr
        530                 535                 540

Tyr Gly Tyr Thr Gly Ala Phe Arg Cys Leu Ala Glu Asn Ala Gly Asp
545                 550                 555                 560

Val Ala Phe Val Lys Asp Val Thr Val Leu Gln Asn Thr Asp Gly Asn
                565                 570                 575

Asn Asn Glu Ala Trp Ala Lys Asp Leu Lys Leu Ala Asp Phe Ala Leu
            580                 585                 590

Leu Cys Leu Asp Gly Lys Arg Lys Pro Val Thr Glu Ala Arg Ser Cys
        595                 600                 605

His Leu Ala Met Ala Pro Asn His Ala Val Val Ser Arg Met Asp Lys
    610                 615                 620

Val Glu Arg Leu Lys Gln Val Leu Leu His Gln Gln Ala Lys Phe Gly
625                 630                 635                 640

Arg Asn Gly Ser Asp Cys Pro Asp Lys Phe Cys Leu Phe Gln Ser Glu
                645                 650                 655

Thr Lys Asn Leu Leu Phe Asn Asp Asn Thr Glu Cys Leu Ala Arg Leu
            660                 665                 670

His Gly Lys Thr Thr Tyr Glu Lys Tyr Leu Gly Pro Gln Tyr Val Ala
        675                 680                 685

Gly Ile Thr Asn Leu Lys Lys Cys Ser Thr Ser Pro Leu Leu Glu Ala
    690                 695                 700

Cys Glu Phe Leu Arg Lys
705                 710

<210> SEQ ID NO 3
<211> LENGTH: 508
<212> TYPE: PRT
<213> ORGANISM: Homo sapiens

<400> SEQUENCE: 3

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140
```

```
Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
        355                 360                 365

Leu Val Leu Asp Lys Trp Leu Leu Pro Arg Asn Pro Pro Ser Glu Asp
    370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
            420                 425                 430

Ser Gln Leu Leu Arg Pro Trp Thr Leu Cys Pro Glu Leu Pro Pro Thr
        435                 440                 445

Pro Pro His Leu Lys Tyr Leu Tyr Leu Val Val Ser Asp Ser Gly Ile
    450                 455                 460

Ser Thr Asp Tyr Ser Ser Gly Asp Ser Gln Gly Ala Gln Gly Gly Leu
465                 470                 475                 480

Ser Asp Gly Pro Tyr Ser Asn Pro Tyr Glu Asn Ser Leu Ile Pro Ala
                485                 490                 495

Ala Glu Pro Leu Pro Pro Ser Tyr Val Ala Cys Ser
            500                 505

<210> SEQ ID NO 4
<211> LENGTH: 241
<212> TYPE: PRT
<213> ORGANISM: Homo sapiens

<400> SEQUENCE: 4

Met Asp His Leu Gly Ala Ser Leu Trp Pro Gln Val Gly Ser Leu Cys
1               5                   10                  15
```

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
            115                 120                 125

Gly Ala Pro Arg Tyr His Arg Val Ile His Ile Asn Glu Val Val Leu
130                 135                 140

Leu Asp Ala Pro Val Gly Leu Val Ala Arg Leu Ala Asp Glu Ser Gly
145                 150                 155                 160

His Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Gly Thr Val Phe Leu Ser Pro Asp Trp Leu Ser Ser Thr
        195                 200                 205

Arg Ala Arg Pro His Val Ile Tyr Phe Cys Leu Leu Arg Val Pro Arg
    210                 215                 220

Pro Asp Ser Ala Pro Arg Trp Arg Ser Trp Arg Ala Ala Pro Ser Val
225                 230                 235                 240

Cys

<210> SEQ ID NO 5
<211> LENGTH: 328
<212> TYPE: PRT
<213> ORGANISM: Homo sapiens

<400> SEQUENCE: 5

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
            115                 120                 125

Gly Ala Pro Arg Tyr His Arg Val Ile His Ile Asn Glu Val Val Leu
130                 135                 140

```
Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Val Gly Gly Leu Val Val Pro Ser Val Pro Gly Leu Pro Cys Phe
305                 310                 315                 320

Leu Gln Pro Asn Cys Arg Pro Leu
                325

<210> SEQ ID NO 6
<211> LENGTH: 2813
<212> TYPE: PRT
<213> ORGANISM: Homo sapiens

<400> SEQUENCE: 6

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
```

```
                180             185             190
Leu Ser Ser Gly Glu Gln Trp Cys Glu Arg Ala Ser Pro Ser Ser
            195                 200             205

Ser Cys Asn Ile Ser Ser Gly Glu Met Gln Lys Gly Leu Trp Glu Gln
    210              215                 220

Cys Gln Leu Leu Lys Ser Thr Ser Val Phe Ala Arg Cys His Pro Leu
225             230                 235                     240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
        260                 265                 270

Arg Thr Cys Ala Gln Glu Gly Met Val Leu Tyr Gly Trp Thr Asp His
    275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305             310                 315                     320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605
```

```
Arg Tyr Asp Val Cys Ser Cys Ser Asp Gly Arg Glu Cys Leu Cys Gly
    610             615             620

Ala Leu Ala Ser Tyr Ala Ala Cys Ala Gly Arg Gly Val Arg Val
625             630             635             640

Ala Trp Arg Glu Pro Gly Arg Cys Glu Leu Asn Cys Pro Lys Gly Gln
            645             650             655

Val Tyr Leu Gln Cys Gly Thr Pro Cys Asn Leu Thr Cys Arg Ser Leu
            660             665             670

Ser Tyr Pro Asp Glu Glu Cys Asn Glu Ala Cys Leu Glu Gly Cys Phe
            675             680             685

Cys Pro Pro Gly Leu Tyr Met Asp Glu Arg Gly Asp Cys Val Pro Lys
690             695             700

Ala Gln Cys Pro Cys Tyr Tyr Asp Gly Glu Ile Phe Gln Pro Glu Asp
705             710             715             720

Ile Phe Ser Asp His His Thr Met Cys Tyr Cys Glu Asp Gly Phe Met
            725             730             735

His Cys Thr Met Ser Gly Val Pro Gly Ser Leu Leu Pro Asp Ala Val
            740             745             750

Leu Ser Ser Pro Leu Ser His Arg Ser Lys Arg Ser Leu Ser Cys Arg
    755             760             765

Pro Pro Met Val Lys Leu Val Cys Pro Ala Asp Asn Leu Arg Ala Glu
770             775             780

Gly Leu Glu Cys Thr Lys Thr Cys Gln Asn Tyr Asp Leu Glu Cys Met
785             790             795             800

Ser Met Gly Cys Val Ser Gly Cys Leu Cys Pro Pro Gly Met Val Arg
            805             810             815

His Glu Asn Arg Cys Val Ala Leu Glu Arg Cys Pro Cys Phe His Gln
        820             825             830

Gly Lys Glu Tyr Ala Pro Gly Glu Thr Val Lys Ile Gly Cys Asn Thr
    835             840             845

Cys Val Cys Arg Asp Arg Lys Trp Asn Cys Thr Asp His Val Cys Asp
850             855             860

Ala Thr Cys Ser Thr Ile Gly Met Ala His Tyr Leu Thr Phe Asp Gly
865             870             875             880

Leu Lys Tyr Leu Phe Pro Gly Glu Cys Gln Tyr Val Leu Val Gln Asp
            885             890             895

Tyr Cys Gly Ser Asn Pro Gly Thr Phe Arg Ile Leu Val Gly Asn Lys
            900             905             910

Gly Cys Ser His Pro Ser Val Lys Cys Lys Lys Arg Val Thr Ile Leu
        915             920             925

Val Glu Gly Gly Glu Ile Glu Leu Phe Asp Gly Glu Val Asn Val Lys
    930             935             940

Arg Pro Met Lys Asp Glu Thr His Phe Glu Val Val Glu Ser Gly Arg
945             950             955             960

Tyr Ile Ile Leu Leu Leu Gly Lys Ala Leu Ser Val Val Trp Asp Arg
            965             970             975

His Leu Ser Ile Ser Val Val Leu Lys Gln Thr Tyr Gln Glu Lys Val
            980             985             990

Cys Gly Leu Cys Gly Asn Phe Asp  Gly Ile Gln Asn Asn  Asp Leu Thr
    995            1000            1005

Ser Ser  Asn Leu Gln Val Glu  Glu Asp Pro Val Asp  Phe Gly Asn
    1010            1015            1020
```

```
Ser Trp Lys Val Ser Ser Gln Cys Ala Asp Thr Arg Lys Val Pro
1025                1030                1035

Leu Asp Ser Ser Pro Ala Thr Cys His Asn Asn Ile Met Lys Gln
1040                1045                1050

Thr Met Val Asp Ser Ser Cys Arg Ile Leu Thr Ser Asp Val Phe
1055                1060                1065

Gln Asp Cys Asn Lys Leu Val Asp Pro Glu Pro Tyr Leu Asp Val
1070                1075                1080

Cys Ile Tyr Asp Thr Cys Ser Cys Glu Ser Ile Gly Asp Cys Ala
1085                1090                1095

Cys Phe Cys Asp Thr Ile Ala Ala Tyr Ala His Val Cys Ala Gln
1100                1105                1110

His Gly Lys Val Val Thr Trp Arg Thr Ala Thr Leu Cys Pro Gln
1115                1120                1125

Ser Cys Glu Glu Arg Asn Leu Arg Glu Asn Gly Tyr Glu Cys Glu
1130                1135                1140

Trp Arg Tyr Asn Ser Cys Ala Pro Ala Cys Gln Val Thr Cys Gln
1145                1150                1155

His Pro Glu Pro Leu Ala Cys Pro Val Gln Cys Val Glu Gly Cys
1160                1165                1170

His Ala His Cys Pro Pro Gly Lys Ile Leu Asp Glu Leu Leu Gln
1175                1180                1185

Thr Cys Val Asp Pro Glu Asp Cys Pro Val Cys Glu Val Ala Gly
1190                1195                1200

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Asp Phe Tyr Cys Ser Arg Leu Leu Asp Leu
1265                1270                1275

Val Phe Leu Leu Asp Gly Ser Ser Arg Leu Ser Glu Ala Glu Phe
1280                1285                1290

Glu Val Leu Lys Ala Phe Val Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Ala Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Lys Val Ile Val Ile Pro
1400                1405                1410

Val Gly Ile Gly Pro His Ala Asn Leu Lys Gln Ile Arg Leu Ile
```

-continued

```
            1415                1420                1425
Glu Lys Gln Ala Pro Glu Asn Lys Ala Phe Val Leu Ser Ser Val
    1430                1435                1440
Asp Glu Leu Glu Gln Gln Arg Asp Glu Ile Val Ser Tyr Leu Cys
    1445                1450                1455
Asp Leu Ala Pro Glu Ala Pro Pro Thr Leu Pro Pro His Met
    1460                1465                1470
Ala Gln Val Thr Val Gly Pro Gly Leu Leu Gly Val Ser Thr Leu
    1475                1480                1485
Gly Pro Lys Arg Asn Ser Met Val Leu Asp Val Ala Phe Val Leu
    1490                1495                1500
Glu Gly Ser Asp Lys Ile Gly Glu Ala Asp Phe Asn Arg Ser Lys
    1505                1510                1515
Glu Phe Met Glu Glu Val Ile Gln Arg Met Asp Val Gly Gln Asp
    1520                1525                1530
Ser Ile His Val Thr Val Leu Gln Tyr Ser Tyr Met Val Thr Val
    1535                1540                1545
Glu Tyr Pro Phe Ser Glu Ala Gln Ser Lys Gly Asp Ile Leu Gln
    1550                1555                1560
Arg Val Arg Glu Ile Arg Tyr Gln Gly Gly Asn Arg Thr Asn Thr
    1565                1570                1575
Gly Leu Ala Leu Arg Tyr Leu Ser Asp His Ser Phe Leu Val Ser
    1580                1585                1590
Gln Gly Asp Arg Glu Gln Ala Pro Asn Leu Val Tyr Met Val Thr
    1595                1600                1605
Gly Asn Pro Ala Ser Asp Glu Ile Lys Arg Leu Pro Gly Asp Ile
    1610                1615                1620
Gln Val Val Pro Ile Gly Val Gly Pro Asn Ala Asn Val Gln Glu
    1625                1630                1635
Leu Glu Arg Ile Gly Trp Pro Asn Ala Pro Ile Leu Ile Gln Asp
    1640                1645                1650
Phe Glu Thr Leu Pro Arg Glu Ala Pro Asp Leu Val Leu Gln Arg
    1655                1660                1665
Cys Cys Ser Gly Glu Gly Leu Gln Ile Pro Thr Leu Ser Pro Ala
    1670                1675                1680
Pro Asp Cys Ser Gln Pro Leu Asp Val Ile Leu Leu Leu Asp Gly
    1685                1690                1695
Ser Ser Ser Phe Pro Ala Ser Tyr Phe Asp Glu Met Lys Ser Phe
    1700                1705                1710
Ala Lys Ala Phe Ile Ser Lys Ala Asn Ile Gly Pro Arg Leu Thr
    1715                1720                1725
Gln Val Ser Val Leu Gln Tyr Gly Ser Ile Thr Thr Ile Asp Val
    1730                1735                1740
Pro Trp Asn Val Val Pro Glu Lys Ala His Leu Leu Ser Leu Val
    1745                1750                1755
Asp Val Met Gln Arg Glu Gly Gly Pro Ser Gln Ile Gly Asp Ala
    1760                1765                1770
Leu Gly Phe Ala Val Arg Tyr Leu Thr Ser Glu Met His Gly Ala
    1775                1780                1785
Arg Pro Gly Ala Ser Lys Ala Val Val Ile Leu Val Thr Asp Val
    1790                1795                1800
Ser Val Asp Ser Val Asp Ala Ala Ala Asp Ala Ala Arg Ser Asn
    1805                1810                1815
```

Arg Val Thr Val Phe Pro Ile Gly Ile Gly Asp Arg Tyr Asp Ala
1820             1825             1830

Ala Gln Leu Arg Ile Leu Ala Gly Pro Ala Gly Asp Ser Asn Val
1835             1840             1845

Val Lys Leu Gln Arg Ile Glu Asp Leu Pro Thr Met Val Thr Leu
1850             1855             1860

Gly Asn Ser Phe Leu His Lys Leu Cys Ser Gly Phe Val Arg Ile
1865             1870             1875

Cys Met Asp Glu Asp Gly Asn Glu Lys Arg Pro Gly Asp Val Trp
1880             1885             1890

Thr Leu Pro Asp Gln Cys His Thr Val Thr Cys Gln Pro Asp Gly
1895             1900             1905

Gln Thr Leu Leu Lys Ser His Arg Val Asn Cys Asp Arg Gly Leu
1910             1915             1920

Arg Pro Ser Cys Pro Asn Ser Gln Ser Pro Val Lys Val Glu Glu
1925             1930             1935

Thr Cys Gly Cys Arg Trp Thr Cys Pro Cys Val Cys Thr Gly Ser
1940             1945             1950

Ser Thr Arg His Ile Val Thr Phe Asp Gly Gln Asn Phe Lys Leu
1955             1960             1965

Thr Gly Ser Cys Ser Tyr Val Leu Phe Gln Asn Lys Glu Gln Asp
1970             1975             1980

Leu Glu Val Ile Leu His Asn Gly Ala Cys Ser Pro Gly Ala Arg
1985             1990             1995

Gln Gly Cys Met Lys Ser Ile Glu Val Lys His Ser Ala Leu Ser
2000             2005             2010

Val Glu Leu His Ser Asp Met Glu Val Thr Val Asn Gly Arg Leu
2015             2020             2025

Val Ser Val Pro Tyr Val Gly Gly Asn Met Glu Val Asn Val Tyr
2030             2035             2040

Gly Ala Ile Met His Glu Val Arg Phe Asn His Leu Gly His Ile
2045             2050             2055

Phe Thr Phe Thr Pro Gln Asn Asn Glu Phe Gln Leu Gln Leu Ser
2060             2065             2070

Pro Lys Thr Phe Ala Ser Lys Thr Tyr Gly Leu Cys Gly Ile Cys
2075             2080             2085

Asp Glu Asn Gly Ala Asn Asp Phe Met Leu Arg Asp Gly Thr Val
2090             2095             2100

Thr Thr Asp Trp Lys Thr Leu Val Gln Glu Trp Thr Val Gln Arg
2105             2110             2115

Pro Gly Gln Thr Cys Gln Pro Ile Leu Glu Glu Gln Cys Leu Val
2120             2125             2130

Pro Asp Ser Ser His Cys Gln Val Leu Leu Pro Leu Phe Ala
2135             2140             2145

Glu Cys His Lys Val Leu Ala Pro Ala Thr Phe Tyr Ala Ile Cys
2150             2155             2160

Gln Gln Asp Ser Cys His Gln Glu Gln Val Cys Glu Val Ile Ala
2165             2170             2175

Ser Tyr Ala His Leu Cys Arg Thr Asn Gly Val Cys Val Asp Trp
2180             2185             2190

Arg Thr Pro Asp Phe Cys Ala Met Ser Cys Pro Pro Ser Leu Val
2195             2200             2205

```
Tyr Asn His Cys Glu His Gly Cys Pro Arg His Cys Asp Gly Asn
    2210            2215            2220

Val Ser Ser Cys Gly Asp His Pro Ser Glu Gly Cys Phe Cys Pro
    2225            2230            2235

Pro Asp Lys Val Met Leu Glu Gly Ser Cys Val Pro Glu Glu Ala
    2240            2245            2250

Cys Thr Gln Cys Ile Gly Glu Asp Gly Val Gln His Gln Phe Leu
    2255            2260            2265

Glu Ala Trp Val Pro Asp His Gln Pro Cys Gln Ile Cys Thr Cys
    2270            2275            2280

Leu Ser Gly Arg Lys Val Asn Cys Thr Thr Gln Pro Cys Pro Thr
    2285            2290            2295

Ala Lys Ala Pro Thr Cys Gly Leu Cys Glu Val Ala Arg Leu Arg
    2300            2305            2310

Gln Asn Ala Asp Gln Cys Cys Pro Glu Tyr Glu Cys Val Cys Asp
    2315            2320            2325

Pro Val Ser Cys Asp Leu Pro Pro Val Pro His Cys Glu Arg Gly
    2330            2335            2340

Leu Gln Pro Thr Leu Thr Asn Pro Gly Glu Cys Arg Pro Asn Phe
    2345            2350            2355

Thr Cys Ala Cys Arg Lys Glu Glu Cys Lys Arg Val Ser Pro Pro
    2360            2365            2370

Ser Cys Pro Pro His Arg Leu Pro Thr Leu Arg Lys Thr Gln Cys
    2375            2380            2385

Cys Asp Glu Tyr Glu Cys Ala Cys Asn Cys Val Asn Ser Thr Val
    2390            2395            2400

Ser Cys Pro Leu Gly Tyr Leu Ala Ser Thr Ala Thr Asn Asp Cys
    2405            2410            2415

Gly Cys Thr Thr Thr Thr Cys Leu Pro Asp Lys Val Cys Val His
    2420            2425            2430

Arg Ser Thr Ile Tyr Pro Val Gly Gln Phe Trp Glu Glu Gly Cys
    2435            2440            2445

Asp Val Cys Thr Cys Thr Asp Met Glu Asp Ala Val Met Gly Leu
    2450            2455            2460

Arg Val Ala Gln Cys Ser Gln Lys Pro Cys Glu Asp Ser Cys Arg
    2465            2470            2475

Ser Gly Phe Thr Tyr Val Leu His Glu Gly Glu Cys Cys Gly Arg
    2480            2485            2490

Cys Leu Pro Ser Ala Cys Glu Val Val Thr Gly Ser Pro Arg Gly
    2495            2500            2505

Asp Ser Gln Ser Ser Trp Lys Ser Val Gly Ser Gln Trp Ala Ser
    2510            2515            2520

Pro Glu Asn Pro Cys Leu Ile Asn Glu Cys Val Arg Val Lys Glu
    2525            2530            2535

Glu Val Phe Ile Gln Gln Arg Asn Val Ser Cys Pro Gln Leu Glu
    2540            2545            2550

Val Pro Val Cys Pro Ser Gly Phe Gln Leu Ser Cys Lys Thr Ser
    2555            2560            2565

Ala Cys Cys Pro Ser Cys Arg Cys Glu Arg Met Glu Ala Cys Met
    2570            2575            2580

Leu Asn Gly Thr Val Ile Gly Pro Gly Lys Thr Val Met Ile Asp
    2585            2590            2595

Val Cys Thr Thr Cys Arg Cys Met Val Gln Val Gly Val Ile Ser
```

```
                2600                2605                2610
Gly Phe Lys Leu Glu Cys Arg Lys Thr Thr Cys Asn Pro Cys Pro
            2615                2620                2625
Leu Gly Tyr Lys Glu Glu Asn Asn Thr Gly Glu Cys Cys Gly Arg
            2630                2635                2640
Cys Leu Pro Thr Ala Cys Thr Ile Gln Leu Arg Gly Gly Gln Ile
            2645                2650                2655
Met Thr Leu Lys Arg Asp Glu Thr Leu Gln Asp Gly Cys Asp Thr
            2660                2665                2670
His Phe Cys Lys Val Asn Glu Arg Gly Glu Tyr Phe Trp Glu Lys
            2675                2680                2685
Arg Val Thr Gly Cys Pro Pro Phe Asp Glu His Lys Cys Leu Ala
            2690                2695                2700
Glu Gly Gly Lys Ile Met Lys Ile Pro Gly Thr Cys Cys Asp Thr
            2705                2710                2715
Cys Glu Glu Pro Glu Cys Asn Asp Ile Thr Ala Arg Leu Gln Tyr
            2720                2725                2730
Val Lys Val Gly Ser Cys Lys Ser Glu Val Glu Val Asp Ile His
            2735                2740                2745
Tyr Cys Gln Gly Lys Cys Ala Ser Lys Ala Met Tyr Ser Ile Asp
            2750                2755                2760
Ile Asn Asp Val Gln Asp Gln Cys Ser Cys Cys Ser Pro Thr Arg
            2765                2770                2775
Thr Glu Pro Met Gln Val Ala Leu His Cys Thr Asn Gly Ser Val
            2780                2785                2790
Val Tyr His Glu Val Leu Asn Ala Met Glu Cys Lys Cys Ser Pro
            2795                2800                2805
Arg Lys Cys Ser Lys
            2810

<210> SEQ ID NO 7
<211> LENGTH: 238
<212> TYPE: PRT
<213> ORGANISM: Homo sapiens

<400> SEQUENCE: 7

Met Leu Thr Thr Leu Leu Pro Ile Leu Leu Ser Gly Trp Ala Phe
1               5                   10                  15

Cys Ser Gln Asp Ala Ser Asp Gly Leu Gln Arg Leu His Met Leu Gln
                20                  25                  30

Ile Ser Tyr Phe Arg Asp Pro Tyr His Val Trp Tyr Gln Gly Asn Ala
            35                  40                  45

Ser Leu Gly Gly His Leu Thr His Val Leu Glu Gly Pro Asp Thr Asn
        50                  55                  60

Thr Thr Ile Ile Gln Leu Gln Pro Leu Gln Glu Pro Glu Ser Trp Ala
65                  70                  75                  80

Arg Thr Gln Ser Gly Leu Gln Ser Tyr Leu Leu Gln Phe His Gly Leu
                85                  90                  95

Val Arg Leu Val His Gln Glu Arg Thr Leu Ala Phe Pro Leu Thr Ile
                100                 105                 110

Arg Cys Phe Leu Gly Cys Glu Leu Pro Pro Glu Gly Ser Arg Ala His
            115                 120                 125

Val Phe Phe Glu Val Ala Val Asn Gly Ser Ser Phe Val Ser Phe Arg
        130                 135                 140
```

```
Pro Glu Arg Ala Leu Trp Gln Ala Asp Thr Gln Val Thr Ser Gly Val
145                 150                 155                 160

Val Thr Phe Thr Leu Gln Gln Leu Asn Ala Tyr Asn Arg Thr Arg Tyr
                165                 170                 175

Glu Leu Arg Glu Phe Leu Glu Asp Thr Cys Val Gln Tyr Val Gln Lys
            180                 185                 190

His Ile Ser Ala Glu Asn Thr Lys Gly Ser Gln Thr Ser Arg Ser Tyr
        195                 200                 205

Thr Ser Leu Val Leu Gly Val Leu Val Gly Ser Phe Ile Ile Ala Gly
    210                 215                 220

Val Ala Val Gly Ile Phe Leu Cys Thr Gly Gly Arg Arg Cys
225                 230                 235

<210> SEQ ID NO 8
<211> LENGTH: 345
<212> TYPE: PRT
<213> ORGANISM: Homo sapiens

<400> SEQUENCE: 8

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
            20                  25                  30

Thr Val Val Pro Leu Lys Thr Phe Tyr Glu Pro Gly Glu Glu Ile Thr
        35                  40                  45

Tyr Ser Cys Lys Pro Gly Tyr Val Ser Arg Gly Gly Met Arg Lys Phe
    50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
        115                 120                 125

Lys Trp Ser Pro Glu Leu Pro Val Cys Ala Pro Ile Ile Cys Pro Pro
    130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
        195                 200                 205

Ser Arg Pro Asp Asn Gly Phe Val Asn Tyr Pro Ala Lys Pro Thr Leu
    210                 215                 220

Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
                245                 250                 255

Met Pro Ser Cys Lys Ala Ser Cys Lys Val Pro Val Lys Lys Ala Thr
            260                 265                 270

Val Val Tyr Gln Gly Glu Arg Val Lys Ile Gln Glu Lys Phe Lys Asn
        275                 280                 285
```

```
Gly Met Leu His Gly Asp Lys Val Ser Phe Phe Cys Lys Asn Lys Glu
    290             295             300
Lys Lys Cys Ser Tyr Thr Glu Asp Ala Gln Cys Ile Asp Gly Thr Ile
305             310             315             320
Glu Val Pro Lys Cys Phe Lys Glu His Ser Ser Leu Ala Phe Trp Lys
                325             330             335
Thr Asp Ala Ser Asp Val Lys Pro Cys
            340             345
```

METHODS AND COMPOSITIONS FOR DIAGNOSIS AND PROGNOSIS OF RENAL INJURY AND RENAL FAILURE

This application is filed under 35 U.S.C. §371 as the U.S. national phase of International Application No. PCT/US2010/023292, filed Feb. 5, 2010, which designated the U.S. and claims the benefit of priority to U.S. Provisional Patent Application 61/150,372 filed Feb. 6, 2009; 61/150,374 filed Feb. 6, 2009; 61/150,393 filed Feb. 6, 2009; 61/162,396 filed Mar. 23, 2009; 61/162,402 filed Mar. 23, 2009; and 61/166,333 filed Apr. 3, 2009, each of which is hereby incorporated in its entirety including all tables, figures, and claims.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |

| Type | Risk Factors |
|---|---|
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, Curr Opin Nephrol Hypertens 14:265-270, 2005 and Chertow et al, J Am Soc Nephrol 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., Crit Care. 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;
"Injury": serum creatinine increased 2.0 fold from baseline OR urine production <0.5 ml/kg/hr for 12 h;
"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:
"Loss": persistent need for renal replacement therapy for more than four weeks.
"ESRD": end stage renal disease—the need for dialysis for more than 3 months.

These criteria are called the RIFLE criteria, which provide a useful clinical tool to classify renal status. As discussed in Kellum, Crit. Care Med. 36: S 141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 µmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 µmol/L accompanied by an acute increase of at least 44 µmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more markers selected from the group consisting of Prostatic acid phosphatase, Lactotransferrin, Soluble erythropoietin receptor, Von Willebrand factor, Soluble endothelial protein C receptor, and Beta-2-glycoprotein 1 (collectively referred to herein as "kidney injury markers, and individually as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

These kidney injury markers may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more kidney injury markers of the present invention in a body fluid sample obtained from the subject. The assay result(s), for example a measured concentration of one or more markers selected from the group consisting of Prostatic acid phosphatase, Lactotransferrin, Soluble erythropoietin receptor, Von Willebrand factor, Soluble endothelial protein C receptor, and Beta-2-glycoprotein 1 is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s), for example a measured concentration of one or more markers selected from the group consisting of Prostatic acid phosphatase, Lactotransferrin, Soluble erythropoietin receptor, Von Willebrand factor, Soluble endothelial protein C receptor, and Beta-2-glycoprotein 1 is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result(s0 is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example a measured concentration of one or more markers selected from the group consisting of Prostatic acid phosphatase, Lactotransferrin, Soluble erythropoietin receptor, Von Willebrand factor, Soluble endothelial protein C receptor, and Beta-2-glycoprotein 1 is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example a measured concentration of one or more markers selected from the group consisting of Prostatic acid phosphatase, Lactotransferrin, Soluble erythropoietin receptor, Von Willebrand factor, Soluble endothelial protein C receptor, and Beta-2-glycoprotein 1 is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

BRIEF DESCRIPTION OF THE FIGURES

FIG. 1 provides data tables determined in accordance with Example 6 for the comparison of marker levels in urine samples collected for Cohort 1 (patients that did not progress beyond RIFLE stage 0) and in urine samples collected from subjects at 0, 24 hours, and 48 hours prior to reaching stage R, I or F in Cohort 2. Tables provide descriptive statistics, AUC analysis, and sensitivity, specificity and odds ratio calculations at various threshold (cutoff) levels for the various markers.

FIG. 2 provides data tables determined in accordance with Example 7 for the comparison of marker levels in urine samples collected for Cohort 1 (patients that did not progress beyond RIFLE stage 0 or R) and in urine samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 3 provides data tables determined in accordance with Example 8 for the comparison of marker levels in urine samples collected for Cohort 1 (patients that reached, but did not progress beyond, RIFLE stage R) and in urine samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 4 provides data tables determined in accordance with Example 9 for the comparison of marker levels in urine samples collected for Cohort 1 (patients that did not progress beyond RIFLE stage 0) and in urine samples collected from subjects at 0, 24 hours, and 48 hours prior to reaching stage F in Cohort 2. Tables provide descriptive statistics, AUC analysis, and sensitivity, specificity and odds ratio calculations at various threshold (cutoff) levels for the various markers.

FIG. 5 provides data tables determined in accordance with Example 6 for the comparison of marker levels in plasma samples collected for Cohort 1 (patients that did not progress beyond RIFLE stage 0) and in plasma samples collected from subjects at 0, 24 hours, and 48 hours prior to reaching stage R, I or F in Cohort 2. Tables provide descriptive statistics, AUC analysis, and sensitivity, specificity and odds ratio calculations at various threshold (cutoff) levels for the various markers.

FIG. 6 provides data tables determined in accordance with Example 7 for the comparison of marker levels in plasma samples collected for Cohort 1 (patients that did not progress beyond RIFLE stage 0 or R) and in plasma samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 7 provides data tables determined in accordance with Example 8 for the comparison of marker levels in plasma samples collected for Cohort 1 (patients that reached, but did not progress beyond, RIFLE stage R) and in plasma samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 8 provides data tables determined in accordance with Example 9 for the comparison of marker levels in plasma samples collected for Cohort 1 (patients that did not progress beyond RIFLE stage 0) and in plasma samples collected from subjects at 0, 24 hours, and 48 hours prior to reaching stage F in Cohort 2. Tables provide descriptive statistics, AUC analysis, and sensitivity, specificity and odds ratio calculations at various threshold (cutoff) levels for the various markers.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more markers selected from the group consisting of Prostatic acid phosphatase, Lactotransferrin, Soluble erythropoietin receptor, Von Willebrand factor, Soluble endothelial protein C receptor, and Beta-2-glycoprotein 1, or one or more markers related thereto, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 μmol/L), a percentage increase in serum creatinine of greater than or equal to 20% (1.2-fold from baseline), or a reduction in urine output (documented oliguria of less than 0. 5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 μmol/l), a percentage increase in serum creatinine of greater than or equal to 50% (1. 5-fold from baseline), or a reduction in urine output (documented oliguria of less than 0.5 ml/kg per hour for at least 6 hours). This term is synonymous with "acute kidney injury" or "AKI."

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

As used herein, the term "Prostatic acid phosphatase" refers to one or more polypeptides present in a biological sample that are derived from the Prostatic acid phosphatase precursor (Swiss-Prot P15309 (SEQ ID NO: 1)).

```
         10         20         30         40         50         60
 MRAAPLLLAR AASLSLGFLF LLFFWLDRSV LAKELKFVTL VFRHGDRSPI DTFPTDPIKE 70         80         90        100        110        120
 SSWPQGFGQL TQLGMEQHYE LGEYIRKRYR KFLNESYKHE QVYIRSTDVD RTLMSAMTNL 130        140        150        160        170        180
 AALFPPEGVS IWNPILLWQP IPVHTVPLSE DQLLYLPFRN CPRFQELESE TLKSEEFQKR 190        200        210        220        230        240
 LHPYKDFIAT LGKLSGLHGQ DLFGIWSKVY DPLYCESVHN FTLPSWATED TMTKLRELSE 250        260        270        280        290        300
 LSLLSLYGIH KQKEKSRLQG GVLVNEILNH MKRATQIPSY KKLIMYSAHD TTVSGLQMAL 310        320        330        340        350        360
 DVYNGLLPPY ASCHLTELYF EKGEYFVEMY YRNETQHEPY PLMLPGCSPS CPLERFAELV 370        380
 GPVIPQDWST ECMTTNSHQG TEDSTD
```

The following domains have been identified in Prostatic acid phosphatase:

| Residues | Length | Domain ID |
|---|---|---|
| 1-32 | 32 | Signal sequence |
| 33-386 | 354 | Prostatic acid phosphatase |

As used herein, the term "Lactotransferrin" refers to one or polypeptides present in a biological sample that are derived from the Lactotransferrin precursor (Swiss-Prot P02788 (SEQ ID NO: 2)).

```
         10         20         30         40         50         60
MKLVFLVLLF LGALGLCLAG RRRSVQWCAV SQPEATKCFQ WQRNMRKVRG PPVSCIKRDS 70         80         90        100        110        120
PIQCIQAIAE NRADAVTLDG GFIYEAGLAP YKLRPVAAEV YGTERQPRTH YYAVAVVKKG 130        140        150        160        170        180
GSFQLNELQG LKSCHTGLRR TAGWNVPIGT LRPFLNWTGP PEPIEAAVAR FFSASCVPGA 190        200        210        220        230        240
DKGQFPNLCR LCAGTGENKC AFSSQEPYFS YSGAFKCLRD GAGDVAFIRE STVFEDLSDE 250        260        270        280        290        300
AERDEYELLC PDNTRKPVDK FKDCHLARVP SHAVVARSVN GKEDAIWNLL RQAQEKFGKD 310        320        330        340        350        360
KSPKFQLFGS PSGQKDLLFK DSAIGFSRVP PRIDSGLYLG SGYFTAIQNL RKSEEEVAAR 370        380        390        400        410        420
RARVVWCAVG EQELRKCNQW SGLSEGSVTC SSASTTEDCI ALVLKGEADA MSLDGGYVYT 430        440        450        460        470        480
AGKCGLVPVL AENYKSQQSS DPDPNCVDRP VEGYLAVAVV RRSDTSLTWN SVKGKKSCHT 490        500        510        520        530        540
AVDRTAGWNI PMGLLFNQTG SCKFDEYFSQ SCAPGSDPRS NLCALCIGDE QGENKCVPNS 550        560        570        580        590        600
NERYYGYTGA FRCLAENAGD VAFVKDVTVL QNTDGNNNEA WAKDLKLADF ALLCLDGKRK 610        620        630        640        650        660
PVTEARSCHL AMAPNHAVVS RMDKVERLKQ VLLHQQAKFG RNGSDCPDKF CLFQSETKNL 670        680        690        700        710
LFNDNTECLA RLHGKTTYEK YLGPQYVAGI TNLKKCSTSP LLEACEFLRK
```

Lactotransferrin is cleaved into several smaller polypeptides which include kaliocin-1, lactoferroxin A, lactoferroxin B, and lactoferroxin C. The following domains have been identified in Lactotransferrin:

| Residues | Length | Domain ID |
|---|---|---|
| 1-19 | 19 | Signal sequence |
| 20-710 | 691 | Lactotransferrin |
| 171-201 | 31 | kaliocin-1 |
| 338-343 | 6 | lactoferroxin A |
| 543-547 | 5 | lactoferroxin B |
| 680-686 | 7 | lactoferroxin C |

As used herein, the term "Soluble erythropoietin receptor" refers to one or more non-membrane-bound polypeptides present in a biological sample that are derived from the Erythropoietin receptor precursor (Swiss-Prot P19235 (SEQ ID NO: 3)).

```
         10         20         30         40         50         60
MDHLGASLWP QVGSLCLLLA GAAWAPPPNL PDPKFESKAA LLAARGPEEL LCFTERLEDL 70         80         90        100        110        120
VCFWEEAASA GVGPGNYSFS YQLEDEPWKL CRLHQAPTAR GAVRFWCSLP TADTSSFVPL 130        140        150        160        170        180
ELRVTAASGA PRYHRVIHIN EVVLLDAPVG LVARLADESG HVVLRWLPPP ETPMTSHIRY 190        200        210        220        230        240
EVDVSAGNGA GSVQRVEILE GRTECVLSNL RGRTRYTFAV RARMAEPSFG GFWSAWSEPV 250        260        270        280        290        300
SLLTPSDLDP LILTLSLILV VILVLLTVLA LLSHRRALKQ KIWPGIPSPE SEFEGLFTTH 310        320        330        340        350        360
KGNFQLWLYQ NDGCLWWSPC TPFTEDPPAS LEVLSERCWG TMQAVEPGTD DEGPLLEPVG 370        380        390        400        410        420
SEHAQDTYLV LDKWLLPRNP PSEDLPGPGG SVDIVAMDEG SEASSCSSAL ASKPSPEGAS 430        440        450        460        470        480
AASFEYTILD PSSQLLRPWT LCPELPPTPP HLKYLYLVVS DSGISTDYSS GDSQGAQGGL 490        500
SDGPYSNPYE NSLIPAAEPL PPSYVACS
``` or a splice variant thereof (SEQ ID NO: 4)

```
         10         20         30         40         50         60
MDHLGASLWP QVGSLCLLLA GAAWAPPPNL PDPKFESKAA LLAARGPEEL LCFTERLEDL 70         80         90        100        110        120
VCFWEEAASA GVGPGNYSFS YQLEDEPWKL CRLHQAPTAR GAVRFWCSLP TADTSSFVPL 130        140        150        160        170        180
ELRVTAASGA PRYHRVIHIN EVVLLDAPVG LVARLADESG HVVLRWLPPP ETPMTSHIRY 190        200        210        220        230        240
EVDVSAGNGA GSVQRGTVFL SPDWLSSTRA RPHVIYFCLL RVPRPDSAPR WRSWRAAPSV

C
```

(or SEQ ID NO: 5)

```
         10         20         30         40         50         60
MDHLGASLWP QVGSLCLLLA GAAWAPPPNL PDPKFESKAA LLAARGPEEL LCFTERLEDL 70         80         90        100        110        120
VCFWEEAASA GVGPGNYSFS YQLEDEPWKL CRLHQAPTAR GAVRFWCSLP TADTSSFVPL 130        140        150        160        170        180
ELRVTAASGA PRYHRVIHIN EVVLLDAPVG LVARLADESG HVVLRWLPPP ETPMTSHIRY 190        200        210        220        230        240
EVDVSAGNGA GSVQRVEILE GRTECVLSNL RGRTRYTFAV RARMAEPSFG GFWSAWSEPV 250        260        270        280        290        300
SLLTPSDLDP LILTLSLILV VILVLLTVLA LLSHRRALKQ KIWPGIPSPE SEFEGLFTTH 310        320
KGNFQVGGLV VPSVPGLPCF LQPNCRPL
```

Erythropoietin receptor is a single-pass type I membrane protein having a large extracellular domain, some or all of which is present in soluble forms of Erythropoietin receptor generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Erythropoietin receptor:

| Residues | Length | Domain ID |
|---|---|---|
| 1-24 | 24 | Signal sequence |
| 25-508 | 484 | Erythropoietin receptor |

-continued

| Residues | Length | Domain ID |
|---|---|---|
| 25-250 | 226 | Extracellular domain |
| 251-273 | 23 | Transmembrane domain |
| 274-508 | 235 | Cytoplasmic domain |

As used herein, the term "Von Willebrand factor" refers to one or polypeptides present in a biological sample that are derived from the Von Willebrand factor precursor (Swiss-Prot P04275 (SEQ ID NO: 6)).

```
         10         20         30         40         50         60
MIPARFAGVL LALALILPGT LCAEGTRGRS STARCSLFGS DFVNTFDGSM YSFAGYCSYL 70         80         90        100        110        120
LAGGCQKRSF SIIGDFQNGK RVSLSVYLGE FFDIHLFVNG TVTQGDQRVS MPYASKGLYL 130        140        150        160        170        180
ETEAGYYKLS GEAYGFVARI DGSGNFQVLL SDRYFNKTCG LCGNFNIFAE DDFMTQEGTL 190        200        210        220        230        240
TSDPYDFANS WALSSGEQWC ERASPPSSSC NISSGEMQKG LWEQCQLLKS TSVFARCHPL 250        260        270        280        290        300
VDPEPFVALC EKTLCECAGG LECACPALLE YARTCAQEGM VLYGWTDHSA CSPVCPAGME 310        320        330        340        350        360
YRQCVSPCAR TCQSLHINEM CQERCVDGCS CPEGQLLDEG LCVESTECPC VHSGKRYPPG 370        380        390        400        410        420
TSLSRDCNTC ICRNSQWICS NEECPGECLV TGQSHFKSFD NRYFTFSGIC QYLLARDCQD
```

-continued

```
        430        440        450        460        470        480
 HSFSIVIETV QCADDRDAVC TRSVTVRLPG LHNSLVKLKH GAGVAMDGQD IQLPLLKGDL 490        500        510        520        530        540
 RIQHTVTASV RLSYGEDLQM DWDGRGRLLV KLSPVYAGKT CGLCGNYNGN QGDDFLTPSG 550        560        570        580        590        600
 LAEPRVEDFG NAWKLHGDCQ DLQKQHSDPC ALNPRMTRFS EEACAVLTSP TFEACHRAVS 610        620        630        640        650        660
 PLPYLRNCRY DVCSCSDGRE CLCGALASYA AACAGRGVRV AWREPGRCEL NCPKGQVYLQ 670        680        690        700        710        720
 CGTPCNLTCR SLSYPDEECN EACLEGCFCP PGLYMDERGD CVPKAQCPCY YDGEIFQPED 730        740        750        760        770        780
 IFSDHHTMCY CEDGFMHCTM SGVPGSLLPD AVLSSPLSHR SKRSLSCRPP MVKLVCPADN 790        800        810        820        830        840
 LRAEGLECTK TCQNYDLECM SMGCVSGCLC PPGMVRHENR CVALERCPCF HQGKEYAPGE 850        860        870        880        890        900
 TVKIGCNTCV CRDRKWNCTD HVCDATCSTI GMAHYLTFDG LKYLFPGECQ YVLVQDYCGS 910        920        930        940        950        960
 NPGTFRILVG NKGCSHPSVK CKKRVTILVE GGEIELFDGE VNVKRPMKDE THFEVVESGR 970        980        990       1000       1010       1020
 YIILLLGKAL SVVWDRHLSI SVVLKQTYQE KVCGLCGNFD GIQNNDLTSS NLQVEEDPVD 1030       1040       1050       1060       1070       1080
 FGNSWKVSSQ CADTRKVPLD SSPATCHNNI MKQTMVDSSC RILTSDVFQD CNKLVDPEPY 1090       1100       1110       1120       1130       1140
 LDVCIYDTCS CESIGDCACF CDTIAAYAHV CAQHGKVVTW RTATLCPQSC EERNLRENGY 1150       1160       1170       1180       1190       1200
 ECEWRYNSCA PACQVTCQHP EPLACPVQCV EGCHAHCPPG KILDELLQTC VDPEDCPVCE 1210       1220       1230       1240       1250       1260
 VAGRRFASGK KVTLNPSDPE HCQICHCDVV NLTCEACQEP GGLVVPPTDA PVSPTTLYVE 1270       1280       1290       1300       1310       1320
 DISEPPLHDF YCSRLLDLVF LLDGSSRLSE AEFEVLKAFV VDMMERLRIS QKWVRVAVVE 1330       1340       1350       1360       1370       1380
 YHDGSHAYIG LKDRKRPSEL RRIASQVKYA GSQVASTSEV LKYTLFQIFS KIDRPEASRI 1390       1400       1410       1420       1430       1440
 ALLLMASQEP QRMSRNFVRY VQGLKKKKVI VIPVGIGPHA NLKQIRLIEK QAPENKAFVL 1450       1460       1470       1480       1490       1500
 SSVDELEQQR DEIVSYLCDL APEAPPPTLP PHMAQVTVGP GLLGVSTLGP KRNSMVLDVA 1510       1520       1530       1540       1550       1560
 FVLEGSDKIG EADFNRSKEF MEEVIQRMDV GQDSIHVTVL QYSYMVTVEY PFSEAQSKGD 1570       1580       1590       1600       1610       1620
 ILQRVREIRY QGGNRTNTGL ALRYLSDHSF LVSQGDREQA PNLVYMVTGN PASDEIKRLP 1630       1640       1650       1660       1670       1680
 GDIQVVPIGV GPNANVQELE RIGWPNAPIL IQDFETLPRE APDLVLQRCC SGEGLQIPTL 1690       1700       1710       1720       1730       1740
 SPAPDCSQPL DVILLLDGSS SFPASYFDEM KSFAKAFISK ANIGPRLTQV SVLQYGSITT 1750       1760       1770       1780       1790       1800
 IDVPWNVVPE KAHLLSLVDV MQREGGPSQI GDALGFAVRY LTSEMHGARP GASKAVVILV 1810       1820       1830       1840       1850       1860
 TDVSVDSVDA AADAARSNRV TVFPIGIGDR YDAAQLRILA GPAGDSNVVK LQRIEDLPTM 1870       1880       1890       1900       1910       1920
 VTLGNSFLHK LCSGFVRICM DEDGNEKRPG DVWTLPDQCH TVTCQPDGQT LLKSHRVNCD 1930       1940       1950       1960       1970       1980
 RGLRPSCPNS QSPVKVEETC GCRWTCPCVC TGSSTRHIVT FDGQNFKLTG SCSYVLFQNK 1990       2000       2010       2020       2030       2040
 EQDLEVILHN GACSPGARQG CMKSIEVKHS ALSVELHSDM EVTVNGRLVS VPYVGGNMEV
```

```
           2050       2060       2070       2080       2090       2100
      NVYGAIMHEV RFNHLGHIFT FTPQNNEFQL QLSPKTFASK TYGLCGICDE NGANDFMLRD 2110       2120       2130       2140       2150       2160
      GTVTTDWKTL VQEWTVQRPG QTCQPILEEQ CLVPDSSHCQ VLLLPLFAEC HKVLAPATFY 2170       2180       2190       2200       2210       2220
      AICQQDSCHQ EQVCEVIASY AHLCRTNGVC VDWRTPDFCA MSCPPSLVYN HCEHGCPRHC 2230       2240       2250       2260       2270       2280
      DGNVSSCGDH PSEGCFCPPD KVMLEGSCVP EEACTQCIGE DGVQHQFLEA WVPDHQPCQI 2290       2300       2310       2320       2330       2340
      CTCLSGRKVN CTTQPCPTAK APTCGLCEVA RLRQNADQCC PEYECVCDPV SCDLPPVPHC 2350       2360       2370       2380       2390       2400
      ERGLQPTLTN PGECRPNFTC ACRKEECKRV SPPSCPPHRL PTLRKTQCCD EYECACNCVN 2410       2420       2430       2440       2450       2460
      STVSCPLGYL ASTATNDCGC TTTTCLPDKV CVHRSTIYPV GQFWEEGCDV CTCTDMEDAV 2470       2480       2490       2500       2510       2520
      MGLRVAQCSQ KPCEDSCRSG FTYVLHEGEC CGRCLPSACE VVTGSPRGDS QSSWKSVGSQ 2530       2540       2550       2560       2570       2580
      WASPENPCLI NECVRVKEEV FIQQRNVSCP QLEVPVCPSG FQLSCKTSAC CPSCRCERME 2590       2600       2610       2620       2630       2640
      ACMLNGTVIG PGKTVMIDVC TTCRCMVQVG VISGFKLECR KTTCNPCPLG YKEENNTGEC 2650       2660       2670       2680       2690       2700
      CGRCLPTACT IQLRGGQIMT LKRDETLQDG CDTHFCKVNE RGEYFWEKRV TGCPPFDEHK 2710       2720       2730       2740       2750       2760
      CLAEGGKIMK IPGTCCDTCE EPECNDITAR LQYVKVGSCK SEVEVDIHYC QGKCASKAMY 2770       2780       2790       2800       2810
      SIDINDVQDQ CSCCSPTRTE PMQVALHCTN GSVVYHEVLN AMECKCSPRK CSK
```

The following domains have been identified in Von Willebrand factor:

| Residues | Length | Domain ID |
|---|---|---|
| 1-24 | 22 | Signal sequence |
| 23-763 | 227 | Von Willebrand antigen 2 |
| 764-2813 | 2050 | Von Willebrand factor |

As used herein, the term "Soluble endothelial protein C receptor" refers to one or more non-membrane-bound polypeptides present in a biological sample that are derived from the Erythropoietin receptor precursor (Swiss-Prot Q9UNN8 (SEQ ID NO: 7)).

```
            10         20         30         40         50         60
      MLTTLLPILL LSGWAFCSQD ASDGLQRLHM LQISYFRDPY HVWYQGNASL GGHLTHVLEG 70         80         90        100        110        120
      PDTNTTIIQL QPLQEPESWA RTQSGLQSYL LQFHGLVRLV HQERTLAFPL TIRCFLGCEL 130        140        150        160        170        180
      PPEGSRAHVF FEVAVNGSSF VSFRPERALW QADTQVTSGV VTFTLQQLNA YNRTRYELRE 190        200        210        220        230
      FLEDTCVQYV QKHISAENTK GSQTSRSYTS LVLGVLVGSF IIAGVAVGIF LCTGGRRC
```

Endothelial protein C receptor is a single-pass type I membrane protein having a large extracellular domain, some or all of which is present in soluble forms of Endothelial protein C receptor generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Endothelial protein C receptor:

| Residues | Length | Domain ID |
|---|---|---|
| 1-17 | 17 | Signal sequence |
| 18-238 | 221 | Erythropoietin receptor |
| 18-210 | 193 | Extracellular domain |
| 211-231 | 21 | Transmembrane domain |
| 232-238 | 7 | Cytoplasmic domain |

As used herein, the term "Beta-2-glycoprotein 1" refers to one or polypeptides present in a biological sample that are derived from the Beta-2-glycoprotein 1 precursor (Swiss-Prot P02749 (SEQ ID NO: 8)).

```
        10         20         30         40         50         60
MISPVLILFS SFLCHVAIAG RTCPKPDDLP FSTVVPLKTF YEPGEEITYS CKPGYVSRGG 70         80         90        100        110        120
MRKFICPLTG LWPINTLKCT PRVCPFAGIL ENGAVRYTTF EYPNTISFSC NTGFYLNGAD 130        140        150        160        170        180
SAKCTEEGKW SPELPVCAPI ICPPPSIPTF ATLRVYKPSA GNNSLYRDTA VFECLPQHAM 190        200        210        220        230        240
FGNDTITCTT HGNWTKLPEC REVKCPFPSR PDNGFVNYPA KPTLYYKDKA TFGCHDGYSL 250        260        270        280        290        300
DGPEEIECTK LGNWSAMPSC KASCKVPVKK ATVVYQGERV KIQEKFKNGM LHGDKVSFFC 310        320        330        340
KNKEKKCSYT EDAQCIDGTI EVPKCFKEHS SLAFWKTDAS DVKPC
```

The following domains have been identified in Beta-2-glycoprotein 1:

| Residues | Length | Domain ID |
|---|---|---|
| 1-19 | 19 | Signal sequence |
| 20-345 | 326 | Beta-2-glycoprotein 1 |

In addition, several naturally occurring variants have been identified:

| Residue | Change |
|---|---|
| 5 | V to A |
| 107 | S to N |
| 154 | R to H |
| 266 | V to L |
| 325 | C to G |
| 335 | W to S |

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the $97.5^{th}$ percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal dectection therory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Cathepsin B (P07858); Ceruloplasmin (P00450); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (000206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itml, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/ (urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{-corrected}} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

EXAMPLE 1

Contrast-induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:
Inclusion Criteria
males and females 18 years of age or older;
undergoing a radiographic/angiographic procedure (such as a CT scan or coronary intervention) involving the intravascular administration of contrast media;
expected to be hospitalized for at least 48 hours after contrast administration;
able and willing to provide written informed consent for study participation and to comply with all study procedures.

Exclusion Criteria
renal transplant recipients;
acutely worsening renal function prior to the contrast procedure;
already receiving dialysis (either acute or chronic) or in imminent need of dialysis at enrollment;
expected to undergo a major surgical procedure (such as involving cardiopulmonary bypass) or an additional imaging procedure with contrast media with significant risk for further renal insult within the 48 hrs following contrast administration;
participation in an interventional clinical study with an experimental therapy within the previous 30 days;
known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age >75 yrs=4 points; hematocrit level <39% for men, <35% for women=3 points; diabetes=3 points; contrast media volume=1 point for each 100 mL; serum creatinine level >1.5 g/dL=4 points OR estimated GFR 40-60 mL/min/1.73 m$^2$=2 points, 20-40 mL/min/1.73 m$^2$=4 points, <20 mL/min/1.73 m$^2$=6 points. The risks assigned are as follows: risk for CIN and dialysis: 5 or less total points=risk of CIN-7.5%, risk of dialysis-0.04%; 6-10 total points=risk of CIN-14%, risk of dialysis-0.12%; 11-16 total points=risk of CIN-26.1%, risk of dialysis-1.09%; >16 total points=risk of CIN-57.3%, risk of dialysis-12.8%.

EXAMPLE 2

Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:
Inclusion Criteria
males and females 18 years of age or older;

undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.

Exclusion Criteria
known pregnancy;
previous renal transplantation;
acutely worsening renal function prior to enrollment (e.g., any category of RIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

EXAMPLE 3

Acutely Ill Subject Sample Collection

The objective of this study is to collect samples from acutely ill patients. Approximately 900 adults expected to be in the ICU for at least 48 hours will be enrolled. To be enrolled in the study, each patient must meet all of the following inclusion criteria and none of the following exclusion criteria:
Inclusion Criteria males and females 18 years of age or older;
Study population 1: approximately 300 patients that have at least one of:
shock (SBP<90 mmHg and/or need for vasopressor support to maintain MAP>60 mmHg and/or documented drop in SBP of at least 40 mmHg); and sepsis;
Study Population 2: Approximately 300 Patients that have at Least One of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study Population 3: Approximately 300 Patients
expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment.

Exclusion Criteria
known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HW) or a hepatitis virus;
meets only the SBP<90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

EXAMPLE 4

Immunoassay Format

Analytes are is measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

Concentrations are expressed in the following examples as follows: Prostatic acid phosphatase—ng/mL, Lactotransferrin—ng/mL, Soluble erythropoietin receptor—pg/mL, Von Willebrand factor—μg/mL, Soluble endothelial protein C receptor—pg/mL, and Beta-2-glycoprotein 1—pg/mL.

EXAMPLE 5

Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

EXAMPLE 6

Kidney Injury Markers for Evaluating Renal Status in Patients at RIFLE Stage 0

Patients from the intensive care unit (ICU) were classified by kidney status as non-injury (0), risk of injury (R), injury (I), and failure (F) according to the maximum stage reached within 7 days of enrollment as determined by the RIFLE criteria.

Two cohorts were defined as (Cohort 1) patients that did not progress beyond stage 0, and (Cohort 2) patients that reached stage R, I, or F within 10 days. To address normal marker fluctuations that occur within patients at the ICU and thereby assess utility for monitoring AKI status, marker levels were measured in urine samples collected for Cohort 1. Marker concentrations were measured in urine samples collected from a subject at 0, 24 hours, and 48 hours prior to reaching stage R, I or F in Cohort 2. In the following tables, the time "prior max stage" represents the time at which a sample is collected, relative to the time a particular patient reaches the lowest disease stage as defined for that cohort, binned into three groups which are +/−12 hours. For example, 24 hr prior for this example (0 vs R, I, F) would mean 24 hr (+/−12 hours) prior to reaching stage R (or I if no sample at R, or F if no sample at R or I).

Each marker was measured by standard immunoassay methods using commercially available assay reagents. A receiver operating characteristic (ROC) curve was generated for each marker and the area under each ROC curve (AUC) was determined. Patients in Cohort 2 were also separated according to the reason for adjudication to stage R, I, or F as being based on serum creatinine measurements (sCr), being based on urine output (UO), or being based on either serum creatinine measurements or urine output. That is, for those patients adjudicated to stage R, I, or F on the basis of serum creatinine measurements alone, the stage 0 cohort may have included patients adjudicated to stage R, I, or F on the basis of urine output; for those patients adjudicated to stage R, I, or F on the basis of urine output alone, the stage 0 cohort may have included patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, for those patients adjudicated to stage R, I, or F on the basis of serum creatinine measurements or urine output, the adjudication method which yielded the most severe RIFLE stage was used.

The ability to distinguish cohort 1 (subjects remaining in RIFLE 0) from Cohort 2 (subjects progressing to RIFLE R, I or F) was determined using ROC analysis. SE is the standard error of the AUC, n is the number of sample or individual patients ("pts," as indicated). Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 1.

EXAMPLE 7

Kidney Injury Markers for Evaluating Renal Status in Patients at RIFLE Stages 0 and R Patients were classified and analyzed as described in Example 6. However, patients that reached stage R but did not progress to stage I or F were grouped with patients from non-injury stage 0 in Cohort 1. Cohort 2 in this example included only patients that progressed to stage I or F. Marker concentrations in urine samples were included for Cohort 1. Marker concentrations in urine samples collected within 0, 24, and 48 hours of reaching stage I or F were included for Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 2.

EXAMPLE 8

Kidney Injury Markers gor Evaluating Renal Status in Patients Progressing from Stage R to Stages I and F Patients were classified and analyzed as described in Example 6, but only those patients that reached Stage R were included in this example. Cohort 1 contained patients that reached stage R but did not progress to stage I or F within 10 days, and Cohort 2 included only patients that progressed to stage I or F. Marker concentrations in urine samples collected within 12 hours of reaching stage R were included in the analysis for both Cohort 1 and 2.

The ability to distinguish cohort 1 (subjects remaining in RIFLE R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 3.

EXAMPLE 9

Kidney Injury Markers for Evaluating Renal Status in Patients at RIFLE Stage 0

Patients were classified and analyzed as described in Example 6. However, patients that reached stage R or I but did not progress to stage F were eliminated from the analysis. Patients from non-injury stage 0 are included in Cohort 1. Cohort 2 in this example included only patients that progressed to stage F. The maximum marker concentrations in urine samples were included for each patient in Cohort 1. The maximum marker concentrations in urine samples collected within 0, 24, and 48 hours of reaching stage F were included for each patient in Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 4.

EXAMPLE 10

Kidney Injury Markers for Evaluating Renal Status in Patients at RIFLE Stage 0

Patients from the intensive care unit (ICU) were classified by kidney status as non-injury (0), risk of injury (R), injury (I), and failure (F) according to the maximum stage reached within 7 days of enrollment as determined by the RIFLE criteria.

Two cohorts were defined as (Cohort 1) patients that did not progress beyond stage 0, and (Cohort 2) patients that reached stage R, I, or F within 10 days. To address normal marker fluctuations that occur within patients at the ICU and thereby assess utility for monitoring AKI status, marker levels were measured in the plasma component of blood samples collected for Cohort 1. Marker concentrations were measured in the plasma component of blood samples collected from a subject at 0, 24 hours, and 48 hours prior to reaching stage R, I or F in Cohort 2. In the following tables, the time "prior max stage" represents the time at which a sample is collected, relative to the time a particular patient reaches the lowest disease stage as defined for that cohort, binned into three groups which are +/−12 hours. For example, 24 hr prior for this example (0 vs R, I, F) would mean 24 hr (+/−12 hours) prior to reaching stage R (or I if no sample at R, or F if no sample at R or I).

Each marker was measured by standard immunoassay methods using commercially available assay reagents. A receiver operating characteristic (ROC) curve was generated for each marker and the area under each ROC curve (AUC) was determined. Patients in Cohort 2 were also separated according to the reason for adjudication to stage R, I, or F as being based on serum creatinine measurements (sCr), being based on urine output (UO), or being based on either serum creatinine measurements or urine output. That is, for those patients adjudicated to stage R, I, or F on the basis of serum creatinine measurements alone, the stage 0 cohort may have included patients adjudicated to stage R, I, or F on the basis of urine output; for those patients adjudicated to stage R, I, or F on the basis of urine output alone, the stage 0 cohort may have included patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, for those patients adjudicated to stage R, I, or F on the basis of serum creatinine measurements or urine output, the adjudication method which yielded the most severe RIFLE stage was used.

The ability to distinguish cohort 1 (subjects remaining in RIFLE 0) from Cohort 2 (subjects progressing to RIFLE R, I or F) was determined using ROC analysis. SE is the standard error of the AUC, n is the number of sample or individual patients ("pts," as indicated). Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 5.

EXAMPLE 11

Kidney Injury Markers for Evaluating Renal Status in Patients at RIFLE Stages 0 and R Patients were classified and analyzed as described in Example 10. However, patients that reached stage R but did not progress to stage I or F were grouped with patients from non-injury stage 0 in Cohort 1. Cohort 2 in this example included only patients that progressed to stage I or F. Marker concentrations in the plasma component of blood samples were included for Cohort 1. Marker concentrations in the plasma component of blood samples collected within 0, 24, and 48 hours of reaching stage I or F were included for Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 6.

EXAMPLE 12

Kidney Injury Markers for Evaluating Renal Status in Patients Progressing from Stage R to Stages I and F Patients were classified and analyzed as described in Example 10, but only those patients that reached Stage R were included in this example. Cohort 1 contained patients that reached stage R but did not progress to stage I or F within 10 days, and Cohort 2 included only patients that progressed to stage I or F. Marker concentrations in the plasma component of blood samples collected within 12 hours of reaching stage R were included in the analysis for both Cohort 1 and 2.

The ability to distinguish cohort 1 (subjects remaining in RIFLE R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 7.

EXAMPLE 13

Kidney Injury Markers for Evaluating Renal Status in Patients at RIFLE Stage 0

Patients were classified and analyzed as described in Example 10. However, patients that reached stage R or I but did not progress to stage F were eliminated from the analysis. Patients from non-injury stage 0 are included in Cohort 1. Cohort 2 in this example included only patients that progressed to stage F. The maximum marker concentrations in the plasma component of blood samples were included from each patient in Cohort 1. The maximum marker concentrations in the plasma component of blood samples collected within 0, 24, and 48 hours of reaching stage F were included from each patient in Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 8.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

---

We claim:

1. A method for evaluating renal status in a subject, comprising:

performing one or more assays configured to detect a kidney injury marker selected from the group consisting of Prostatic acid phosphatase, Lactotransferrin, Soluble erythropoietin receptor, Von Willebrand factor, and Soluble endothelial protein C receptor on a body fluid sample obtained from the subject by introducing a body fluid sample obtained from the subject into an assay instrument which, for each kidney injury marker being assayed, (i) contacts all or a portion of the body fluid sample with a binding reagent which specifically binds for detection the kidney injury marker being assayed and (ii) generates an assay result indicative of binding of the kidney injury marker being assayed to the binding reagent to provide one or more assay results;

correlating the assay result(s) generated by the assay instrument to a likelihood that the subject is at risk of a future acute renal injury within 72 hours of the time at which the body fluid sample is obtained from the subject by using the assay result to assign the subject to a predetermined subpopulation of individuals having a known predisposition of a future acute renal injury within 72 hours; and treating the subject based on the predetermined subpopulation of individuals to which the patient is assigned, wherein the treatment comprises one or more of initiating renal replacement therapy, withdrawing delivery of compounds that are known to be damaging to the kidney, delaying or avoiding procedures that are known to be damaging to the kidney, and modifying diuretic administration.

2. A method according to claim 1, wherein said risk of a future acute renal injury is a risk of future acute renal failure (ARF).

3. A method according to claim 2, wherein said assay result(s) comprise one or more of:

(i) a measured concentration of Prostatic acid phosphatase,
(ii) a measured concentration of Lactotransferrin,
(iii) a measured concentration of Soluble erythropoietin receptor,
(iv) a measured concentration of Von Willebrand factor, and
(v) a measured concentration of Soluble endothelial protein C receptor.

4. A method according to claim 1, wherein the subject is selected for evaluation of renal status based on the pre-existence in the subject of one or more known risk factors for prerenal, intrinsic renal, or postrenal ARF.

5. A method according to claim 1, wherein the subject is selected for evaluation of renal status based on an existing diagnosis of one or more of congestive heart failure, preeclampsia, eclampsia, diabetes mellitus, hypertension, coronary artery disease, proteinuria, renal insufficiency, glomerular filtration below the normal range, cirrhosis, serum creatinine above the normal range, sepsis, injury to renal function, reduced renal function, or ARF, or based on undergoing or having undergone major vascular surgery, coronary artery bypass, or other cardiac surgery, or based on exposure to NSAIDs, cyclosporines, tacrolimus, aminoglycosides, foscarnet, ethylene glycol, hemoglobin, myoglobin, ifosfamide, heavy metals, methotrexate, radiopaque contrast agents, or strep tozotocin.

6. A method according to claim 1, wherein said risk of a future acute renal injury is a risk within 48 hours of the time at which the body fluid sample is obtained.

7. A method according to claim 1, wherein said risk of a future acute renal injury is a risk within 24 hours of the time at which the body fluid sample is obtained.

* * * * *